US011897873B2

(12) United States Patent
Roberts et al.

(10) Patent No.: US 11,897,873 B2
(45) Date of Patent: *Feb. 13, 2024

(54) KAPPA OPIOID RECEPTOR ANTAGONISTS AND PRODUCTS AND METHODS RELATED THERETO

(71) Applicants: The Scripps Research Institute, La Jolla, CA (US); BlackThorn Therapeutics, Inc., San Francisco, CA (US)

(72) Inventors: Edward Roberts, Fallbrook, CA (US); Miguel A. Guerrero, San Diego, CA (US); Mariangela Urbano, Del Mar, CA (US); Hugh Rosen, La Jolla, CA (US); Robert M. Jones, South San Francisco, CA (US); Candace Mae Laxamana, South San Francisco, CA (US); Xianrui Zhao, South San Francisco, CA (US); Eric Douglas Turtle, Belmont, CA (US)

(73) Assignees: BLACKTHORN THERAPEUTICS, INC., San Francisco, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/390,531

(22) Filed: Jul. 30, 2021

(65) Prior Publication Data

US 2022/0162202 A1 May 26, 2022

Related U.S. Application Data

(60) Continuation of application No. 16/846,136, filed on Apr. 10, 2020, now Pat. No. 11,124,504, which is a division of application No. 15/924,119, filed on Mar. 16, 2018, now Pat. No. 10,676,469.

(60) Provisional application No. 62/609,960, filed on Dec. 22, 2017, provisional application No. 62/585,447, filed on Nov. 13, 2017, provisional application No. 62/473,209, filed on Mar. 17, 2017.

(51) Int. Cl.
*C07D 413/14* (2006.01)
*A61P 25/00* (2006.01)
*A61P 25/06* (2006.01)

(52) U.S. Cl.
CPC ............ *C07D 413/14* (2013.01); *A61P 25/00* (2018.01); *A61P 25/06* (2018.01)

(58) Field of Classification Search
CPC ......... C07D 413/14; A61P 25/00; A61P 25/06
See application file for complete search history.

(56) References Cited

U.S. PATENT DOCUMENTS

| | | | |
|---|---|---|---|
| 9,682,966 B2 | 6/2017 | Roberts et al. | |
| 10,118,915 B2 | 11/2018 | Roberts et al. | |
| 10,676,469 B2 * | 6/2020 | Roberts | A61P 25/06 |
| 11,124,504 B2 * | 9/2021 | Roberts | A61P 25/00 |
| 2015/0210673 A1 | 7/2015 | Roberts et al. | |
| 2018/0099954 A1 | 4/2018 | Roberts et al. | |

FOREIGN PATENT DOCUMENTS

| | | |
|---|---|---|
| WO | 2010/100405 A1 | 9/2010 |
| WO | 2014/028829 A1 | 2/2014 |

OTHER PUBLICATIONS

Guerrero; J. Med. Chem. 2019, 62, 1761-1780. DOI: 10.1021/acs.jmedchem.8b01679 (Year: 2019).

Urbano; Bioorg. Med. Chem. Lett. 2014, 24, 2021-2032. DOI: 10.1016/j.bmcl.2014.03.040 (Year: 2014).

Guerrero; Optimization and characterization of an opioid kappa receptor (OPRK1) antagonist. In Probe Reports from the NIH Molecular Libraries Program [Internet]; National Center for Biotechnology Information: Bethesda, MD, 2013; https://www.ncbi.nlm.nih.gov/books/NBK179827/ (accessed Sep. 5, 2019). (Year: 2013).

* cited by examiner

*Primary Examiner* — Daniel R Carcanague
(74) *Attorney, Agent, or Firm* — Seed IP Law Group LLP

(57) ABSTRACT

Compounds are provided that antagonize the kappa-opioid receptor (KOR) and products containing such compounds, as well as to methods of their use and synthesis. Such compounds have the structure of Formula (I), or a pharmaceutically acceptable isomer, racemate, hydrate, solvate, isotope or salt thereof:

(I)

wherein X, Y, $R^1$, $R^2$, $R^4$, $R^5$, $R^6$, $R^7$, $R^8$ and $R^{11}$ are as defined herein.

6 Claims, 18 Drawing Sheets

TH Immunohistochemistry

KAPPA OPIOID RECEPTOR ANTAGONISTS AND PRODUCTS AND METHODS RELATED THERETO

STATEMENT OF GOVERNMENT INTEREST

This invention was made with government support under grant 1uh2ns093030-01 awarded by the national institute of neurological disorders and stroke (ninds), an institute within the national institute of health (nih). The government has certain rights in the invention.

FIELD OF THE INVENTION

The invention relates to kappa-opioid receptor (KOR) antagonists and to products containing the same, as well as to methods of their use and preparation.

BACKGROUND

The kappa-opioid receptor (KOR) is encoded by the OPRK1 gene and is a member of the opioid receptor family which binds the opioid peptide dynorphin as the primary endogenous ligand. The KOR has a wide, yet distinct distribution in the brain, spinal cord, and in peripheral tissues, and particularly in brain areas implicated in reward, cognitive function and stress responsiveness. Evidence indicates that dynorphins are elevated under painful and stressful conditions, and that KOR disruption produces anti-stress effects. Such findings have led to development of KOR antagonists for treatment of depressive, anxiety, addictive disorders, as well as other psychiatric conditions associated with stress. Development of KOR antagonists is summarized in the article entitled "Antagonists of the Kappa Opioid Receptor" by Urbano et al., *Bioorganic & Medicinal Chemistry Letters*, 24:2021-2032, 2014.

Pharmacological studies with prototypical KOR antagonists (i.e., the morphinan-derived ligands nor-BNI and GNTI, and the non-morphinan JDTic), have confirmed the therapeutic potential of the KOR/dynorphin system. However, such prototypical KOR antagonists display delayed onset of action in the range of hours to days, followed by antagonism effects lasting weeks at minimally effective doses. Furthermore, such compounds showed poor blood-brain barrier penetration. Thus, more recent research has focused on the development of short-acting KOR antagonists with improved pharmacokinetics.

KOR antagonists have been extensively studied because they block a prominent stress-induced neuroadaptation; namely, elevated expression of dynorphin in the nucleus accumbens (NAc). The NAc is an element of the mesolimbic system which plays a role in motivation and the pathology of psychiatric disorders. Stress, as well as repeated exposure to drugs of abuse, triggers a complex sequence of intracellular events involving the transcription factor CREB, a cAMP response element binding protein, in the NAc. As explained by Carlezon et al. in "Kappa Opioid Antagonists for Psychiatric Disorders: From Bench to Clinical Trials" (*Depression and Anxiety*, 33:895-906, 2016), CREB-mediated increases in the expression of dynorphin produce depressive-like signs, which KOR antagonists mitigate. According to the model set forth by Carlezon et al., stress activates CREB in the NAc, which leads to an increase in dynorphin expression. Increased dynorphin, in turn, promotes activation of KORs. KORs are expressed on the cell bodies and terminals of mesocorticolimbic dopamine (DA) neurons and activation of KORs inhibit DA release. Treatment with a KOR antagonist blocks the action of dynorphin, restoring DA function, and thereby providing antidepressant- and anxiolytic-like effects in various animal models.

Such mechanisms of action, as well as the rather extensive development and testing of KOR antagonists to date, including recent clinical study results (e.g., CERC-501 and ALKS-5461), provide strong evidence that KOR antagonists may have therapeutic effects in humans suffering from a wide range of disorders, including mood disorders, anxiety disorders and substance use disorders as defined, for example, in the Diagnostic and Statistical Manual of Mental Disorder (DSM). Another framework for classifying psychopathology disorders is the Research Domain Criteria (RDoC) project, which aims to classify such disorders based on dimensions of observable behavior and neurobiological dimensions. In this context, KOR antagonists have therapeutic effect on at least two types of RDoC-defined domains; namely, those related to reward and those related to adverse effects of stress. Within these domains, use of KOR antagonists for treatment of anhedonia ("positive valence system"), and for blocking the adverse effects of stress ("negative valence system"), have been recognized.

As a result of the advances made in this field, KOR antagonists are recognized for their utility in treating major depression and disorders related to substance abuse or addiction, particularly in the context of rapidly acting treatments which avoid the drawbacks associated with the prototypical KOR antagonists discussed above. Other studies have shown that KOR antagonists may be particularly useful for the treatment of stress-mediated symptoms, as well as for treating social anxiety disorder and phobias. Prophylactic therapy has also been suggested to prevent adverse conditions arising from stress, and in this regard KOR antagonism has been proposed as a preventative treatment of PTSD in individuals at risk of the same. Other therapeutic applications of KOR antagonism include the treatment of impairment in reward-related function as it frequently occurs in patients with mood and anxiety spectrum disorders, and which may also occur with other types of conditions such as schizophrenia or a schizoaffective disorder.

In summary, KOR antagonism provides significant promise for the treatment of a wide variety of disorders and conditions. As a result, a number of compounds are currently in development that are highly selective and potent KOR antagonists for treating a variety of conditions, such as substance use disorders, major depression, anhedonia, and stress-related symptoms. However, and despite the advances made in this field, there remains a need for new and improved KOR antagonists, as well as for pharmaceutical products containing the same, and for methods related to their use and manufacture.

SUMMARY OF THE INVENTION

The present invention is directed to compounds that antagonize the kappa opioid receptor (KOR), to compositions containing the same, and to methods of their preparation and use for treatment of a disease or condition wherein antagonism of a KOR is medically indicated or beneficial.

In an embodiment, compounds are provided having the structure of Formula (I), or a pharmaceutically acceptable isomer, racemate, hydrate, solvate, isotope or salt thereof:

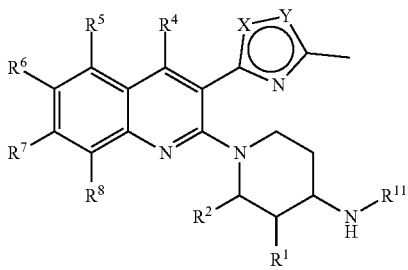

(I)

wherein X, Y, R¹, R², R⁴, R⁵, R⁶, R⁷, R⁸ and R¹¹ are as defined below.

In an embodiment, a pharmaceutical composition is provided comprising a compound having the structure of Formula (I), or a pharmaceutically acceptable isomer, racemate, hydrate, solvate, isotope or salt thereof, in combination with a pharmaceutically acceptable carrier, diluent or excipient.

In an embodiment, use of a compound having the structure of Formula (I), or a pharmaceutically acceptable isomer, racemate, hydrate, solvate, isotope, or salt thereof, for the manufacture of a medicament is provided.

In an embodiment, a method is provided for antagonizing the KOR, the method comprising contacting the receptor with an effective amount of a compound having the structure of Formula (I), or a pharmaceutically acceptable isomer, racemate, hydrate, solvate, isotope or salt thereof, or a pharmaceutical composition comprising the same.

In an embodiment, a method is provided for treatment of a neuropsychiatric or behavioral condition, whether organic, stress-induced or iatrogenic, that is characterized by elevations in serum prolactin and respond to KOR antagonist administration with a reduction in serum prolactin. Such method comprises administering to the subject an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject.

In an embodiment, a method is provided for treatment of a malcondition in a subject for which antagonism of the KOR is medically indicated. Such method comprises administering to the subject an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject.

In an embodiment, a method is provided for treatment of an addictive disorder, including disorders related to substance abuse or addiction, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method is provided for treatment of central nervous system (CNS)-related disorder, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method is provided for treatment of an anxiety disorder, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject. In one embodiment, the anxiety disorder is a social anxiety disorder. In one embodiment, the anxiety disorder is a generalized anxiety disorder (GAD). In one embodiment, the anxiety disorder is phobia. In one embodiment, the anxiety disorder is a stress-related disorder.

In an embodiment, a method is provided for treatment of a depressive disorder, depression, or depressive illness, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject. In one embodiment, the depressive disorder is major depression.

In an embodiment, a method is provided for treatment of a mood disorder, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject. In one embodiment, the mood disorder is anhedonia. In one embodiment, the mood disorder is major depression.

In an embodiment, a method is provided for treatment of a schizophrenia or a schizoaffective disorder, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject.

In an embodiment, a method is provided for treatment of obesity or an eating disorder, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject.

In an embodiment, a method is provided for treatment of migraine, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject.

In an embodiment, a method is provided for treatment of postnatal depression, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method is provided for treatment of disorders of mood and behavior associated with neurodegenerative diseases, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method of synthesis is provided for a compound having the structure of Formula (I), or a pharmaceutically acceptable isomer, racemate, hydrate, solvate, isotope or salt thereof.

In an embodiment, a pharmaceutical composition is provided comprising a compound having the structure of Formula (I), or a pharmaceutically acceptable isomer, racemate, hydrate, solvate, isotope or salt thereof, in combination with at least one pharmaceutically acceptable carrier, diluent or excipient.

DETAILED DESCRIPTION OF THE INVENTION

Figure 1A:
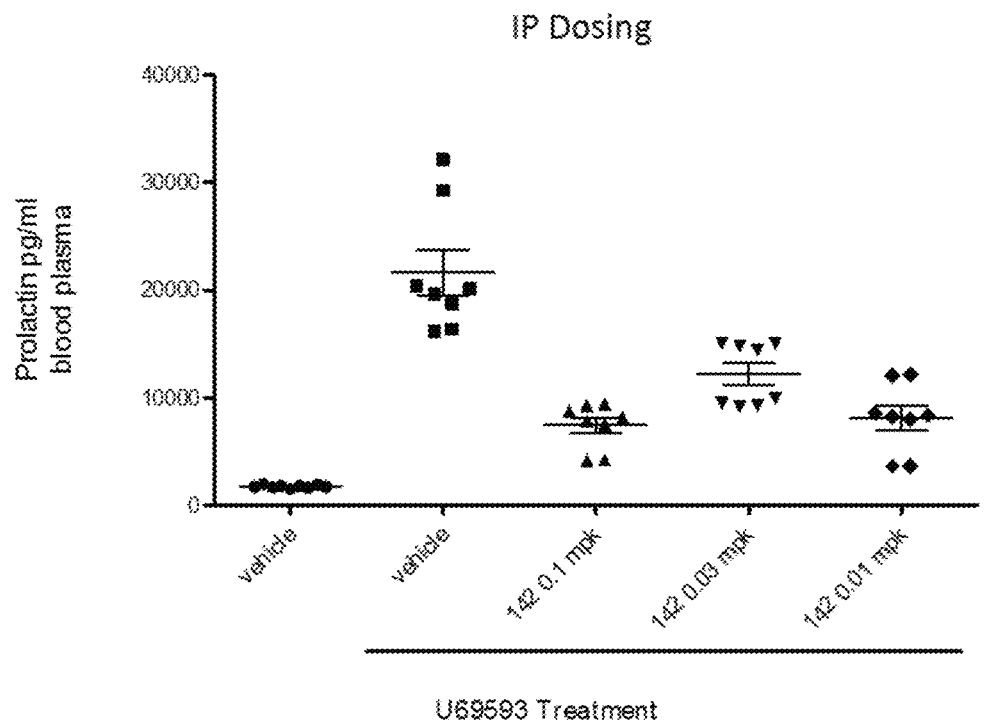
FIGS. 1A and 1B illustrate the activity of a representative compound, Compound 142, to serve as an antagonist in an OPRK1 agonist-induced prolactin challenge to 8-10 week old male C57BL/6J mice following IP dosing (FIG. 1A) and PO dosing (FIG. 1B).

As mentioned above, the invention relates to compounds that antagonize the kappa opioid receptor (KOR) (also referred to herein as KOR antagonists), to products comprising the same, and to methods for their use and synthesis.

In one embodiment, compounds are provided having the structure of Formula (I), or a pharmaceutically acceptable isomer, racemate, hydrate, solvate, isotope or salt thereof:

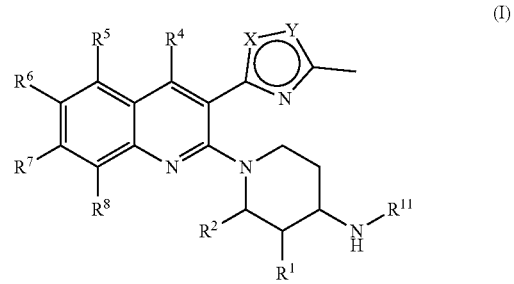

(I)

wherein
X is O when Y is N or X is N when Y is O;
$R^1$ is H, lower alkyl, or halo;
$R^2$ is H or lower alkyl;
$R^4$ and $R^8$ are each independently H, lower alkyl, halo or cyano, wherein at least one of $R^4$ and $R^8$ is not H or when both $R^4$ and $R^8$ are H $R^7$ is not H;
$R^5$ and $R^7$ are each independently H, halo or cyano, wherein at least one of $R^5$ and $R^7$ is H;

$R^6$ is lower alkyl, lower haloalkyl, lower alkoxy, lower haloalkoxy, cycloalkoxy, lower alkynyl, cycloalkyl, halo or cyano, wherein $R^6$ is not lower alkyl when $R^8$ is lower alkyl;

$R^{11}$ is $-(CH_2)_{0-1}R^{12}$ wherein $R^{12}$ is

[chemical structures]

and n is an integer from 1-5.

In one embodiment, compounds are provided having the structure of Formula (I), or a pharmaceutically acceptable isomer, racemate, hydrate, solvate, isotope or salt thereof, wherein X is O when Y is N or X is N when Y is O;

$R^1$ is H or F;

$R^4$ and $R^8$ are each independently hydrogen, lower alkyl, halo or cyano, wherein at least one of $R^4$ and $R^8$ is not hydrogen or when both $R^4$ and $R^8$ are hydrogen $R^7$ is not hydrogen;

$R^5$ and $R^7$ are each independently hydrogen, halo or cyano, wherein at least one of $R^5$ and $R^7$ is H;

$R^6$ is lower alkyl, lower haloalkyl, lower alkoxy, lower haloalkoxy, lower alkynyl, cycloalkyl, halo or cyano, wherein $R^6$ is not lower alkyl when $R^8$ is lower alkyl;

$R^{11}$ is $-(CH_2)_{0-1}R^{12}$ wherein $R^{12}$ is h

[chemical structures]

and n is an integer from 1-5.

In another embodiment, compounds are provided having the structure of Formula (I), or a pharmaceutically acceptable isomer, racemate, hydrate, solvate, isotope or salt thereof, wherein X is O when Y is N or X is N when Y is O;

$R^1$ is H or F;

$R^2$ is H or lower alkyl;

$R^4$ and $R^8$ are each independently H, lower alkyl, halo or cyano, wherein at least one of $R^4$ and $R^8$ is not H or when both $R^4$ and $R^8$ are H $R^7$ is not H;

$R^5$ and $R^7$ are each independently H, halo or cyano, wherein at least one of $R^5$ and $R^7$ is H;

$R^6$ is lower alkyl, lower haloalkyl, lower alkoxy, lower haloalkoxy, lower alkynyl, cycloalkyl, halo or cyano, wherein $R^6$ is not lower alkyl when $R^8$ is lower alkyl;

$R^{11}$ is $-(CH_2)_{0-1}R^1$ wherein R is

[chemical structures]

and n is an integer from 1-5.

In one embodiment, $R^1$ is H or F.

As used herein, "KOR" and "OPRK1" refer to the kappa-opioid receptor (KOR) that is encoded by the OPRK1 gene. "KOR" and "OPRK1" are used interchangeably herein.

As used herein, "DOR" and "OPRD" refer to the delta-opioid receptor (DOR) that is encoded by the OPRD gene. "DOR" and "OPRD" are used interchangeably herein.

As used herein, "MOR" and "OPRM1" refer to the mu-opioid receptor (MOR) that is encoded by the OPRM1 gene. "MOR" and "OPRM1" are used interchangeably herein.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

"Halo" or "halogen" refers to fluorine, chlorine, bromine and iodine.

"Cyano" refers to —CN.

"Lower haloalkyl" refers to a lower alkyl as defined above with one or more hydrogen atoms replaced with halogen. Examples of lower haloalkyl groups include, but are not limited to, —CF$_3$, —CH$_2$CF$_3$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, iso-propoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, —OCF$_3$, —OCH$_2$CF$_3$, and the like.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diasteromerically" pure means a level of enantiomeric or diasteromeric enrichment of one enantiomer with respect to the other enantiomer or diasteromer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out).

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon 13 and/or 14 atoms, wherein one or more hydrogen atoms are replaced with deuterium and/or tritium, and/or wherein one or more fluorine atoms are replaced by fluorine 19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

Co-crystal forms of compounds having the structure of Formula (I) are also included within the scope of this invention; namely, solids that are crystalline single phase materials composed of two or more different molecular and/or ionic compounds generally in a stoichiometric ratio which are neither solvates nor simple salts.

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int J. Pharm.*, 33, 201-217, 1986) (incorporated by reference herein).

Pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic and sulfonic classes of organic acids, examples of which include formic acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Although pharmaceutically unacceptable salts are not generally useful as medicaments, such salts may be useful, for example as intermediates in the synthesis of compounds having the structure of Formula I, for example in their purification by recrystallization.

In more specific embodiments, compounds are provided having the structure of any one of Formulas (II) through (XX). or a pharmaceutically acceptable isomer, racemate, hydrate, solvate, isotope or salt thereof:

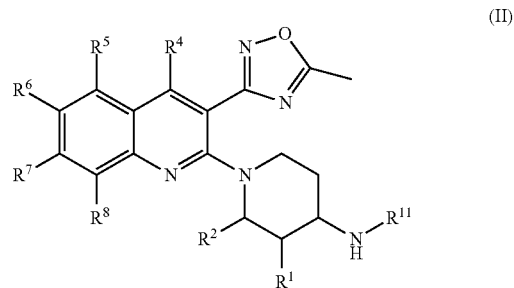

(II)

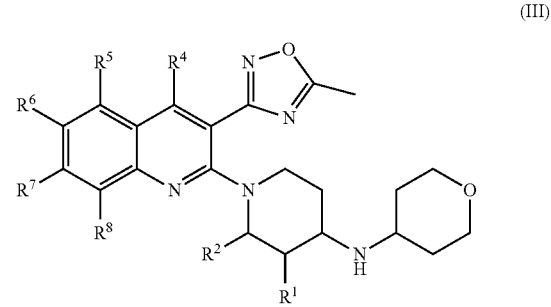

(III)

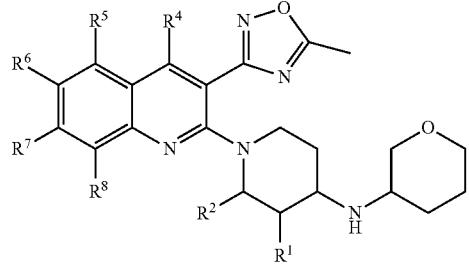
(IV)
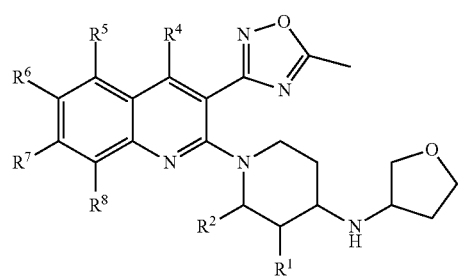
(V)
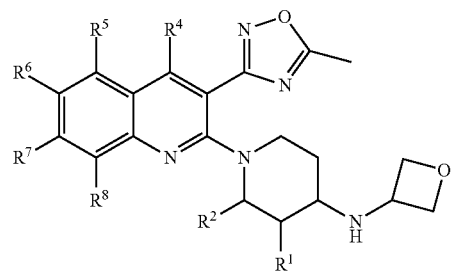
(VI)
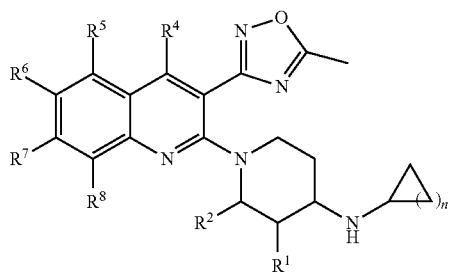
(VII)
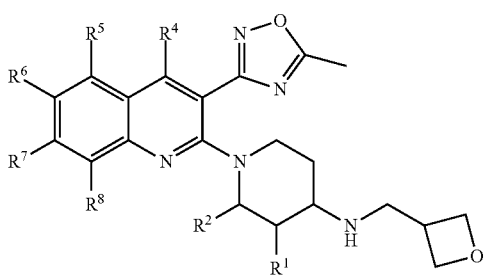
(VIII)
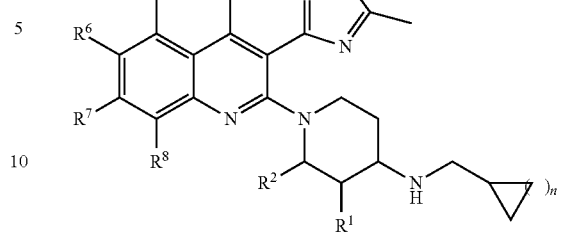
(IX)
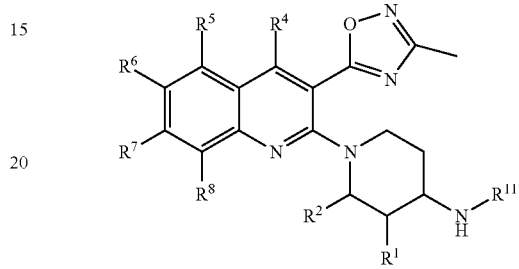
(X)
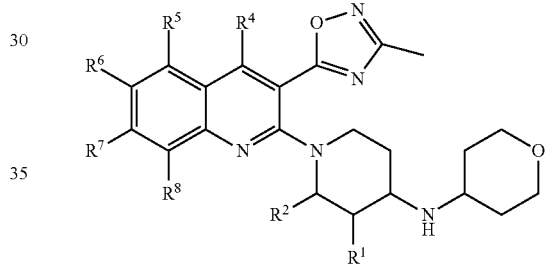
(XI)
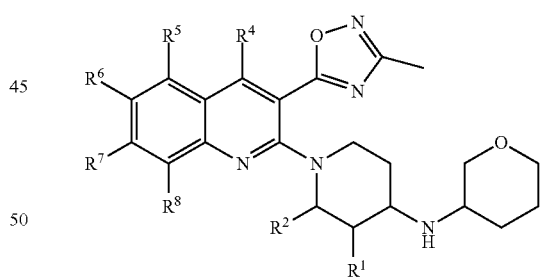
(XII)
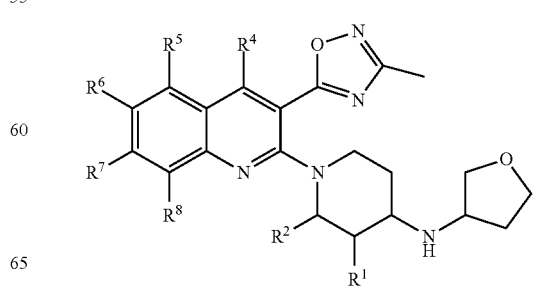
(XIII)

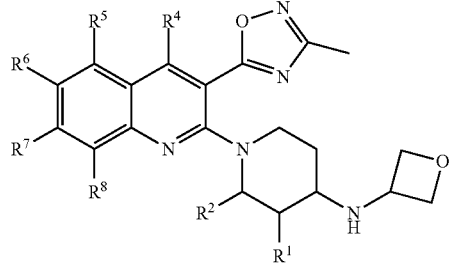
(XIV)
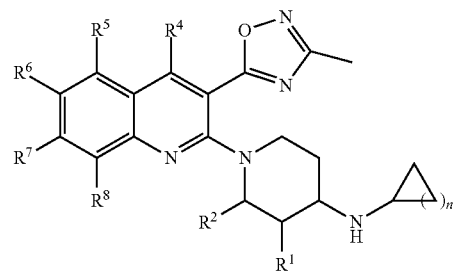
(XV)
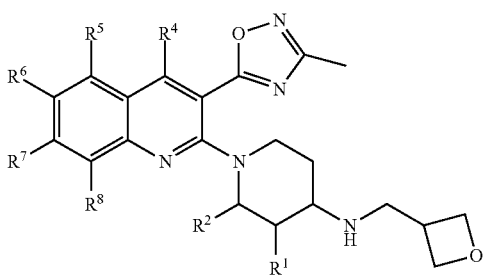
(XVI)
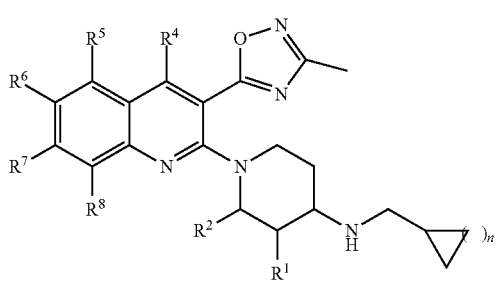
(XVII)
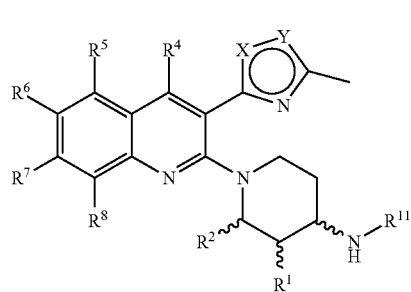
(XVIII)
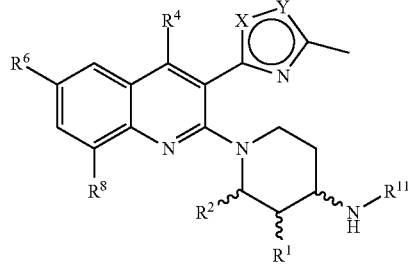
(XIX)
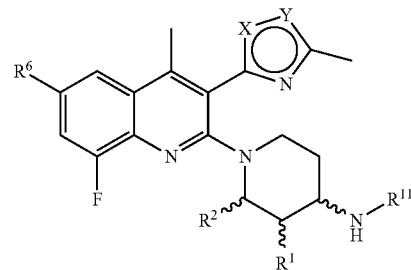
(XX)
In further embodiments, $R^2$ is H and compounds are provided having the structure of any one of Formulas (I-A) through (XX-A), or a pharmaceutically acceptable isomer, racemate, hydrate, solvate, isotope or salt thereof.
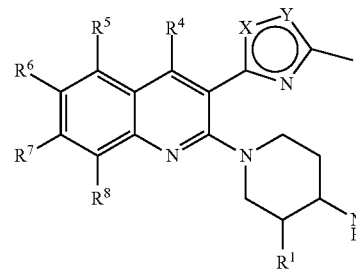
(I-A)
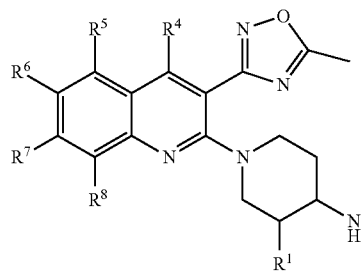
(II-A)
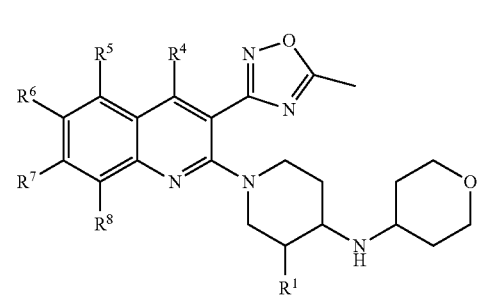
(III-A)

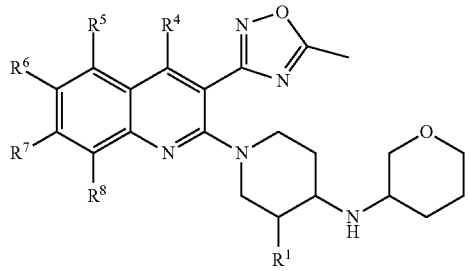
(IV-A)
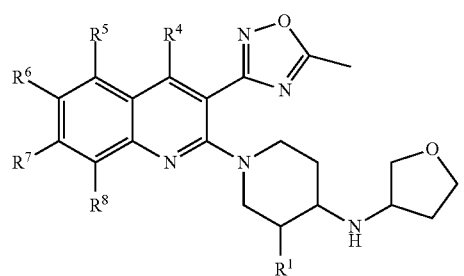
(V-A)
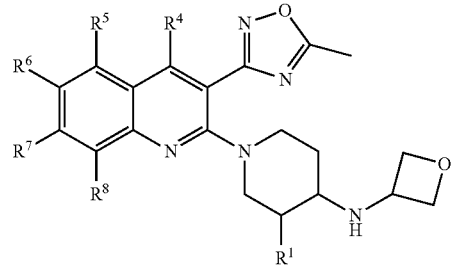
(VI-A)
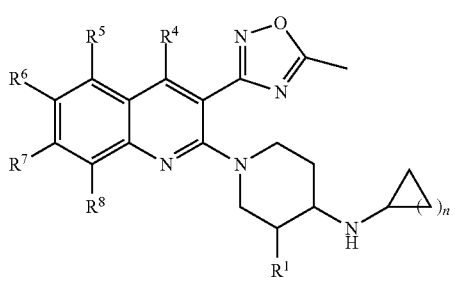
(VII-A)
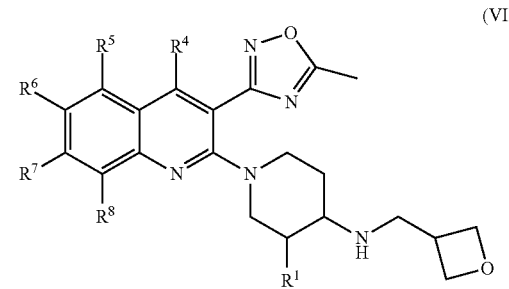
(VIII-A)
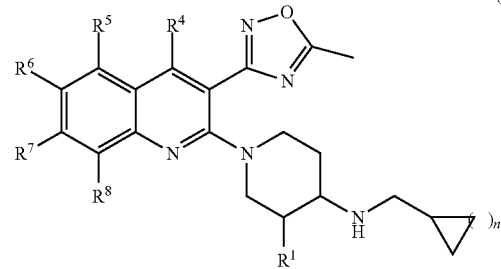
(IX-A)
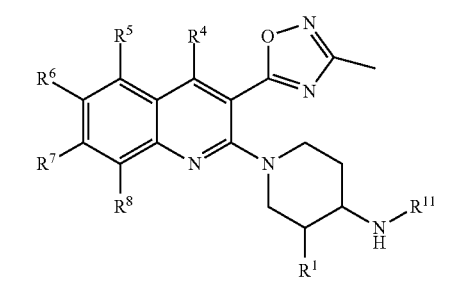
(X-A)
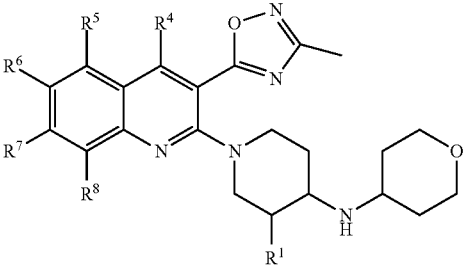
(XI-A)
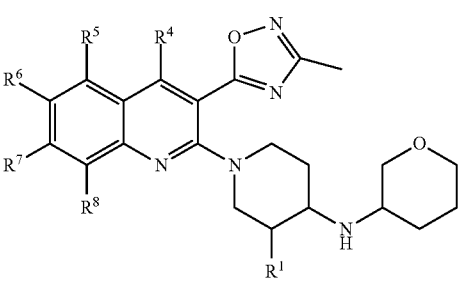
(XII-A)
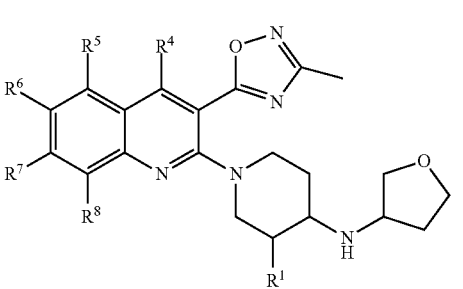
(XIII-A)

(XIV-A)
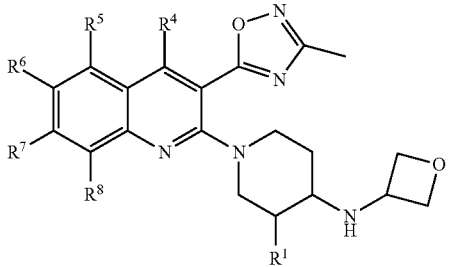
(XV-A)
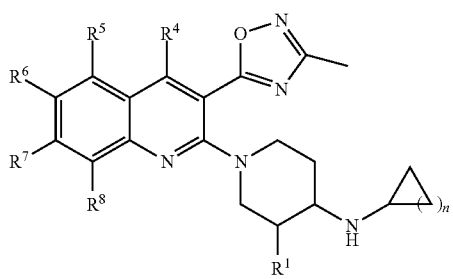
(XVI-A)
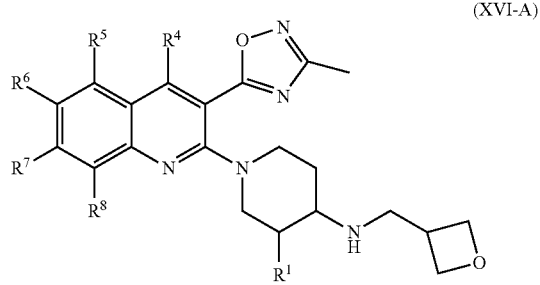
(XVII-A)
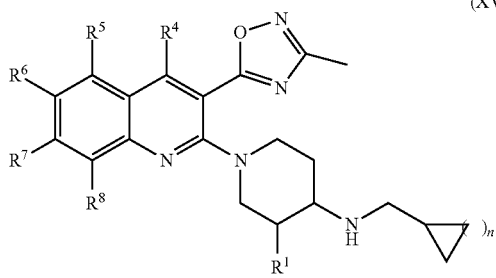
(XVIII-A)
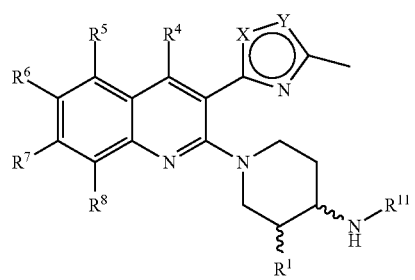
(XIX-A)
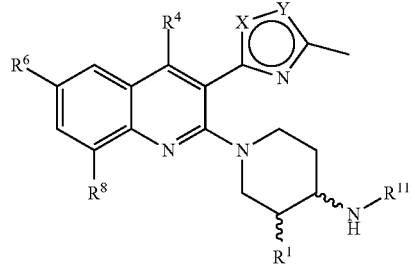
(XX-A)
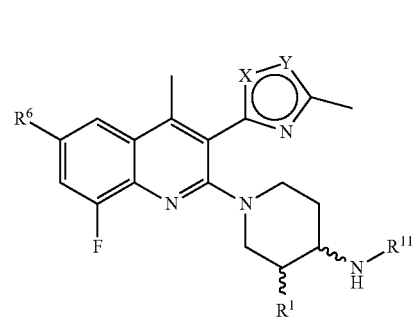
In further embodiments, $R^1$ is H and compounds are provided having the structure of any one of Formulas (I-B) through (XX-B), or a pharmaceutically acceptable isomer, racemate, hydrate, solvate, isotope or salt thereof.
(I-B)
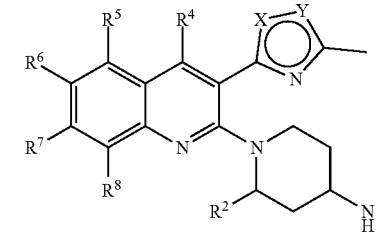
(II-B)
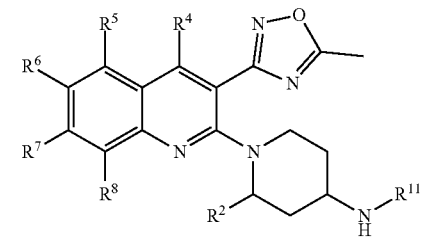
(III-B)
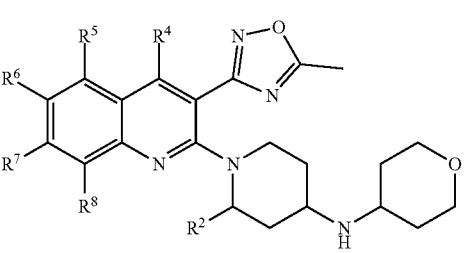

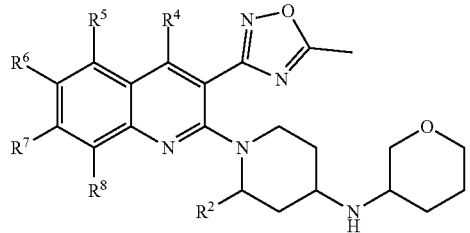
(IV-B)
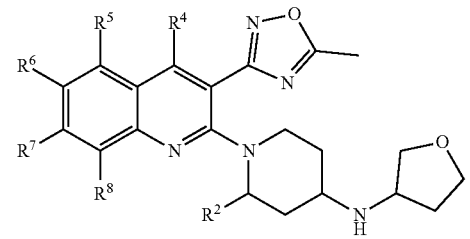
(V-B)
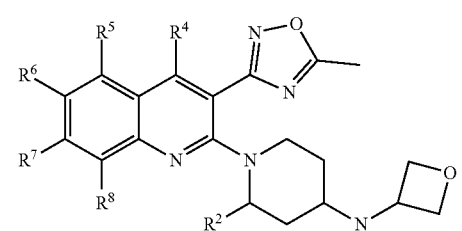
(VI-B)
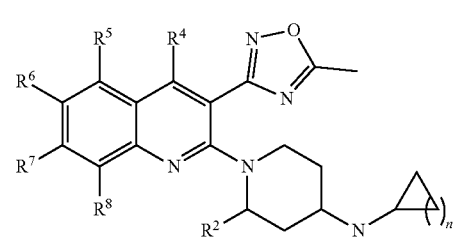
(VII-B)
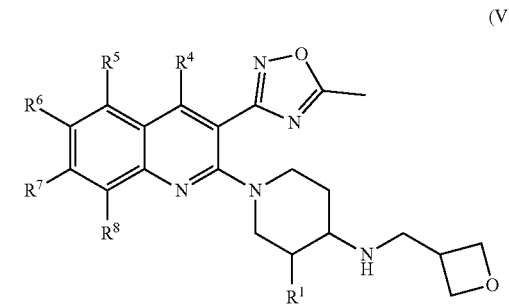
(VIII-B)
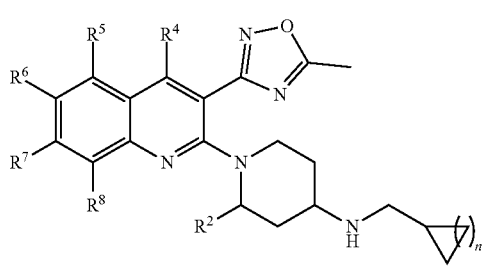
(IX-B)
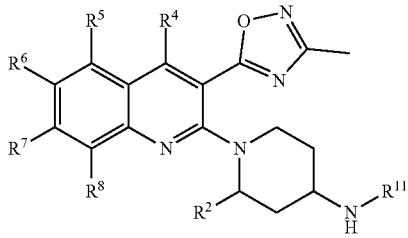
(X-B)
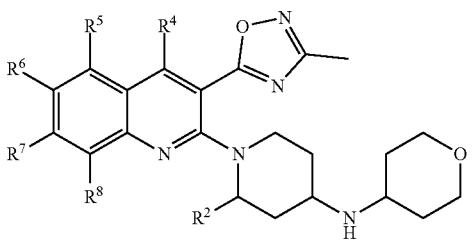
(XI-B)
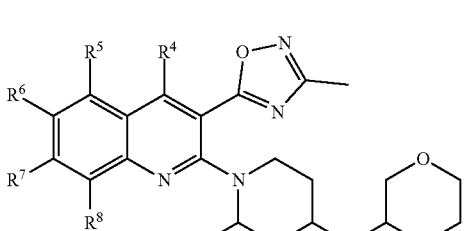
(XII-B)
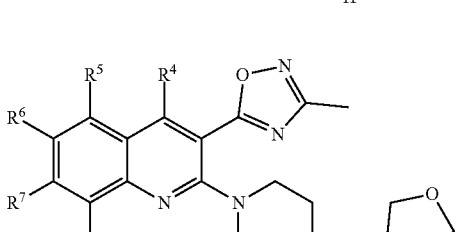
(XIII-B)
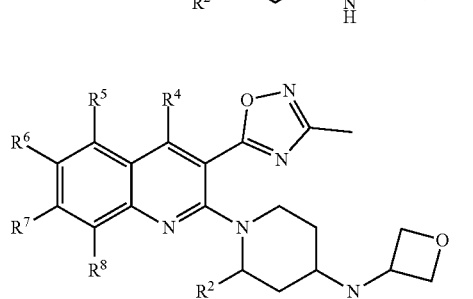
(XIV-B)
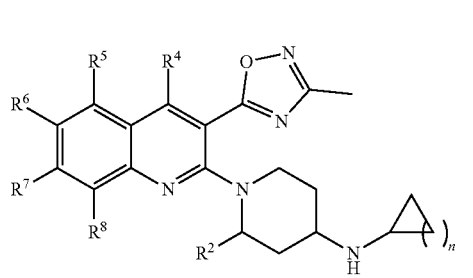
(XV-B)

-continued

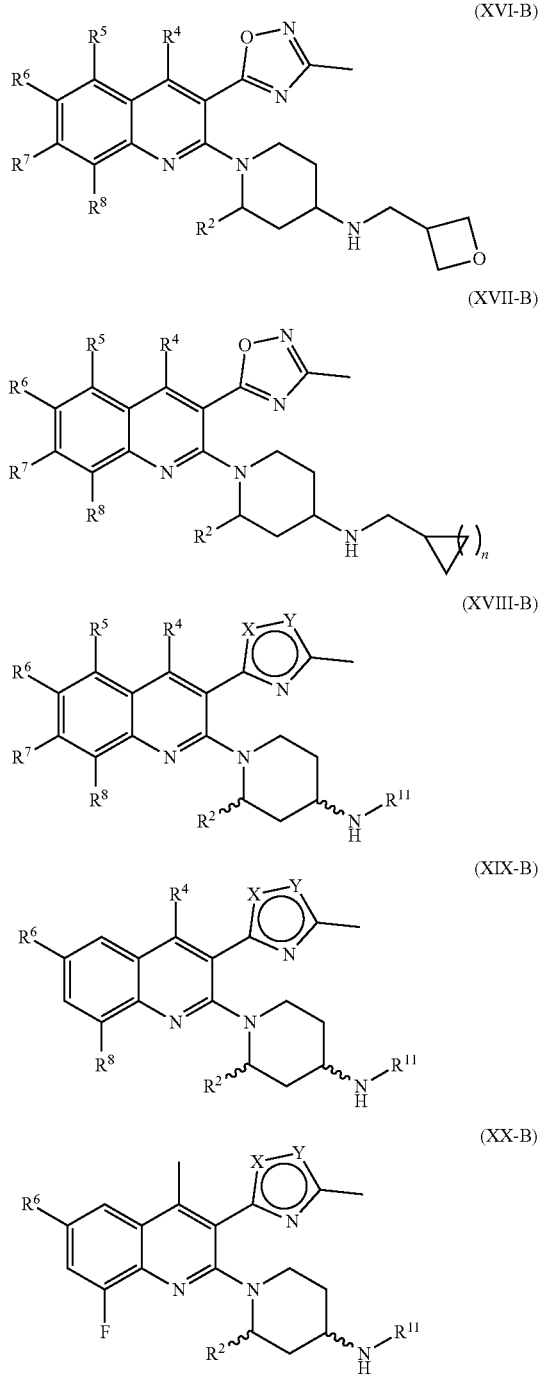

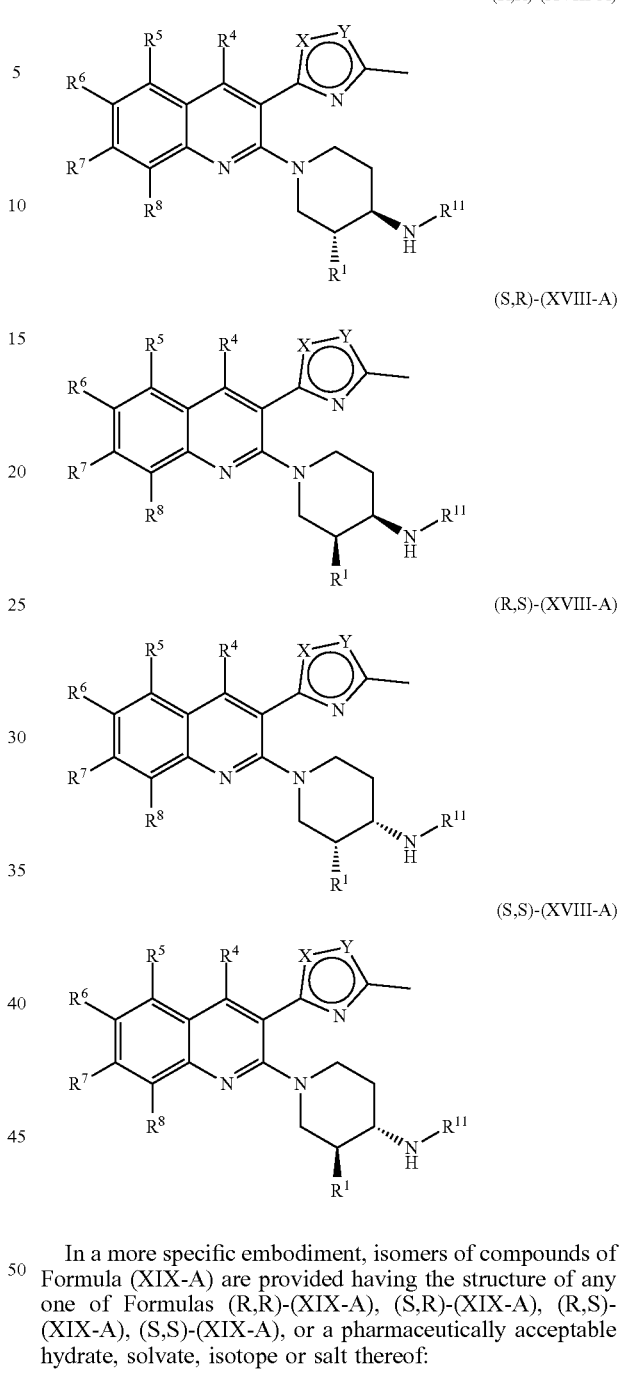

In a more specific embodiment, isomers of compounds of Formula (XVIII-A) are provided having the structure of any one of Formulas (R,R)-(XVIII-A), (S,R)-(XVIII-A), (R,S)-(XVIII-A), (S,S)-(XVIII-A), or a pharmaceutically acceptable hydrate, solvate, isotope or salt thereof:

In a more specific embodiment, isomers of compounds of Formula (XIX-A) are provided having the structure of any one of Formulas (R,R)-(XIX-A), (S,R)-(XIX-A), (R,S)-(XIX-A), (S,S)-(XIX-A), or a pharmaceutically acceptable hydrate, solvate, isotope or salt thereof:

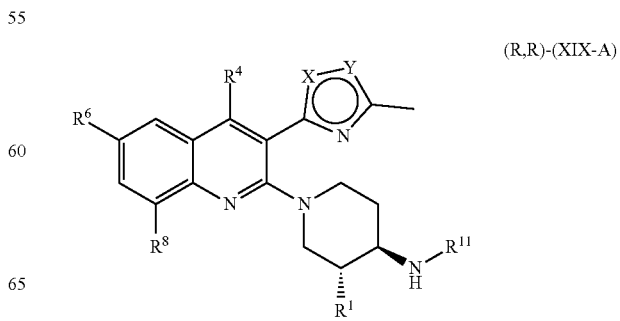

(S,R)-(XIX-A)
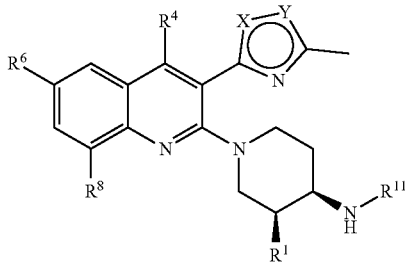

(R,S)-(XIX-A)
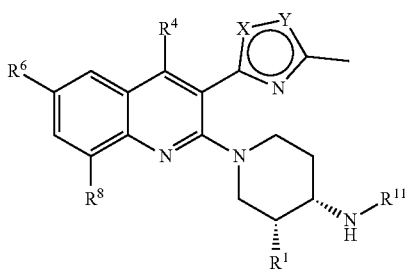

(S,S)-(XIX-A)
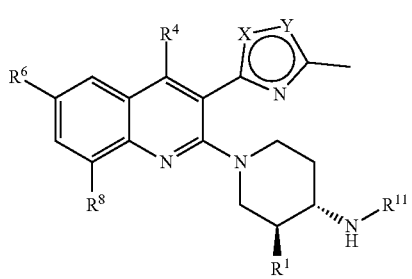

In a more specific embodiment, isomers of compounds of Formula (XX-A) are provided having the structure of any one of Formulas (R,R)-(XX-A), (S,R)-(XX-A), (R,S)-(XX-A), (S,S)-(XX-A), or a pharmaceutically acceptable hydrate, solvate, isotope or salt thereof:

(R,R)-(XX-A)
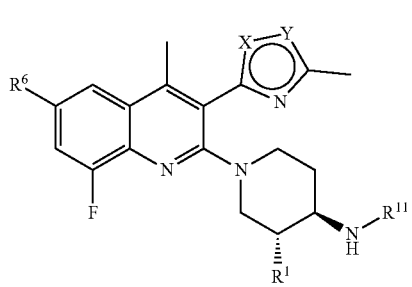

(S,R)-(XX-A)
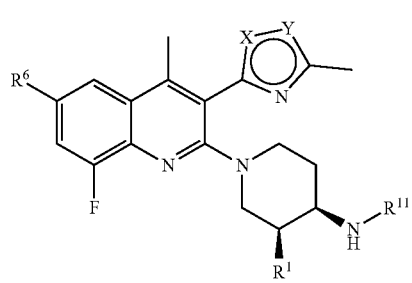

(R,S)-(XX-A)
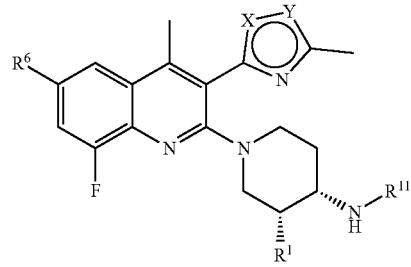

(S,S)-(XX-A)
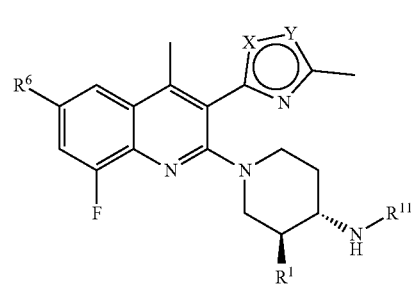

In a more specific embodiment, isomers of compounds of Formula (XVIII-B) are provided having the structure of any one of Formulas (R,R)-(XVIII-B), (S,R)-(XVIII-B), (R,S)-(XVIII-B), (S,S)-(XVIII-B), or a pharmaceutically acceptable hydrate, solvate, isotope or salt thereof:

(R,R)-(XVIII-B)
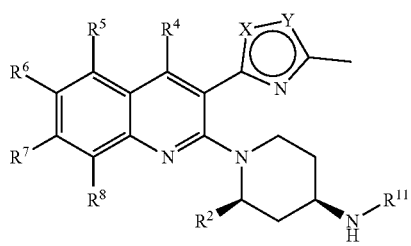

(S,R)-(XVIII-B)
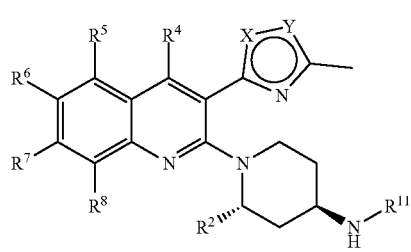

(R,S)-(XVIII-B)
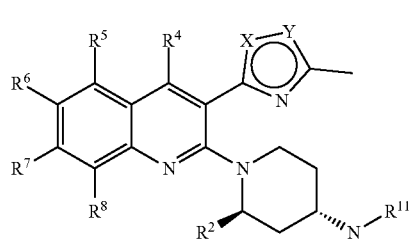

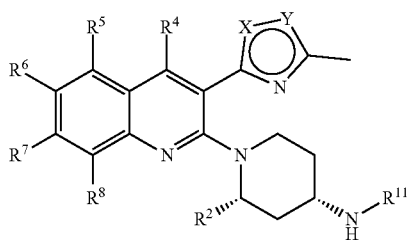
(S,S)-(XVIII-B)

In a more specific embodiment, isomers of compounds of Formula (XIX-B) are provided having the structure of any one of Formulas (R,R)-(XIX-B), (S,R)-(XIX-B), (R,S)-(XIX-B), (S,S)-(XIX-B), or a pharmaceutically acceptable hydrate, solvate, isotope or salt thereof:

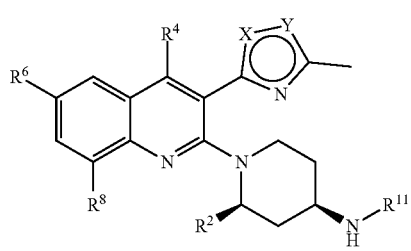
(R,R)-(XIX-B)

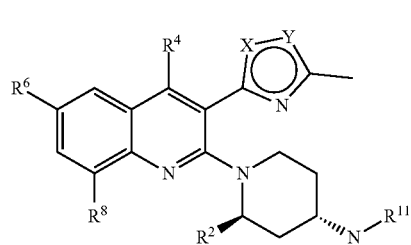
(S,R)-(XIX-B)

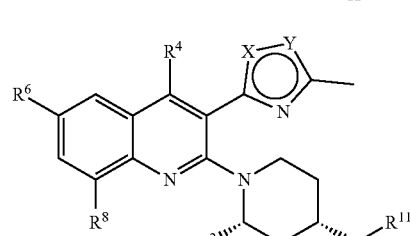
(R,S)-(XIX-B)

(S,S)-(XIX-B)

In a more specific embodiment, isomers of compounds of Formula (XX-B) are provided having the structure of any one of Formulas (R,R)-(XX-B), (S,R)-(XX-B), (R,S)-(XX-B), (S,S)-(XX-B), or a pharmaceutically acceptable hydrate, solvate, isotope or salt thereof:

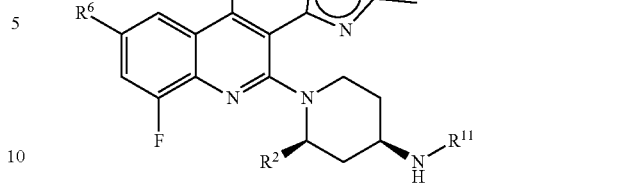
(R,R)-(XX-B)

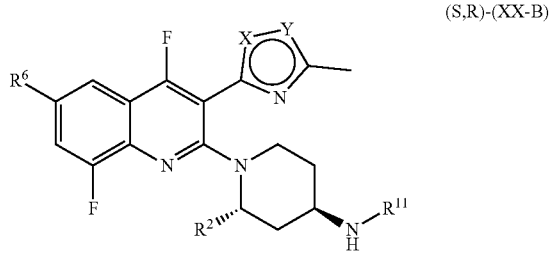
(S,R)-(XX-B)

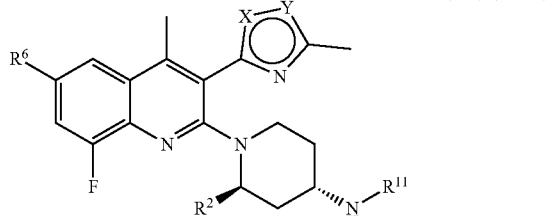
(R,S)-(XX-B)

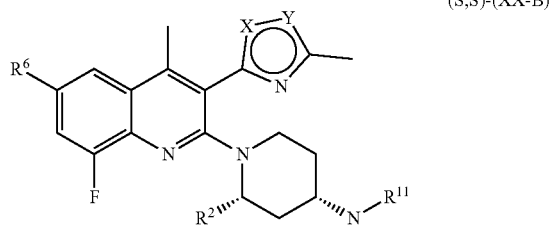
(S,S)-(XX-B)

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is lower alkyl, halo or cyano and $R^8$ is H.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is lower alkyl and $R^8$ is H, and more specifically wherein $R^4$ is methyl and R is H.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is halo and $R^8$ is H, and more specifically wherein $R^4$ is F or Cl and $R^8$ is H.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is cyano and $R^8$ is H.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is H and $R^8$ is lower alkyl, halo or cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is H and $R^8$ is lower alkyl, and more specifically wherein $R^4$ is H and $R^8$ is methyl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is H and $R^8$ is halo, and more specifically wherein $R^4$ is H and $R^8$ is F or Cl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is H and $R^8$ is cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ and $R^8$ are each independently lower alkyl, halo or cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ and $R^8$ are each independently methyl, F, Cl or cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is methyl and $R^8$ is F, Cl or cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^4$ is F, Cl or cyano and $R^8$ is methyl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^5$ and $R^7$ are both H.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^5$ is H and $R^7$ is F or cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^5$ is halo or cyano and $R^7$ is H, and more specifically wherein $R^5$ is F or cyano and $R^7$ is H.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^6$ is lower alkyl, and more specifically $R^6$ is methyl or ethyl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^6$ is lower haloalkyl, and more specifically $R^6$ is —$CH_2CF_3$.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^6$ is cyclopropyl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^6$ is lower alkoxy, and more specifically $R^6$ is methoxy.

In further embodiments, compounds are provided having the structure of any one of Formulas (I) through (XX), Formulas (I-B) through (XX-B), or a pharmaceutically acceptable isomer, racemate, hydrate, solvate, isotope or salt thereof, wherein $R^2$ is lower alkyl, and more specifically methyl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein $R^{11}$ is and more specifically $R^{11}$ is , or

.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein:

$R^4$ is H;
$R^5$ is H;
$R^6$ is lower alkyl, and more specifically methyl or ethyl;
$R^7$ is H;
$R^8$ is halo, and more specifically, F or Cl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein:
$R^4$ is lower alkyl, and more specifically methyl;
$R^5$ is H;
$R^6$ is lower alkyl, and more specifically methyl or ethyl;
$R^7$ is H;
$R^8$ is halo, and more specifically, F or Cl.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein:
$R^4$ is lower alkyl, and more specifically methyl;
$R^5$ is H;
$R^6$ is lower alkyl, and more specifically methyl or ethyl;
$R^7$ is H;
$R^8$ is cyano.

In further embodiments, compounds are provided having the structure of any one of Formulas (I) through (XX), Formulas (I-A) through (XX-A), Formulas (I-B) through (XX-B), or a pharmaceutically acceptable isomer, racemate, hydrate, solvate, isotope or salt thereof, wherein:
$R^4$ is cyano;
$R^5$ is H;
$R^6$ is lower alkyl, and more specifically methyl or ethyl;
$R^7$ is H;
$R^8$ is H or halo.

In a more specific embodiment, compounds are provided having the structure of Formula (II), or a pharmaceutically acceptable isomer, racemate, hydrate, solvate, isotope or salt thereof:

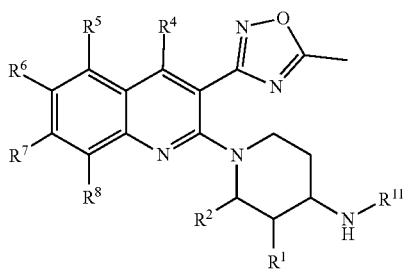

(II)

wherein:
$R^1$ is H or F;
$R^2$ is H or lower alkyl;
$R^4$ is H, $CH_3$, Cl or CN;
$R^5$ is H or F;
$R^6$ is Cl, Br, F, CN, $CH_3$, $CF_3$, $CH_2CH_3$, $CHFCH_3$, $CF_2CH_3$, $CH_2CH_2F$, $CH_2CF_3$, $CH(CH_3)_2$, C≡$CCH_3$, cyclopropyl, cyclobutyl, $OCH_3$, $OCF_3$, $OCH_2CH_3$ or $OCH(CH_3)_2$;
$R^7$ is H or F;
$R^8$ is H, F, Cl, or CN;
$R^{11}$ is —$(CH_2)_{0-1}R^{12}$ wherein $R^{12}$ is,

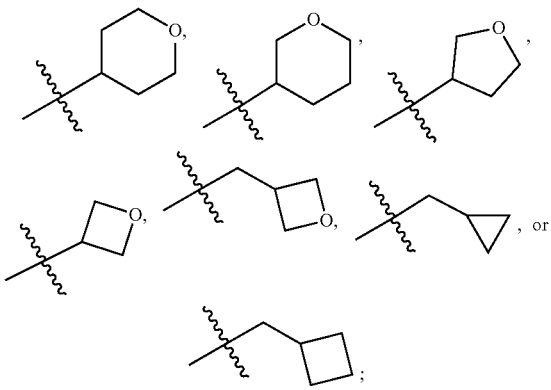

wherein
at least one of $R^5$ and $R^7$ is H;
when $R^2$ is H, at least one of $R^4$ and $R^8$ is not H or when $R^2$, $R^4$, and $R^8$ are H, $R^7$ is not H; and
$R^6$ is not lower alkyl when $R^8$ is lower alkyl.

In a more specific embodiment, compounds are provided having the structure of Formula (X), or a pharmaceutically acceptable isomer, racemate, hydrate, solvate, isotope or salt thereof:

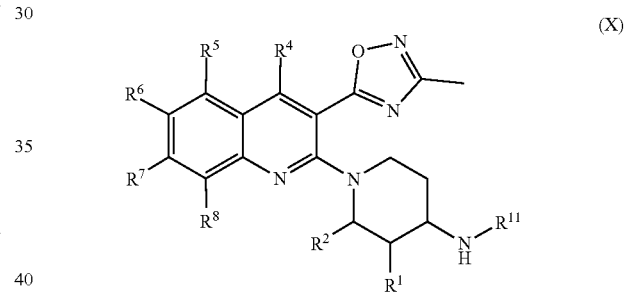

(X)

wherein:
$R^1$ is H or F;
$R^2$ is H or lower alkyl;
$R^4$ is H, $CH_3$, Cl or CN;
$R^5$ is H or F;
$R^6$ is Cl, Br, F, CN, $CH_3$, $CF_3$, $CH_2CH_3$, $CHFCH_3$, $CF_2CH_3$, $CH_2CH_2F$, $CH_2CF_3$, $CH(CH_3)_2$, C≡$CCH_3$, cyclopropyl, cyclobutyl, $OCH_3$, $OCF_3$, $OCH_2CH_3$ or $OCH(CH_3)_2$;
$R^7$ is H or F;
$R^8$ is H, F, Cl, or CN;
$R^{11}$ is —$(CH_2)_{0-1}R^{12}$ wherein $R^{12}$ is,

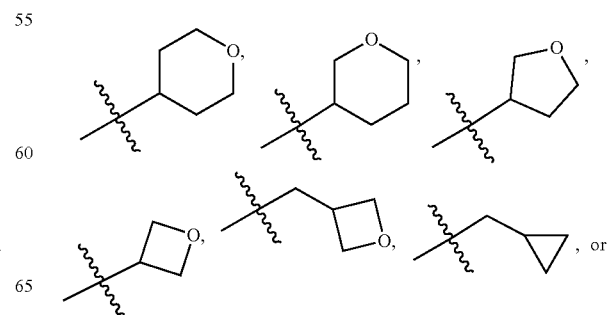

-continued

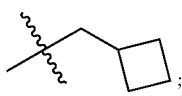

wherein
at least one of $R^5$ and $R^7$ is H;
when $R^2$ is H, at least one of $R^4$ and $R^8$ is not H or when $R^2$, $R^4$, and $R^8$ are H, $R^7$ is not H; and
$R^6$ is not lower alkyl when $R^8$ is lower alkyl.

Representative compounds include the compounds listed in Table 1, as well as pharmaceutically acceptable isomers, racemates, hydrates, solvates, isotopes, and salts thereof.

TABLE 1-continued
Representative Compounds
| No. | Structure |
|---|---|
| 11 | 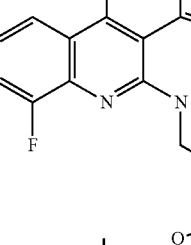 |
| 12 | 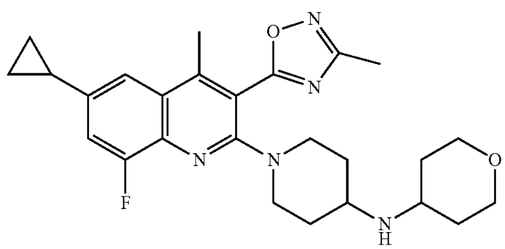 [SMILES: Cc1noc(-c2c(N3CCC(NC4CCOCC4)CC3)nc3c(F)cc(C4CC4)cc3c2C)n1] |
| 13 | 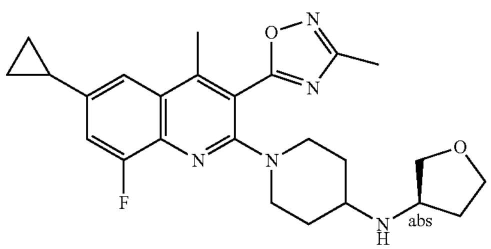 [SMILES: Cc1noc(-c2c(N3CCC(N[C@@H]4CCOC4)CC3)nc3c(F)cc(C4CC4)cc3c2C)n1] |
| 14 | 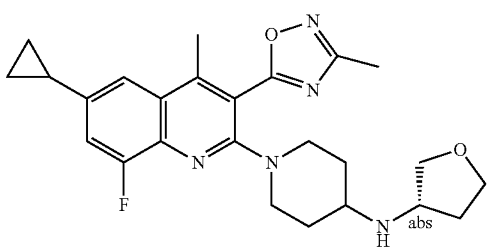 [SMILES: Cc1noc(-c2c(N3CCC(N[C@H]4CCOC4)CC3)nc3c(F)cc(C4CC4)cc3c2C)n1] |
| 15 | 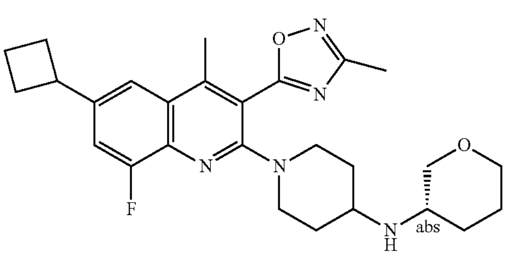 [SMILES: Cc1noc(-c2c(N3CCC(N[C@H]4CCCOC4)CC3)nc3c(F)cc(C4CCC4)cc3c2C)n1] |
| 16 | 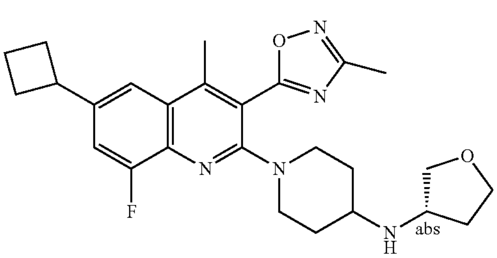 [SMILES: Cc1noc(-c2c(N3CCC(N[C@H]4CCOC4)CC3)nc3c(F)cc(C4CCC4)cc3c2C)n1] |
TABLE 1-continued
Representative Compounds
| No. | Structure |
|---|---|
| 17 | 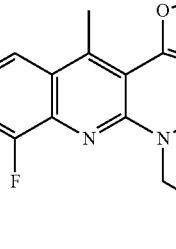 |
| 18 | 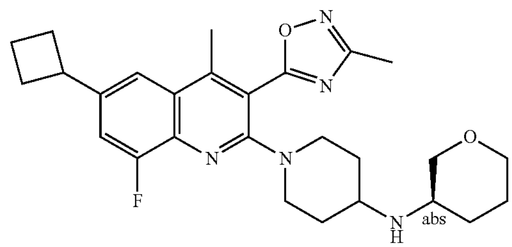 [SMILES: Cc1noc(-c2c(N3CCC(N[C@@H]4CCCOC4)CC3)nc3c(F)cc(C4CCC4)cc3c2C)n1] |
| 19 | 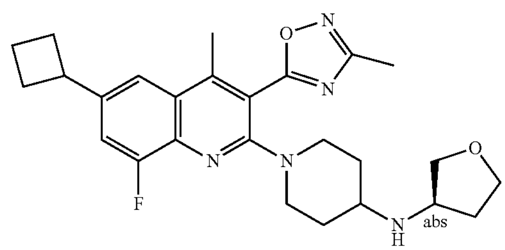 [SMILES: Cc1noc(-c2c(N3CCC(N[C@@H]4CCOC4)CC3)nc3c(F)cc(C4CCC4)cc3c2C)n1] |
| 20 | 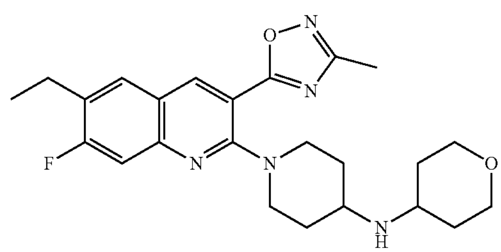 [SMILES: CCc1cc2cc(-c3nc(C)no3)c(N3CCC(NC4CCOCC4)CC3)nc2cc1F] |
| 21 | 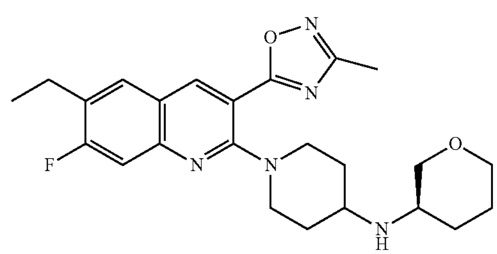 [SMILES: CCc1cc2cc(-c3nc(C)no3)c(N3CCC(N[C@@H]4CCCOC4)CC3)nc2cc1F] |
| 22 | 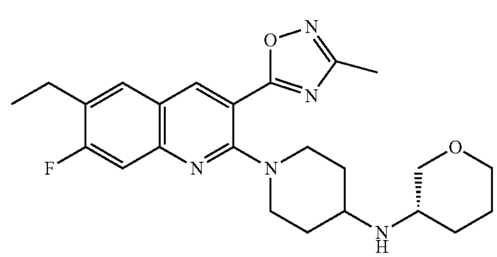 [SMILES: CCc1cc2cc(-c3nc(C)no3)c(N3CCC(N[C@H]4CCCOC4)CC3)nc2cc1F] |

TABLE 1-continued

Representative Compounds

| No. | Structure |
|---|---|
| 23 | (chemical structure) |
| 24 | (chemical structure) |
| 25 | (chemical structure) |
| 26 | (chemical structure) |
| 27 | (chemical structure) |
| 28 | (chemical structure) |
| 29 | (chemical structure) |
| 30 | (chemical structure) |
| 31 | (chemical structure) |
| 32 | (chemical structure) |
| 33 | (chemical structure) |
| 34 | (chemical structure) |

TABLE 1-continued
Representative Compounds
| No. | Structure |
|---|---|
| 35 | 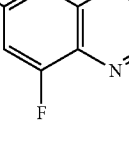 |
| 36 | 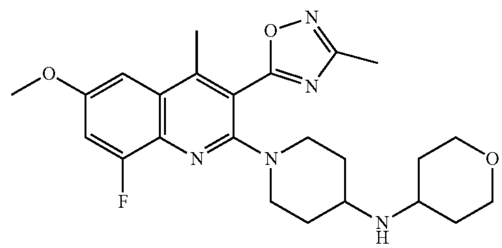 [SMILES: COc1cc(F)c2nc(N3CCC(NC4CCOCC4)CC3)c(-c3nc(C)no3)c(C)c2c1] |
| 37 | 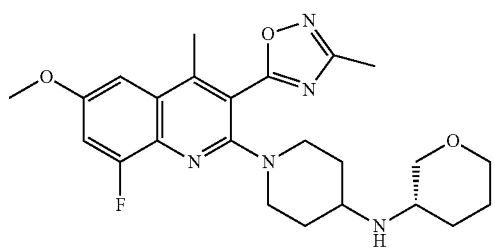 |
| 38 | 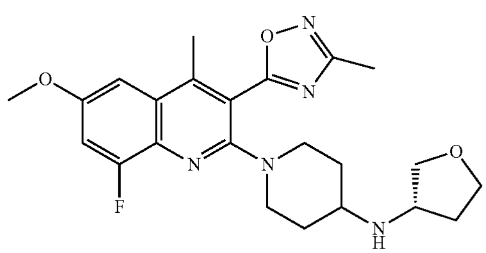 |
| 39 | 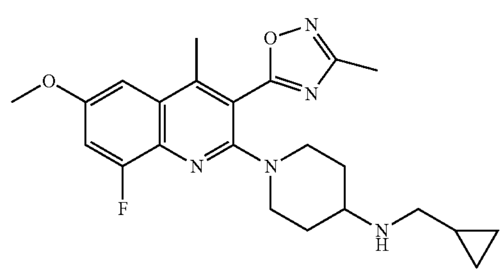 [SMILES: COc1cc(F)c2nc(N3CCC(NCC4CC4)CC3)c(-c3nc(C)no3)c(C)c2c1] |
| 40 | 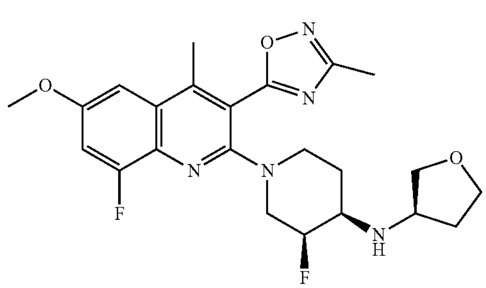 [SMILES: COc1cc(F)c2nc(N3CC[C@@H](N[C@@H]4CCOC4)[C@@H](F)C3)c(-c3nc(C)no3)c(C)c2c1] |
TABLE 1-continued
Representative Compounds
| No. | Structure |
|---|---|
| 41 | 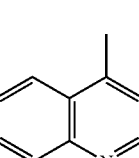 |
| 42 | 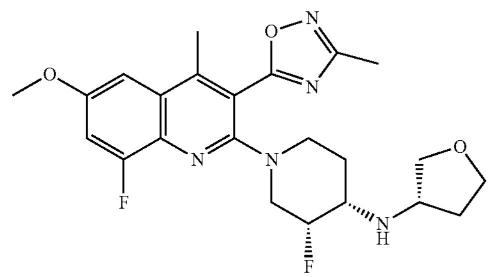 [SMILES: COc1cc(F)c2nc(N3CC[C@H](N[C@H]4CCOC4)[C@H](F)C3)c(-c3nc(C)no3)c(C)c2c1] |
| 43 | 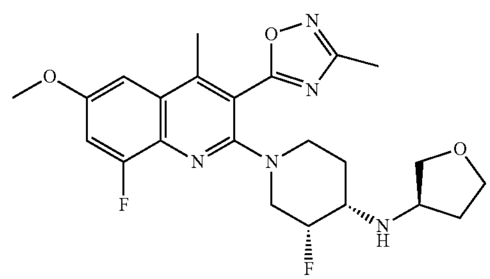 [SMILES: COc1cc(F)c2nc(N3CC[C@H](N[C@@H]4CCOC4)[C@H](F)C3)c(-c3nc(C)no3)c(C)c2c1] |
| 44 | 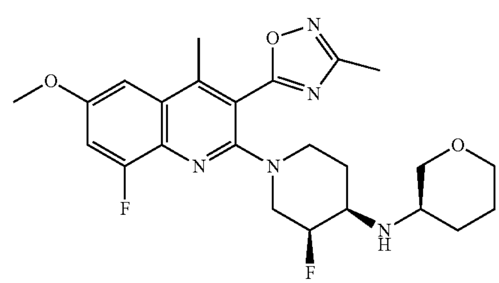 [SMILES: COc1cc(F)c2nc(N3CC[C@@H](N[C@@H]4CCCOC4)[C@@H](F)C3)c(-c3nc(C)no3)c(C)c2c1] |
| 45 | 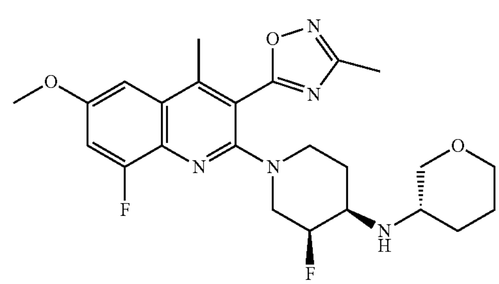 [SMILES: COc1cc(F)c2nc(N3CC[C@@H](N[C@H]4CCCOC4)[C@@H](F)C3)c(-c3nc(C)no3)c(C)c2c1] |

TABLE 1-continued

Representative Compounds

| No. | Structure |
|---|---|
| 46 | 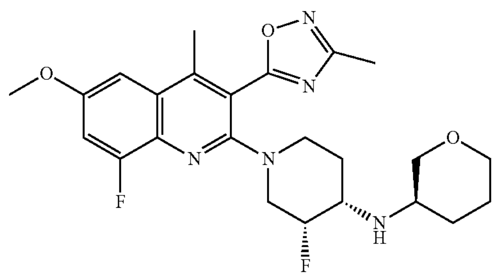 [SMILES: COc1cc(F)c2nc(N3CC[C@H](N[C@@H]4CCCOC4)[C@H](F)C3)c(-c3nc(C)no3)c(C)c2c1] |
| 47 | 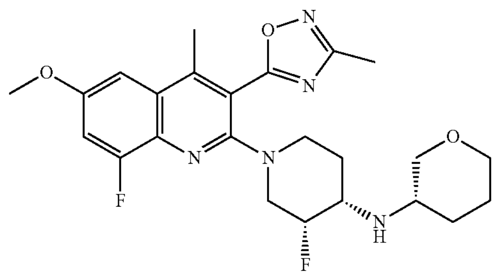 [SMILES: COc1cc(F)c2nc(N3CC[C@H](N[C@H]4CCCOC4)[C@H](F)C3)c(-c3nc(C)no3)c(C)c2c1] |
| 48 | 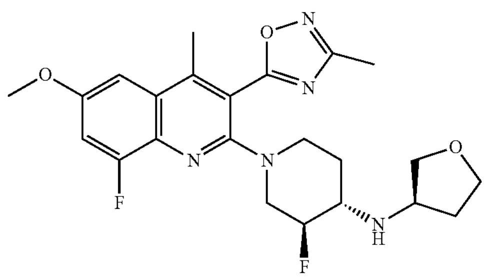 [SMILES: COc1cc(F)c2nc(N3CC[C@H](N[C@@H]4CCOC4)[C@@H](F)C3)c(-c3nc(C)no3)c(C)c2c1] |
| 49 | 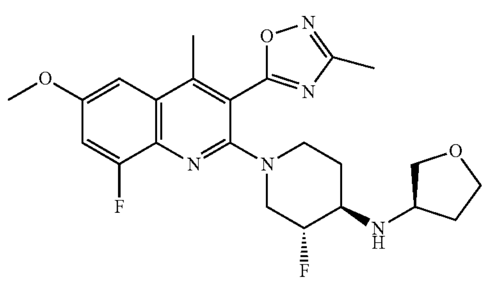 [SMILES: COc1cc(F)c2nc(N3CC[C@@H](N[C@@H]4CCOC4)[C@H](F)C3)c(-c3nc(C)no3)c(C)c2c1] |
| 50 | 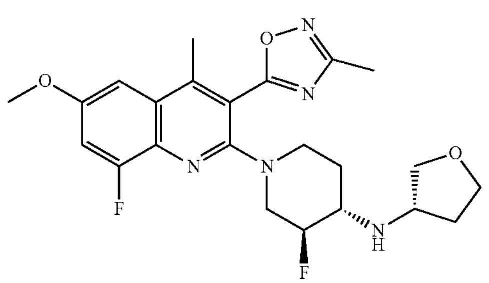 [SMILES: COc1cc(F)c2nc(N3CC[C@H](N[C@H]4CCOC4)[C@@H](F)C3)c(-c3nc(C)no3)c(C)c2c1] |
| 51 | |
| 52 | |
| 53 | |
| 54 | |
| 55 | |

TABLE 1-continued

Representative Compounds

| No. | Structure |
|---|---|
| 56 | (structure) |
| 57 | (structure) |
| 58 | (structure) |
| 59 | (structure) |
| 60 | (structure) |
| 61 | (structure) |
| 62 | (structure) |
| 63 | (structure) |
| 64 | (structure) |
| 65 | (structure) |
| 66 | (structure) |

TABLE 1-continued

Representative Compounds

| No. | Structure |
|-----|-----------|
| 67 | 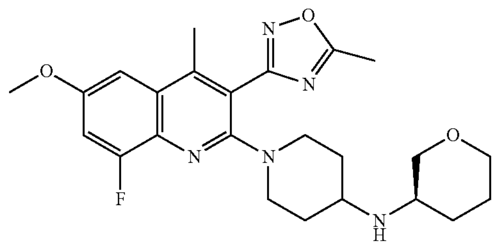 |
| 68 | 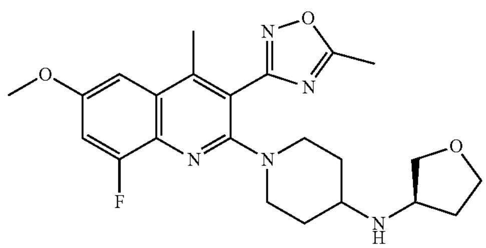 |
| 69 | 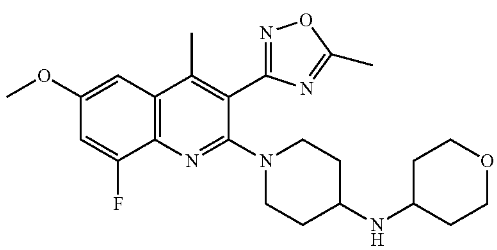 [SMILES: COc1cc(F)c2nc(N3CCC(NC4CCOCC4)CC3)c(-c3noc(C)n3)c(C)c2c1] |
| 70 | 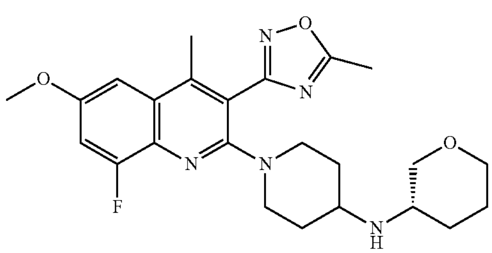 [SMILES: COc1cc(F)c2nc(N3CCC(N[C@H]4CCCOC4)CC3)c(-c3noc(C)n3)c(C)c2c1] |
| 71 | 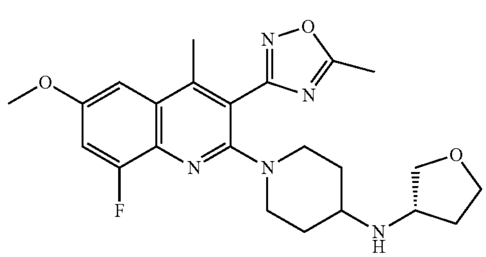 [SMILES: COc1cc(F)c2nc(N3CCC(N[C@H]4CCOC4)CC3)c(-c3noc(C)n3)c(C)c2c1] |
| 72 | 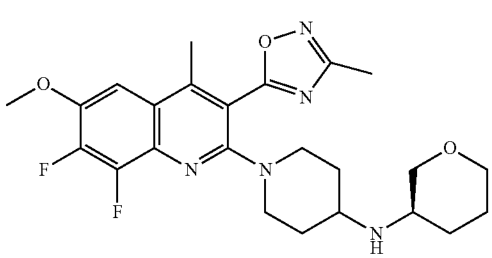 [SMILES: COc1cc2c(C)c(-c3nc(C)no3)c(N3CCC(N[C@@H]4CCCOC4)CC3)nc2c(F)c1F] |
| 73 | |
| 74 | |
| 75 | |
| 76 | |
| 77 | |
| 78 | |

TABLE 1-continued

Representative Compounds

| No. | Structure |
|---|---|
| 79 | 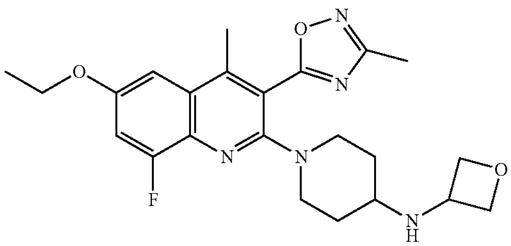 [SMILES: CCOc1cc(F)c2nc(N3CCC(NC4COC4)CC3)c(-c3nc(C)no3)c(C)c2c1] |
| 80 | 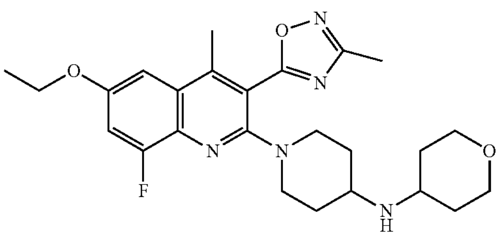 [SMILES: CCOc1cc(F)c2nc(N3CCC(NC4CCOCC4)CC3)c(-c3nc(C)no3)c(C)c2c1] |
| 81 | 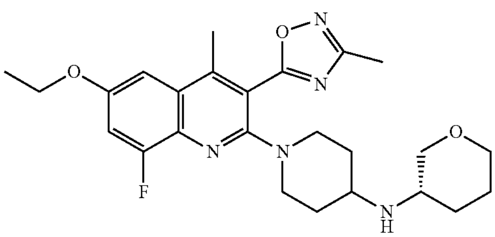 [SMILES: CCOc1cc(F)c2nc(N3CCC(N[C@H]4CCCOC4)CC3)c(-c3nc(C)no3)c(C)c2c1] |
| 82 | 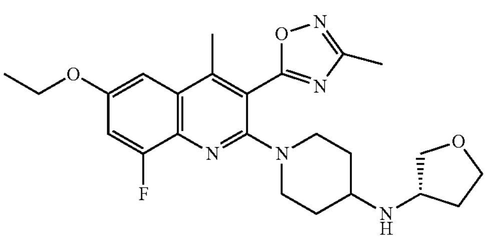 [SMILES: CCOc1cc(F)c2nc(N3CCC(N[C@H]4CCOC4)CC3)c(-c3nc(C)no3)c(C)c2c1] |
| 83 | 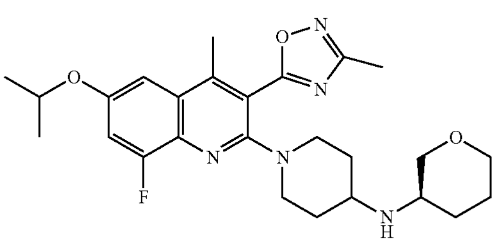 [SMILES: Cc1noc(-c2c(N3CCC(N[C@@H]4CCCOC4)CC3)nc3c(F)cc(OC(C)C)cc3c2C)n1] |
| 84 | 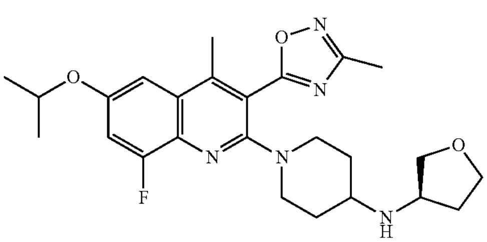 [SMILES: Cc1noc(-c2c(N3CCC(N[C@@H]4CCOC4)CC3)nc3c(F)cc(OC(C)C)cc3c2C)n1] |
| 85 | |
| 86 | |
| 87 | |
| 88 | |
| 89 | |
| 90 | |

TABLE 1-continued

Representative Compounds

| No. | Structure |
|---|---|
| 91 | 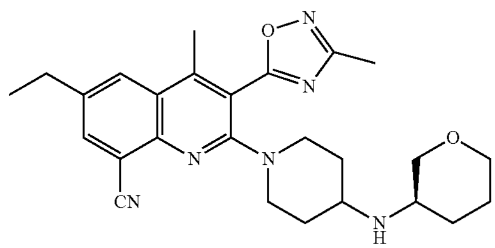 [SMILES: CCc1cc(C#N)c2nc(N3CCC(N[C@@H]4CCCOC4)CC3)c(-c3nc(C)no3)c(C)c2c1] |
| 92 | 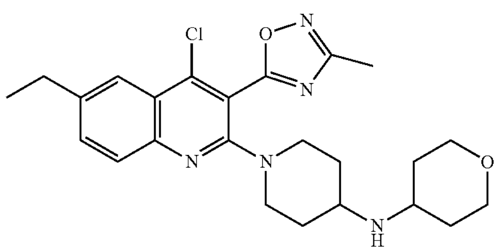 [SMILES: CCc1ccc2nc(N3CCC(NC4CCOCC4)CC3)c(-c3nc(C)no3)c(Cl)c2c1] |
| 93 | 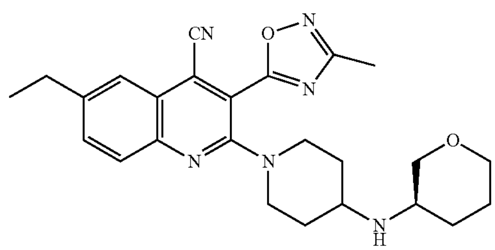 [SMILES: CCc1ccc2nc(N3CCC(N[C@@H]4CCCOC4)CC3)c(-c3nc(C)no3)c(C#N)c2c1] |
| 94 | 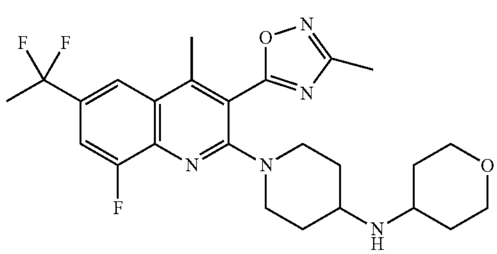 [SMILES: Cc1noc(-c2c(N3CCC(NC4CCOCC4)CC3)nc3c(F)cc(C(C)(F)F)cc3c2C)n1] |
| 95 | 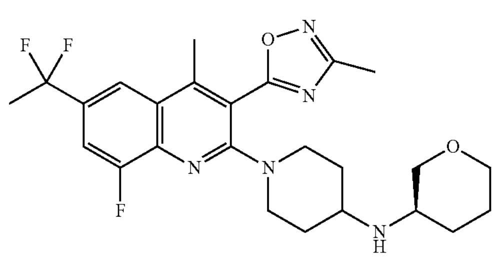 [SMILES: Cc1noc(-c2c(N3CCC(N[C@@H]4CCCOC4)CC3)nc3c(F)cc(C(C)(F)F)cc3c2C)n1] |
| 96 | 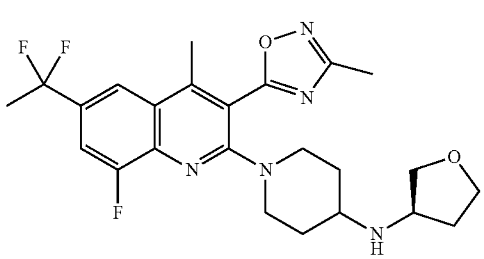 [SMILES: Cc1noc(-c2c(N3CCC(N[C@@H]4CCOC4)CC3)nc3c(F)cc(C(C)(F)F)cc3c2C)n1] |
| 97 | |
| 98 | |
| 99 | |
| 100 | |
| 101 | |
| 102 | |

TABLE 1-continued

Representative Compounds

| No. | Structure |
|-----|-----------|
| 103 | 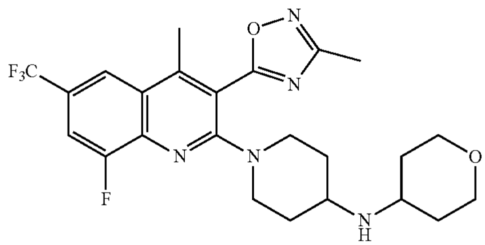 [SMILES: Cc1noc(-c2c(N3CCC(NC4CCOCC4)CC3)nc3c(F)cc(C(F)(F)F)cc3c2C)n1] |
| 104 | 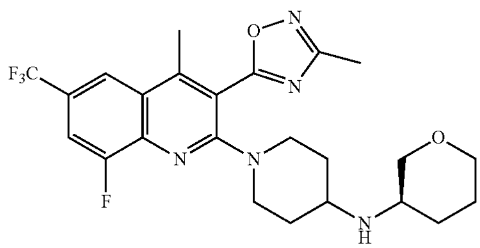 [SMILES: Cc1noc(-c2c(N3CCC(N[C@@H]4CCCOC4)CC3)nc3c(F)cc(C(F)(F)F)cc3c2C)n1] |
| 105 | 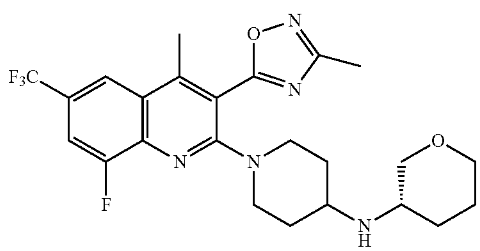 [SMILES: Cc1noc(-c2c(N3CCC(N[C@H]4CCCOC4)CC3)nc3c(F)cc(C(F)(F)F)cc3c2C)n1] |
| 106 | 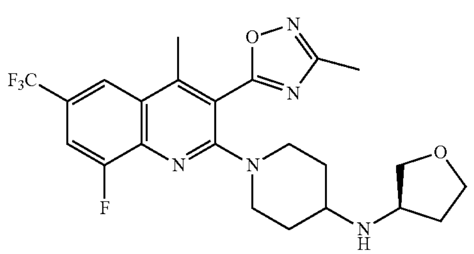 [SMILES: Cc1noc(-c2c(N3CCC(N[C@@H]4CCOC4)CC3)nc3c(F)cc(C(F)(F)F)cc3c2C)n1] |
| 107 | 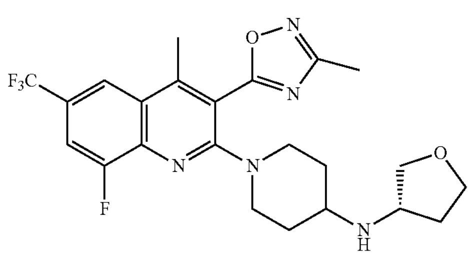 [SMILES: Cc1noc(-c2c(N3CCC(N[C@H]4CCOC4)CC3)nc3c(F)cc(C(F)(F)F)cc3c2C)n1] |
| 108 | 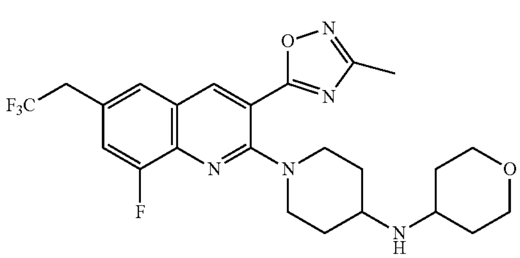 [SMILES: Cc1noc(-c2cc3cc(CC(F)(F)F)cc(F)c3nc2N2CCC(NC3CCOCC3)CC2)n1] |
| 109 | |
| 110 | |
| 111 | |
| 112 | |
| 113 | |
| 114 | |

TABLE 1-continued

Representative Compounds

| No. | Structure |
|---|---|
| 115 | (structure) |
| 116 | (structure) |
| 117 | (structure) |
| 118 | (structure) |
| 119 | (structure) |
| 120 | (structure) |
| 121 | (structure) |
| 122 | (structure) |
| 123 | (structure) |
| 124 | (structure) |
| 125 | (structure) |

TABLE 1-continued

Representative Compounds

| No. | Structure |
|---|---|
| 126 | 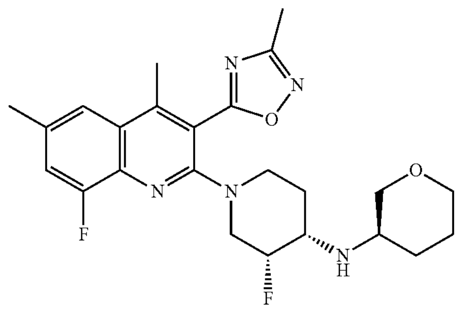 [SMILES: Cc1cc(F)c2nc(N3CC[C@H](N[C@@H]4CCCOC4)[C@H](F)C3)c(-c3nc(C)no3)c(C)c2c1] |
| 127 | 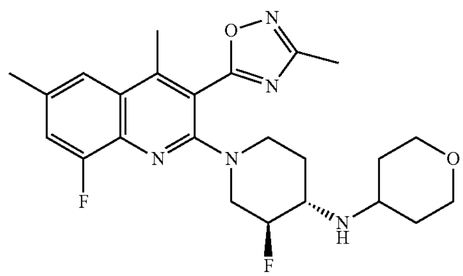 [SMILES: Cc1cc(F)c2nc(N3CC[C@H](NC4CCOCC4)[C@@H](F)C3)c(-c3nc(C)no3)c(C)c2c1] |
| 128 | 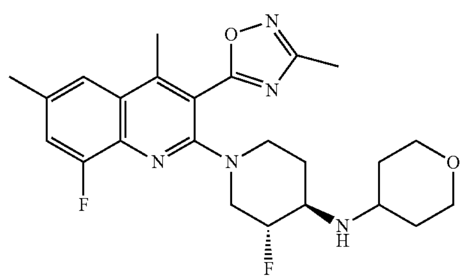 [SMILES: Cc1cc(F)c2nc(N3CC[C@@H](NC4CCOCC4)[C@H](F)C3)c(-c3nc(C)no3)c(C)c2c1] |
| 129 | 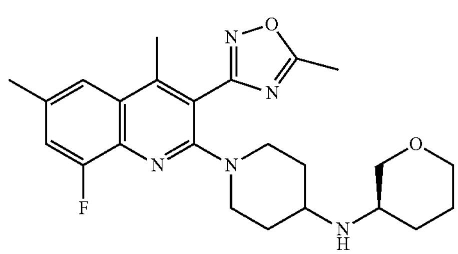 [SMILES: Cc1cc(F)c2nc(N3CCC(N[C@@H]4CCCOC4)CC3)c(-c3noc(C)n3)c(C)c2c1] |
| 130 | 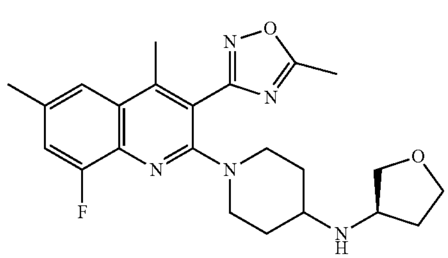 [SMILES: Cc1cc(F)c2nc(N3CCC(N[C@@H]4CCOC4)CC3)c(-c3noc(C)n3)c(C)c2c1] |
| 131 | |
| 132 | |
| 133 | |
| 134 | |
| 135 | |

TABLE 1-continued

Representative Compounds

| No. | Structure |
|---|---|
| 136 | 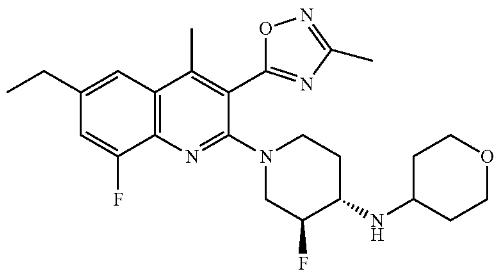 [SMILES: CCc1cc(F)c2nc(N3CC[C@H](NC4CCOCC4)[C@H](F)C3)c(-c3nc(C)no3)c(C)c2c1] |
| 137 | 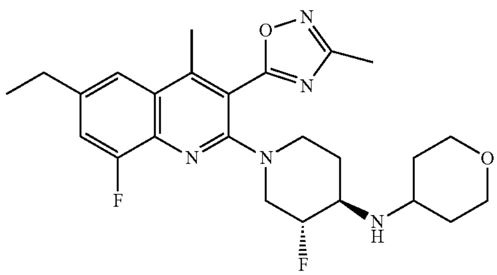 [SMILES: CCc1cc(F)c2nc(N3CC[C@@H](NC4CCOCC4)[C@H](F)C3)c(-c3nc(C)no3)c(C)c2c1] |
| 138 | 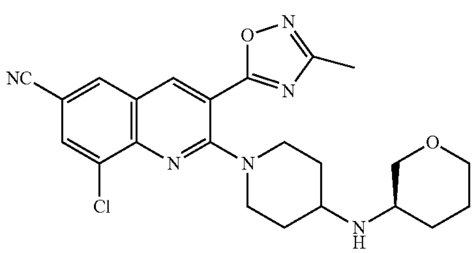 [SMILES: Cc1noc(-c2cc3cc(C#N)cc(Cl)c3nc2N2CCC(N[C@@H]3CCCOC3)CC2)n1] |
| 139 | 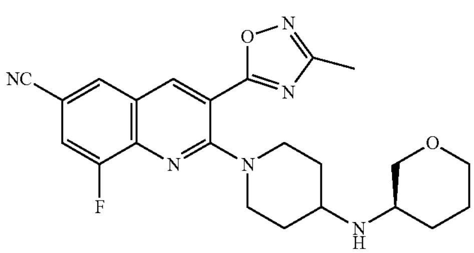 [SMILES: Cc1noc(-c2cc3cc(C#N)cc(F)c3nc2N2CCC(N[C@@H]3CCCOC3)CC2)n1] |
| 140 | 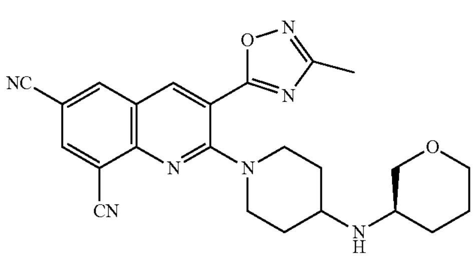 |
| 141 | 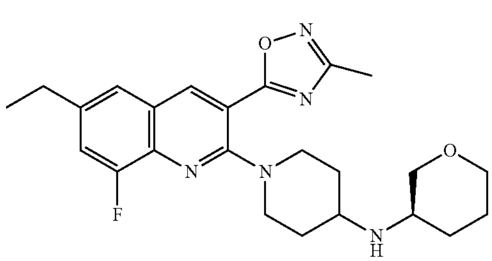 [SMILES: CCc1cc(F)c2nc(N3CCC(N[C@@H]4CCCOC4)CC3)c(-c3nc(C)no3)cc2c1] |
| 142 | |
| 143 | |
| 144 | |
| 145 | |
| 146 | |
| 147 | |

TABLE 1-continued

Representative Compounds

| No. | Structure |
|---|---|
| 148 | 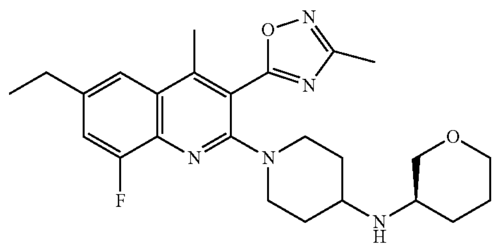 |
| 149 | 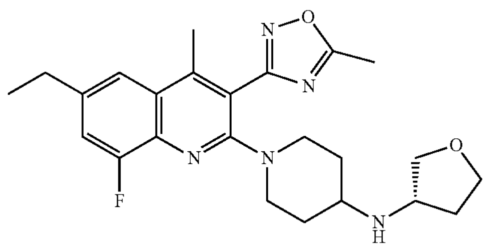 [SMILES: CCc1cc(F)c2nc(N3CCC(N[C@H]4CCOC4)CC3)c(-c3noc(C)n3)c(C)c2c1] |
| 150 | 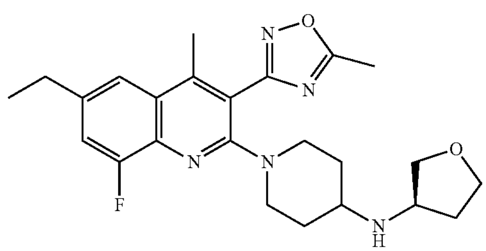 [SMILES: CCc1cc(F)c2nc(N3CCC(N[C@@H]4CCOC4)CC3)c(-c3noc(C)n3)c(C)c2c1] |
| 151 | 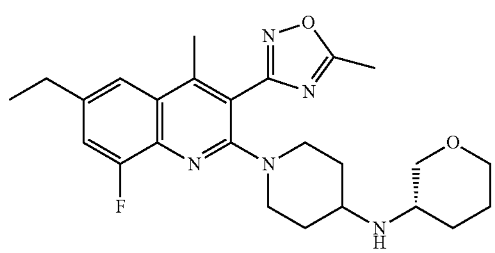 [SMILES: CCc1cc(F)c2nc(N3CCC(N[C@H]4CCCOC4)CC3)c(-c3noc(C)n3)c(C)c2c1] |
| 152 | 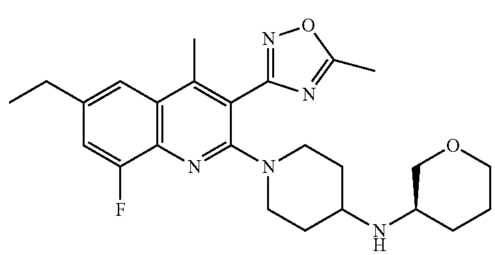 [SMILES: CCc1cc(F)c2nc(N3CCC(N[C@@H]4CCCOC4)CC3)c(-c3noc(C)n3)c(C)c2c1] |
| 153 | 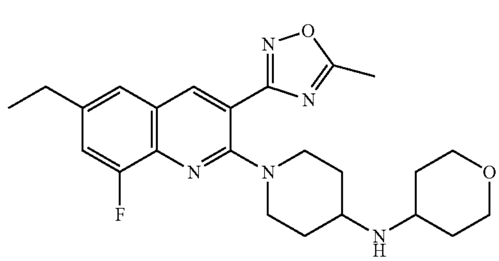 [SMILES: CCc1cc(F)c2nc(N3CCC(NC4CCOCC4)CC3)c(-c3noc(C)n3)cc2c1] |
| 154 | |
| 155 | |
| 156 | |
| 157 | |
| 158 | |
| 159 | |

TABLE 1-continued

Representative Compounds

| No. | Structure |
|---|---|
| 160 | 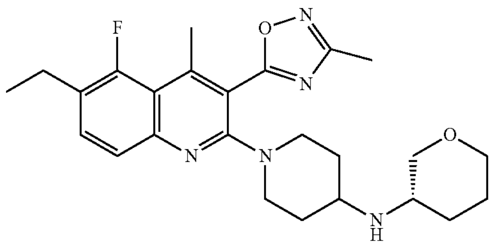 [SMILES: CCc1ccc2nc(N3CCC(N[C@H]4CCCOC4)CC3)c(-c3nc(C)no3)c(C)c2c1F] |
| 161 | 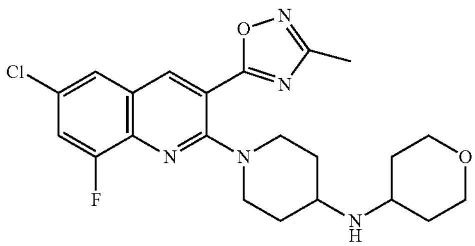 [SMILES: Cc1noc(-c2cc3cc(Cl)cc(F)c3nc2N2CCC(NC3CCOCC3)CC2)n1] |
| 162 | 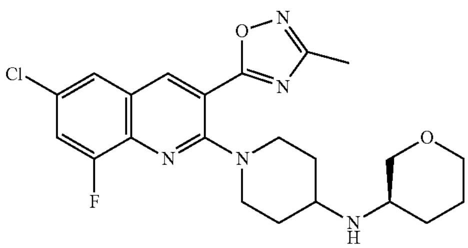 [SMILES: Cc1noc(-c2cc3cc(Cl)cc(F)c3nc2N2CCC(N[C@@H]3CCCOC3)CC2)n1] |
| 163 | 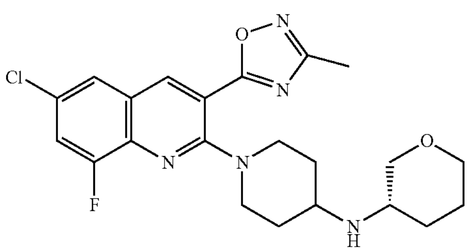 [SMILES: Cc1noc(-c2cc3cc(Cl)cc(F)c3nc2N2CCC(N[C@H]3CCCOC3)CC2)n1] |
| 164 | 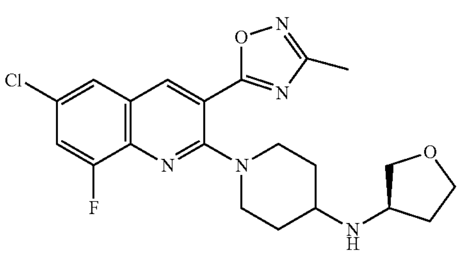 [SMILES: Cc1noc(-c2cc3cc(Cl)cc(F)c3nc2N2CCC(N[C@@H]3CCOC3)CC2)n1] |
| 165 | 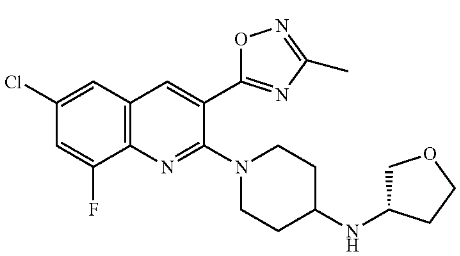 [SMILES: Cc1noc(-c2cc3cc(Cl)cc(F)c3nc2N2CCC(N[C@H]3CCOC3)CC2)n1] |
| 166 | |
| 167 | |
| 168 | |
| 169 | |
| 170 | |

TABLE 1-continued

Representative Compounds

| No. | Structure |
|---|---|
| 171 | 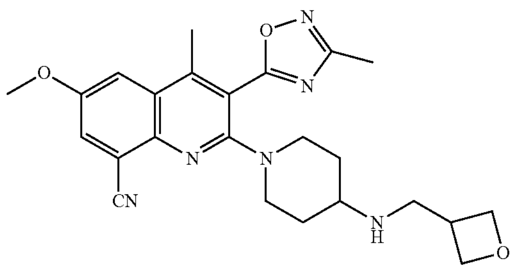 [SMILES: COc1cc(C#N)c2nc(N3CCC(NCC4COC4)CC3)c(-c3nc(C)no3)c(C)c2c1] |
| 172 | 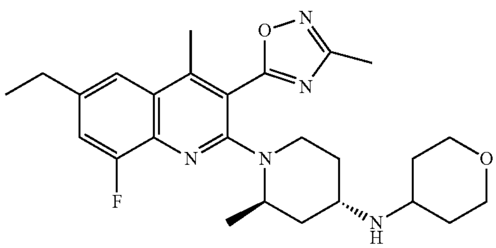 [SMILES: CCc1cc(F)c2nc(N3CC[C@H](NC4CCOCC4)C[C@H]3C)c(-c3nc(C)no3)c(C)c2c1] |
| 173 | 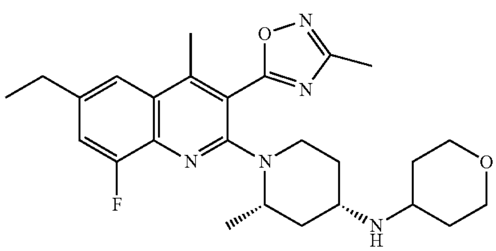 [SMILES: CCc1cc(F)c2nc(N3CC[C@H](NC4CCOCC4)C[C@@H]3C)c(-c3nc(C)no3)c(C)c2c1] |
| 174 | 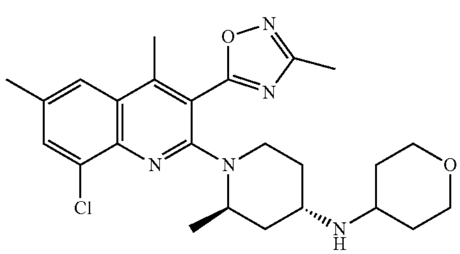 [SMILES: Cc1cc(Cl)c2nc(N3CC[C@H](NC4CCOCC4)C[C@H]3C)c(-c3nc(C)no3)c(C)c2c1] |
| 175 | 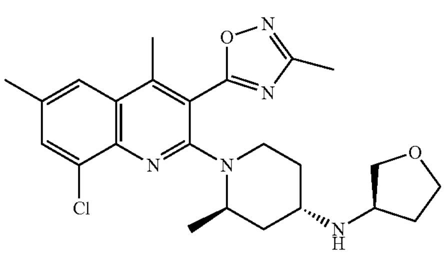 [SMILES: Cc1cc(Cl)c2nc(N3CC[C@H](N[C@@H]4CCOC4)C[C@H]3C)c(-c3nc(C)no3)c(C)c2c1] |
| 176 | 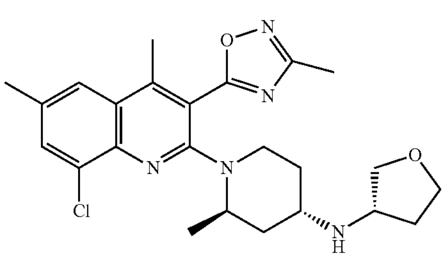 [SMILES: Cc1cc(Cl)c2nc(N3CC[C@H](N[C@H]4CCOC4)C[C@H]3C)c(-c3nc(C)no3)c(C)c2c1] |
| 177 | |
| 178 | |
| 179 | |
| 180 | |
| 181 | |
| 182 | |

TABLE 1-continued

Representative Compounds

| No. | Structure |
|---|---|
| 183 | 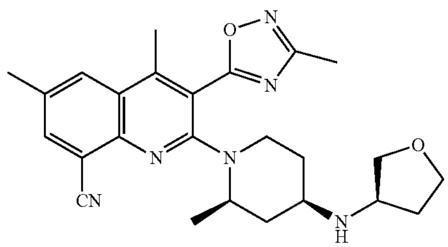 [SMILES: Cc1cc(C#N)c2nc(N3CC[C@@H](N[C@@H]4CCOC4)C[C@H]3C)c(-c3nc(C)no3)c(C)c2c1] |
| 184 | 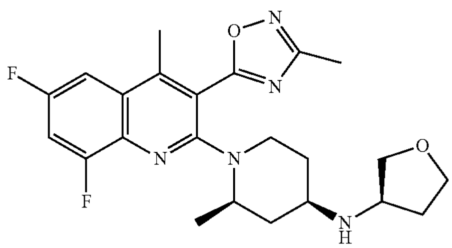 [SMILES: Cc1noc(-c2c(N3CC[C@@H](N[C@@H]4CCOC4)C[C@H]3C)nc3c(F)cc(F)cc3c2C)n1] |
| 185 | 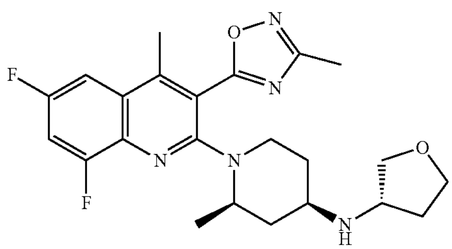 [SMILES: Cc1noc(-c2c(N3CC[C@@H](N[C@H]4CCOC4)C[C@H]3C)nc3c(F)cc(F)cc3c2C)n1] |
| 186 | 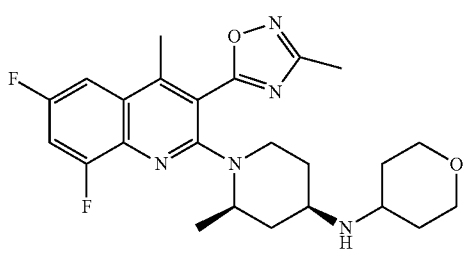 [SMILES: Cc1noc(-c2c(N3CC[C@@H](NC4CCOCC4)C[C@H]3C)nc3c(F)cc(F)cc3c2C)n1] |
| 187 | 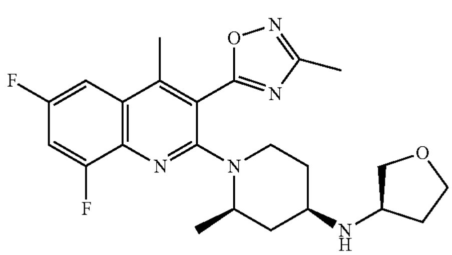 [SMILES: Cc1noc(-c2c(N3CC[C@@H](N[C@@H]4CCOC4)C[C@H]3C)nc3c(F)cc(F)cc3c2C)n1] |
| 188 | 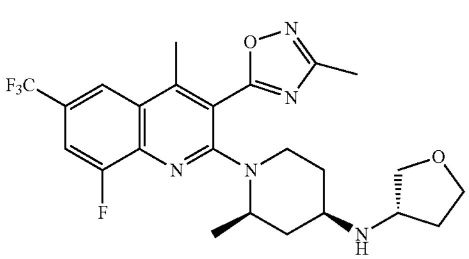 [SMILES: Cc1noc(-c2c(N3CC[C@@H](N[C@H]4CCOC4)C[C@H]3C)nc3c(F)cc(C(F)(F)F)cc3c2C)n1] |
| 189 | |
| 190 | |
| 191 | |
| 192 | |
| 193 | |
| 194 | |

TABLE 1-continued

Representative Compounds

| No. | Structure |
|---|---|
| 195 | 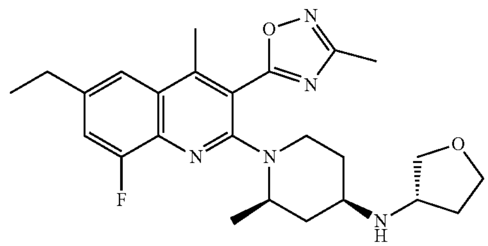 [SMILES: CCc1cc(F)c2nc(N3CC[C@@H](N[C@H]4CCOC4)C[C@H]3C)c(-c3nc(C)no3)c(C)c2c1] |
| 196 | 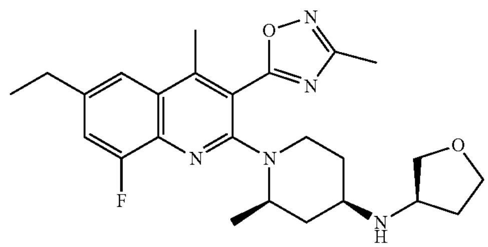 [SMILES: CCc1cc(F)c2nc(N3CC[C@@H](N[C@@H]4CCOC4)C[C@H]3C)c(-c3nc(C)no3)c(C)c2c1] |
| 197 | 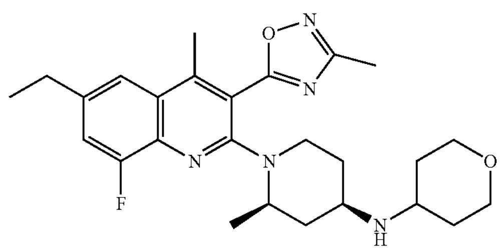 |
| 198 | 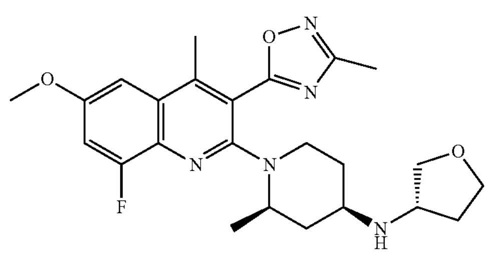 [SMILES: COc1cc(F)c2nc(N3CC[C@@H](N[C@H]4CCOC4)C[C@H]3C)c(-c3nc(C)no3)c(C)c2c1] |
| 199 | 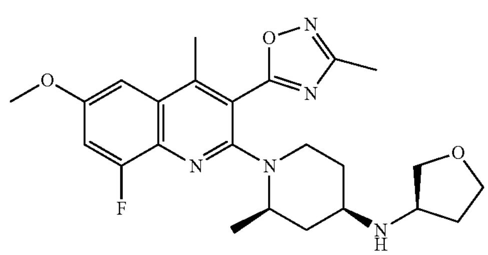 [SMILES: COc1cc(F)c2nc(N3CC[C@@H](N[C@@H]4CCOC4)C[C@H]3C)c(-c3nc(C)no3)c(C)c2c1] |
| 200 | 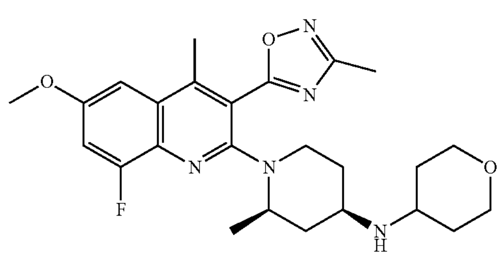 [SMILES: COc1cc(F)c2nc(N3CC[C@@H](NC4CCOCC4)C[C@H]3C)c(-c3nc(C)no3)c(C)c2c1] |
| 201 | |
| 202 | |
| 203 | |
| 204 | |
| 205 | |
| 206 | |

TABLE 1-continued

Representative Compounds

| No. | Structure |
|-----|-----------|
| 207 | 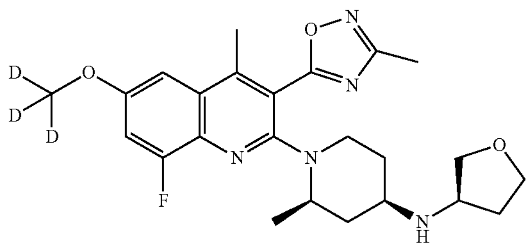 [SMILES: [2H]C([2H])([2H])Oc1cc(F)c2nc(N3CC[C@@H](N[C@@H]4CCOC4)C[C@H]3C)c(-c3nc(C)no3)c(C)c2c1] |
| 208 | 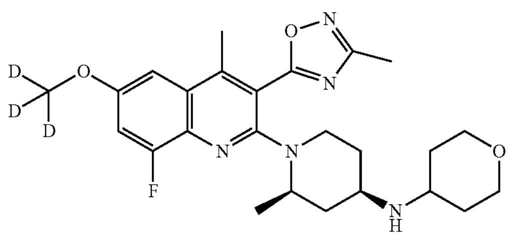 [SMILES: [2H]C([2H])([2H])Oc1cc(F)c2nc(N3CC[C@@H](NC4CCOCC4)C[C@H]3C)c(-c3nc(C)no3)c(C)c2c1] |
| 209 | 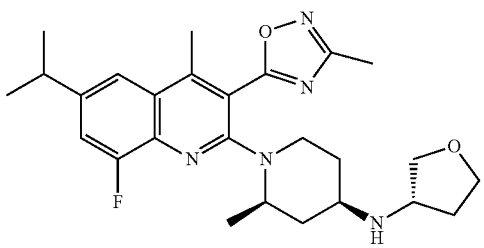 [SMILES: Cc1noc(-c2c(N3CC[C@@H](N[C@H]4CCOC4)C[C@H]3C)nc3c(F)cc(C(C)C)cc3c2C)n1] |
| 210 | 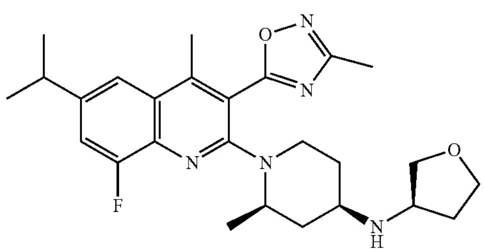 |
| 211 | 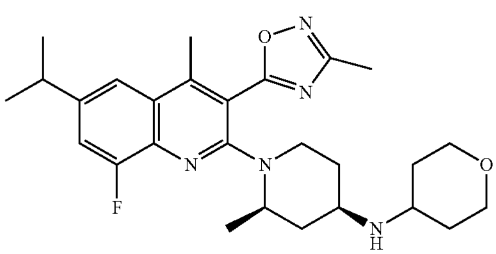 [SMILES: Cc1noc(-c2c(N3CC[C@@H](NC4CCOCC4)C[C@H]3C)nc3c(F)cc(C(C)C)cc3c2C)n1] |
| 212 | 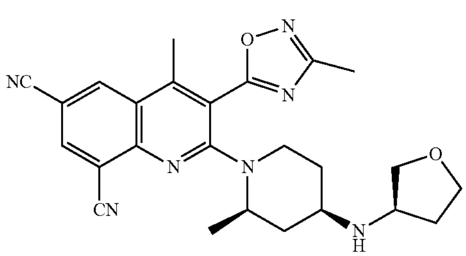 [SMILES: Cc1noc(-c2c(N3CC[C@@H](N[C@@H]4CCOC4)C[C@H]3C)nc3c(C#N)cc(C#N)cc3c2C)n1] |
| 213 | |
| 214 | |
| 215 | |
| 216 | |
| 217 | |
| 218 | |

TABLE 1-continued

Representative Compounds

| No. | Structure |
|---|---|
| 219a | 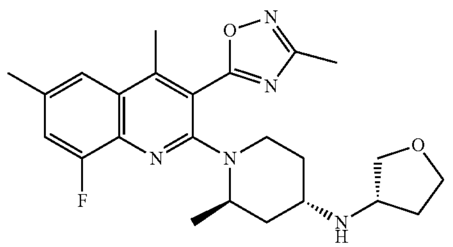 [SMILES: Cc1cc(F)c2nc(N3CC[C@H](N[C@H]4CCOC4)C[C@H]3C)c(-c3nc(C)no3)c(C)c2c1] |
| 219b | 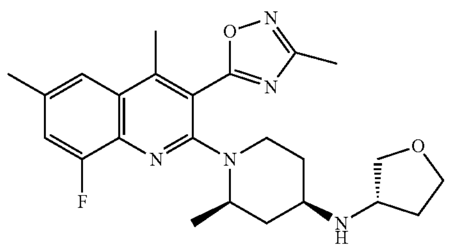 [SMILES: Cc1cc(F)c2nc(N3CC[C@@H](N[C@H]4CCOC4)C[C@H]3C)c(-c3nc(C)no3)c(C)c2c1] |
| 220a | 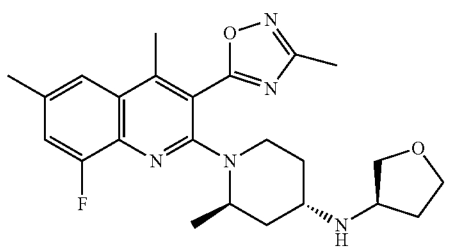 [SMILES: Cc1cc(F)c2nc(N3CC[C@H](N[C@@H]4CCOC4)C[C@H]3C)c(-c3nc(C)no3)c(C)c2c1] |
| 220b | 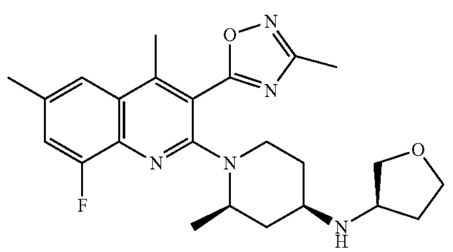 [SMILES: Cc1cc(F)c2nc(N3CC[C@@H](N[C@@H]4CCOC4)C[C@H]3C)c(-c3nc(C)no3)c(C)c2c1] |
| 221 | 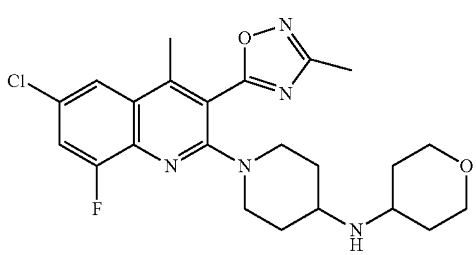 [SMILES: Cc1noc(-c2c(N3CCC(NC4CCOCC4)CC3)nc3c(F)cc(Cl)cc3c2C)n1] |
| 222 | 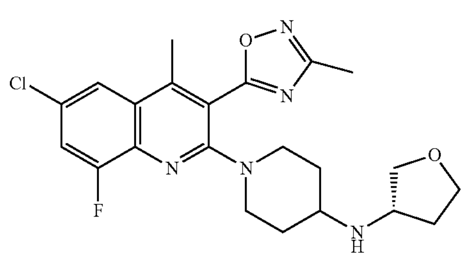 [SMILES: Cc1noc(-c2c(N3CCC(N[C@H]4CCOC4)CC3)nc3c(F)cc(Cl)cc3c2C)n1] |
| 223 | |
| 224 | |
| 225 | |
| 226 | |
| 227 | |
| 228 | |

TABLE 1-continued
Representative Compounds
| No. | Structure |
|---|---|
| 229 | 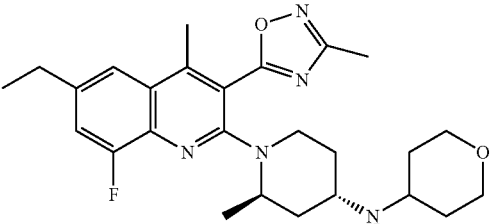 |
| 230 | 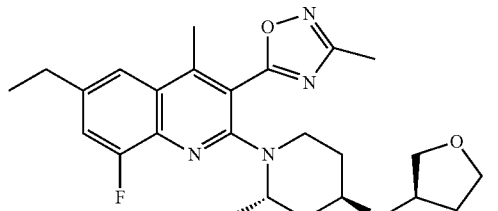 |
| 231 | 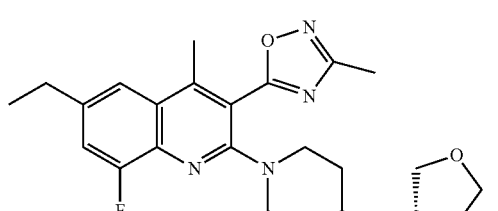 |
| 232 | 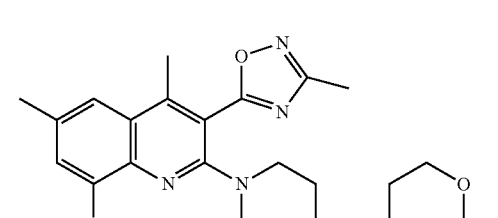 |
| 233 | 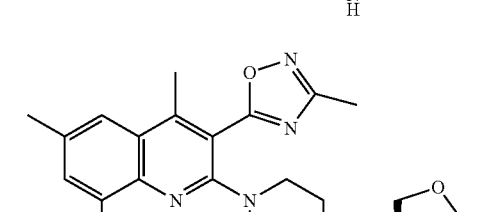 |
| 234 | 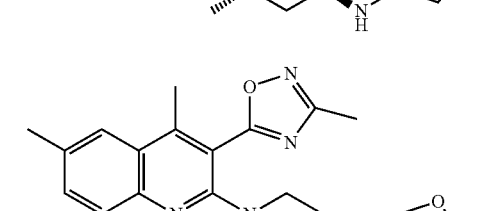 |
| 235 | 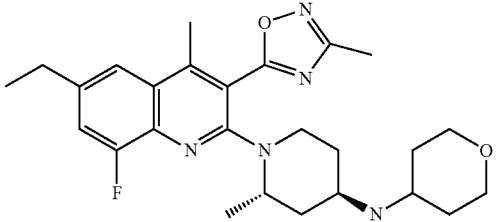 |
| 236a | 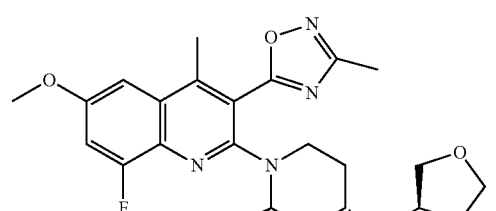 |
| 236b | 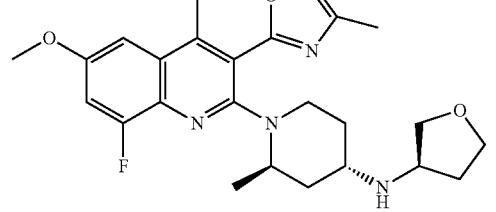 |
| 237a | 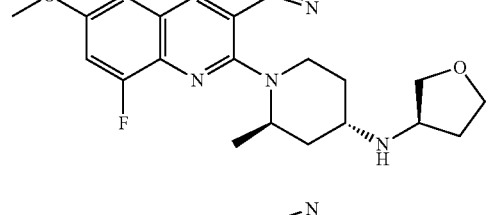 |
| 237b | 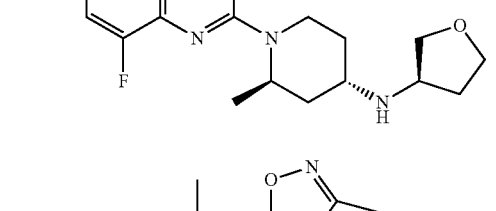 |
| 238 | 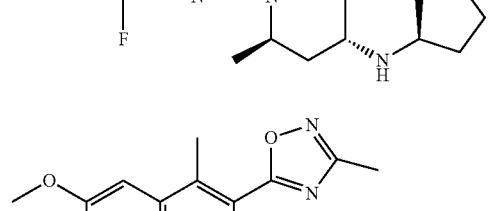 |

TABLE 1-continued

Representative Compounds

| No. | Structure |
|---|---|
| 239 | 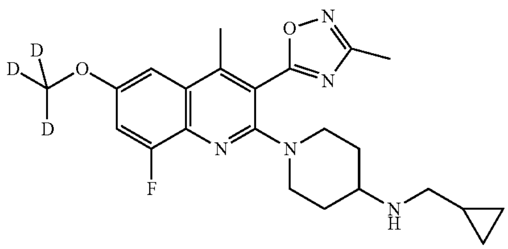 [SMILES: [2H]C([2H])([2H])Oc1cc(F)c2nc(N3CCC(NCC4CC4)CC3)c(-c3nc(C)no3)c(C)c2c1] |
| 240 | 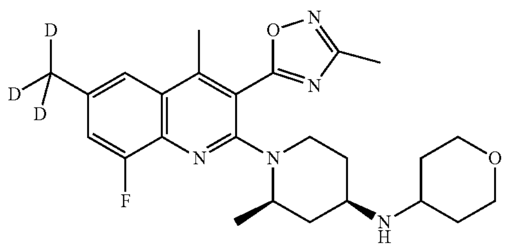 [SMILES: [2H]C([2H])([2H])c1cc(F)c2nc(N3CC[C@@H](NC4CCOCC4)C[C@H]3C)c(-c3nc(C)no3)c(C)c2c1] |
| 241 | 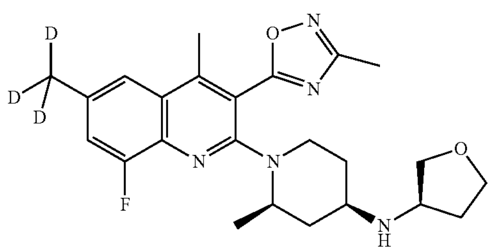 [SMILES: [2H]C([2H])([2H])c1cc(F)c2nc(N3CC[C@@H](N[C@@H]4CCOC4)C[C@H]3C)c(-c3nc(C)no3)c(C)c2c1] |
| 242 | 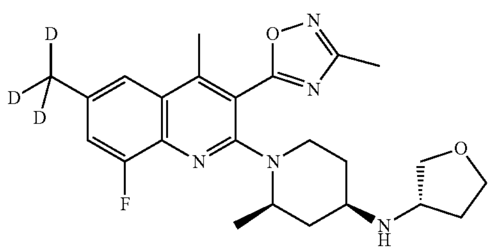 [SMILES: [2H]C([2H])([2H])c1cc(F)c2nc(N3CC[C@@H](N[C@H]4CCOC4)C[C@H]3C)c(-c3nc(C)no3)c(C)c2c1] |
| 243 | 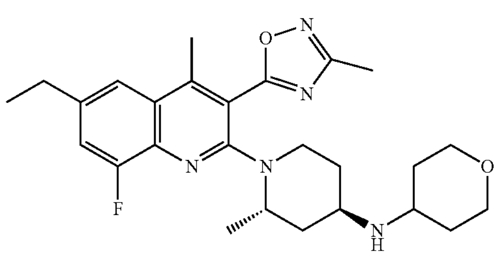 [SMILES: CCc1cc(F)c2nc(N3CC[C@@H](NC4CCOCC4)C[C@@H]3C)c(-c3nc(C)no3)c(C)c2c1] |
| 244 | 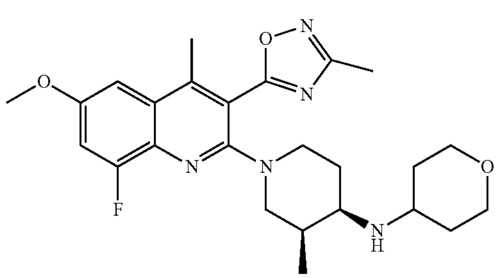 [SMILES: COc1cc(F)c2nc(N3CC[C@@H](NC4CCOCC4)[C@@H](C)C3)c(-c3nc(C)no3)c(C)c2c1] |
| 245 | |
| 246 | |
| 247 | |
| 248 | |
| 249 | |

TABLE 1-continued
Representative Compounds
| No. | Structure |
|---|---|
| 250 | 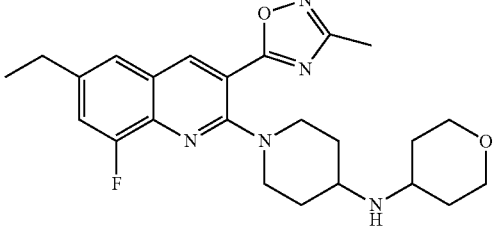 |
| 251 | 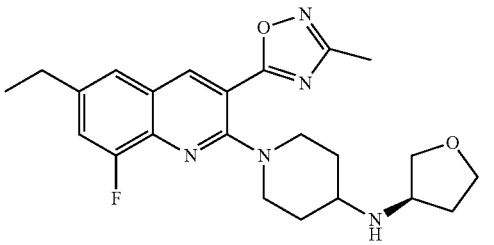 [SMILES: CCc1cc(F)c2nc(N3CCC(N[C@@H]4CCOC4)CC3)c(-c3nc(C)no3)cc2c1] |
| 252 | 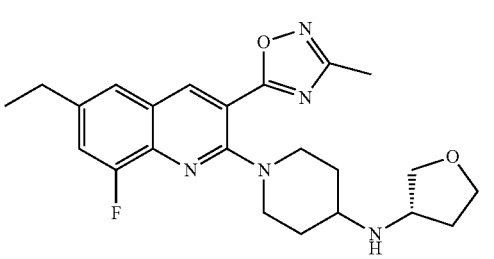 [SMILES: CCc1cc(F)c2nc(N3CCC(N[C@H]4CCOC4)CC3)c(-c3nc(C)no3)cc2c1] |
| 253 | 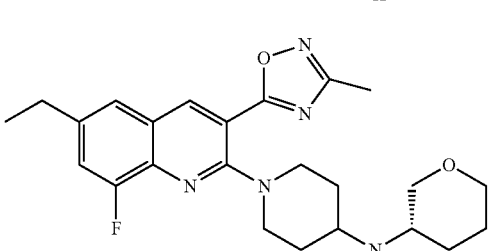 |
| 254 | 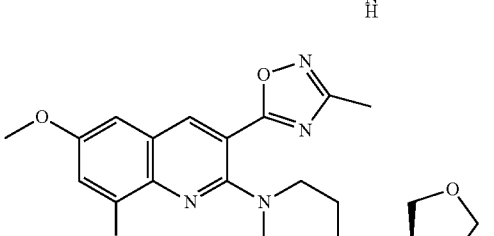 |
| 255 | 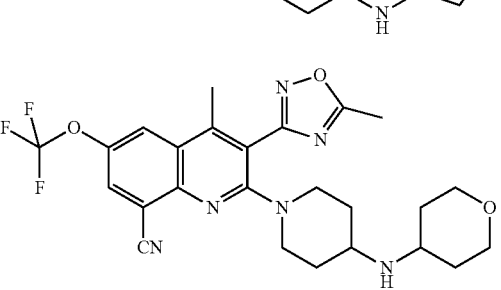 |
| 256 | 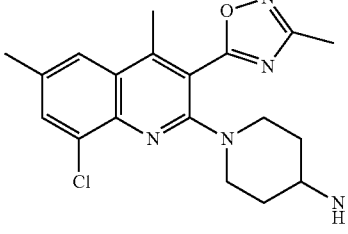 |
| 257 | 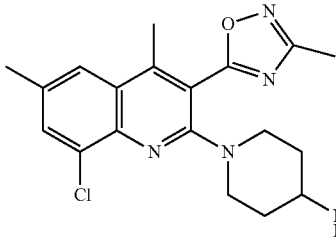 |
| 258 | 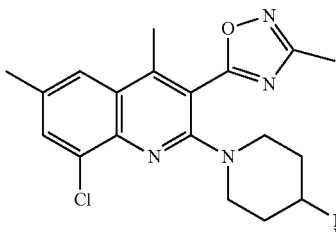 |
| 259 | 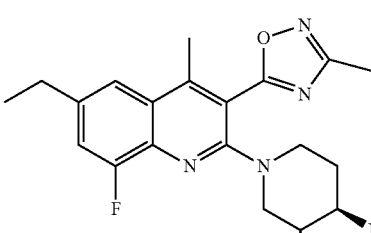 |
| 260 | 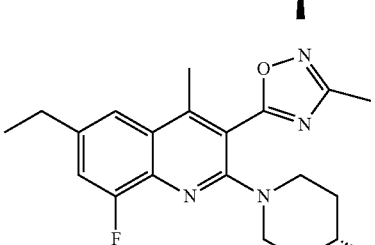 |
| 261 | 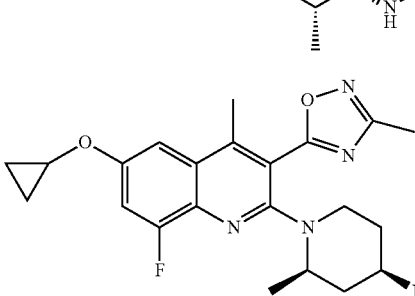 |

TABLE 1-continued

Representative Compounds

| No. | Structure |
|---|---|
| 262 | *(chemical structure)* |
| 263 | *(chemical structure)* |
| 264 | *(chemical structure)* |
| 265 | *(chemical structure)* |

In certain embodiments, the invention provides a pharmaceutical composition comprising a compound of the invention together with at least one pharmaceutically acceptable carrier, diluent or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the *Physicians' Desk Reference*, incorporated herein by reference.

When used to prevent the onset disease or condition, the compounds provided herein will be administered to a subject at risk for developing the condition, typically on the advice and under the supervision of a physician, at the dosage levels described above. Subjects at risk for developing a particular disease or condition generally include those that have a family history of the same, or those who have been identified by genetic testing or screening to be particularly susceptible to developing the disease or condition.

Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method is provided for antagonizing the KOR, the method comprising contacting the receptor with an effective amount of a compound having the structure of Formula (I) through (XVII), or a pharmaceutically acceptable isomer, racemate, hydrate, solvate, isotope or salt thereof, or a pharmaceutical composition comprising the same.

The term "antagonism" is used herein to encompass molecules that interact in some way with a receptor and thereby function as an antagonist, either by binding to the receptor at the binding site of its natural ligand or at locations other than the binding site. The "kappa opioid receptor" or "KOR" is a member of the opioid receptor family which binds the opioid peptide dynorphin as the primary endogenous ligand. The phrase to "KOR antagonism" used herein to encompass molecules that interact in some way with KOR and thereby function as an antagonist, either by binding to KOR at the site of dynorphin, or at a location other than the binding site (i.e., allosteric binding).

In an embodiment, a method is provided for treatment of a neuropsychiatric or behavioral condition, whether organic, stress-induced or iatrogenic, that is characterized by elevations in serum prolactin and respond to KOR antagonist administration with a reduction in serum prolactin. Such method comprises administering to the subject an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for duration sufficient to provide a beneficial effect to the subject.

In a further embodiment, a method is provided for treatment of a malcondition in a subject for which antagonism of the KOR is medically indicated. Such method comprises administering to the subject an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for duration sufficient to provide a beneficial effect to the subject.

As used herein, a "subject" means both mammals and non-mammals. Mammals include, for example, humans; non-human primates, e.g., apes and monkeys; cattle; horses; sheep; and goats. Non-mammals include, for example, fish and birds.

"Treating" or "treatment" within the meaning herein refers to an alleviation of symptoms associated with a disorder or disease, or inhibition of further progression or worsening of those symptoms, or prevention or prophylaxis of the disease or disorder in certain conditions.

The expression "effective amount", when used to describe use of a compound of the invention in providing therapy to a subject suffering from a disorder or malcondition mediated by KOR refers to the amount of a compound of the invention that is effective to bind to as an antagonist the KOR in the individual's tissues, wherein the KOR is implicated in the disorder, wherein such binding occurs to an extent sufficient to produce a beneficial therapeutic effect on the subject.

The term "malcondition" is used to describe any disease, disorder or condition, and are used interchangeably, and in the context of this application refers to a disease, disorder or condition wherein KOR plays a role in the biochemical mechanisms involved in the malcondition, or symptoms thereof, such that a therapeutically beneficial effect can be achieved by acting on such KOR.

In certain embodiments, the present invention provides a method for antagonizing a KOR with a compound of the invention. The method involves contacting the receptor with a suitable concentration of the compound to antagonize the receptor. The contacting can take place in vitro, for example in carrying out an assay to determine the KOR inhibition activity of an inventive compound undergoing experimentation related to a submission for regulatory approval.

In certain embodiments, the method for antagonizing a KOR can also be carried out in vivo, that is, within the living body of a mammal, such as a human patient or a test animal (referred to as a "subject" herein). The inventive compound can be supplied to the living organism via one of the routes as described above, e.g., orally, or can be provided locally within the body tissues. In the presence of the inventive compound, inhibition of the receptor takes place, and the effect thereof can be studied.

Methods of treatments provided by the invention include administration of a compound of the invention, alone or in combination with another pharmacologically active agent or second medicament to a subject or patient having a malcondition for which antagonizing the KOR is medically indicated, such as: an addictive disorder, including disorders related to substance abuse or addiction; CNS-related disorders; anxiety disorders; depressive disorders; mood disorders; schizophrenia or schizoaffective disorders; stress-related disorders; obesity and eating disorder; migraine; postnatal depression; neurodegenerative diseases and disorders, including disorders of mood and behavior associated with neurodegenerative diseases; postnatal depression; anesthesia and/or sedation; epilepsy; status epilepticus; and seizure.

In an embodiment, a method is provided for treatment of an addictive disorder, including a disorders related to substance abuse or addiction, and compulsive behavior, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for a duration sufficient to provide a beneficial effect to the subject.

Disorders related to substance abuse or addiction as described herein can include gambling, drug addiction, drug abuse, alcohol dependence, alcohol abuse, substance-induced depression and mood disorders induced by substances such as alcohol, nicotine, amphetamine, methamphetamine, cocaine, opiate addiction, heroin addiction, benzodiazepines and the like.

In an embodiment, a method is provided for treatment of CNS-related disorder, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

CNS-related disorders include substance abuse related disorders and/or withdrawal syndromes, mood disorders, anxiety disorders, schizophrenia spectrum disorders, pain, personality disorders, autism spectrum disorders, eating disorder; sleep disorder; disorders of memory and/or cognition, head shock and traumatic brain injury; vascular diseases and cognitive disorders.

Exemplary CNS conditions include substance abuse disorders and/or withdrawal syndromes (including addiction to opiates, cocaine, and/or alcohol); mood disorders (including depression, dysthymic disorder, bipolar disorder); anxiety disorders and including compulsive disorders such as obsessive-compulsive disorder (OCD), social phobia, generalized anxiety disorder (GAD), social anxiety disorder; stress, post-traumatic stress disorder (PTSD); schizophrenia spectrum disorders (including schizophrenia, schizoaffective disorder); pain (including migraine, neuropathic pain, injury related pain syndromes, acute pain, chronic pain); personality disorders (including anti-social personality disorder, obsessive compulsive personality disorder); autism spectrum disorders (ASD) (including autism, monogenetic causes of autism such as synaptophathy's, e.g., Rett syndrome, Fragile X syndrome, Angelman syndrome); eating disorders; sleep disorders (including insomnia); disorders of memory and/or cognition (including attention disorders (e.g., attention deficit hyperactivity disorder (ADHD)), dementia (including Alzheimer's type dementia, Lewis body type dementia, vascular type dementia), head shock and traumatic brain injury (TBI); vascular diseases (including stroke, ischemia, vascular malformations) and cognitive disorders (including Alzheimer's disease and other forms of dementia).

In an embodiment, a method is provided for treatment of an anxiety disorder, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for a duration sufficient to provide a beneficial effect to the subject.

Anxiety disorder is a blanket term covering several different forms of abnormal and pathological fear and anxiety. Current psychiatric diagnostic criteria recognize a wide variety of anxiety disorders, including generalized anxiety disorder, panic disorder, stress-related disorders, obsessive compulsive disorder, phobia, social anxiety disorder, separation anxiety disorder and post-traumatic stress disorder (PTSD). In one embodiment, the anxiety disorder is a social anxiety disorder. In one embodiment, the anxiety disorder is phobia. In one embodiment, the anxiety disorder is a stress-related disorder. In one embodiment, the anxiety related disorder is PTSD.

Generalized anxiety disorder is a common chronic disorder characterized by long-lasting anxiety that is not focused on any one object or situation. A person suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attack's potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from social phobia, specific phobia, agoraphobia, phobia of an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

In an embodiment, a method is provided for treatment of a depressive disorder, depression, or depressive illness, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of such disorders include major depression, drug-resistant depression, dysthymia and bipolar disorder. In an embodiment, a method is provided for treatment of a mood disorder, or a affective disorder comprising administering to a subject in need thereof an effective amount of a compound having the structure of Formula (I) through (XVII, or a pharmaceutically acceptable isomer, racemate, hydrate, solvate, isotope or salt thereof, or a pharmaceutical composition comprising the same, at a frequency and for duration sufficient to provide a beneficial effect to the subject.

Examples of a mood disorder or a affective disorder include major depressive disorder (MDD); bipolar disorder; anhedonia; dysthymia; major depression, Psychotic major depression (PMD), or psychotic depression; postpartum depression; seasonal affective disorder (SAD); and catatonic depression is a rare and severe form of major depression involving disturbances of motor behavior and other symptoms The terms "anhedonia" and "anhedonic symptom" are used interchangeably and is defined as the inability to experience pleasure from activities usually found enjoyable, e.g. exercise, hobbies, music, sexual activities or social interactions. The terms "anhedonia" and "anhedonic symptom" are closely related to criterion of "depressive disorder with melancholic features" which is defined in DSM-5 as melancholic depression characterized by a loss of pleasure in most or all activities, a failure of reactivity to pleasurable stimuli, a quality of depressed mood more pronounced than that of grief or loss, a worsening of symptoms in the morning hours, early morning waking, psychomotor retardation, excessive weight loss, or excessive guilt. The term "treatment of depressive disorder with melancholic features" comprises treatment of both the depressive disorder and melancholic features associated herewith. In one embodiment, the mood disorder is anhedonia. In one embodiment, the mood disorder is major depression. In one embodiment, the mood disorder is seasonal affective disorder (SAD).

In other embodiments, a method is provided for treatment of a schizophrenia or a schizoaffective disorder, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for duration sufficient to provide a beneficial effect to the subject.

In other embodiments, a method is provided for treatment of obesity or an eating disorder, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for duration sufficient to provide a beneficial effect to the subject. Obesity and eating disorders as described here can include bulimia, anorexia nervosa, and the like.

In other embodiments, a method is provided for treatment of migraine, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for duration sufficient to provide a beneficial effect to the subject. In another embodiment, prophylactic therapy is provided to prevent migraine. In this regard KOR antagonism is proposed as a preventative treatment of migraine in individuals at risk of the same.

In an embodiment, a method is provided for treatment of postnatal depression, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for a duration sufficient to provide a beneficial effect to the subject.

Immediately after birth, progesterone levels decrease dramatically leading to the onset of postnatal depression (PND). The symptoms of PND range from mild depression to psychosis requiring hospitalization. PND is also associated with severe anxiety and irritability. PND-associated depression is not amenable to treatment by classic antidepressants, and women experiencing PND show an increased incidence of premenstrual syndrome (PMS).

In other embodiments, a method is provided for treatment of a neurodegenerative disease or disorder, including disorders of mood and behavior associated with neurodegenerative diseases; anesthesia and/or sedation; epilepsy; seizure; diabetes, diabetic complications, diabetic retinopathy; sexual/reproductive disorders; hypertension; cerebral hemorrhage; congestive heart failure; atherosclerosis; rheumatoid arthritis; hyperlipidemia, hypertriglycemia, hyperglycemia, hyperlipoproteinemia; compulsive behavior disorders (such as paw licking in dog) and spinal damage, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for duration sufficient to provide a beneficial effect to the subject.

In an embodiment, a method is provided for treatment of disorders of mood and behavior associated with a neurodegenerative disease or disorder, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for a duration sufficient to provide a beneficial effect to the subject.

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

In an embodiment, a method is provided for anesthesia and/or sedation, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for a duration sufficient to provide a beneficial effect to the subject.

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience. Sedation is the reduction of irritability or agitation by administration of a pharmacological agent, generally to facilitate a medical procedure or diagnostic procedure. Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired. Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endrotracheal tube tolerance and ventilator synchronization, often with neuromuscular blocking agents.

Duration of sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life. Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

In an embodiment, a method is provided for treatment of epilepsy, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

In an embodiment, a method is provided for treatment of status epilepticus, comprising administering to a subject in need thereof an effective amount of a compound having the structure of Formula (I), or a pharmaceutically acceptable isomer, racemate, hydrate, solvate, isotope or salt thereof, or a pharmaceutical composition comprising the same, at a frequency and for a duration sufficient to provide a beneficial effect to the subject.

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

In an embodiment, a method is provided for treatment of seizure, comprising administering to a subject in need thereof an effective amount of a compound having the structure of Formula (I) through (XVII), or a pharmaceutically acceptable isomer, racemate, hydrate, solvate, isotope or salt thereof, or a pharmaceutical composition comprising the same, at a frequency and for a duration sufficient to provide a beneficial effect to the subject.

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly. Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time." Myoclonic seizures consist of sporadic jerks, usually on both sides of the body. Patients sometimes describe the jerks as brief electrical shocks. When violent, these seizures may result in dropping or involuntarily throwing objects. Clonic seizures are repetitive, rhythmic jerks that involve both sides of the body at the same time. Tonic seizures are characterized by stiffening of the muscles. Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Compounds having the structure of Formula (I), as well as the sub-structures for Formulas (II) through (XVII), can be synthesized using standard synthetic techniques known to those of skill in the art. For examples, compounds of the present invention can be synthesized using the general synthetic procedures set forth in Schemes 1 and 2.

To this end, the reactions, processes and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

-continued

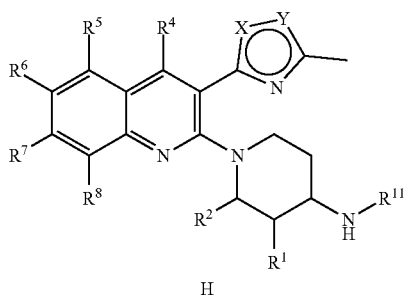

H

Reagents and conditions: i) A(1.0 equiv.), B (1.2 equiv.), POCl₃, 110° C., 1 h; ii) 1,4-dioxa-8-azaspiro[4,5]decane (1.2 equiv.), DIPEA (1.2 equiv.), EtOH, 120° C., 18 h, 33% (over two steps); iii) 10% aq. H₂SO₄, THF, 45° C., 2 h, quantitative yield; iv) amine (2.0 equiv.), NaBH(OAc)₃ (3.0 equiv.), AcOH (3.0 equiv.), DIPEA (2.0 equiv.), 1,2-dichloroethane (DCE), room temperature (RT), 18 h, 93% yield.

Scheme 1

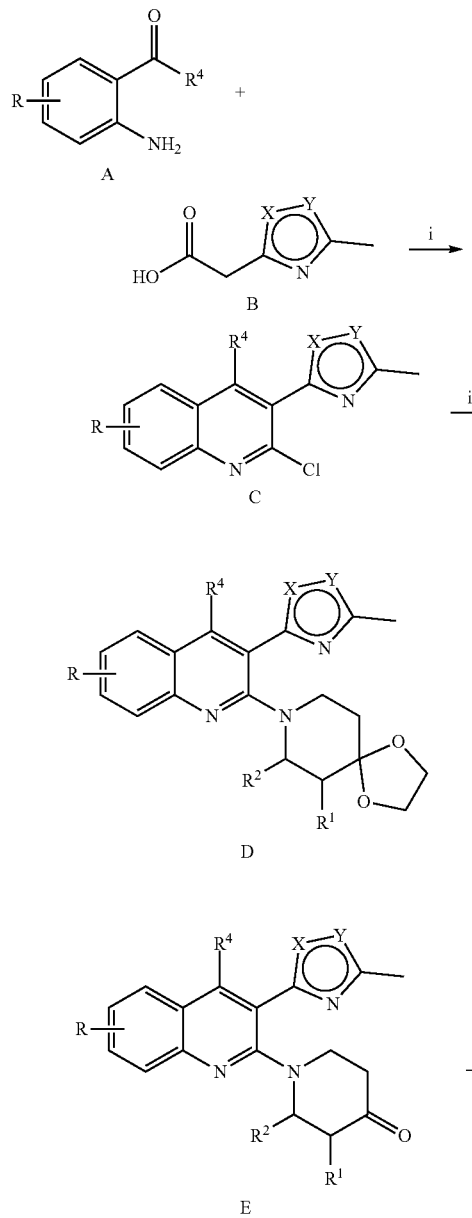

Scheme 2

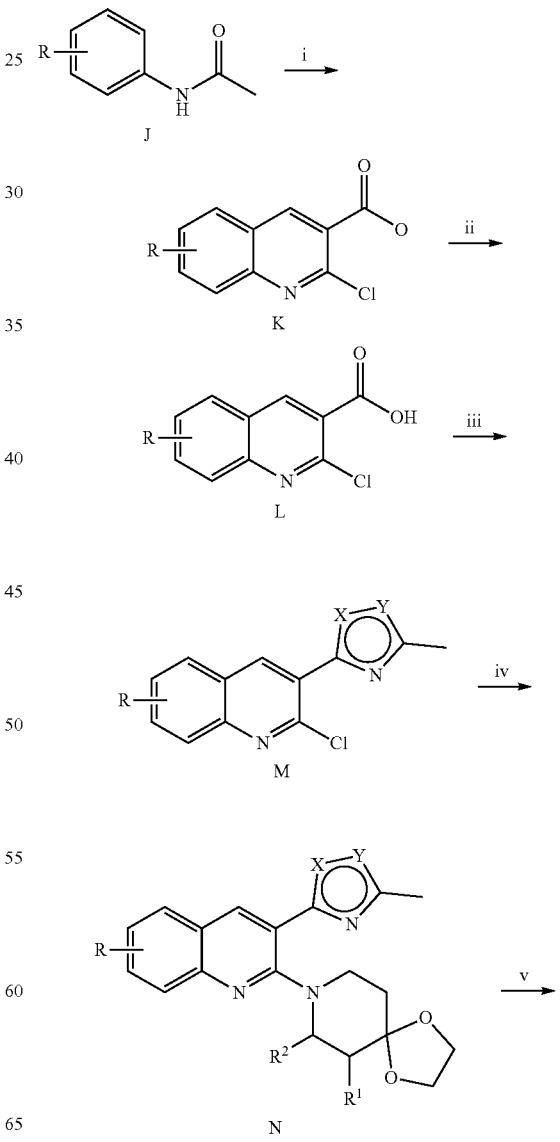

-continued

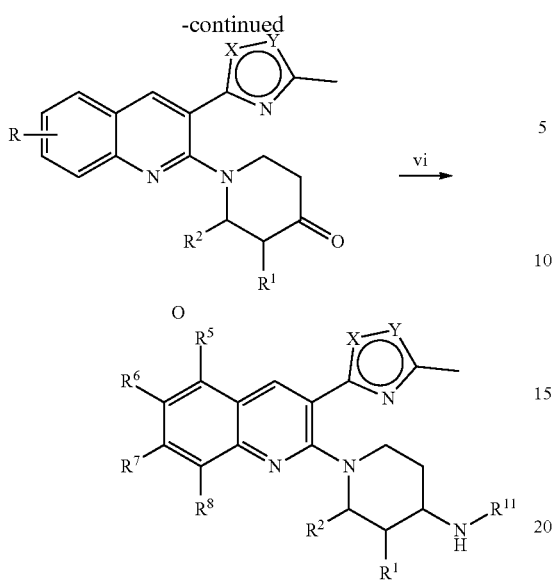

Reagents and conditions: i) DMF (2.5 equiv.), POCl₃ (7.0 equiv.), 0 to 75° C., 48 h, 36-39%; ii) NaH₂PO₄ (5.0 equiv.), NaClO₂ (3.0 equiv.), Na₂SO₃ (4.0 equiv.), CH₃CN, 94-98%; iii) a) 15 (1.0 equiv.), SOCl₂ (3.0 equiv.), CH₂Cl₂, DMF (catalytic), 50° C., 2 h, b) Acetamidoxime (1.2 equiv.), DIPEA (1.2 equiv.), dioxane, 100° C., 4 h, 48-54%; iv) 1,4-dioxa-8-azaspiro[4,5]decane (1.2 equiv.), DIPEA (2.0 equiv.), EtOH, 125° C., overnight, 70-73%; v) 10% aq. H₂SO₄, THF, 45° C., 2 h, 73-78%; vi) Amine (2.0 equiv.), NaBH(OAc)₃ (2.0 equiv.), AcOH (2.0 equiv.), DIPEA (2.0 equiv.), 1,2-dichloroethane, RT, overnight.

EXAMPLES

The invention is further illustrated by the following examples. The examples below are non-limiting and are merely representative of various aspects of the invention. Solid and dotted wedges within the structures herein disclosed illustrate relative stereochemistry, with absolute stereochemistry depicted only when specifically stated or delineated.

General Methods

Analytical high-performance liquid chromatography-mass spectrometry (HPLC-MS) was performed utilizing Shimadzu LC-2030C HPLC system, paired with Shimadzu LC-2020 mass detector (electrospray ionization, ESI). The RP-HPLC column was Shimadzu C18 (3 um, 50×4.6 mm). HPLC Method 1:50~100% acetonitrile in water (0.1% formic acid) as mobile phase, flow rate 1.0 mL/min, and 5 min run time. HPLC Method 2: 10~100% acetonitrile in water (0.1% formic acid) as mobile phase, flow rate 1.0 mL/min, and 10 min run time.

Preparative HPLC purification was performed utilizing Interchim PF4250 system, and the fraction collection was triggered by UV absorbance at 254 nm. The reverse-phase HPLC column was Phenomenex 00D-4454-U0-AX (Gemini 5 um NX-C18, 100×30 mm). Prep-HPLC Method 1: 5-85% acetonitrile in water as the mobile phase, flow rate 35 mL/min, and 20 min run time. Prep-HPLC Method 2: 5-85% acetonitrile in water (0.05% trifluoroacetic acid) as the mobile phase, flow rate 35 mL/min, and 20 min run time.

Normal phase flash column chromatography was performed utilizing either Biotage Isolera One system or Interchim PF4250 system. The silica gel columns were purchased from either Teledyne (RediSep Rf) or Biotage (SNAP Ultra). The mobile phase was either ethyl acetate in hexanes or methanol in dichloromethane with various ratios, and the fraction collection was triggered by UV absorbance at 254 nm.

The microwave reaction was performed on Biotage Initiator (max. 400 W with internal temperature monitor).

All the starting materials and reagents are commercially available and were used as it is.

Example 1

Compound 1

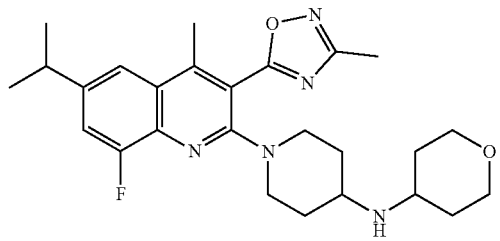

Step 1: Synthesis of Compound Int-1-1c

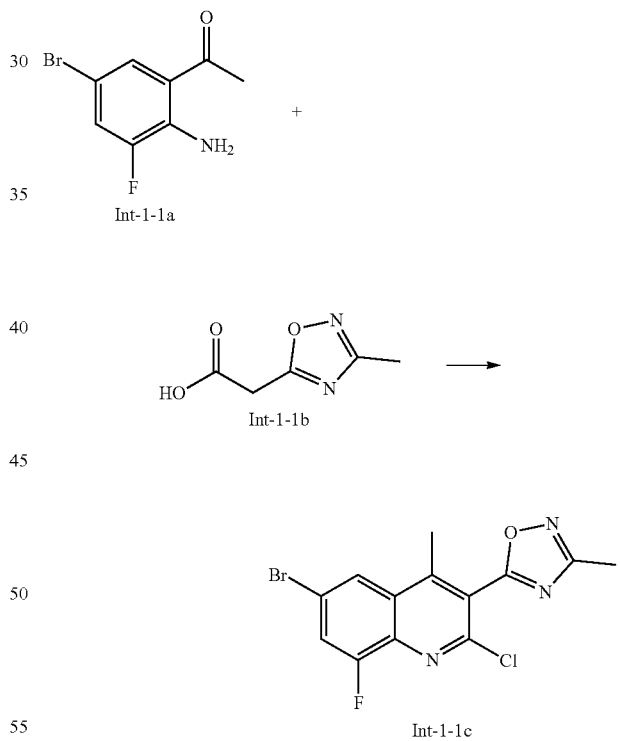

A mixture of aniline Int-1-1a (1.52 g, 6.5 mmol), oxadiazole acid Int-1-1b (1.12 g, 7.9 mmol) and POCl₃ (10 mL) was stirred at 110° C. for 1 h. After cooling to room temperature, excess POCl₃ was removed under reduced pressure. To the residue, H₂O was added at 0° C., and the mixture was stirred at 0° C. for 10 min. The precipitated crude chloroquinoline Int-1-1c was filtered, washed with H₂O and dried under reduced pressure. The crude product Int-1-1c was used for the next reaction without further purification.

Step 2: Synthesis of Compound Int-1-1d

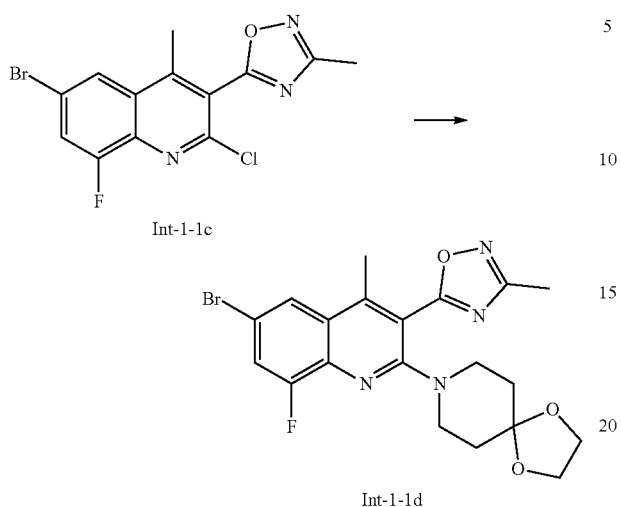

To a suspension of crude chloroquinoline Int-1-1c (2.33 g, 6.5 mmol) and DIPEA (1.4 mL, 7.9 mmol) in EtOH (33 mL) was added 1,4-dioxa-8-azaspiro[4,5]decane (1.0 mL, 7.9 mmol) at room temperature. The mixture was then heated at 120° C. overnight. After cooling to room temperature, the mixture was concentrated and purified by column chromatography (Hexanes/EtOAc gradient) to give quinoline Int-1-1d as dark brown solid (1.0 g, 33% yield over two steps). LCMS: (M+1) m/z=463, 465.

Step 3: Synthesis of Compound Int-1-1e

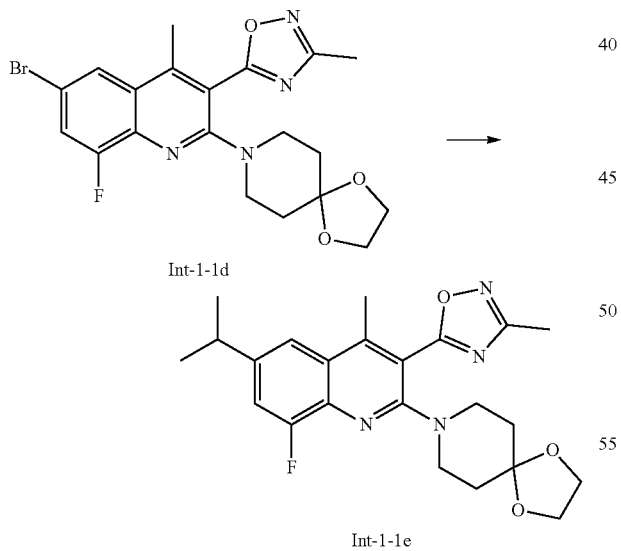

To a suspension of compound Int-1-1d (0.85 g, 1.83 mmol), Pd(OAc)$_2$ (41 mg, 0.09 mmol) and P(tBu)$_3$·HBF$_4$ (32 mg, 0.11 mmol) in THF (10 mL) was added 1M ZnBr$_2$ in THF (0.55 mL) at room temperature. To the mixture, 2M iPrMgCl in THF (3.3 mL, 6.6 mmol) was added over 30 min at room temperature, and the resulting mixture was stirred at ambient temperature overnight. The mixture was poured into ice and partitioned between EtOAc (50 mL) and 1% aq. HCl (50 mL). The organic layer was washed with brine (50 mL), dried over Na$_2$SO$_4$ and concentrated. The residue was purified by column chromatography (1-10% EtOAc in CH$_2$Cl$_2$), then preparative-TLC to give 6-isopropylquinoline Int-1-1e as yellow oil (0.37 g, 47% yield). LCMS: (M+1) m/z=427.

Step 4: Synthesis of Compound Int-1-1f

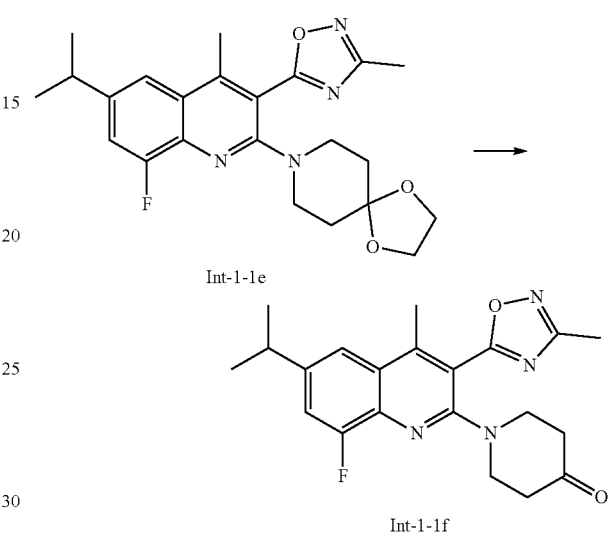

To a solution of Int-1-1e (0.23 g, 0.55 mmol) in THF (2.5 mL) was added 10% aq. H$_2$SO$_4$ (5 mL) at room temperature. The mixture was then stirred at 45° C. for 2 h. After cooling to room temperature, the mixture was neutralized with sat. aq. Na$_2$CO$_3$ and extracted with EtOAc (2×20 mL). The combined organic layers were dried over Na$_2$SO$_4$ and concentrated to dryness. The ketone Int-1-1f (yellow oil) was used for the next reaction without further purification. (210 mg, quantitative yield). LCMS: (M+1) m/z=383.

Step 5: Synthesis of Compound 1

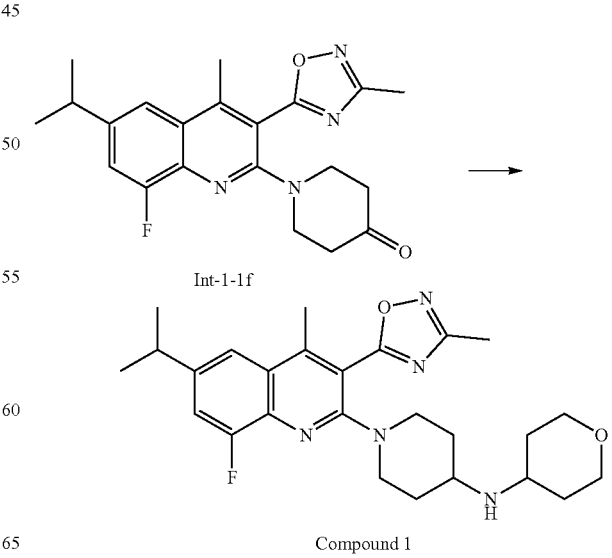

A mixture of Int-1-1f (10.5 mg, 0.027 mmol), tetrahydro-2H-pyran-4-amine (0.054 mmol) and DIPEA (10 μL, 0.054 mmol) in 1,2-dichloroethane (1.5 mL) was stirred at room temperature for 10 min. To the mixture, NaBH(OAc)$_3$ (17.4 mg, 0.081 mmol) and AcOH (5 μL, 0.081 mmol) were added. The resulting mixture was stirred at room temperature overnight. After filtration through Celite, the filtrate was concentrated under reduced pressure. The reside was purified by preparative-TLC (CH$_2$Cl$_2$:MeOH=96:4) to give Compound 1 (93% yield). LCMS: (M+1) m/z=468.

Examples 2-7

The procedure of Example 1 was used to produce Compounds 2-7, except that tetrahydro-2H-pyran-4-amine in Step 5 is replaced by (R)-tetrahydro-2H-pyran-3-amine to yield Compound 2, LCMS: (M+1) m/z=468; (S)-tetrahydro-2H-pyran-3-amine to yield Compound 3, LCMS: (M+1) m/z=468); (R)-tetrahydrofuran-3-amine to yield Compound 4, LCMS: (M+1) m/z=454); (S)-tetrahydrofuran-3-amine to yield Compound 5, LCMS: (M+1) m/z=454); cyclopropylmethanamine to yield Compound 6, LCMS: (M+1) m/z=438); and cyclobutylmethanamine to yield Compound 7, LCMS: (M+1) m/z=452), respectively.

Examples 8-10

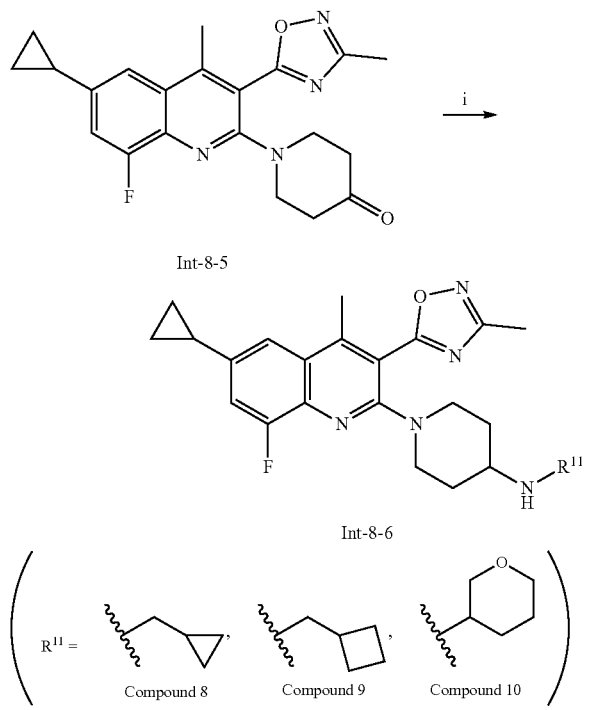

Synthesis of Compound 8

Int-8-5 was prepared from Int-11-42 and 1,4-dioxa-8-azaspiro[4,5]decane in two steps using conditions analogous to the general methods used for the synthesis of Int-1-1d and Int-1-1f.

A mixture of Int-8-5, (11 mg, 0.029 mmol) and cyclopropylmethanamine (4.1 mg, 0.058 mmol) in 1,2-dichloroethane (0.2 mL) was stirred at RT for 10 min. To the mixture, NaBH(OAc)$_3$ (12 mg, 0.058 mmol) and AcOH (3.3 μL, 0.058 mmol) were added. The resulting mixture was stirred RT overnight. The reaction mixture was concentrated under reduced pressure. The residue was purified by preparative-TLC (CH$_2$Cl$_2$:MeOH=95:5) to give Compound 8 as yellow solid (8.8 mg, 0.020 mmol). LCMS: (M+1) m/z=436, 437.

Synthesis of Compound 9

A mixture of Int-8-5 (11 mg, 0.029 mmol), cyclobutylmethanamine hydrochloride (7.0 mg, 0.058 mmol) and DIPEA (10 μL, 0.058 mmol) in 1,2-dichloroethane (0.2 mL) was stirred at RT for 10 min. To the mixture, NaBH(OAc)$_3$ (12 mg, 0.058 mmol) and AcOH (3.3 μL, 0.058 mmol) were added. The resulting mixture was stirred RT overnight. The reaction mixture was concentrated under reduced pressure. The residue was purified by preparative-TLC (CH$_2$Cl$_2$:MeOH=95:5) to give Compound 9 as yellow solid (9.0 mg, 0.020 mmol). LCMS: (M+1) m/z=450, 451.

Synthesis of Compound 10

A mixture of Int-8-5 (11 mg, 0.029 mmol), (S)-tetrahydro-2H-pyran-3-amine hydrochloride (7.9 mg, 0.058 mmol) and DIPEA (10 μL, 0.058 mmol) in 1,2-dichloroethane (0.2 mL) was stirred at RT for 10 min. To the mixture, NaBH(OAc)$_3$ (12 mg, 0.058 mmol) and AcOH (3.3 μL, 0.058 mmol) were added. The resulting mixture was stirred RT overnight. The reaction mixture was concentrated under reduced pressure. The residue was purified by preparative-TLC (CH$_2$Cl$_2$:MeOH=95:5) to give Compound 10 yellow solid (9.7 mg, 0.021 mmol). LCMS: (M+1) m/z=466, 467.

Examples 11-12

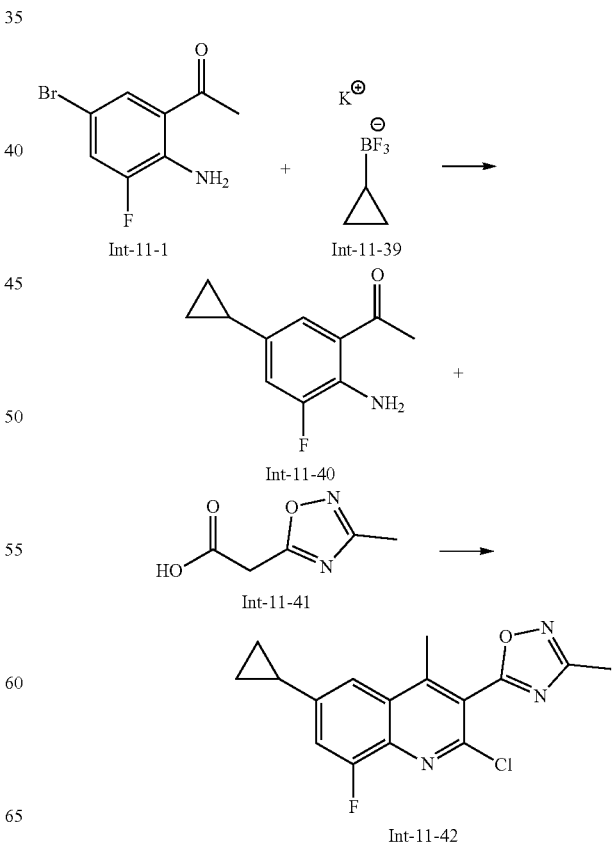

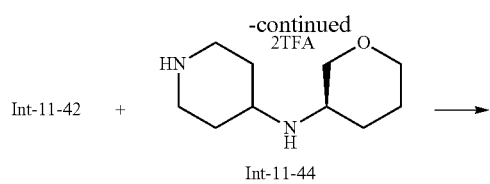

Int-11-44

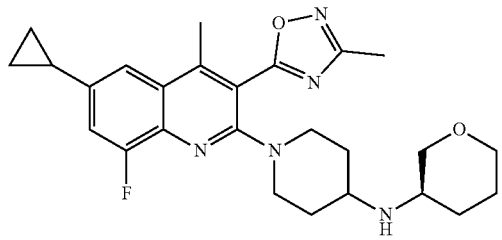

Compound 11

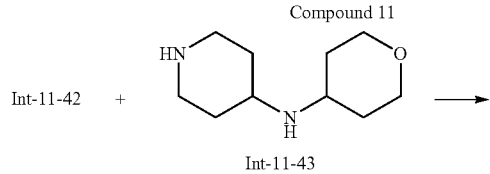

Int-11-43

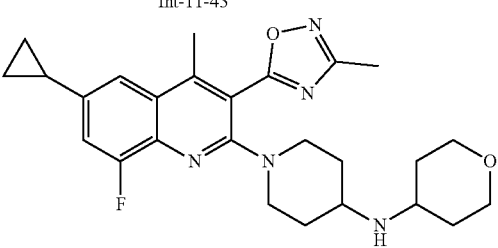

Compound 12

Synthesis of 40

A mixture of bromide Int-11-1 (1.0 equiv.), potassium cyclopropyltrifluoroborate (3.0 equiv.), $K_3PO_4$ (3.3 equiv.) and $Pd(PPh_3)_4$ (0.02 equiv.) in toluene:$H_2O$ (3:1) was heated at 100° C. overnight. The mixture was concentrated under reduced pressure and the product purified by column chromatography using hexanes/$CH_2Cl_2$ (9:1). The product was obtained as a pale yellow solid in 39-41% yield. LCMS: (M+1) m/z=194.

Synthesis of 42

A mixture of Int-11-40 (1.0 equiv.) and Int-11-41 (1.0 equiv.) in $POCl_3$ was heated at 80° C. for 1 h. The excess $POCl_3$ was removed under reduced pressure. The residue was quenched with ice and the mixture was stirred for 15 min. The pale brown product was collected by filtration and used in the next step without further purification (53-55% yield). LCMS: (M+1) m/z=318.

Synthesis of Compound 11

A mixture of Int-11-42 (1.0 equiv.), Int-11-44 (2.0 equiv.) and DIPEA (4.0 equiv.) in ethanol was heated at 130° C. overnight. The mixture was concentrated under reduced pressure and the product purified by preparative-TLC ($CH_2Cl_2$:MeOH=95:5) to give Compound 11 in 62-64% yield as a pale yellow oil. LCMS: (M+1) m/z=466.

Synthesis of Compound 12

A mixture of Int-11-42 (1.0 equiv.), Int-11-43 (2.0 equiv.) and DIPEA (2.0 equiv.) in ethanol was heated at 130° C. overnight. The mixture was concentrated under reduced pressure and the product purified by preparative-TLC ($CH_2Cl_2$:MeOH=95:5) to give Compound 12 in 67-69% yield as a pale yellow solid. LCMS: (M+1) m/z=466.

Examples 13-14

Compound 13 and Compound 14 were obtained according to the procedure for Compound 11 and Compound 12, employing appropriate intermediates. Compound 13 was obtained as a pale yellow solid in 69% yield (last step). LCMS: (M+1) m/z=452. Compound 14 was obtained as a pale yellow solid in 73% yield (last step). LCMS: (M+1) m/z=452.

Examples 15-16

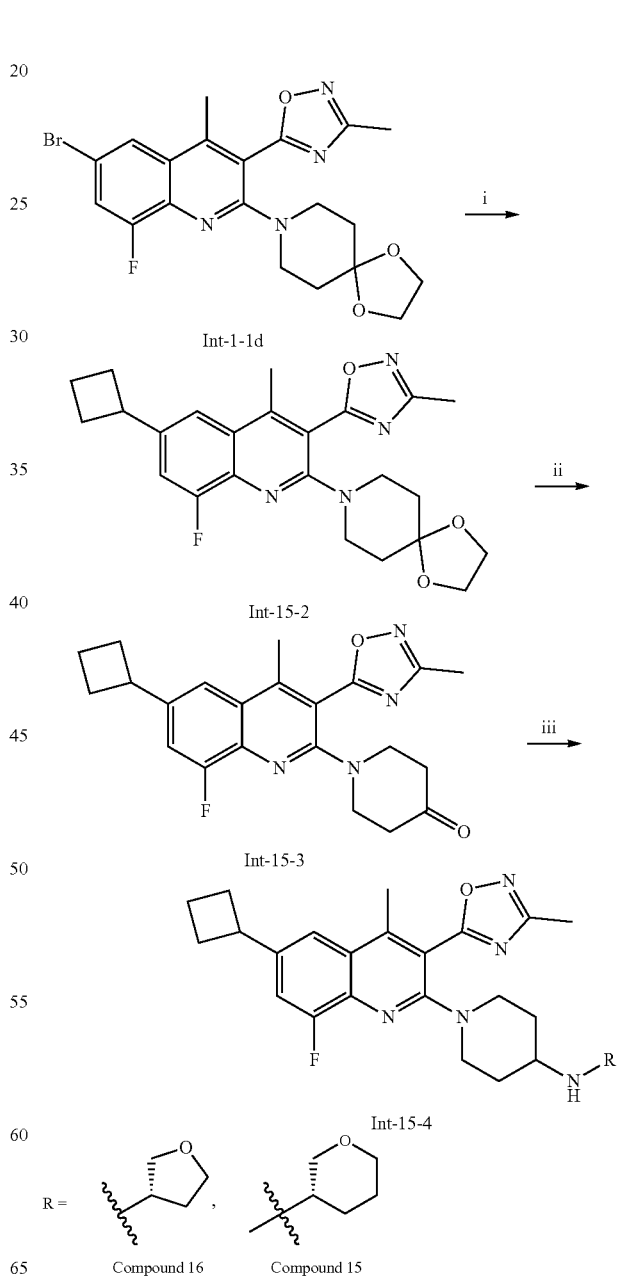

Synthesis of Int-15-2

To a mixture of Int-1-1d (227 mg, 0.49 mmol), potassium cyclobutyltrifluoroborate (159 mg, 0.98 mmol), Cs₂CO₃ (479 mg, 1.47 mmol), CataCXium (18 mg, 0.049 mmol) and Pd(OAc)₂ (11 mg, 0.049 mmol), were added toluene (1.8 mL) and H₂O (0.16 mL). The reaction mixture was degassed under vacuum and purged with nitrogen, then heated at 100° C. overnight. The reaction mixture was cooled to RT, filtered (Whatman syringe filters, 0.2 μM pore size), dry loaded onto silica gel, and purified by column chromatography (Hexanes/EtOAc gradient) to afford the Int-15-2 as a yellow solid (86 mg, 39% yield). LCMS: (M+1) m/z=439.

Synthesis of 3

To a solution of Int-15-2 (68 mg, 0.15 mmol) in THF (0.5 mL) was added 10% aq. H₂SO₄ (1.1 mL) at room temperature. The mixture was then stirred at 45° C. for 4 h. After cooling to RT, the mixture was neutralized with sat. aq. Na₂CO₃ and extracted with EtOAc (2×10 mL). The combined organic layers were dried over Na₂SO₄ and concentrated to dryness. The ketone Int-15-3 was used in the next step without further purification (56 mg, quantitative yield). LCMS: (M+1) m/z=395.

Synthesis of Compound 15

A mixture of Int-15-3 (10 mg, 0.025 mmol), (S)-tetrahydro-2H-pyran-3-amine hydrochloride (7 mg, 0.051 mmol) and DIPEA (9 μL, 0.051 mmol) in 1,2-dichloroethane (0.2 mL) was stirred at RT for 10 min. To the mixture, NaBH(OAc)₃ (11 mg, 0.051 mmol) and AcOH (3 μL, 0.051 mmol) were added. The resulting mixture was stirred RT overnight. The reaction mixture was concentrated under reduced pressure. The residue was purified by preparative-TLC (CH₂Cl₂:MeOH=95:5) to give Compound 15 as yellow solid (10.2 mg, 84% yield). LCMS: (M+1) m/z=480, 481.

Synthesis of Compound 16

A mixture of Int-15-3 (10 mg, 0.025 mmol) and (S)-tetrahydrofuran-3-amine (4.4 mg, 0.051 mmol) in 1,2-dichloroethane (0.2 mL) was stirred at RT for 10 min. To the mixture, NaBH(OAc)₃ (11 mg, 0.051 mmol) and AcOH (3 μL, 0.051 mmol) were added. The resulting mixture was stirred RT overnight. The reaction mixture was concentrated under reduced pressure. The residue was purified by preparative-TLC (CH₂Cl₂:MeOH=95:5) to give Compound 16 as yellow solid (10 mg, 84% yield). LCMS: (M+1) m/z=466, 467.

Example 17

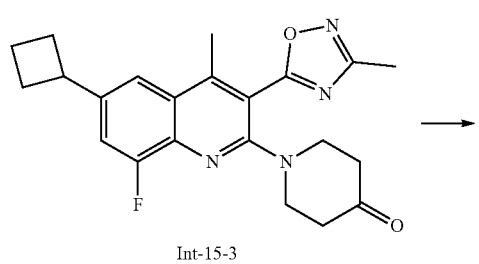

Int-15-3

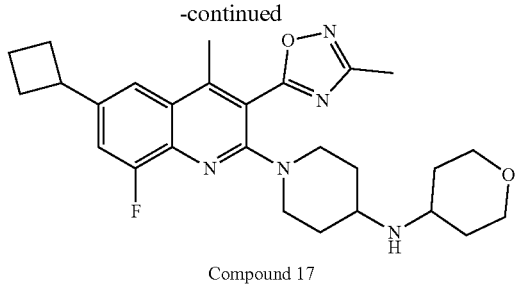

Compound 17

To a solution of 1-(6-cyclobutyl-8-fluoro-4-methyl-3-(3-methyl-1,2,4-oxadiazol-5-yl)quinolin-2-yl)piperidin-4-one (Int-15-3, 12 mg, 0.03 mmol) and tetrahydro-2H-pyran-4-amine (6.2 mg, 0.061 mmol) in 1,2-dichloroethane (0.2 mL) was added acetic acid (3.7 mg, 0.061 mmol), followed by sodium triacetoxyborohydride (13 mg, 0.061 mmol), and the reaction mixture was stirred at 25° C. for 6 h. The reaction was quenched with methanol and sodium carbonate aqueous solution to pH=10. The mixture was then extracted with ethyl acetate twice. The organic layers were combined, washed with brine, dried over magnesium sulfate and finally evaporated to dryness. The residue was purified by prep-HPLC to yield Compound 17 (8.0 mg, 55% yield) as white solid. LCMS: (M+1) m/z=480; Retention time: 2.79 min (Method 1).

Example 18

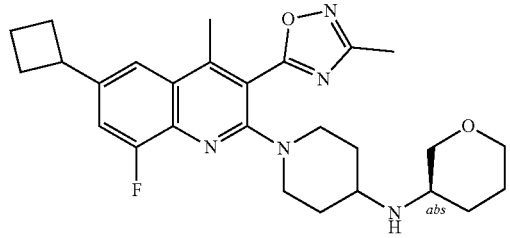

Compound 18

Preparation of Compound 18 was the same as 1-(6-cyclobutyl-8-fluoro-4-methyl-3-(3-methyl-1,2,4-oxadiazol-5-yl)quinolin-2-yl)-N-(tetrahydro-2H-pyran-4-yl)piperidin-4-amine (Compound 17) by replacing tetrahydro-2H-pyran-4-amine with (R)-tetrahydro-2H-pyran-3-amine hydrochloride (2.0 eq) and N,N-diisopropylethylamine (2.0 eq). LCMS: (M+1) m/z=480; Retention time: 3.10 min (Method 1).

Example 19

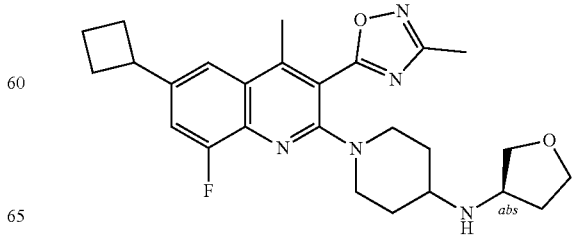

Compound 19

Preparation of Compound 19 was the same as 1-(6-cyclobutyl-8-fluoro-4-methyl-3-(3-methyl-1,2,4-oxadiazol-5-yl)quinolin-2-yl)-N-(tetrahydro-2H-pyran-4-yl)piperidin-4-amine (Compound 17) by replacing tetrahydro-2H-pyran-4-amine with (R)-tetrahydrofuran-3-amine hydrochloride (2.0 eq) and N,N-diisopropylethylamine (2.0 eq). LCMS: (M+1) m/z=466; Retention time: 2.67 min (Method 1).

Examples 20-29

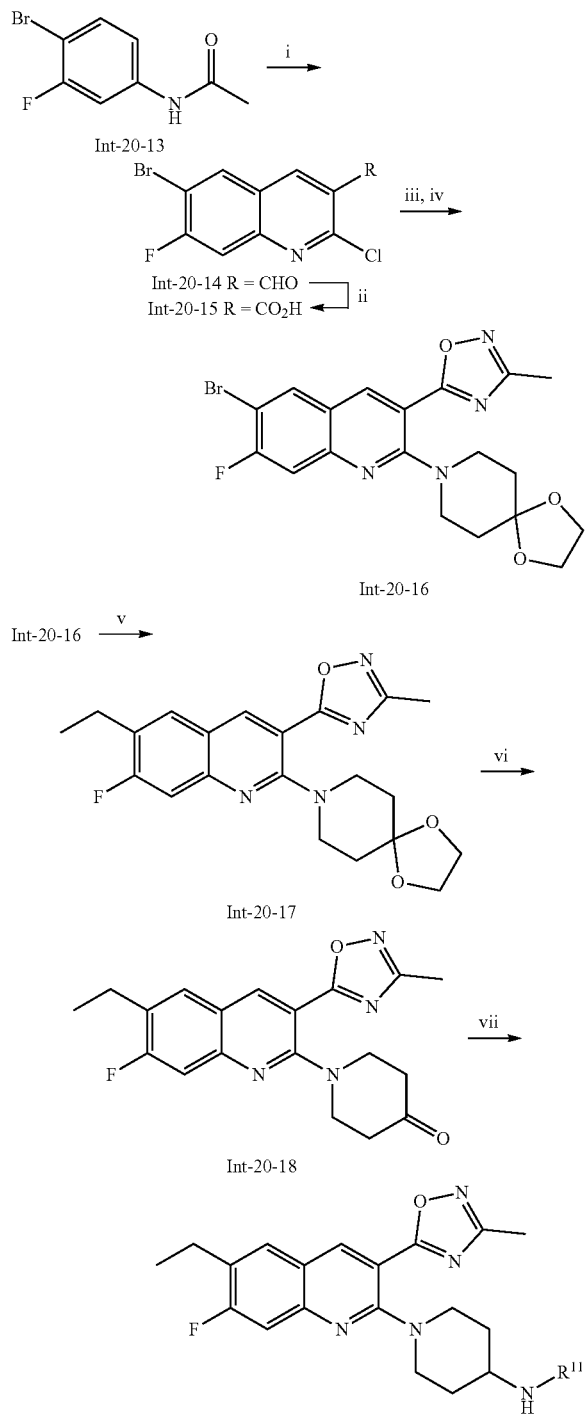

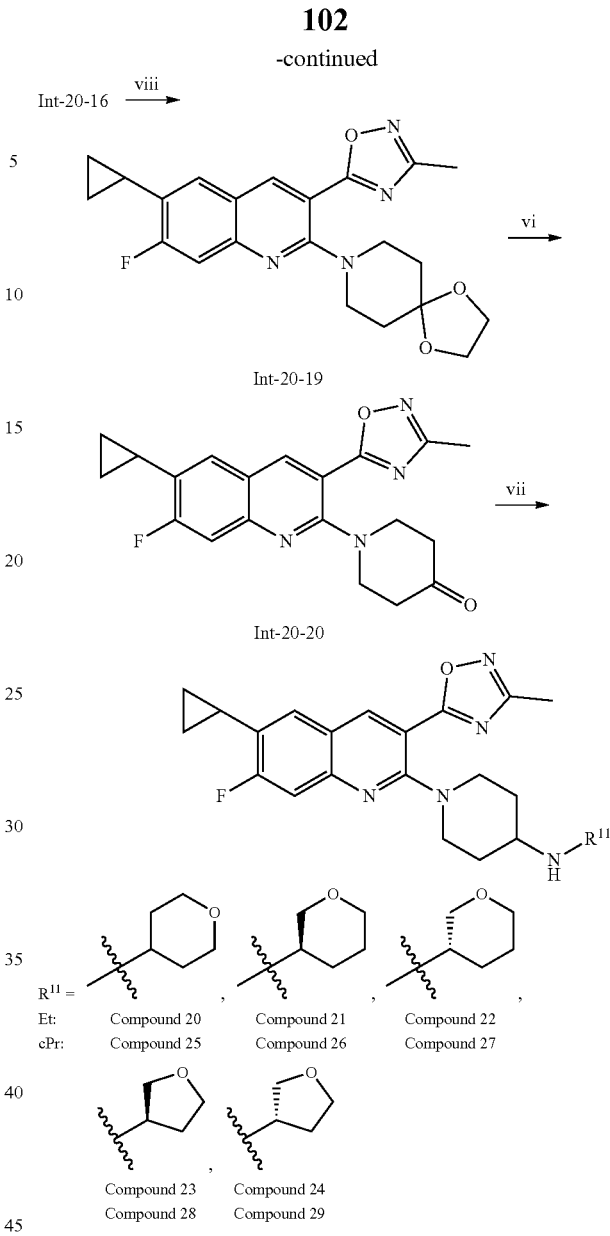

R[11] =

| | | |
|---|---|---|
| Et: | Compound 20 | Compound 21 | Compound 22 |
| cPr: | Compound 25 | Compound 26 | Compound 27 |

Compound 23  Compound 24
Compound 28  Compound 29

Reagents and conditions: i) DMF (2.5 equiv.), POCl₃ (7.0 equiv.), 0 to 75° C., 48 h, 36-39%; ii) NaH₂PO₄ (5.0 equiv.), NaClO₂ (3.0 equiv.), NaSO₃ (4.0 equiv.), CH₃CN, 94-98%; iii) a) 15 (1.0 equiv.), SOCl₂ (3.0 equiv.), CH₂Cl₂, 50 oC, 2 h, b) Acetamidoxime (1.2 equiv.), DIPEA (1.2 equiv.), dioxane, 100° C., 4 h, 48-54%; iv 1,4-dioxa-8-azaspiro[4,5]decane (1.2 equiv.), DIPEA (2.0 equiv.), EtOH, 125° C., overnight, 70-73%; v) 16 (1.0 equiv.), Et₃B (2.0 equiv.), Cs₂CO₃ (2.0 equiv.), Pd(dppf)Cl₂•CH₂Cl₂ (1/20 equiv.), THF, 70° C., 1.5 h, 27-29%; vi) 10% aq. H₂SO₄, THF, 45 oC, 2 h, 73-78%; vii) Amine (2.0 equiv.), NaBH(OAc)₃ (2.0 equiv.), AcOH (2.0 equiv.), DIPEA (2.0 equiv.), 1,2-dichloroethane, rt, overnight; viii) cPrMgBr (3.2 equiv.), Pd(OAc)₂ (2.0 equiv.), P(tBu)₃•BF₄ (0.1 equiv.), 1M ZnBr₂ in THF (0.3 equiv.), THF, RT, 25-28%.

Synthesis of Int-20-14

DMF (2.5 equiv.) was slowly added to POCl₃ (7.0 equiv.) at 0° C., the mixture was stirred at RT for additional 30 min followed by the addition of amide Int-20-13 in a single portion. The mixture was stirred at RT for 30 min and then for 48 h at 75° C. The mixture was quenched with ice-water and stirred for 30 min. The solid Int-20-14 was collected and used without further purification. LCMS: (M+1) m/z=287, 289.

Synthesis of Int-20-15

To a suspended mixture of aldehyde Int-20-14 (1.0 equiv.) in $CH_3CN$ was slowly added an aqueous solution of $NaH_2PO_4$ (5.0 equiv.) followed by the addition of $NaClO_2$ (3.0 equiv.). The mixture was stirred overnight at RT. The mixture was quenched with $Na_2SO_3$ and stirred for 30 min at RT followed by acidification (pH 1-2) with 2M HCl. The product was extracted with EtOAc four times, dried over $Na_2SO_4$ and concentrated under reduced pressure. The crude Int-20-15 was used without further purification LCMS: (M−1) m/z=301, 303.

Synthesis of Int-20-16

To a mixture of acid Int-20-15 (1.0 equiv.) and $SOCl_2$ (3.0 equiv.) in $CH_2Cl_2$ was added a drop of DMF and the reaction was heated at 50° C. for 2 h. The mixture was concentrated under reduced pressure. The crude was dissolved in anhydrous dioxane and slowly added to as solution of acetamidoxime (1.2 equiv.) and DIPEA (1.2 equiv.) in dioxane at 0° C. The mixture was stirred at RT for 30 min and 4 h at 100° C. The mixture was diluted with water, and the solid was collected and used without further purification. LCMS: (M+1) m/z=441, 443.

A solution of the product from the previous step (1.0 equiv.), 1,4-dioxa-8-azaspiro[4,5]decane (1.2 equiv.) and DIPEA (2.0 equiv.) in EtOH was heated at 125° C. overnight. After cooling to room temperature, the mixture was concentrated under reduced pressure and purified by column chromatography (hexanes/EtOAc) to give ketal Int-20-16 as pale yellow solid. LCMS: (M+1) m/z=449, 451.

Synthesis of Int-20-17

To a suspension of Int-20-16 (1.0 equiv.), $Cs_2CO_3$ (2.0 equiv.) and $Pd(dppf)Cl_2 \cdot CH_2Cl_2$ (1/20 equiv.) in THF, 1M solution of $Et_3B$ (2.0 equiv.) in THF was added and the reaction was heated at 70° C. for 1.5 h. After cooling to RT the crude was filtered through celite and purified by column chromatography (hexanes:EtOAc) to afford Int-20-17 as a pale yellow solid. LCMS: (M+1) m/z=399.

Synthesis of Int-20-18

A solution of ketal Int-20-17 (1.0 equiv.) in THF and 10% aq. $H_2SO_4$ was stirred at 45° C. for 2 h. After cooling to RT, the mixture was neutralized with sat. aq. NaOH and extracted with EtOAc. The organic phase was dried over $Na_2SO_4$ and concentrated under reduced pressure to give ketone Int-20-18 as a pale yellowish solid (90-95% yield), which was used in the next step without further purification LCMS: (M+1) m/z=355.

Synthesis of Compounds 20-24

A mixture of ketone Int-20-18 (1.0 equiv.), amine (2.0 equiv.), DIPEA (2.0 equiv.), $NaBH(OAc)_3$ (2.0 equiv.) and AcOH (2.0 equiv.) in 1,2-dichloroethane was stirred at RT overnight. The mixture was filtrated through celite, concentrated under reduced pressure and purified by HPLC to give the desired products. Compound 20 was obtained as a pale yellow solid in 92-94% yield. LCMS: (M+1) m/z=440. Compound 21 was obtained as a pale yellow solid in 78-80% yield. LCMS: (M+1) m/z=440. Compound 22 was obtained as a pale yellow solid in 79-80% yield. LCMS: (M+1) m/z=440. Compound 23 was obtained as a pale brown solid in 82-83% yield. LCMS: (M+1) m/z=426. Compound 24 was obtained as a pale yellow solid in 86-87% yield. LCMS: (M+1) m/z=426.

Synthesis of Int-20-19

To a suspension of compound Int-20-16 (1.0 equiv.), $Pd(OAc)_2$ (0.2 equiv.) and $P(tBu)_3 \cdot HBF_4$ (0.1 equiv.) in anhydrous THF was added 1M $ZnBr_2$ in THF (0.3 equiv.) at RT. To the mixture, 1M cPrMgBr in THF (3.2 equiv.) was added over 30 min at RT and the resulting mixture was stirred overnight. The mixture was quenched with ice/$NH_4Cl$ solution and extracted with EtOAc. The organic layer was washed with brine, dried over $Na_2SO_4$ and concentrated. The crude was used without further purification because no difference in Rf was observed between the remaining bromide Int-20-16 (~30%) and the product Int-20-19. LCMS: (M+1) m/z=411.

Synthesis of Int-20-20

A solution of the above mixture in THF/10% aq. $H_2SO_4$ was stirred at 45° C. for 2 h. After cooling to RT, the mixture was neutralized with sat. aq. NaOH and extracted with EtOAc, dried over $Na_2SO_4$ and concentrated under reduced pressure. The product was purified by column chromatography using hexanes/EtOAc, and ketone Int-20-20 was obtained as a pale yellow solid (20-25% yield). LCMS: (M+1) m/z=367.

Synthesis of Compounds 25-29

A mixture of ketone Int-20-20 (1.0 equiv.), the appropriate amine (2.0 equiv.), DIPEA (2.0 equiv.), $NaBH(OAc)_3$ (2.0 equiv.) and AcOH (2.0 equiv.) in 1,2-dichloroethane was stirred at RT overnight. The mixture was filtrated through celite, concentrated under reduced pressure and purified by HPLC to give the titled compounds. Compound 25 was obtained as a pale yellow solid in 87-88% yield. LCMS: (M+1) m/z=452. Compound 26 was obtained as a pale yellow solid in 68-69% yield. LCMS: (M+1) m/z=452. Compound 27 was obtained as a pale yellow solid in 72-73% yield. LCMS: (M+1) m/z=452. Compound 28 was obtained as a pale yellow solid in 69-70% yield. LCMS: (M+1) m/z=438. Compound 29 was obtained as a pale yellow solid in 75-76% yield. LCMS: (M+1) m/z=438.

Example 30

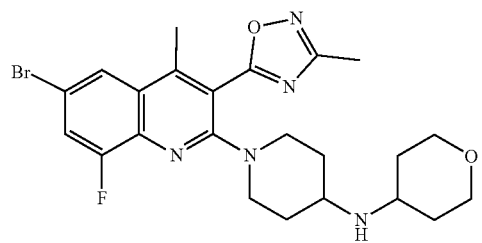

Compound 30

Step 1:

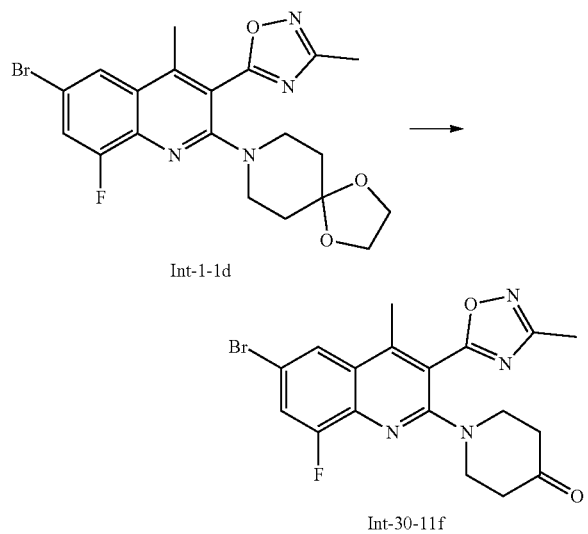

To a solution of 8-(6-bromo-8-fluoro-4-methyl-3-(3-methyl-1,2,4-oxadiazol-5-yl)quinolin-2-yl)-1,4-dioxa-8-azaspiro[4.5]decane (Int-1-1d, 258 mg, 0.56 mmol) in tetrahydrofuran (3 mL) was added sulfuric acid solution (10% aq., 3 mL), and the reaction was stirred at 45° C. for 3 h. The mixture was neutralized with sodium carbonate solution to pH 10, and extracted with ethyl acetate twice. The organic layers were combined, washed with brine, dried over Na$_2$SO$_4$ and concentrated under reduced pressure to give 1-(6-bromo-8-fluoro-4-methyl-3-(3-methyl-1,2,4-oxadiazol-5-yl)quinolin-2-yl)piperidin-4-one (Int-30-11f) as brown solid (248 mg), which was used in the next step without further purification. LCMS (ESI): m/z 419 (M+H); Retention time: 2.93 min (Method 1).

Step 2:

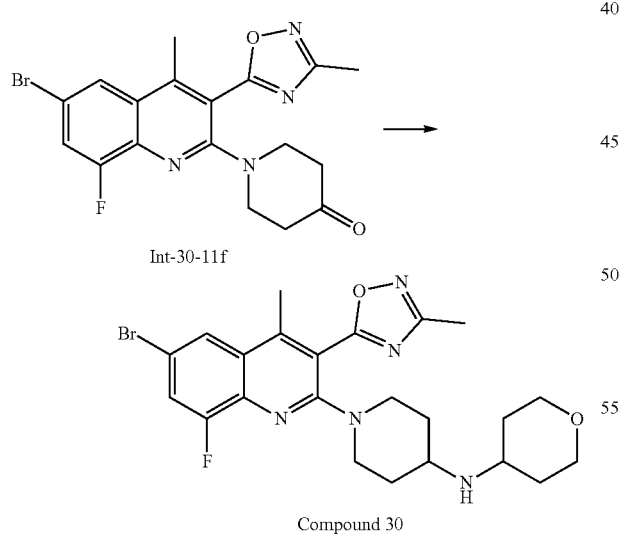

Preparation of Compound 30 was the same as 1-(6-cyclobutyl-8-fluoro-4-methyl-3-(3-methyl-1,2,4-oxadiazol-5-yl)quinolin-2-yl)-N-(tetrahydro-2H-pyran-4-yl)piperidin-4-amine (Compound 17) by replacing 1-(6-cyclobutyl-8-fluoro-4-methyl-3-(3-methyl-1,2,4-oxadiazol-5-yl)quinolin-2-yl)piperidin-4-one with 1-(6-bromo-8-fluoro-4-methyl-3-(3-methyl-1,2,4-oxadiazol-5-yl)quinolin-2-yl)piperidin-4-one (Int-30-11f). LCMS (ESI): m/z 504 (M+H); Retention time: 2.34 min (Method 1).

Example 31

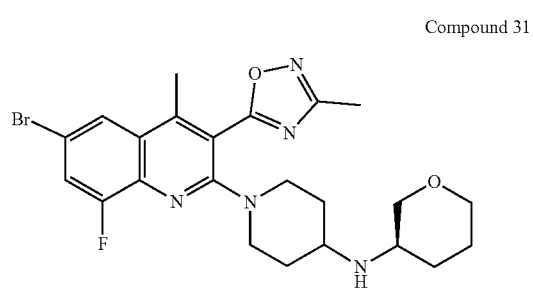

Compound 31

Preparation of Compound 31 was the same as Step 2 in Example 30, where tetrahydro-2H-pyran-4-amine was replaced with (R)-tetrahydro-2H-pyran-3-amine hydrochloride (2.0 equiv.) and N,N-diisopropylethylamine (2.0 equiv.). LCMS (ESI): m/z 504 (M+H); Retention time: 2.48 min (Method 1).

Example 32

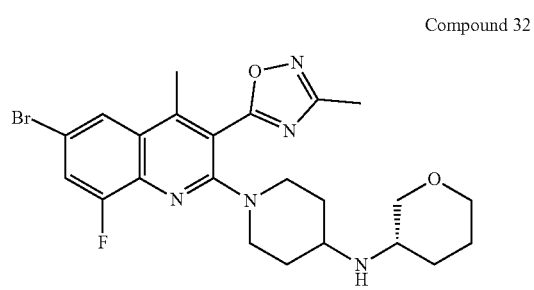 [SMILES: Cc1noc(-c2c(N3CCC(N[C@H]4CCCOC4)CC3)nc3c(F)cc(Br)cc3c2C)n1]

Compound 32

The procedure to make Compound 32 was the same as Step 2 in Example 30 where tetrahydro-2H-pyran-4-amine was replaced with tetrahydro-2H-pyran-4-amine with (S)-tetrahydro-2H-pyran-3-amine hydrochloride (2.0 equiv.) and N,N-diisopropylethylamine (2.0 equiv.). LCMS (ESI): m/z 504 (M+H); Retention time: 2.45 min (Method 1).

Examples 33-35

Synthesis of 2-amino-5-bromo-3-fluorobenzoic acid Int-33-14b

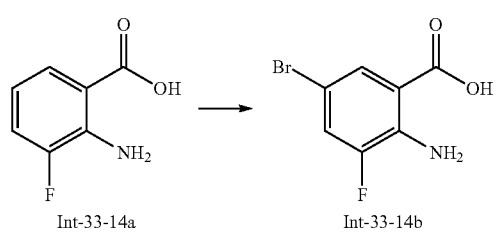 [SMILES: Nc1c(F)cccc1C(=O)O ; Nc1c(F)cc(Br)cc1C(=O)O]

To a suspension of 2-amino-3-fluorobenzoic acid Int-33-14a (15.36 g, 99 mmol) in CH$_2$Cl$_2$ (247.5 mL) was added N-bromosuccinimide (17.62 g, 99 mmol). The mixture was stirred at room temperature overnight. The product was collected by vacuum filtration to give 2-amino-5-bromo-3-fluorobenzoic acid Int-33-14b as an off-white solid (20.81 g, 90% yield), which was used in the next step without further purification. LCMS: (M−1) m/z=232, 234.

Synthesis of
1-(2-amino-5-methoxy-3-fluorophenyl)ethanone 14f

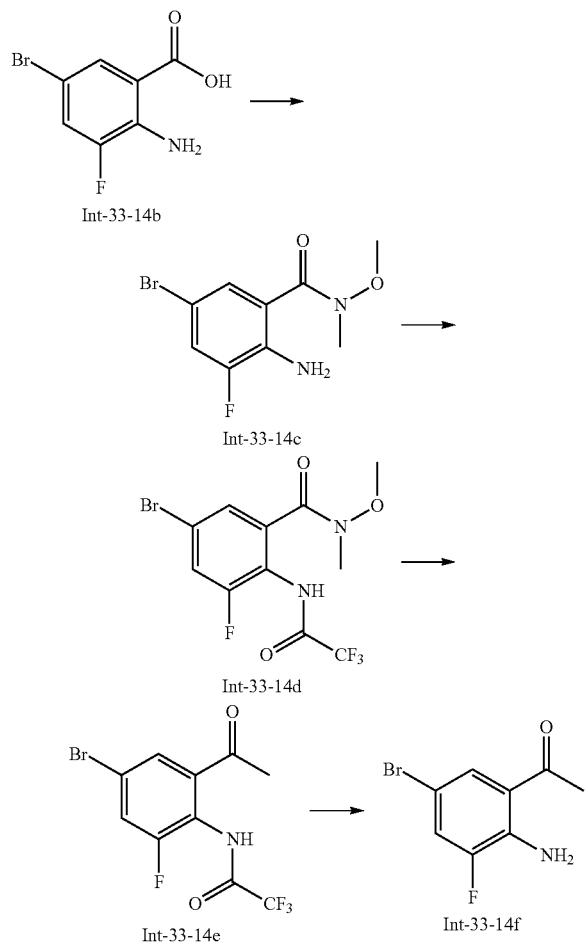

A mixture of Int-33-14b (13.38 g, 57.17 mmol), N,O-dimethylhydroxylamine hydrochloride (10 g, 102.9 mmol), DIPEA (19.9 mL), EDCI (13.15 g, 68.8 mmol) and HOBt (9.27 g, 68.6 mmol) in DMF (142 mL) was stirred at room temperature for 4 h. Then, the reaction was diluted with 100 mL of EtOAc and washed sequentially with 1M NaOH, 1M HCl and brine to obtain Int-33-14c as a brown oil (8.6 g, 85% yield), which was used in the next step without further purification. LCMS: (M+1) m/z=277, 279.

To a solution of Int-33-14c (6.0 g, 22 mmol) in CH$_2$Cl$_2$ (75 mL) at 0° C., TEA (3.6 mL, 26 mmol) was added, followed by dropwise addition of trifluoroacetic anhydride (3.9 mL, 28 mmol). The reaction was stirred at room temperature overnight. Sat. aq. NaHCO$_3$ solution was then added and the organic phase was separated and washed with water. The organic layer was dried over Na$_2$SO$_4$ and concentrated to dryness to afford Int-33-14d as a yellow solid (9.4 g, 80% yield), which was used in the next step without further purification. LCMS: (M+1) m/z=371, 373.

To a solution of Int-33-14d (0.180 g, 0.554 mmol) in THF (1 mL) at −78° C., 3M solution of MeMgCl in THF (0.66 mL, 2.22 mmol) was added, and the reaction was stirred at room temperature for 2 h. The reaction was poured into ice, acidified to pH 2 with 2M HCl and extracted with EtOAc. The combined organic layers were dried over Na$_2$SO$_4$ and concentrated to dryness to afford Int-33-14e as a yellow oil, which was used in the next step without further purification. LCMS: (M+1) m/z=328.

To a solution of Int-33-14e (0.138 g, 0.370 mmol) in MeOH (0.75 mL), 2 M aq. solution of NaOH (0.75 mL) was added, the reaction was heated at 90° C. for 1.5 h. Water was added and the product was extracted with EtOAc and concentrated to dryness. Int-33-14f was obtained as a yellow solid (0.110 g, 92% yield), which was used in the next step without further purification. LCMS: (M+1) m/z=232.

Synthesis of 2-chloroquinoline Int-33-14h

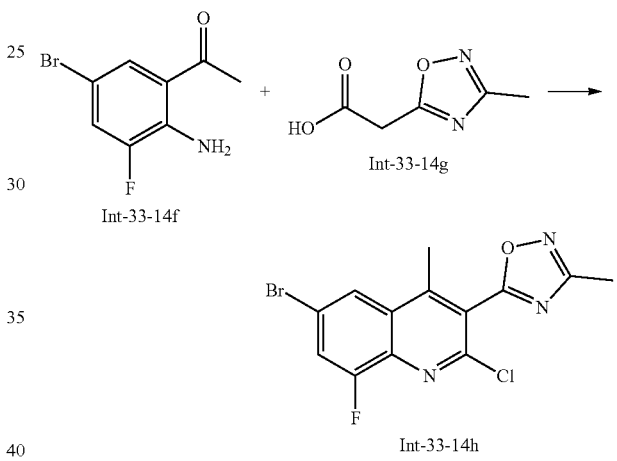

A solution of 2-(3-methyl-1,2,4-oxadiazol-5-yl)acetic acid Int-33-14 g (72 mg, 0.50 mmol) in POCl$_3$ (1.5 mL) was stirred at 50° C. for 5 min before ketone Int-33-14f (92 mg, 0.50 mmol) was added. The mixture was heated to 110° C. for 1 h. The excess POCl$_3$ was removed under vacuum. To the residue was added sat. aq. solution of NaHCO$_3$, and the product was extracted with EtOAc. The combined organic layers were dried over Na$_2$SO$_4$ and concentrated to dryness. The crude product was purified by column chromatography (hexanes/EtOAc) to give 2-chloroquinoline Int-33-14h as a yellow solid (69 mg, 45% yield). LCMS: (M+1) m/z=357.

Synthesis of ketal Int-33-14i

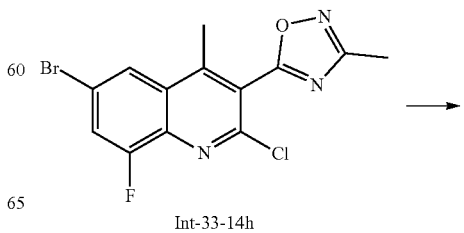

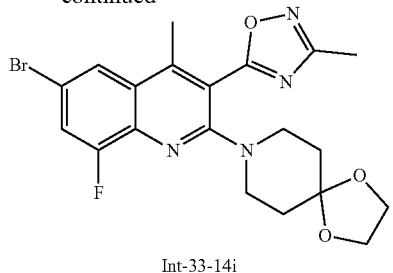

Int-33-14i

To a suspension of Int-33-14h (56 mg, 0.182 mmol) in EtOH (0.4 mL), 1,4-dioxa-8-azaspiro[4,5]decane (29 mg, 0.200 mmol) and DIPEA (38 µL, 0.218 mmol) were added. The mixture was subjected to microwave irradiation at 110° C. for 45 min. The mixture was concentrated under reduced pressure and purified by column chromatography (hexanes/EtOAc) to give ketal Int-33-14i as yellow solid (60 mg, 80% yield). LCMS: (M+1) m/z=464.

Synthesis of 8-(8-fluoro-6-methoxy-4-methyl-3-(3-methyl-1,2,4-oxadiazol-5-yl)quinolin-2-yl)-1,4-dioxa-8-azaspiro[4.5]decane Int-33-14i

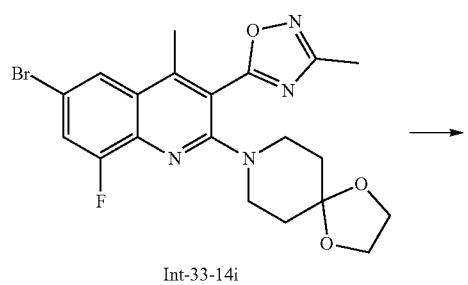

Int-33-14i

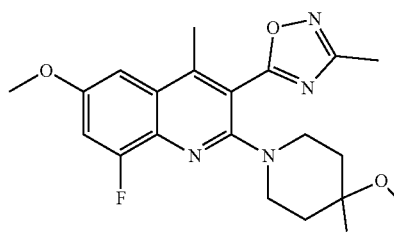

Int-33-14j

To a microwave crimp vial, Int-33-14i (1.08 g, 2.89 mmol), Pd₂(dba)₃ (0.119 g, 0.130 mmol), tBuXPhos (0.116 g, 0.275 mmol), and KB(OMe)₄ (1.51 g, 8.68 mmol) were added and the atmosphere was changed three times with nitrogen before DMF (3 mL) was added. The mixture was heated to 100° C. for 2 h. After cooling to room temperature, the crude product was filtered through celite and purified by column chromatography (hexanes/EtOAc) to afford Int-33-14j as a yellow solid (0.348 g, 37% yield). LCMS: (M+1) m/z=415.

Synthesis of ketone Int-33-14k

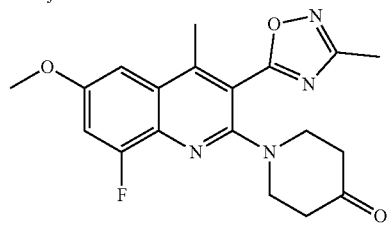

Int-33-14j

Int-33-14k

To a solution of ketal Int-33-14j (60 mg, 0.145 mmol) in THF (0.5 mL) was added 10% aq. H₂SO₄ (0.71 mL). The mixture was stirred at 45° C. for 2 h. After cooling to room temperature, the mixture was neutralized with sat. aq. Na₂CO₃ and extracted with EtOAc, dried over Na₂SO₄ and concentrated to dryness to give ketone Int-33-14k as a yellow oil (224 mg, 90% yield), which was used in the next step without further purification. LCMS: (M+1) m/z=371.

Synthesis of Compound 33

A mixture of ketone Int-33-14k (10 mg, 0.027 mmol), 3-(R)-aminotetrahydropyran HCl (5.6 mg, 0.040 mmol), DIPEA (4 µL, 0.030 mmol), and AcOH (2 µL, 0.054 mmol) in 1,2-dichloroethane (0.1 mL) was stirred at room temperature for 15 minutes before NaBH(OAc)₃ (11.5 mg, 0.0540 mmol) was added. The mixture was stirred at room temperature for 5 hrs. The mixture was concentrated under reduced pressure and purified by preparative-TLC (CH₂Cl₂: MeOH=95:5) to give Compound 33 as a yellow solid (4.3 mg, 35% yield). LCMS: (M+1) m/z=456.

Synthesis of Compound 34

A mixture of ketone Int-33-14k (20 mg, 0.054 mmol), 3-(R)-aminotetrahydrofuran (7.1 mg, 0.081 mmol), and AcOH (5 µL, 0.11 mmol) in 1,2-dichloroethane (0.1 mL) was stirred at room temperature for 15 minutes before NaBH(OAc)₃ (22.9 mg, 0.108 mmol) was added. The mixture was stirred at room temperature for 5 hrs. The mixture was concentrated under reduced pressure and purified by preparative-TLC (CH₂Cl₂:MeOH=95:5) to give Compound 34 as a yellow solid (10 mg, 42% yield). LCMS: (M+1) m/z=442.

Synthesis of Compound 35

A mixture of ketone Int-33-14k (10 mg, 0.027 mmol), 3-oxetaneamine (3.0 mg, 0.040 mmol), and AcOH (2.0 µL, 0.054 mmol) in 1,2-dichloroethane (0.1 mL) was stirred at room temperature for 15 minutes before NaBH(OAc)₃ (11.5 mg, 0.0540 mmol) was added. The mixture was stirred at Examples 36-39

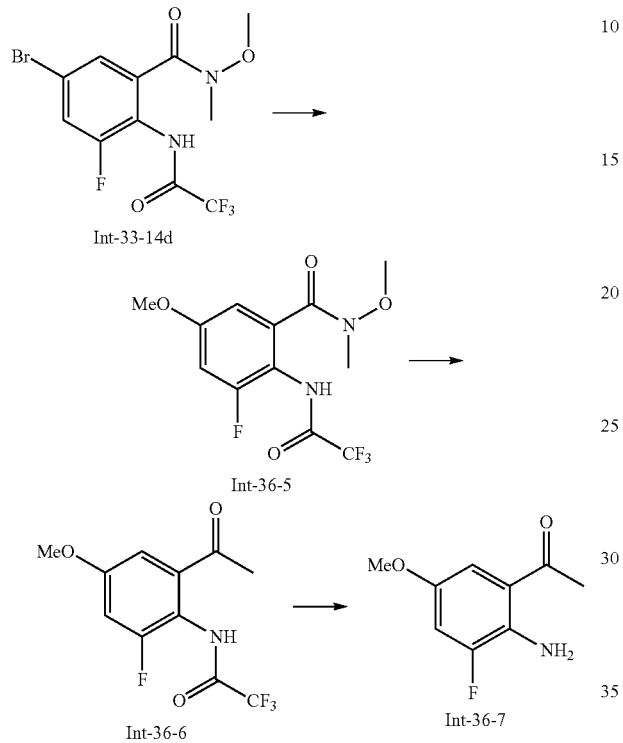

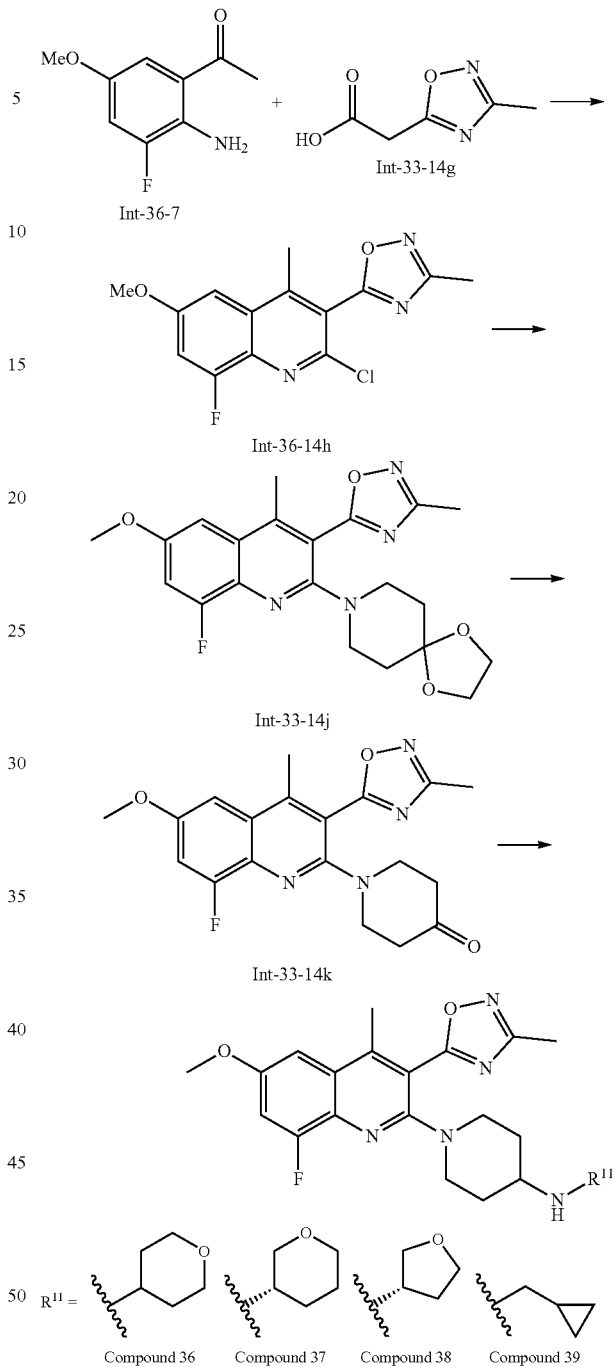

Synthesis of Int-36-7

To a microwave crimp vial Int-33-14d (1.08 g, 2.89 mmol), Pd$_2$(dba)$_3$ (0.119 g, 0.130 mmol), tBuXPhos (0.116 g, 0.275 mmol), and KB(OMe)$_4$ (1.51 g, 8.68 mmol) were added and the atmosphere was changed three times with nitrogen before DMF (3 mL) was filled. The mixture was heated to 100° C. for 2 h. After cooling to room temperature, the crude product was filtered through celite and purified by column chromatography (hexanes:EtOAc) to afford Int-36-5 as a yellow solid (0.348 g, 27.9% yield). LCMS: (M+1) m/z=325.

To a solution of Int-36-5 (0.180 g, 0.554 mmol) in THF (1 mL) at −78° C., 3M solution of MeMgCl in THF (0.66 mL, 2.22 mmol) was added, and the reaction was stirred at room temperature for 2 h. The reaction was poured into ice, acidified (pH=2) with 2M HCl and extracted with EtOAc. The combined organic layers were dried over Na$_2$SO$_4$ and concentrated to dryness to afford Int-36-6 as a yellow oil, which was used in the next step without further purification. LCMS: (M+1) m/z=280.

To a solution of Int-36-6 (0.138 g, 0.370 mmol) in MeOH (0.75 mL), 2 M aq. solution of NaOH (0.75 mL) was added, the reaction was heated at 90° C. for 1.5 h. Water was added and the product was extracted into EtOAc and concentrated under vacuum to obtain Int-36-7 as a yellow solid (0.110 g, 92% yield), which was used in the next step without further treatment. LCMS: (M+1) m/z=182.

Synthesis of Int-36-14h

A solution of 2-(3-methyl-1,2,4-oxadiazol-5-yl)acetic acid Int-33-14 g (72 mg, 0.50 mmol) in POCl$_3$ (1.5 mL) was stirred at 50° C. for 5 min before ketone Int-36-7 (92 mg, 0.50 mmol) was added. The mixture was heated to 110° C. for 1 h. The excess POCl$_3$ was removed under vacuum. To the residue was added sat. aq. solution of NaHCO$_3$, and the product was extracted with EtOAc. The combined organic layers were dried over Na$_2$SO$_4$ and concentrated to dryness. The crude product was purified by column chromatography (hexanes/EtOAc) to give 2-chloroquinoline Int-36-14h as a yellow solid (69 mg, 45% yield). LCMS: (M+1) m/z=307, 309.

Synthesis of Int-33-14i

To a suspension of Int-36-14h (56 mg, 0.18 mmol) in EtOH (0.4 mL), 1,4-dioxa-8-azaspiro[4,5]decane (29 mg, 0.20 mmol) and DIPEA (38 μL, 0.22 mmol) were added. The mixture was subjected to microwave irradiation at 110° C. for 45 min. The mixture was concentrated under reduced pressure and purified by column chromatography (hexanes/EtOAc) to give ketal Int-33-14j as yellow oil (60 mg, 80% yield). LCMS: (M+1) m/z=415.

Synthesis of Int-33-14k

To a solution of ketal Int-33-14j (60 mg, 0.15 mmol) in THF (0.5 mL) was added 10% aq. $H_2SO_4$ (0.71 mL). The mixture was stirred at 45° C. for 2 h. After cooling to room temperature, the mixture was neutralized with sat. aq. $Na_2CO_3$ and extracted with EtOAc, dried over $Na_2SO_4$ and concentrated to dryness to give ketone Int-33-14k as a yellowish oil (224 mg, 90% yield), which was used in the next step without further purification LCMS: (M+1) m/z=371.

Synthesis of Compound 36

A mixture of ketone Int-33-14k (10 mg, 0.027 mmol), 4-aminotetrahydropyran (4.1 mg, 0.040 mmol), and AcOH (2.0 μL, 0.054 mmol) in 1,2-dichloroethane (0.1 mL) was stirred at room temperature for 15 min before NaBH(OAc)$_3$ (11.5 mg, 0.0540 mmol) was added. The mixture was stirred at room temperature for 5 hrs. The mixture was concentrated under reduced pressure and purified by preparative-TLC ($CH_2Cl_2$:MeOH=95:5) to afford Compound 36 as a yellow solid (2.5 mg, 20% yield). LCMS: (M+1) m/z=456.

Synthesis of Compound 37

A mixture of ketone Int-33-14k (10 mg, 0.027 mmol), 3-(S)-aminotetrahydropyran HCl (4.1 mg, 0.030 mmol), DIPEA (4 μL, 0.030 mmol), and AcOH (2 μL, 0.054 mmol) in 1,2-dichloroethane (0.1 mL) was stirred at room temperature for 15 min before NaBH(OAc)$_3$ (11.5 mg, 0.0540 mmol) was added. The mixture was stirred at room temperature for 5 hrs. The mixture was concentrated under reduced pressure and purified by preparative-TLC ($CH_2Cl_2$:MeOH=95:5) to afford Compound 37 as a yellow solid (2.3 mg, 18.7% yield). LCMS: (M+1) m/z=456.

Synthesis of Compound 38

A mixture of ketone Int-33-14k (10 mg, 0.027 mmol), 3-(S)-aminotetrahydrofuran (3.5 mg, 0.040 mmol), and AcOH (2 μL, 0.054 mmol) in 1,2-dichloroethane (0.1 mL) was stirred at room temperature for 15 min before NaBH(OAc)$_3$ (11.5 mg, 0.0540 mmol) was added. The mixture was stirred at room temperature for 5 hrs. The mixture was concentrated under reduced pressure and purified by preparative-TLC ($CH_2Cl_2$:MeOH=95:5) to give Compound 38 as a yellow solid (2.5 mg, 20% yield). LCMS: (M+1) m/z=442.

Synthesis of Compound 39

A mixture of ketone Int-33-14k (10 mg, 0.027 mmol), cyclopropylmethanamine (2.9 mg, 0.040 mmol), and AcOH (2 μL, 0.054 mmol) in 1,2-dichloroethane (0.1 mL) was stirred at room temperature for 15 min before NaBH(OAc)$_3$ (11.5 mg, 0.0540 mmol) was added. The mixture was stirred at room temperature for 5 hrs. The mixture was concentrated under reduced pressure and purified by preparative-TLC ($CH_2Cl_2$:MeOH=95:5) to give Compound 39 as a yellow solid (2.5 mg, 20% yield). LCMS: (M+1) m/z=426.

Examples 40-82

Synthesis of Compound 40

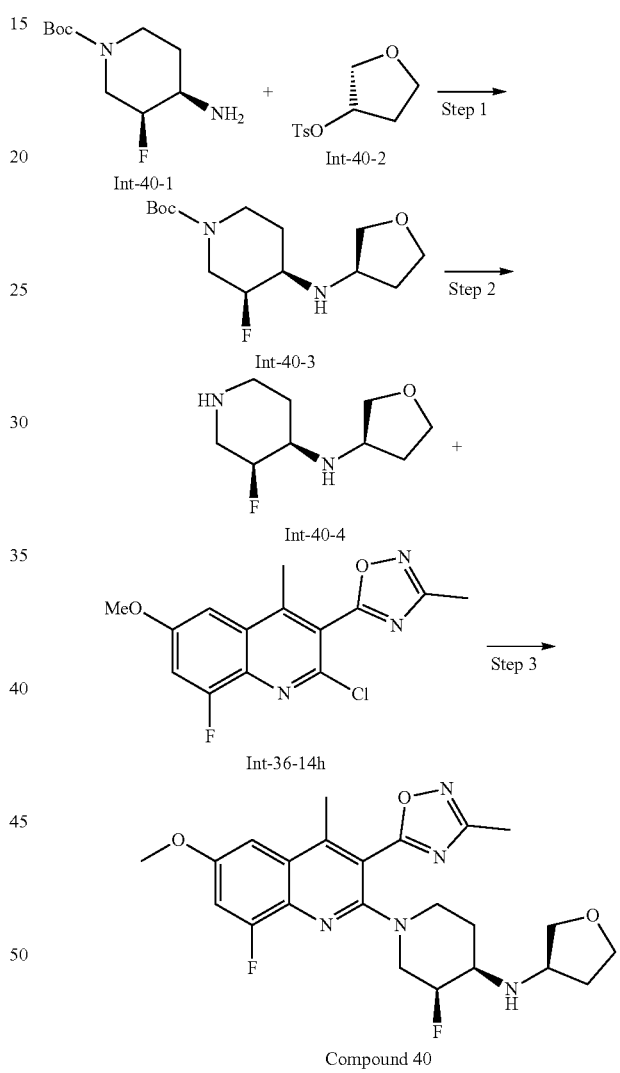

Step 1: A mixture of tert-butyl (3S,4R)-4-amino-3-fluoropiperidine-1-carboxylate (300 mg, 1.38 mmol), (S)-tetrahydrofuran-3-yl methanesulfonate (344 mg, 2.07 mmol), and $K_2CO_3$ (286 mg, 2.07 mmol) in DMF (1.5 mL) was stirred at 72-85° C. for 18 h. After evaporation of the solvent, the residue was purified by chromatography (Silica gel, 0-10% MeOH/DCM) to give tert-butyl (3S,4R)-3-fluoro-4-(((R)-tetrahydrofuran-3-yl)amino)piperidine-1-carboxylate (129 mg, 32% yield) as white solid. LCMS (ESI): m/z 289 (M+H); Retention time: 1.47 min (Method 1).

Step 2: A solution of the above product (65 mg, 0.22 mmol) in TFA (0.35 mL, 4.5 mmol) in CH$_2$Cl$_2$ (1 mL) was stirred at 25° C. for 1 h. The solution was diluted with CH$_2$Cl$_2$ and MeOH, washed by NaHCO$_3$ (sat. aq.), dried over MgSO$_4$, and finally concentrated under reduced pressure. The residue was used without further purification. LCMS (ESI): m/z 189 (M+H).

Step 3: This step was similar to the last step in the synthesis of Compound 134, the solvents were selected among dixoane, ethanol, acetonitrile, and/or DMF, and the temperature varied from 120° C. to 155° C. Compound 40 (20 mg, 23% yield) was obtained as yellow solid after RP-HPLC purification. LCMS (ESI): m/z 460 (M+H); Retention time: 2.00 min (Method 1).

Compounds 41-43 were obtained as disclosed above for Compound 40 using the appropriate fluorine-substituted piperidine(s) with the desired stereochemistry and the appropriate amines. Compound 41 (10.9 mg, 24% yield) was obtained as white solid after prep-TLC purification. LCMS (ESI): m/z 460 (M+H); Retention time: 4.18 min (Method 2). Compound 42 (2.9 mg, 6.4% yield) was obtained as white solid after prep-TLC purification. LCMS (ESI): m/z 460 (M+H); Retention time: 1.74 min (Method 1). Compound 43 (25 mg, 34% yield) was obtained as yellow solid after RP-HPLC purification. LCMS (ESI): m/z 460 (M+H); Retention time: 1.88 min (Method 1). Compounds 44-59 are obtained as disclosed below for Compounds 134-137 using the appropriate amines with the desired stereochemistry, and intermediate Int-36-14h described above for the preparation of Compounds 36-39.

Examples 55 and 58

Synthesis of Compound 55

Compound 55

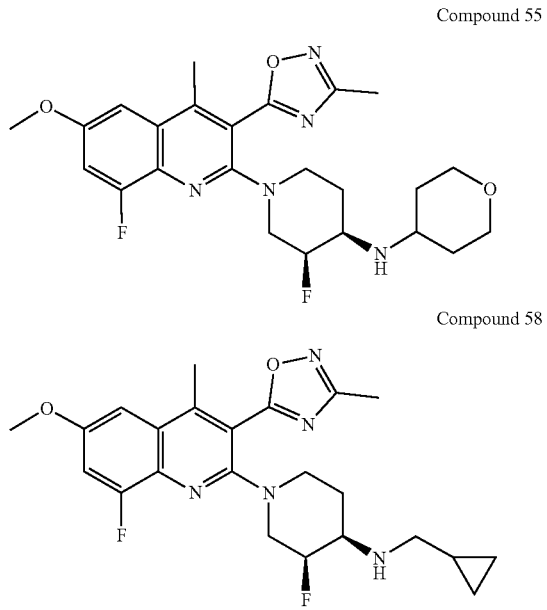

Compound 58

Compound 55 (1.3 mg, 7% yield) was obtained as yellow solid after RP-HPLC purification. LCMS (ESI): m/z 474 (M+H); Retention time: 2.00 min (Method 1). Compound 58 (41 mg, 50% yield) was obtained as off-white solid after RP-HPLC purification. LCMS (ESI): m/z 444 (M+H); Retention time: 2.03 min (Method 1).

Synthesis of Compounds 60-61

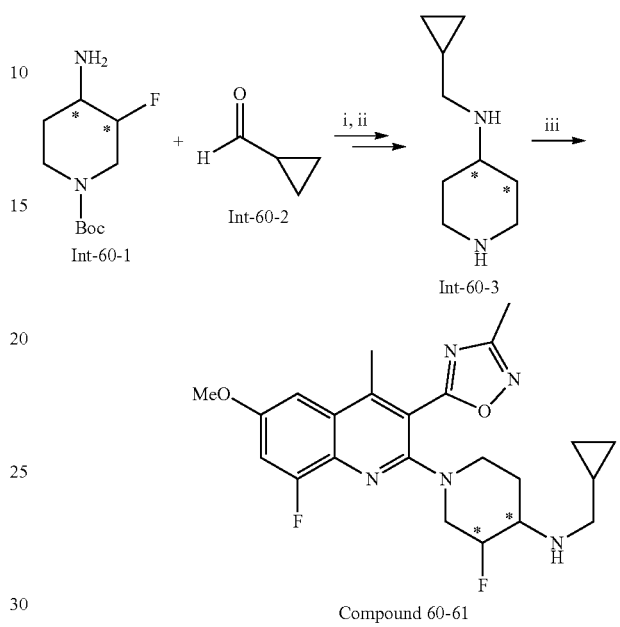

Compound 60-61

Compounds 60-61 are obtained according to the procedure described for Compounds 40-59, employing amine Int-60-3 with the appropriate stereochemistry, and intermediate Int-118-7, preparation of which is described in example 118.

Synthesis of Compounds 62-66

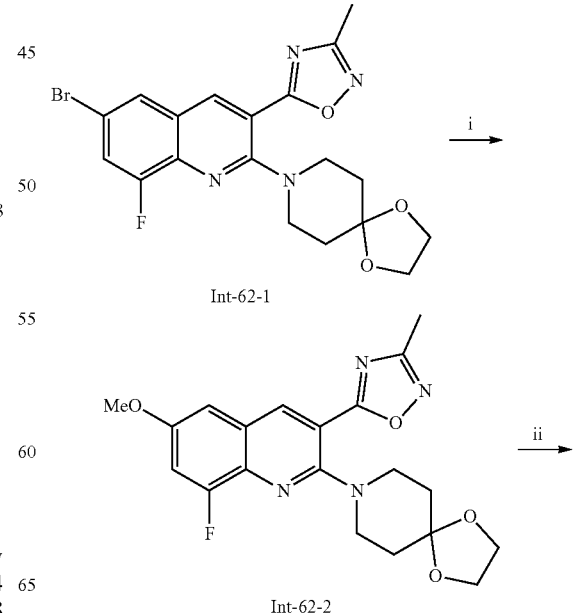

Int-62-1

Int-62-2

-continued

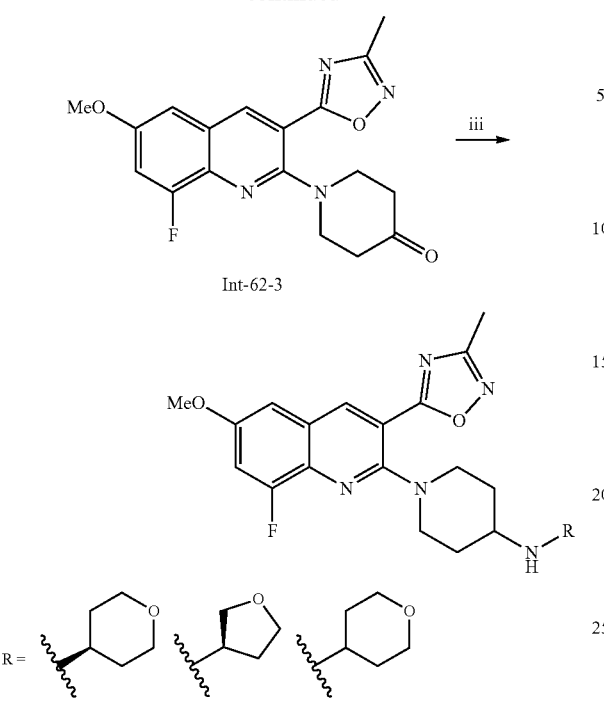

Compounds 62-66 are obtained as disclosed below for Compound 141 starting from intermediate Int-62-1 and according to the synthetic method employed for Compound 35.

Synthesis of Compounds 67-71

Compounds 67-71 are obtained in the manner disclosed above for Compounds 36-39.

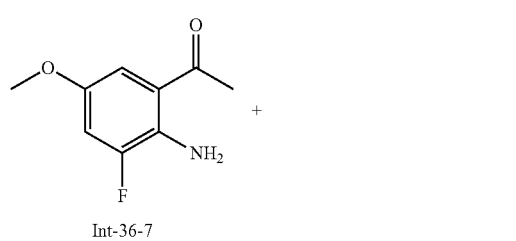

-continued

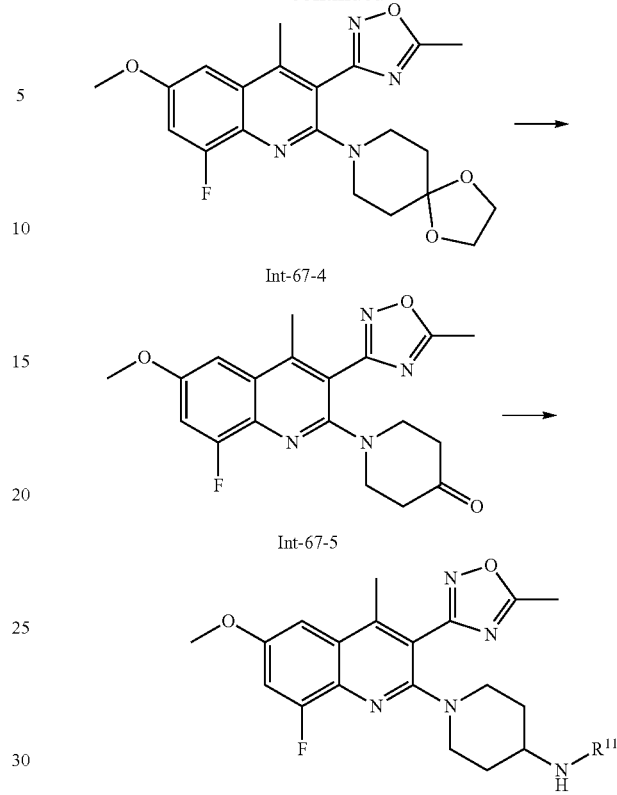

Synthesis of Compounds 72-76

Compounds 72-76 are obtained in the manner disclosed above for Compounds 36-39, starting with intermediate Int-156-28 described for the preparation of Compounds 156-158 below.

Synthesis of Compounds 77-82

Compounds 77-82 are obtained in the manner disclosed above for Compound 35.

Compound 78 was obtained as off-white solid after RP-HPLC purification. LCMS (ESI): m/z 456 (M+H); Retention time: 4.00 min (Method 2).

Compound 80 was obtained as off-white solid after RP-HPLC purification. LCMS (ESI): m/z 470 (M+H); Retention time: 3.88 min (Method 2).

Examples 83-84

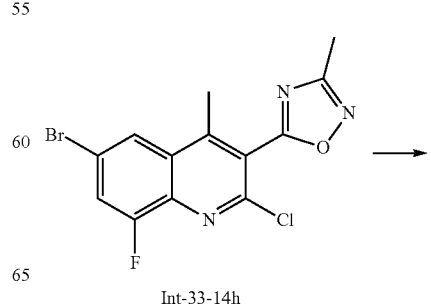

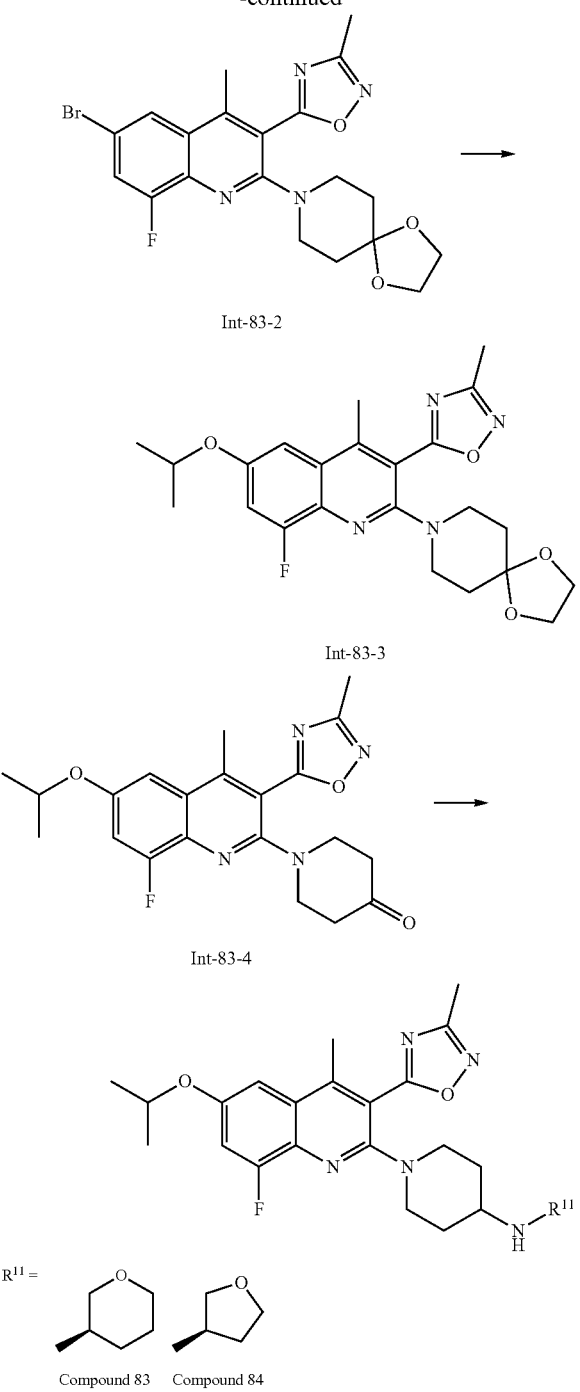

Compound 83    Compound 84

Synthesis of Int-83-2

To a suspension of Int-33-14h (1009 mg, 2.830 mmol) in EtOH (0.4 mL), 1,4-dioxa-8-azaspiro[4,5]decane (449.8 mg, 3.141 mmol) and DIPEA (0.59 mL, 3.4 mmol) were added. The mixture was subjected to microwave irradiation at 120° C. for 45 min. The mixture was concentrated under reduced pressure and purified by column chromatography (hexanes/EtOAc) to give ketal Int-83-2 as yellow oil (1198 mg, 91.4% yield). LCMS: (M+1) m/z=463, 465.

Synthesis of Int-83-3

A microwave crimp vial was charged with allylpalladium chloride dimer (2.0 mg, 0.0054 mmol), $Cs_2CO_3$ (527.4 mg, 1.619 mmol), RockPhos (7.6 mg, 0.015 mmol) and Int-83-2 (500 mg, 1.07 mmol). The atmosphere was changed 3 times with nitrogen before isopropylalcohol (163 uL, 2.15 mmol) and toluene (2 mL) were added. The mixture was heated to 90° C. overnight. After cooling to room temperature, the crude product was filtered through celite and diluted with EtOAc. Water was added and the layers were separated. The aqueous layer was extracted three times with EtOAc. The organic layers were combined and washed with brine then dried over $Na_2SO_4$. The solvent was removed in vacuo and the crude product was purified via reverse phase chromatography (20-100% $ACN:H_2O$) to afford Int-83-3 as a yellow solid (52 mg, 15% yield). LCMS(M+1) m/z=443.

Synthesis of Int-83-4

To a solution of ketal Int-83-3 (60 mg, 0.14 mmol) in THF (0.5 mL) was added 10% aq. $H_2SO_4$ (0.71 mL) was added. The mixture was stirred at 45° C. for 2 h. After cooling to room temperature, the mixture was neutralized with sat. aq. $Na_2CO_3$ and extracted with EtOAc, dried over $Na_2SO_4$ and concentrated to dryness to give ketone Int-83-4 as a yellowish oil (224 mg, 90% yield), which was used in the next step without further purification LCMS: (M+1) m/z=399.

Synthesis of Compound 83

A mixture of ketone Int-83-4 (10 mg, 0.025 mmol), 3-(R)-aminotetrahydropyran HCl (5.2 mg, 0.038 mmol), DIPEA (4.0 µL, 0.03 mmol), and AcOH (2 µL, 0.050 mmol) in 1,2-dichloroethane (0.1 mL) was stirred at room temperature for 15 min before $NaBH(OAc)_3$ (10.6 mg, 0.0502 mmol) was added. The mixture was stirred at room temperature for 5 hrs. The mixture was concentrated under reduced pressure and purified by preparative-TLC ($CH_2Cl_2$:MeOH=95:5) to give Compound 83 as a yellow solid (1.83 mg, 15.1% yield). LCMS: (M+1) m/z=484.

Synthesis of Compound 84

A mixture of ketone Int-83-4 (10 mg, 0.025 mmol), 3-(R)-aminotetrahyfuran (3.3 mg, 0.037 mmol), and AcOH (2 µL, 0.050 mmol) in 1,2-dichloroethane (0.1 mL) was stirred at room temperature for 15 min before $NaBH(OAc)_3$ (10.6 mg, 0.050 mmol) was added. The mixture was stirred at room temperature for 5 hrs. The mixture was concentrated under reduced pressure and purified by preparative-TLC ($CH_2Cl_2$:MeOH=95:5) to give Compound 84 as a yellow solid (2.8 mg, 20% yield). LCMS: (M+1) m/z=470.

Example 85

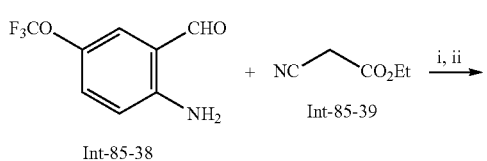

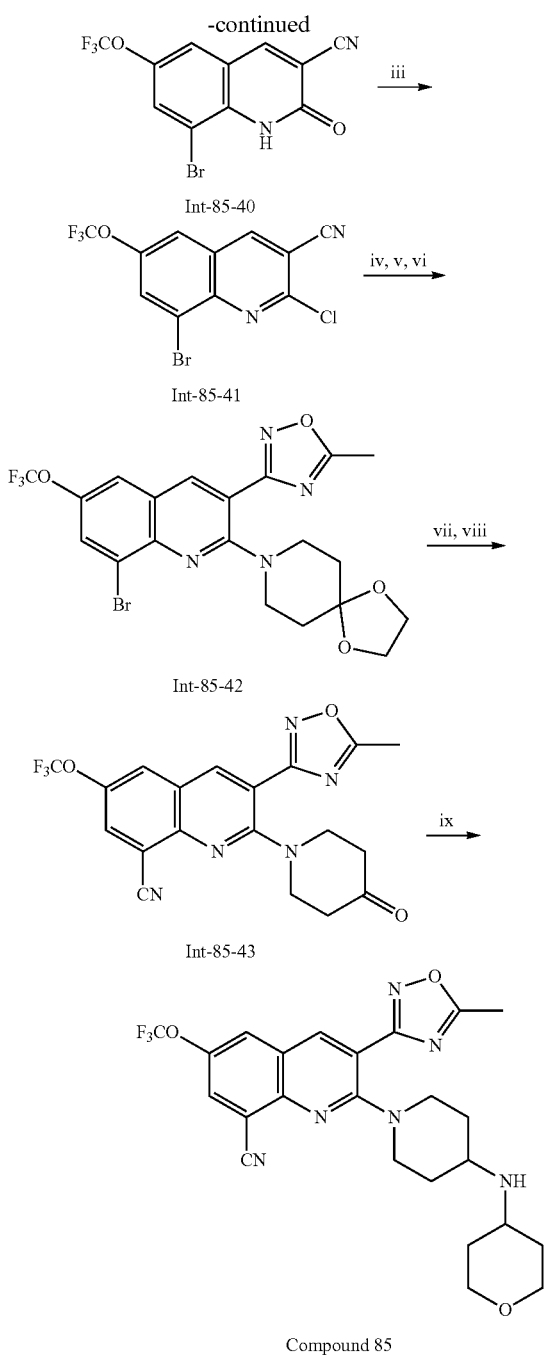

Synthesis of Int-85-40

To a solution of Int-85-38 (1.0 equiv.) in $CH_2Cl_2$ was added NBS (1.05 equiv.) and the mixture was stirred at RT for 18 h. The mixture was concentrated and purified by column chromatography using $CH_2Cl_2$. LCMS: (M+1) m/z=283, 285. A mixture of the intermediate aldehyde (1.0 equiv.), Int-85-39 (2.0 equiv.) and $NH_4OAc$ (5.0 equiv.) in dioxane was heated at 90° C. for 18 h. The mixture was concentrated, and the crude was diluted with water (3×) and extracted with hexanes:EtOAc (9:1) (2×). The organic solution was concentrated under reduced pressure and the product was used without further purification. LCMS: (M+1) m/z=332, 334.

Synthesis of Int-85-41

A mixture of Int-85-40 (1.0 equiv.) and $POCl_3$ was heated at 120° C. for 18 h. The mixture was concentrated under reduced pressure, quenched with ice/water and basified with $NaHCO_3$. The product was extracted with $CH_2Cl_2$ (3×), the organic phase was dried over $Na_2SO_4$ and concentrated. The product (Int-85-41) was used without further purification. LCMS: (M+1) m/z=350, 352.

Synthesis of Int-85-42

A mixture of Int-85-41 (1.0 equiv.), 1,4-dioxa-8-azaspiro[4,5]decane (2.0 equiv.) and DIPEA (2.0 equiv.) in iPrOH was heated at 110° C. for 18 h. After cooling to room temperature, the mixture was concentrated under reduced pressure and purified by column chromatography (EtOAc/hexanes) to give the corresponding ketal. LCMS: (M+1) m/z=458, 460.

A mixture of ketal (1.0 equiv.), $NH_2OH \cdot HCl$ (5.0 equiv.) and $Na_2CO_3$ (5.0 equiv.) in iPrOH was heated at 120° C. for 18 h. The mixture was cooled to RT, filtrated and concentrated under reduced pressure. The solid was used without further purification. LCMS: (M+1) m/z=491, 493.

A mixture of amidoxime (1.0 equiv.), $Ac_2O$ (1.1 equiv.) and DIPEA (1.1 equiv.) in dioxane was heated at 100° C. for 18 h. The mixture was concentrated under reduced pressure and the product was purified by column chromatography using hexanes:EtOAc to yield Int-85-42. LCMS: (M+1) m/z=515, 517.

Synthesis of Int-85-43

A mixture of Int-85-42 (1.0 equiv.), KI (1.0 equiv.), zinc cyanide (3.0 equiv.), $Pd(OAc)_2$ (0.2 equiv.), dppe (0.3 equiv.), $Na_2CO_3$ (3.0 equiv.) and TMEDA (1.0 equiv.) in DMF was heated at 130° C. overnight. The mixture was diluted with EtOAc and washed with brine (3×). The organic phase was concentrated and the product was purified by preparative-TLC. LCMS: (M+1) m/z=462.

A mixture of the previous product in THF/10% aq. $H_2SO_4$ was stirred at 45° C. for 2 h. After cooling to room temperature, the mixture was neutralized with sat. aq. $NaHCO_3$ and the product extracted with EtOAc (3×). The organic phase was dried over $Na_2SO_4$ and concentrated under reduced pressure to give ketone Int-85-43, which was used in the next step without further purification LCMS: (M+1) m/z=418.

Synthesis of Compound 85

A mixture of ketone Int-85-43 (1.0 equiv.), 4-aminotetrahydropyran (2.0 equiv.), $NaBH(OAc)_3$ (2.0 equiv.) and AcOH (2.0 equiv.) in 1,2-dichloroethane was stirred at room temperature overnight. The mixture was filtrated through celite, concentrated under reduced pressure and purified by HPLC to give Compound 85 as a yellow solid in 84-86% yield. LCMS: (M+1) m/z=503.

Example 86

Compound 86 was obtained according to the procedure disclosed below for Compound 88, starting from ketone Int-88-24 and the opportune amine, as a pale yellow solid in 49-51% yield. LCMS: (M+1) m/z=470.

Example 87

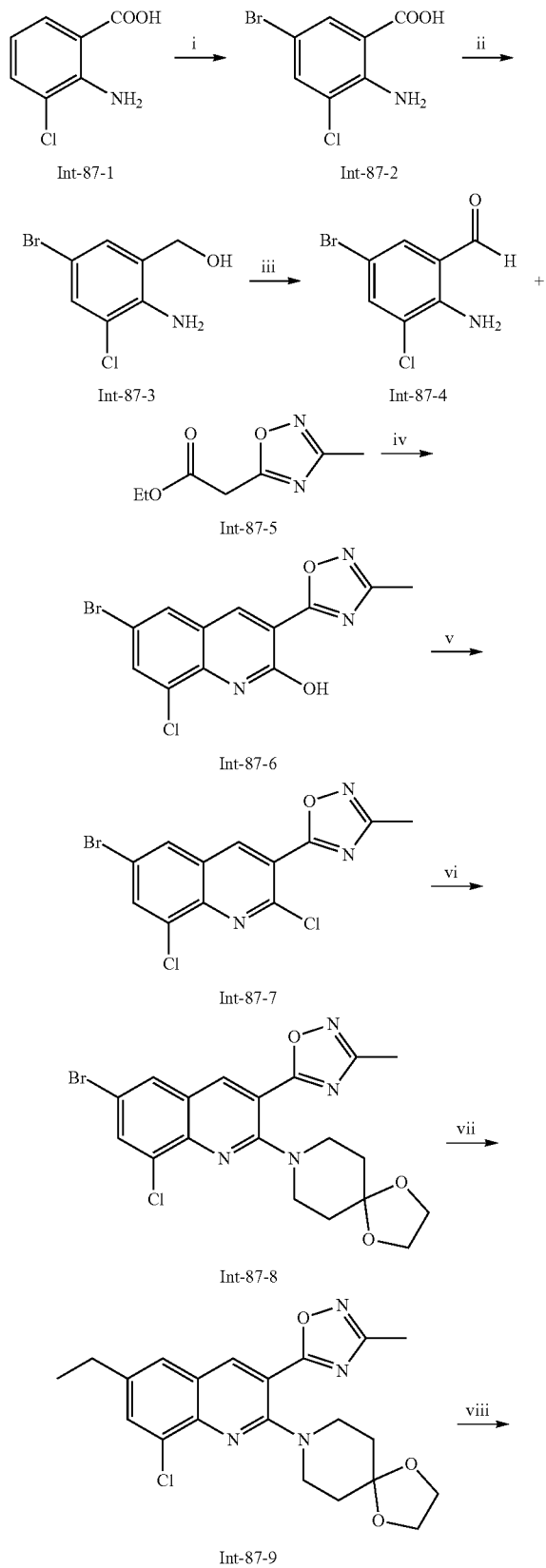

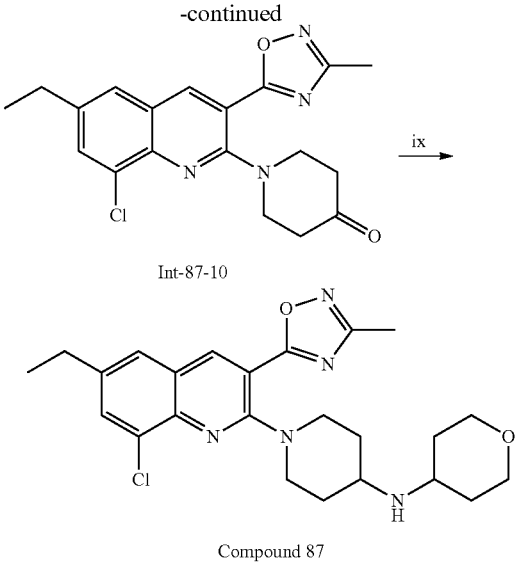

Synthesis of Int-87-2

To a suspension of 2-amino-3-chlorobenzoic acid Int-87-1 (4.57 g, 26.6 mmol) in $CH_2Cl_2$ (100 mL) was added N-bromosuccimide (4.74 g, 26.6 mmol). The mixture was stirred at room temperature for 2.5 h. The product was filtered, washed with $CH_2Cl_2$ and dried under reduced pressure to give Int-87-2 as an off-white solid (5.67 g, 85% yield). LCMS: (M−1) m/z=248, 250.

Synthesis of Int-87-3

To a solution of Int-87-2 (5.41 g, 21.6 mmol) in THF (50 mL) was added a 1M solution of $BH_3 \cdot THF$ complex in THF (108 mL, 108 mmol) dropwise at 0° C. The mixture was then stirred at room temperature for 18 h. The reaction was quenched by slow addition of MeOH at 0° C. After the removal of volatiles under reduced pressure, the residue was partitioned between EtOAc and brine. The organic layer was dried over $Na_2SO_4$ and concentrated. Product Int-87-3 as a pink solid was used for the next reaction without further purification (quantitative yield).

Synthesis of Int-87-4

A mixture of Int-87-3 (5.10 g, 21.6 mmol) and activated $MnO_2$ (11.2 g, 129.4 mmol) in $CH_2Cl_2$ (100 mL) was stirred at room temperature overnight. After filtration through Celite, the filtrate was concentrated. The residue was purified with a short silica gel column to give Int-87-4 as a yellow solid (5.06 g, quantitative yield).

Synthesis of Int-87-6

A mixture of aldehyde Int-87-4 (1.52 g, 6.48 mmol), oxadiazole ester Int-87-5 (1.10 g, 6.48 mmol) and p-TSA (0.15 g, 10 wt %) was heated at 150° C. for 1 h. After cooling to room temperature, $CH_2Cl_2$:MeOH (9:1, v/v, 20 mL) and hexanes:EtOAc (8:2, v/v, 20 mL) were added, and the resulting mixture was stirred vigorously. The desired product precipitated from solution during evaporation of solvents under reduced pressure. The solid was filtered, washed with $H_2O$ and dried under reduced pressure. Product 6 as a brown

Synthesis of Int-87-7

A mixture of Int-87-6 (0.50 g, 1.47 mmol) and POCl$_3$ (5 mL) was stirred at 110° C. for 1 h. After cooling to room temperature, excess POCl$_3$ was removed under reduced pressure. To the residue, H$_2$O was added at 0° C. The mixture was stirred at 0° C. for 10 min. The precipitated solid was filtered, washed with H$_2$O and dried under the reduced pressure to give Int-87-7 as a pale brown solid, which was used for the next reaction without further purification (447 mg, 85% yield).

Synthesis of Int-87-8

A mixture of Int-87-7 (272 mg, 0.76 mmol), 1,4-dioxa-8-azaspiro[4,5]decane (0.20 mL, 1.52 mmol) and DIPEA (0.26 mL, 1.52 mmol) in EtOH (7.6 mL) was heated at 120° C. overnight. After cooling to room temperature, the mixture was concentrated and purified by column chromatography (Hexanes/EtOAc gradient) to give Int-87-8 as a yellow oil (287 mg, 82% yield). LCMS: (M+1) m/z=465, 467.

Synthesis of Int-87-9

To a mixture of Int-87-8 (287 mg, 0.62 mmol), K$_2$CO$_3$ (170 mg, 1.24 mmol) and Pd(PPh$_3$)$_4$ (71 mg, 0.062 mmol) in THF (12 mL) was added 1M solution of Et$_3$B in THF (1.3 mL, 1.24 mmol) at room temperature. The mixture was then heated at 70° C. overnight. After cooling to room temperature, the mixture was filtered through Celite. The filtrated was concentrated and purified by column chromatography (Hexanes/EtOAc gradient) to give Int-87-9 as a yellow oil (70 mg, 27% yield). LCMS: (M+1) m/z=415.

Synthesis of Int-87-10

To a solution of Int-87-9 (70 mg, 0.17 mmol) in THF (1 mL) was added 10% aq. H$_2$SO$_4$ (2 mL, v/v). The mixture was stirred at 45° C. for 2 h. After cooling to room temperature, the mixture was neutralized with sat. aq. Na$_2$CO$_3$ and extracted with EtOAc (×2). The combined organic extracts were dried over Na$_2$SO$_4$ and concentrated to dryness. Product Int-87-10, a yellow solid, was used for the next reaction without further purification. (62 mg, quantitative yield). LCMS: (M+1) m/z=371.

Synthesis of Compound 87

A mixture of ketone Int-87-10 (10.9 mg, 0.029 mmol), tetrahydro-2H-pyran-4-amine (6.0 mg, 0.058 mmol) and DIPEA (10 μL, 0.058 mmol) in 1,2-dichloroethane (1.0 mL) was stirred at room temperature for 10 min. To the mixture, NaBH(OAc)$_3$ (18.4 mg, 0.087 mmol) and AcOH (5 μL, 0.087 mmol) were added. The resulting mixture was stirred at room temperature for 18 h. After filtration through Celite, the filtrate was concentrated. The residue was purified by preparative-TLC (EtOAc:iPrOH=9:1) to give Compound 87 as a yellow oil (12.0 mg, 91% yield). LCMS: (M+1) m/z=456.

Example 88

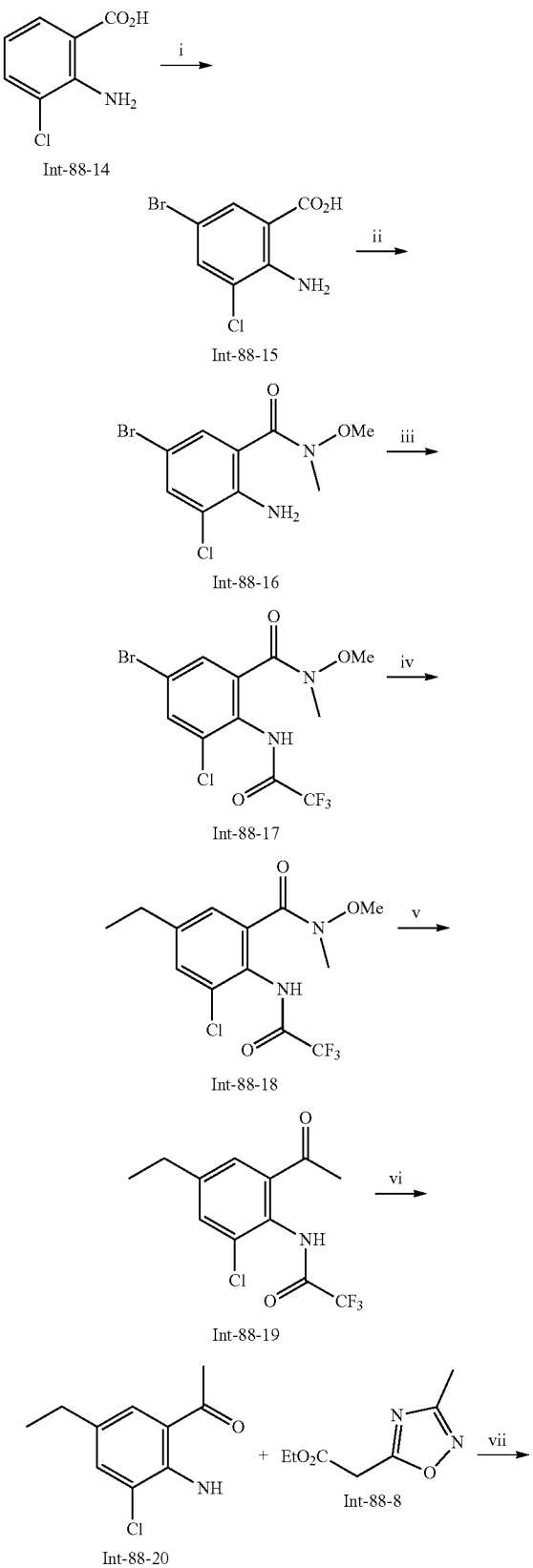

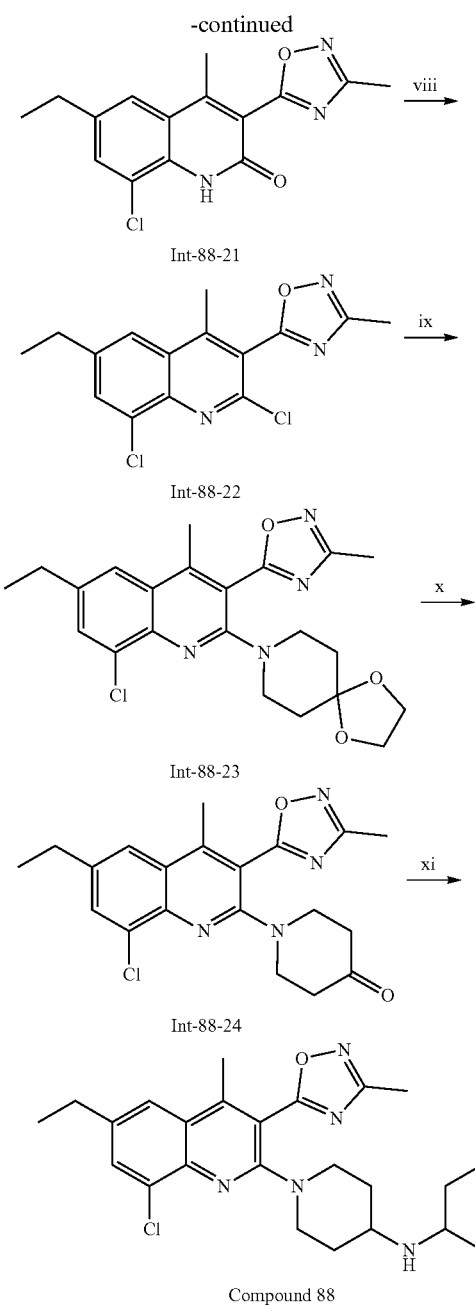

Reagents and conditions: i) DMF (2.5 equiv.), POCl₃ (7.0 equiv.), 0 to 75° C., 48 h, 36-39%; ii) NaH₂PO₄ (5.0 equiv.), NaClO₂ (3.0 equiv.), Na₂SO₃ (4.0 equiv.), CH₃CN, 94-98%; iii) a) Int-20-15 (1.0 equiv.), SOCl₂ (3.0 equiv.), CH₂Cl₂, 50° C., 2 h, b) Acetamidoxime (1.2 equiv.), DIPEA (1.2 equiv.), dioxane, 100° C., 4 h, 48-54%; iv 1,4-dioxa-8-azaspiro[4,5]decane (1.2 equiv.), DIPEA (2.0 equiv.), EtOH, 125° C., overnight, 70-73%; v) Int-20-16 (1.0 equiv.), Et₃B (2.0 equiv.), Cs₂CO₃ (2.0 equiv.), Pd(dppf)Cl₂•CH₂Cl₂ (1/20 equiv.), THF, 70° C., 1.5 h, 27-29%; vi) 10% aq. H₂SO₄, THF, 45° C., 2 h, 73-78%; vii) Amine (2.0 equiv.), NaBH(OAc)₃ (2.0 equiv.), AcOH (2.0 equiv.), DIPEA (2.0 equiv.), 1,2-dichloroethane, rt, overnight; viii) cPrMgBr (3.2equiv.), Pd(OAc)₂ (0.2 equiv.), P(tBu)₃•HBF₄ (0.1 equiv.), 1M ZnBr₂ in THF (0.3 equiv.), THF, RT, 25-28%.

Synthesis of Int-88-15

A suspension of acid Int-88-14 (1.0 equiv.) and NBS (1.0 equiv.) in CH₂Cl₂ was stirred at room temperature overnight. The product was collected by filtration to give acid Int-88-15 as an off-white solid (84-86% yield), which was used in the next step without further purification. LCMS: (M−1) m/z=247, 249.

Synthesis of Int-88-16

A mixture of Int-88-15 (1.0 equiv.), N,O-dimethylhydroxylamine hydrochloride (1.8 equiv.), DIPEA (2.0 equiv.), EDCI (1.2 equiv.) and HOBt (1.2 equiv.) in DMF was stirred at room temperature for 4 h. The reaction was diluted with EtOAc and washed sequentially with sat. aq. NaHCO₃ and brine, and concentrated under vacuum to obtain Int-88-16 as brown oil (84-86% yield). The product was used in the next step without further purification. LCMS: (M+1) m/z=292, 294.

Synthesis of Int-88-17

To a solution of Int-88-16 (1.0 equiv.) and TEA (1.2 equiv.) in CH₂Cl₂ at 0° C. was added dropwise trifluoroacetic anhydride (1.3 equiv.). The reaction was stirred at room temperature overnight. The mixture was washed with sat. aq. NaHCO₃ solution and brine (2×). The organic layer was dried over Na₂SO₄ and concentrated to afford Int-88-17 as a paled yellow solid (90-92% yield), which was used in the next step without further purification. LCMS: (M−1) m/z=386, 388.

Synthesis of Int-88-18

To a suspension of Int-88-17 (1.0 equiv.), Cs₂CO₃ (3.0 equiv.) and Pd(dppf)Cl₂ (0.02 equiv.) in THF a 1M solution of Et₃B in THF (3.0 equiv.) was added, and the reaction was heated at 70° C. for 1.5 h. After cooling to room temperature, the crude was filtered through celite and purified by column chromatography (hexanes:EtOAc) to afford Int-88-18 as a yellow solid (45-47% yield). LCMS: (M+1) m/z=339.

Synthesis of Int-88-19

To a solution of Int-88-18 (1.0 equiv.) in THF at 0° C. was added a 1.4 M solution of MeMgBr in THF:toluene (5.0 equiv.), and the reaction was stirred at room temperature for 2.5 h. The reaction was quenched with ice, acidified to pH 2 with 2M HCl and extracted with EtOAc (2×). The combined organic layers were dried over Na₂SO₄ and concentrated to afford Int-88-19 as yellow solid (85-87% yield), which was used in the next step without further purification. LCMS: (M−1) m/z=294.

Synthesis of Int-88-20

To a solution of Int-88-19 (1.0 equiv.) in MeOH was added 2 M aq. solution of NaOH (1.7 equiv.) and the reaction was heated at 90° C. for 3 h. The mixture was diluted with water and the solid collected by filtration to obtain Int-88-20 as a yellow solid (80-82% yield), which was used in the next step without further purification. LCMS: (M+1) m/z=198.

Synthesis of Int-88-21

A mixture of ketone Int-88-20 (1.0 equiv.), Int-88-8 (2.0 equiv.) and p-TsOH (cat.) was stirred at 150° C. for 2 h. After cooling to room temperature, the reaction mixture was washed consecutively with EtOAc:hexanes (8:2, v/v) (2×)

and water to give quinolone Int-88-21 as a yellow solid (19-21% yield). LCMS: (M+1) m/z=304.

Synthesis of Int-88-22

A suspension of Int-88-21 in POCl₃ was stirred at 110° C. for 2 h. The excess of POCl₃ was removed under reduced pressure. The crude was quenched with sat. aq. solution of NaHCO₃ and the product was extracted with EtOAc (3×). The combined organic layers were dried over Na₂SO₄ and concentrated. The product was purified by column chromatography (Hexanes/EtOAc) to give 2-chloroquinoline Int-88-22 as a pale yellow solid (97-98% yield). LCMS: (M+1) m/z=322, 324.

Synthesis of Int-88-23

A suspension of Int-88-22 (1.0 equiv.), 1,4-dioxa-8-azaspiro[4,5]decane (2.0 equiv.) and DIPEA (2.0 equiv.) in EtOH was heated at 110° C. overnight. After cooling to room temperature, the mixture was concentrated under reduced pressure and purified by column chromatography (Hexanes/EtOAc) to give ketal Int-88-23 as pale yellow solid (73-75% yield). LCMS: (M+1) m/z=429.

Synthesis of Int-88-24

To a solution of ketal Int-88-23 in THF was added 10% aq. H₂SO₄ and the mixture was stirred at 45° C. for 2 h. After cooling to room temperature, the mixture was neutralized with sat. aq. Na₂CO₃ and extracted with EtOAc (3×), dried over Na₂SO₄ and concentrated to give ketone Int-88-24 as a yellow solid (83-85% yield), which was used in the next step without further purification. LCMS: (M+1) m/z=385.

Synthesis of Compound 88

A mixture of ketone Int-88-24 (1.0 equiv.), 4-aminotetrahydropyran (1.5 equiv.), NaBH(OAc)₃ (2.0 equiv.) and AcOH (2.0 equiv.) in 1,2-dichloroethane was stirred at room temperature overnight. The mixture was concentrated under reduced pressure and purified by preparative-TLC (CH₂Cl₂: MeOH=95:5) to give Compound 88 as a yellow solid (89-90% yield). LCMS: (M+1) m/z=470.

Example 89

Compound 89 was obtained according to the procedure disclosed below for Compound 91 as pale yellow solid in 96% yield (last step). LCMS: (M+1) m/z=447.

Example 90

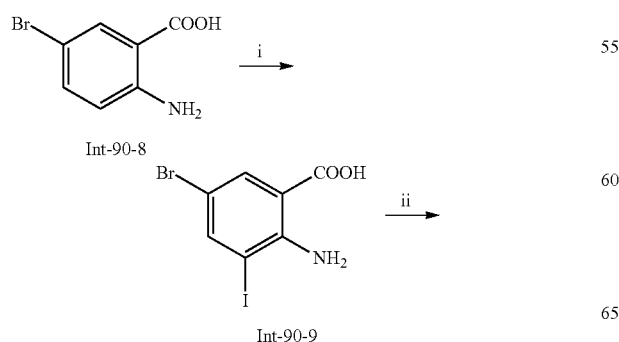

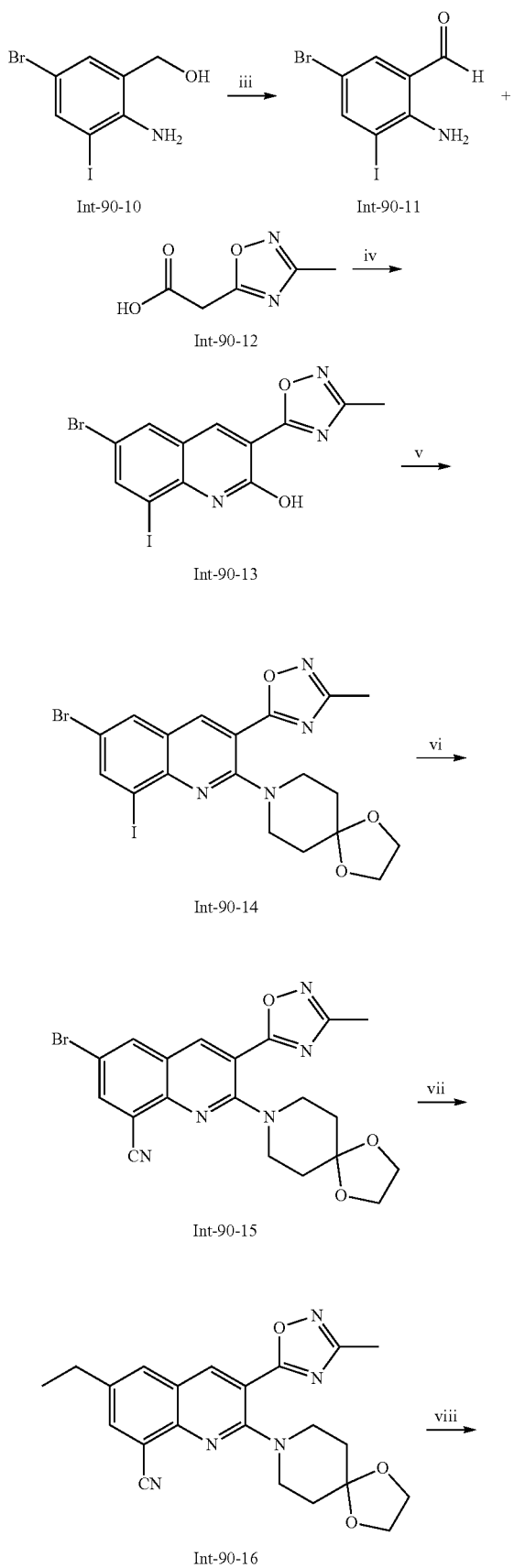

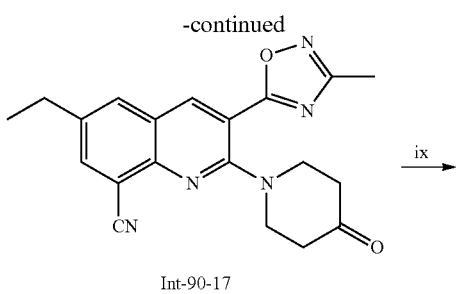

Int-90-17

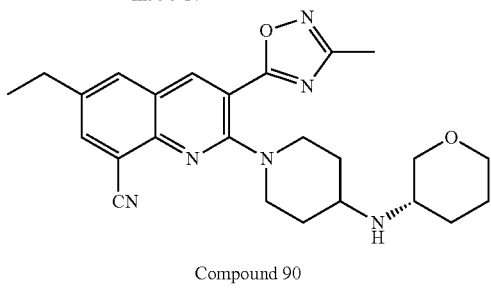

Compound 90

Synthesis of Int-90-11

To a suspension of 2-amino-5-bromobenzoic acid Int-90-8 (10.80 g, 50.0 mmol) in CH$_2$Cl$_2$ (200 mL) was added N-iodosuccinimide (11.25 g, 50.0 mmol). The mixture was stirred at room temperature for 4 h. The product was filtered, washed with CH$_2$Cl$_2$ and dried under reduced pressure to give iodobenzoic acid Int-90-9 as a light brown solid. To a solution of Int-90-9 (13.51 g, 39.5 mmol) in THF (100 mL) was added dropwise a solution of BH$_3$·THF complex (1M in THF, 200 mL, 200 mmol) at 0° C. The mixture was then stirred at room temperature overnight. The reaction was quenched by MeOH at 0° C. slowly. After removing the solvent to dryness, the crude alcohol Int-90-10 was dissolved in CH$_2$Cl$_2$ (200 mL), and activated MnO$_2$ (20.60 g, 237 mmol) was added. The mixture was stirred at room temperature overnight. The crude product was purified with a short silica gel path to give aldehyde Int-90-11 as a yellow solid (10.3 g, 63% yield over three steps). LCMS: (M−1) m/z=324, 326.

Synthesis of Int-90-14

A mixture of aldehyde Int-90-11 (4.50 g, 13.8 mmol), oxadiazole acid Int-90-12 (2.36 g, 16.6 mmol) and POCl$_3$ (14 mL) was stirred at 110° C. for 1 h. After cooling to room temperature, excess POCl$_3$ was removed under reduced pressure. To this residue, H$_2$O was added at 0° C. The mixture was stirred at 0° C. for 10 min. The crude chloride Int-90-13 was filtered, washed with H$_2$O and dried under reduced pressure. To a suspension of Int-90-13 in EtOH (70 mL) were added 1,4-dioxa-8-azaspiro[4,5]decane (3.5 mL, 27.6 mmol) and DIPEA (4.8 mL, 27.6 mmol) at room temperature. The mixture was then heated at 120° C. overnight. After cooling to room temperature, the mixture was concentrated and purified by column chromatography (hexanes/EtOAc gradient) to give quinoline Int-90-14 as yellow oil (2.61 g, 34% yield over two steps). LCMS: (M+1) m/z=557, 559.

Synthesis of Int-90-15

A mixture of Int-90-14 (2.35 g, 4.22 mmol), Zn(CN)$_2$ (0.50 g, 4.22 mmol), Zn powder (30 mg, 0.42 mmol) and Pd(PPh$_3$)$_4$ (0.50 g, 0.42 mmol) in THF/DMF (60 mL, 1:1 (v/v)) was heated at 80° C. overnight. After cooling to room temperature, the mixture was filtered through Celite and the filtrate was concentrated. The residue was purified by column chromatography (hexanes/EtOAc) to give cyanoquinoline Int-90-15 as yellow oil (0.86 g, 45% yield). LCMS: (M+1) m/z=456, 458.

Synthesis of Int-90-16

To a mixture of Int-90-15 (0.86 g, 1.88 mmol), K$_2$CO$_3$ (0.52 g, 3.76 mmol) and Pd(PPh$_3$)$_4$ (0.22 g, 0.19 mmol) in DMF (20 mL) was added 1M solution of Et$_3$B in THF (3.8 mL, 3.80 mmol) at room temperature. The mixture was then heated at 70° C. overnight. After cooling to room temperature, the mixture was partitioned between brine (30 mL) and EtOAc (30 mL). The aqueous layer was extracted with EtOAc (30 mL) and the combined organic layers were dried over Na$_2$SO$_4$ and concentrated. The residue was purified by column chromatography (hexanes/EtOAc gradient) to give ethylquinoline 16 as yellow oil (0.23 g, 30% yield). LCMS: (M+1) m/z=406.

Synthesis of Int-90-17

To a solution of Int-90-16 (0.14 g, 0.35 mmol) in THF (1 mL) was added 10% aq. H$_2$SO$_4$ (5 mL, v/v). The mixture was stirred at 45° C. for 2 h. After cooling to room temperature, the mixture was neutralized with sat. aq. Na$_2$CO$_3$ and extracted with EtOAc (2×20 mL). The combined organic layers were dried over Na$_2$SO$_4$ and concentrated to dryness. The ketone Int-90-17 as a yellow solid was used for the next reaction without further purification. (116 mg, 92% yield). LCMS: (M+1) m/z=362.

Synthesis of Compound 90

A mixture of ketone Int-90-17 (14.4 mg, 0.04 mmol), (S)-3-aminotetrahydropyran hydrochloride (11.0 mg, 0.08 mmol) and DIPEA (14 µL, 0.08 mmol) in 1,2-dichloroethane (1.5 mL) was stirred at room temperature for 10 min. To the mixture were added NaBH(OAc)$_3$ (25.4 mg, 0.12 mmol) and AcOH (7 µL, 0.12 mmol). The resulting mixture was stirred at room temperature overnight. After filtration through Celite, the filtrate was concentrated under reduced pressure. The residue was purified by preparative-TLC (CH$_2$Cl$_2$:MeOH=95:5) to give Compound 90 as yellow oil (15.6 mg, 88% yield). LCMS: (M+1) m/z=447.

Example 91

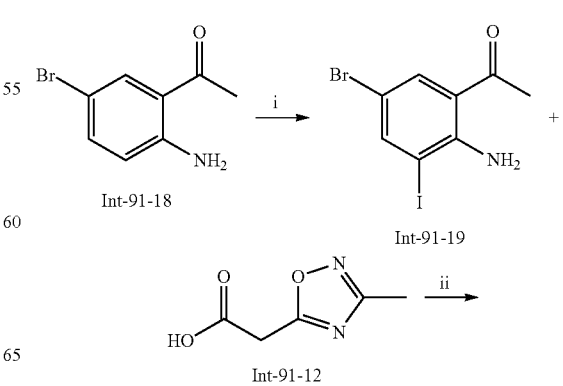

-continued

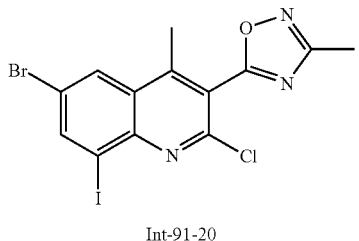

Int-91-20

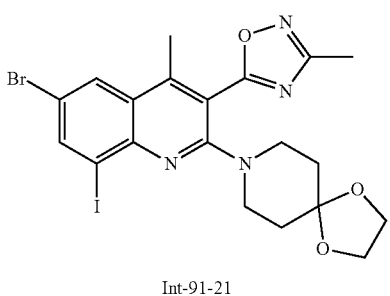

Int-91-21

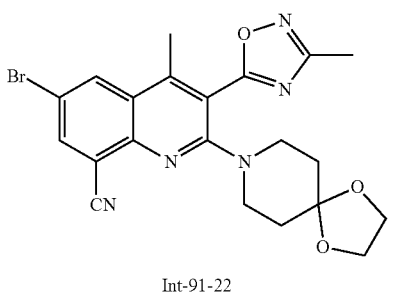

Int-91-22

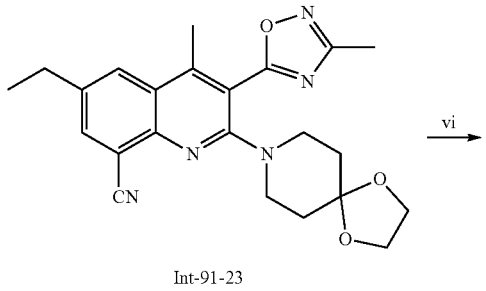

Int-91-23

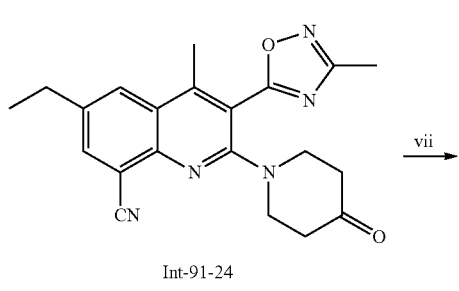

Int-91-24

-continued

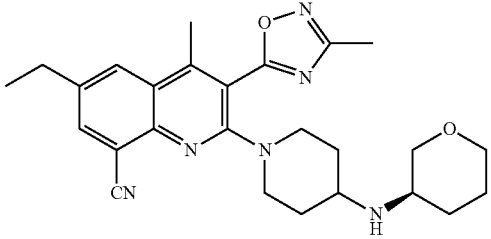

Compound 91

Reagents and conditions: i) Int-91-18 (1.0 equiv.), PyICl (1.0 equiv.), MeOH, reflux, 18 h, 69%; ii) Int-91-19 (1.0 equiv.), Int-91-12 (1.2 equiv.), POCl₃, 110° C., 1 h; iii) 1,4-dioxa-8-azaspiro[4,5]decane (2.0 equiv.), DIPEA (2.0 equiv.), EtOH, 120° C., 18 h, 30% (two steps); iv) Zn(CN)₂ (1.0 equiv.), Zn (0.1 equiv.), Pd(PPh₃)₄ (0.1 equiv.), THF/DMF, 80° C., 18 h, 86%; v) Et₃B (2.0 equiv.), K₂CO₃ (2.0 equiv.), Pd(PPh₃)₄ (0.1 equiv.), DMF, 70° C., 57%; vi) 10% aq. H₂SO₄, THF, 45° C., 2 h, 89%; vii) amine (2.0 equiv.), NaBH(OAc)₃ (3.0 equiv.), AcOH (3.0 equiv.), DIPEA (2.0 equiv.), 1,2-dichloroethane, RT, 18 h, 93%.

Synthesis of Int-91-19

A mixture of 2-amino-5-bromoacetophenone Int-91-18 (4.6 g, 21.5 mmol) and pyridinium iodochloride (5.2 g, 21.5 mmol) in MeOH (54 mL) was refluxed overnight. After cooling to room temperature, the mixture was concentrated. The residue was purified by column chromatography (hexanes/EtOAc gradient) to give iodoacetophenone Int-91-19 as a yellow solid (5.04 g, 69% yield). LCMS: (M+1) m/z=340, 342.

Synthesis of Int-91-21

A mixture of ketone Int-91-19 (5.02 g, 14.8 mmol), oxadiazole acid Int-91-12 (2.52 g, 17.7 mmol) and POCl₃ (15 mL) was stirred at 110° C. for 1 h. After cooling to room temperature, excess POCl₃ was removed under reduced pressure. To this residue, H₂O was added at 0° C. The mixture was stirred at 0° C. for 10 min. The crude chloride Int-91-20 was filtered, washed with H₂O and dried under reduced pressure. To a suspension of Int-91-20 in EtOH (74 mL) were added 1,4-dioxa-8-azaspiro[4,5]decane (3.8 mL, 29.6 mmol) and DIPEA (5.2 mL, 29.6 mmol) at room temperature. The mixture was then heated at 120° C. overnight. After cooling to room temperature, the mixture was concentrated and purified by column chromatography (hexanes/EtOAc gradient) to give quinoline Int-91-21 as yellow oil (2.54 g, 30% yield over two steps). LCMS: (M+1) m/z=571, 573.

Synthesis of Int-91-22

A mixture of Int-91-21 (1.28 g, 2.24 mmol), Zn(CN)₂ (0.26 g, 2.24 mmol), Zn powder (15 mg, 0.22 mmol) and Pd(PPh₃)₄ (0.26 g, 0.22 mmol) in THF/DMF (22 mL, 1:1 (v/v)) was heated at 80° C. overnight. After cooling to room temperature, the mixture was filtered through Celite and the filtrate was concentrated. The residue was purified by column chromatography (hexanes/EtOAc gradient) to give cyanoquinoline Int-91-22 as a light green solid (0.90 g, 86% yield). LCMS: (M+1) m/z=470, 472.

Synthesis of Int-91-23

To a mixture of Int-91-22 (0.90 g, 1.91 mmol), K₂CO₃ (0.53 g, 3.82 mmol) and Pd(PPh₃)₄ (0.22 g, 0.19 mmol) in DMF (20 mL) was added 1M solution of Et$_3$B in THF (3.8 mL, 3.8 mmol) at room temperature. The mixture was then heated at 70° C. overnight. After cooling to room temperature, the mixture was partitioned between brine (30 mL) and EtOAc (30 mL). The aqueous layer was extracted with EtOAc (30 mL) and the combined organic layers were dried over Na$_2$SO$_4$ and concentrated. The residue was purified by column chromatography (hexanes/EtOAc gradient) to give ethylquinoline Int-91-23 as yellow oil (0.45 g, 57% yield). LCMS: (M+1) m/z=420.

Synthesis of Int-91-24

To a solution of Int-91-23 (0.45 g, 1.08 mmol) in THF (4 mL) was added 10% aq. H$_2$SO$_4$ (12 mL, v/v). The mixture was stirred at 45° C. for 2 h. After cooling to room temperature, the mixture was neutralized with sat. aq. Na$_2$CO$_3$ and extracted with EtOAc (2×30 mL). The combined organic layers were dried over Na$_2$SO$_4$ and concentrated to dryness. The ketone Int-91-24 as an orange solid was used for the next reaction without further purification. (0.36 g, 89% yield). LCMS: (M+1) m/z=376.

Synthesis of Compound 91

A mixture of ketone Int-91-24 (15.1 mg, 0.04 mmol), (R)-3-aminotetrahydropyran hydrochloride (11.0 mg, 0.08 mmol) and DIPEA (14 µL, 0.08 mmol) in 1,2-dichloroethane (1.5 mL) was stirred at room temperature for 10 min. To the mixture were added NaBH(OAc)$_3$ (25.4 mg, 0.12 mmol) and AcOH (7 µL, 0.12 mmol). The resulting mixture was stirred at room temperature overnight. After filtration through Celite, the filtrate was concentrated under reduced pressure. The reside was purified by preparative-TLC (EtOAc:iPrOH=9:1) to give Compound 91 as a yellow solid (17.2 mg, 93% yield). LCMS: (M+1) m/z=461.

Examples 92-93

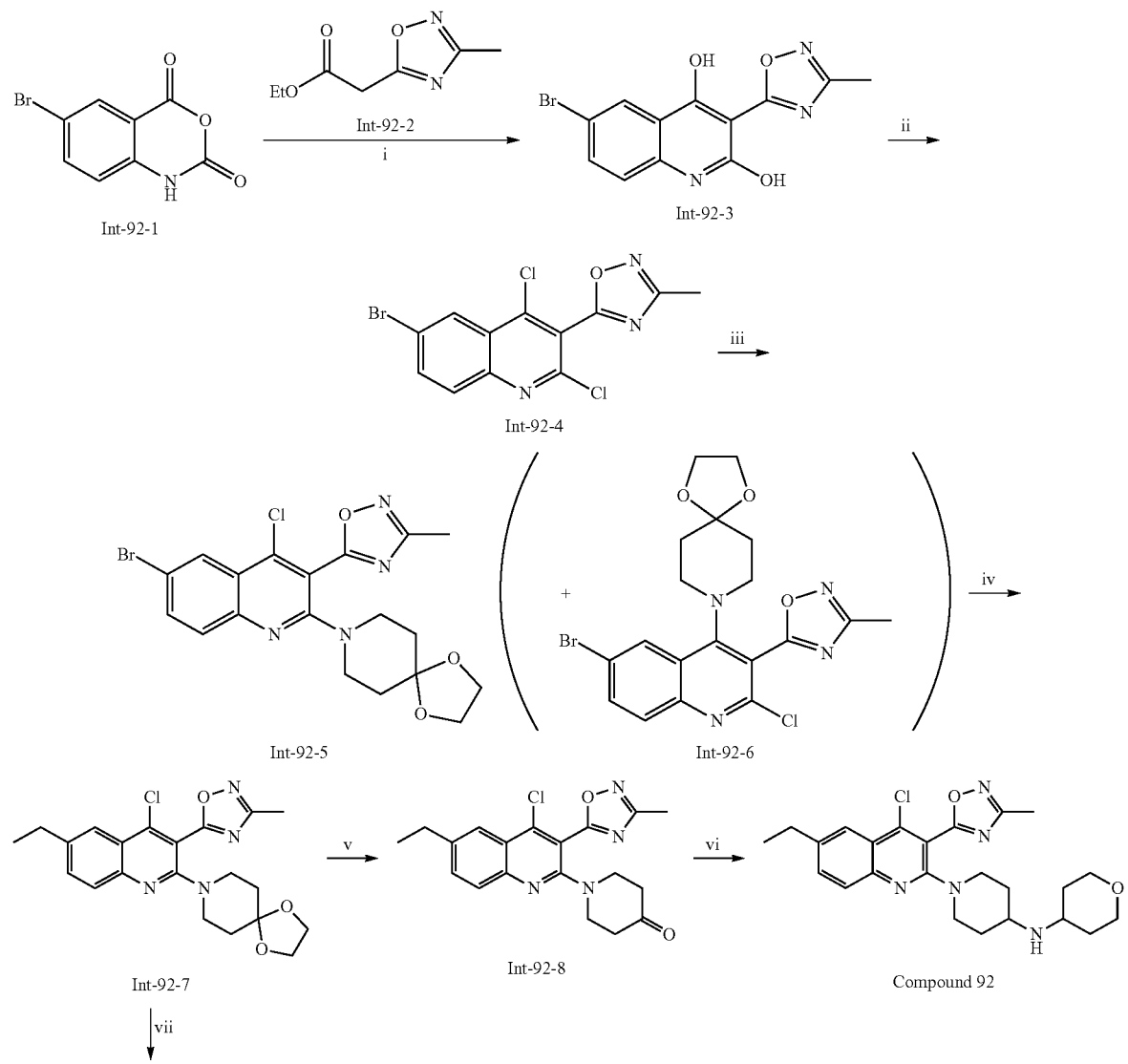

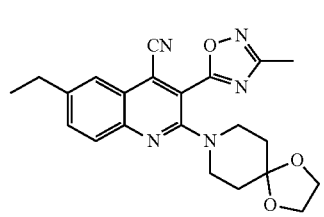 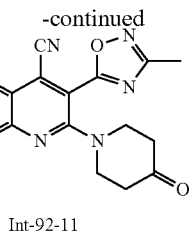 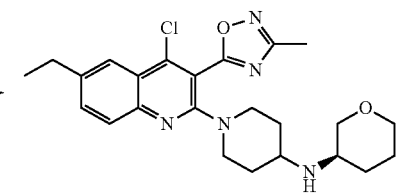

Int-92-10 → Int-92-11 → Compound 93

Reagents and conditions: i) Int-92-1 (1.0 equiv.), Int-142-9 (1.5 equiv.), NaH (1.0 equiv.), DMF, 120° C., 4 h; ii) POCl₃, 110° C., 1.5 h, 19% in two steps; iii) Int-92-4 (1.0 equiv.), 1,4-dioxa-8-azaspiro[4,5]decane (2.0 equiv.), Pd(PPh₃)₄ (0.1 equiv.), 1,4-dioxane, 80° C., 3 h, 11% for Int-92-5 (and 48% for Int-92-6); iv) 5 (1.0 eqiv.), Et₃B (1.2 equiv.), K₂CO₃ (2.0 equiv.), Pd(PPh₃)₄ (0.1 equiv.), THF/DMF, 70° C., overnight, 67%; v) 10% aq. H₂SO₄, THF, 45° C., 2 h, 80%; vi) Int-92-8 (1.0 equiv.), amine (2.0 equiv.), NaBH(OAc)₃ (3.0 equiv.), AcOH (3.0 equiv.), DIPEA (2.0 equiv.), 1,2-dichloroethane, RT, overnight, 62%; vii) 7 (1.0 equiv.), KCN (2.0 equiv.), DMSO, 110° C., overnight, 30%; viii) 10% aq. H₂SO₄, THF, 45° C., 1.5 h, quantitative yield; ix) Int-92-11 (1.0 equiv.), amine (2.0 equiv.), NaBH(OAc)₃ (3.0 equiv.), AcOH (3.0 equiv.), DIPEA (2.0 equiv.), 1,2-dichloroethane, RT, 18 h, 61%.

Synthesis of Int-92-3

To a suspension of NaH (60% in oil, 0.83 g, 20.7 mmol) in DMF (60 mL) was added oxadiazole ester Int-92-2 (5.30 g, 31.0 mmol) dropwise at 0° C. The mixture was stirred at 0° C. for 10 min followed by the addition of 5-bromoisatoic anhydride Int-92-1 (5.00 g, 20.7 mmol). The mixture was then heated at 120° C. for 4 h. After cooling to room temperature, the reaction was quenched by addition of H₂O, and acidified with conc. HCl (pH=4-5 by pH paper). The mixture was extracted with CH₂Cl₂ (×3), and combined organic extracts were dried over Na₂SO₄ and concentrated to dryness. Product Int-92-3, a dark brown oil, was used for the next reaction without further purification.

Synthesis of Int-92-4

A mixture of Int-92-3 (6.67 g, 20.7 mmol) and POCl₃ (5 mL) was stirred at 110° C. for 1.5 h. After cooling to room temperature, excess POCl₃ was removed under the reduced pressure. To the residue, was added H₂O at 0° C. The mixture was partitioned between CH₂Cl₂ and sat. aq. NaHCO₃. The aqueous layer was separated and extracted with CH₂Cl₂ (×2). The combined organic layers were dried over Na₂SO₄ and concentrated. The residue was purified by column chromatography (Hexanes/EtOAc gradient) to give Int-92-4 as a yellow solid (1.41 g, 19% yield in two steps).

Synthesis of Int-92-5

A mixture of Int-92-4 (4.29 g, 11.95 mmol), 1,4-dioxa-8-azaspiro[4,5]decane (3.0 mL, 23.90 mmol) and Pd(PPh₃)₄ (1.38 g, 1.12 mmol) in 1,4-dioxane (80 mL) was heated at 80° C. for 3 h. After cooling to room temperature, the mixture was filtered through Celite. The filtrated was concentrated and purified by column chromatography (Hexanes/EtOAc gradient) to give Int-92-5 as a pale yellow solid (0.59 g, 11% yield) and 4-aminated Int-92-6 as a pale yellow crystal (2.67 g, 48% yield). The structure of Int-92-6 was confirmed by X-ray crystallography. LCMS: (M+1) m/z=465, 467.

Synthesis of Int-92-7

To a mixture of Int-92-5 (590 mg, 1.27 mmol), K₂CO₃ (350 mg, 2.54 mmol) and Pd(PPh₃)₄ (146 mg, 0.127 mmol) in THF/DMF (1:1, v/v, 12 mL) was added 1M solution of Et₃B in THF (1.52 mL, 1.52 mmol) at room temperature. The mixture was then heated at 70° C. overnight. After cooling to room temperature, the mixture was filtered through Celite. The filtrated was concentrated and purified by column chromatography (Hexanes/EtOAc gradient) to give Int-92-7 as a yellow oil (352 mg, 67% yield). LCMS: (M+1) m/z=415.

Synthesis of Int-92-8

To a solution of Int-92-7 (125 mg, 0.30 mmol) in THF (3 mL) was added 10% aq. H₂SO₄ (5 mL, v/v). The mixture was stirred at 45° C. for 2 h. After cooling to room temperature, the mixture was neutralized with sat. aq. Na₂CO₃ and extracted with EtOAc (×2). The combined organic extracts were dried over Na₂SO₄ and concentrated. The residue was purified by column chromatography (Hexanes/EtOAc gradient) to give Int-92-8 as a yellow oil (88.7 mg, 80% yield). LCMS: (M+1) m/z=371.

Synthesis of Compound 92

A mixture of ketone Int-92-8 (10.0 mg, 0.027 mmol), 4-aminotetrahydropyran (5.5 mg, 0.054 mmol) and DIPEA (10 µL, 0.054 mmol) in 1,2-dichloroethane (1.5 mL) was stirred at room temperature for 10 min. To the mixture, NaBH(OAc)₃ (17.0 mg, 0.081 mmol) and AcOH (5 µL, 0.081 mmol) were added. The resulting mixture was stirred at room temperature overnight. After filtration through Celite, the filtrate was concentrated. The reside was purified by preparative-TLC (CH₂Cl₂:MeOH=93:7) to give Compound 92 as a yellow oil (7.6 mg, 62% yield). LCMS: (M+1) m/z=456.

Synthesis of Int-92-10

A mixture of Int-92-7 (334 mg, 0.805 mmol) and KCN (105 mg, 1.61 mmol) in DMSO (10 mL) was heated at 110° C. overnight. After cooling to room temperature, the mixture was partitioned between EtOAc and brine. The aqueous layer was separated and extracted with EtOAc (×3). The combined organic layers were dried over Na₂SO₄ and concentrated. The residue was purified by column chromatography (Hexanes/EtOAc) followed by preparative-TLC (Hexanes:EtOAc=6:1) to give Int-92-10 as a yellow solid (97 mg, 30% yield). LCMS: (M+1) m/z=406.

Synthesis of Int-92-11

To a solution of Int-92-10 (23 mg, 0.057 mmol) in THF (1 mL) was added 10% aq. H₂SO₄ (1 mL, v/v). The mixture was stirred at 45° C. for 1.5 h. After cooling to room temperature, the mixture was neutralized with sat. aq.

Na₂CO₃ and extracted with EtOAc (×2). The combined organic extracts were dried over Na₂SO₄ and concentrated to dryness. Product Int-92-11 as a yellow oil was used for the next reaction without further purification. (20.5 mg, quantitative yield). LCMS: (M+1) m/z=362.

Synthesis of Compound 93

A mixture of ketone Int-92-11 (10.2 mg, 0.028 mmol), (R)-3-aminotetrahydropyran (7.7 mg, 0.056 mmol) and DIPEA (10 μL, 0.056 mmol) in 1,2-dichloroethane (1.5 mL) was stirred at room temperature for 10 min. To the mixture, NaBH(OAc)₃ (17.8 mg, 0.084 mmol) and AcOH (5 μL, 0.084 mmol) were added. The resulting mixture was stirred at room temperature overnight. After filtration through Celite, the filtrate was concentrated. The reside was purified by preparative-TLC (CH₂Cl₂:MeOH=95:5) to give Compound 93 as an orange oil (7.7 mg, 61% yield). LCMS: (M+1) m/z=447.

Examples 94-96

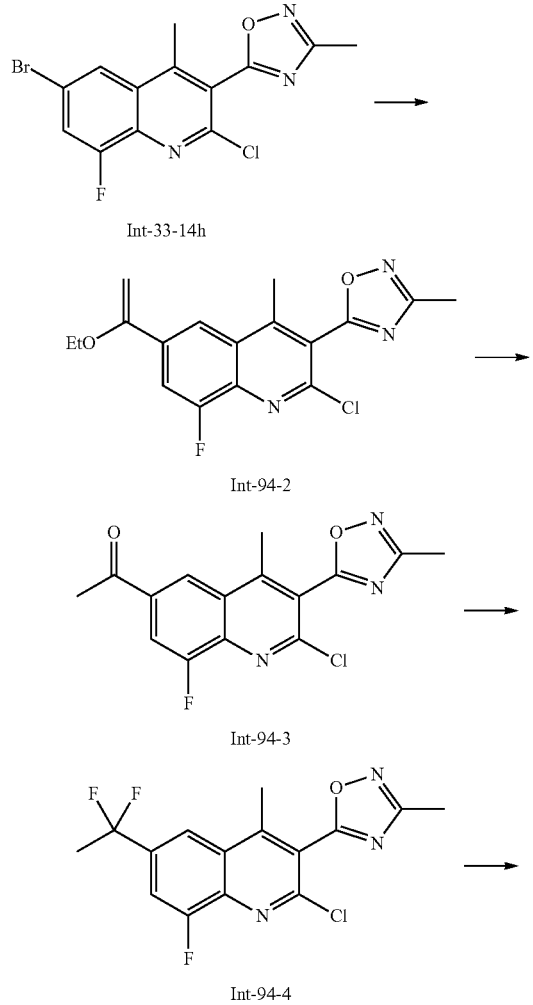

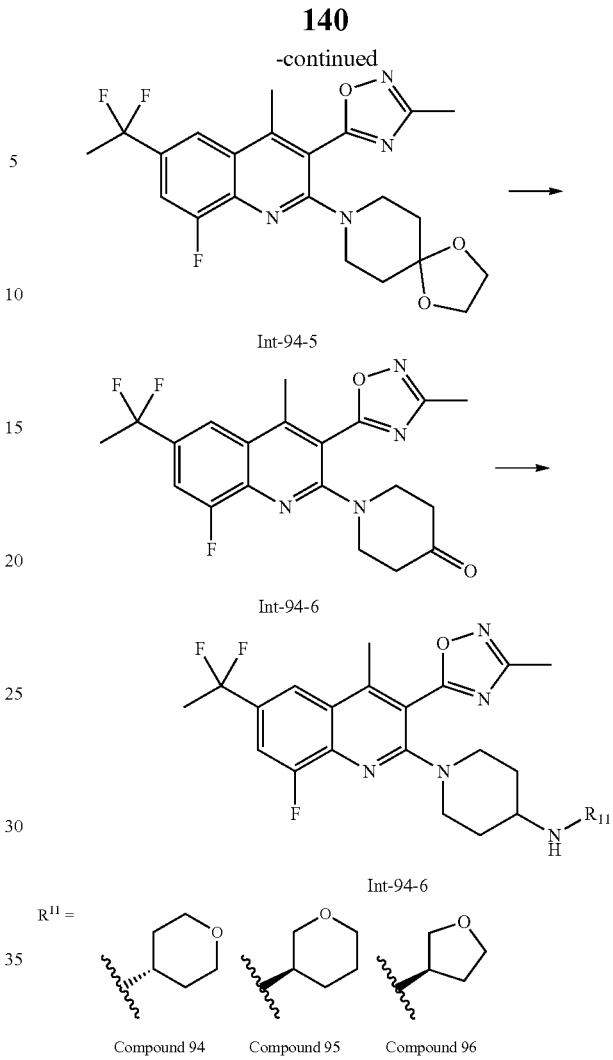

Synthesis of Int-94-2

A solution of Int-33-14h (1.753 g, 4.92 mmol) and tributyl-(1-ethoxyvinyl)tin (2.33 mL, 6.89 mmol) in toluene (15 mL) was degassed with nitrogen. Bis(triphenylphosphine)palladium(II)dichloride (172.7 mg, 0.245 mmol, 5 mol %) was added, and the reaction mixture was heated at 80° C. overnight. The reaction mixture was cooled to RT, and filtered on celite pad. The filtrate was evaporated, and the residue was purified by silica gel chromatography (Hexanes:EtOAc=90:1) to afford Int-94-2 as a white solid (537 mg, 31% yield). LCMS: (M+1) m/z=348, 350.

Synthesis of Int-94-3

To a mixture of Int-94-2 (537 mg, 1.54 mmol) in 1,4-dioxane (3 mL) was added 2 M hydrochloric acid (3 mL). The reaction mixture was stirred at RT for 30 min. 1,4-dioxane was removed under reduced pressure. The product was collected by vacuum filtration, rinsed sequentially with water and Hexanes to provide Int-94-3 as an off-white solid (480 mg, 97% yield). LCMS: (M+1) m/z=320, 322.

Synthesis of Int-94-4

To a mixture of Int-94-3 (100 mg, 0.31 mmol) in dichloromethane (1.5 mL) was added diethylaminosulfur trifluoride (0.25 mL, 1.88 mmol) at 0° C. The reaction mixture was stirred at RT overnight. Additional diethylaminosulfur trifluoride (0.21 mL, 1.58 mmol) was added at 0° C., and the reaction was kept stirring at RT for additional 48 h. The reaction mixture was slowly poured into a saturated aqueous NaHCO₃ solution. The organic layer was separated, and the aqueous layer was extracted with dichloromethane (3×20 mL). The combined organic layers were dried over Na₂SO₄ and the solvent was evaporated under reduced pressure. The residue was purified by preparative-TLC (Hexanes:EtOAc=80:20) to provide Int-94-4 as a white solid (62.4 mg, 59% yield). LCMS: (M+1) m/z=342, 344.

Synthesis of Int-94-5

To a suspension of Int-94-4 (40 mg, 0.12 mmol) in EtOH (0.5 mL) were added 1,4-dioxa-8-azaspiro[4,5]decane (0.030 mL, 0.24 mmol) and DIPEA (0.041 mL, 0.24 mmol). The reaction mixture was heated with microwave at 130° C. for 40 min. The mixture was concentrated and purified by preparative-TLC (Hexanes:EtOAc=80:20) to provide Int-94-5 as a yellow solid (43 mg, 89% yield). LCMS: (M+1) m/z=449.

Synthesis of Int-94-6

To a solution of Int-94-5 (43 mg, 0.096 mmol) in THF (0.4 mL) was added 10% aq. H₂SO₄ (0.8 mL) at RT. The mixture was then stirred at 45° C. for 4 h. After cooling to RT, the mixture was neutralized with saturated aq. Na₂CO₃ and extracted with EtOAc (2×10 mL). The combined organic layers were dried over Na₂SO₄ and concentrated to dryness. The ketone Int-94-6 (38 mg, 98%; yellow oil) was used in the next step without further purification. LCMS: (M+1) m/z=405.

Synthesis of Compound 94

A mixture of Int-94-6 (11 mg, 0.027 mmol), tetrahydro-2H-pyran-4-amine (5.5 mg, 0.054 mmol) in 1,2-dichloroethane (0.2 mL) was stirred at RT for 10 min. To the mixture NaBH(OAc)₃ (11.4 mg, 0.054 mmol) and AcOH (3 μl, 0.054 mmol) were added. The resulting mixture was stirred at RT overnight. The reaction mixture was directly purified by preparative-TLC (CH₂Cl₂:MeOH=95:5) to give Compound 94 as off-white solid (6.0 mg, 45% yield). LCMS: (M+1) m/z=490.

Synthesis of Compound 95

A mixture of Int-94-6 (11 mg, 0.027 mmol), (R)-tetrahydro-2H-pyran-3-amine hydrochloride (7.4 mg, 0.054 mmol) and DIPEA (9.4 μL, 0.054 mmol) in 1,2-dichloroethane (0.2 mL) was stirred at RT for 10 min. To the mixture NaBH(OAc)₃ (11.4 mg, 0.054 mmol) and AcOH (3 μL, 0.054 mmol) were added. The resulting mixture was stirred at RT overnight. The reaction mixture was directly purified by preparative-TLC (CH₂Cl₂:MeOH=95:5) to give Compound 95 as a white solid (6.0 mg, 45% yield). LCMS: (M+1) m/z=490.

Synthesis of Compound 96

A mixture of Int-94-6 (11 mg, 0.027 mmol) and (R)-tetrahydrofuran-3-amine (4.7 mg, 0.054 mmol) in 1,2-dichloroethane (0.2 mL) was stirred at RT for 10 min. To the mixture NaBH(OAc)₃ (11.4 mg, 0.054 mmol) and AcOH (3 μl, 0.054 mmol) were added. The resulting mixture was stirred at RT overnight. The reaction mixture was directly purified by preparative-TLC (CH₂Cl₂:MeOH=95:5) to give Compound 96 as an off-white solid (2.0 mg, 16% yield). LCMS: (M+1) m/z=476.

Examples 97-98

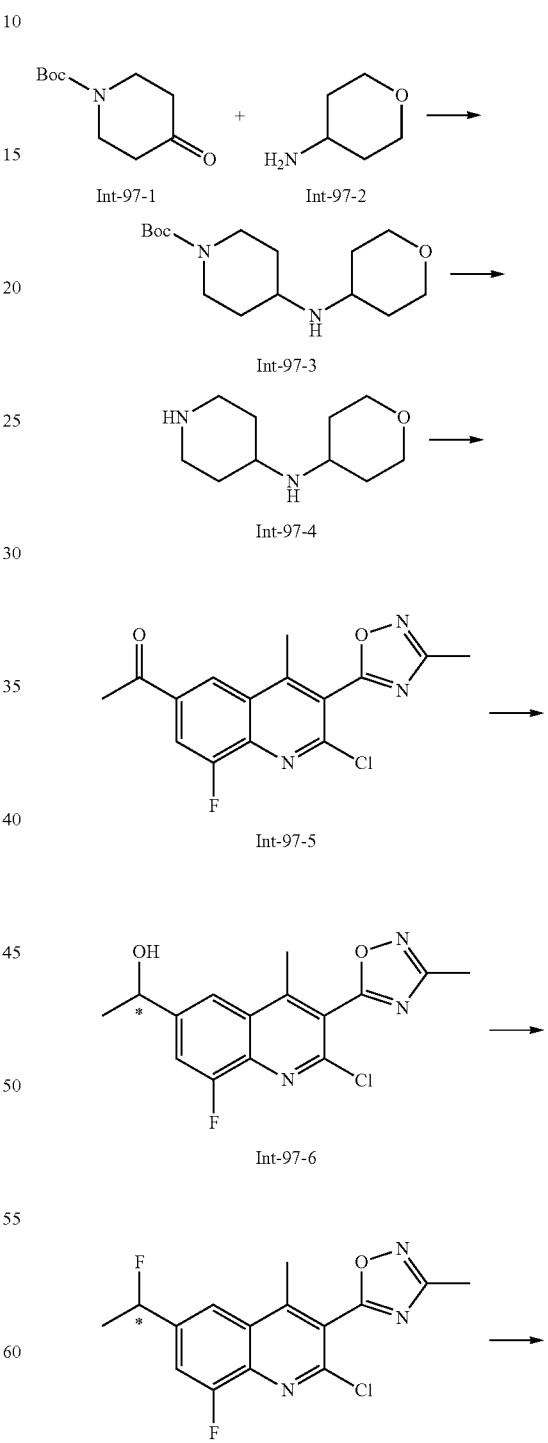

-continued

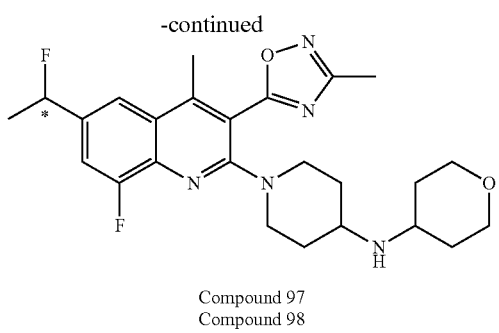

Compound 97
Compound 98

Synthesis of Int-97-3

A mixture of Int-97-1 (1.37 g, 6.89 mmol) and tetrahydro-2H-pyran-4-amine Int-97-2 (1.395 g, 13.79 mmol) in 1,2-dichloroethane (20 mL) was stirred at RT for 10 min. To the mixture NaBH(OAc)$_3$ (2.92 g, 3.79 mmol) and AcOH (0.78 mL, 13.79 mmol)) were added. The reaction mixture was stirred at RT overnight. The solvent was evaporated under reduced pressure, and the residue was partitioned between saturated aqueous solution of Na$_2$CO$_3$ and EtOAc. The organic phase was separated, and the aqueous layer was extracted with EtOAc (2×40 mL). The combined organic phase was dried over Na$_2$SO$_4$ and evaporated under reduced pressure. The product was purified by column chromatography (CH$_2$Cl$_2$:MeOH=97:3) to afford Int-97-3 as yellow oil (1.716 g, 88% yield). LC-MS: (M+1) m/z=285.

Synthesis of Int-97-4

To a solution of Int-97-3 (1.716 g, 6.03 mmol) in CH$_2$Cl$_2$ (10 mL) was added dropwise trifluoroacetic acid (9.2 mL, 120.67 mmol). The reaction mixture was stirred at RT for 1 h, then the solvent and the excess of trifluoroacetic acid were evaporated under reduced pressure. The residue was partitioned between 2M NaOH solution and EtOAc. The organic phase was separated, and the aqueous phase was back-extracted with EtOAc (3×20 mL). The combined organic phase was washed with water (2×5 mL), dried over Na$_2$SO$_4$ and evaporated under reduced pressure to provide Int-97-4 as yellow oil which was used in the next step without further purification (1.1 g, quantitative yield).
LCMS: (M+1) m/z=185.

Synthesis of Int-97-5

Same as synthesis of intermediate Int-94-3 described above for Compounds 94-96.

Synthesis of Int-97-6

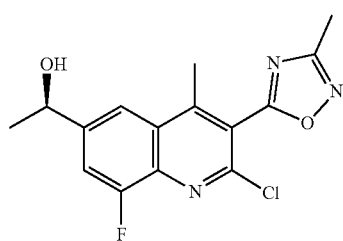

Dichloro (p-cymene) ruthenium(II) dimer (0.38 mg, 0.6 μmol) and (1R,2R)-(−)-N-p-tosyl-1,2-diphenylethylenediamine (0.55 mg, 1.5 μmol) were suspended in water (0.25 mL). The mixture was degassed with nitrogen, then heated at 70° C. for 90 min under nitrogen. The resulting mixture was allowed to cool down to RT. Ketone Int-97-5 (40 mg, 0.125 mg), sodium formate (42.5 mg, 0.625 mmol) and anhydrous THE (0.12 mL) were added, and the reaction was degassed with nitrogen. The reaction mixture was stirred at 40° C. for 2.5 h. The reaction mixture was diluted with EtOAc, and washed with brine. The aqueous phase was extracted with EtOAc. The combined organic layers were dried over Na$_2$SO$_4$ and evaporated under reduced pressure. The residue was purified by preparative-TLC (Hexanes:EtOAc=70:30) to provide the title compound as a white solid (33.0 mg, 82% yield, ee not determined). LCMS: (M+1) m/z=322, 324.

Synthesis of Int-97-7

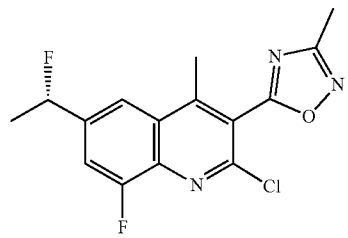 [SMILES: Cc1noc(-c2c(Cl)nc3c(F)cc([C@H](C)F)cc3c2C)n1]

N-(Trimethylsilyl)morpholine (60 μL, 0.336 mmol) was added dropwise to a solution of DAST (43 μL, 0.328 mmol) in dry CH$_2$Cl$_2$ (0.2 mL) at −78° C. The resulting solution was stirred at RT for 2.5 h. The reaction mixture was cooled at −78° C. and a solution of (R)-1-(2-chloro-8-fluoro-4-methyl-3-(3-methyl-1,2,4-oxadiazol-5-yl)quinolin-6-yl)ethan-1-ol Int-97-6 (33 mg, 0.10 mmol) in dry CH$_2$Cl$_2$ (0.4 mL) was added dropwise. The reaction mixture was stirred at RT overnight. The reaction mixture was then slowly poured into 10 mL of saturated NaHCO$_3$ solution. The organic layer was separated and the aqueous phase extracted with additional CH$_2$Cl$_2$ (3×10 mL). The combined organic phase was dried over Na$_2$SO$_4$ and evaporated under reduced pressure. The residue was purified by preparative-TLC (Hexanes:EtOAc=80:20) to provide the desired compound as a yellow oil (14.6 mg, 45% yield, ee not determined). LCMS: (M+1) m/z=324, 326.

Synthesis of Compound 97

A mixture of (S)-5-(2-chloro-8-fluoro-6-(1-fluoroethyl)-4-methylquinolin-3-yl)-3-methyl-1,2,4-oxadiazole Int-97-7 (13.8 mg, 0.0426 mmol), N-(tetrahydro-2H-pyran-4-yl)piperidin-4-amine 4 (9 mg, 0.047 mmol) and DIPEA (8 μL, 0.047 mmol) in DMF (0.2 mL) was heated at 120° C. overnight. The reaction mixture was diluted with brine and EtOAc. The organic phase was separated, and washed with brine (2×5 mL). The organic phase was dried over Na$_2$SO$_4$ and concentrated to dryness. The residue was purified by preparative-TLC (CH$_2$Cl$_2$:MeOH=96:4) to provide Compound 97 as a yellow solid (5.0 mg, 25% yield, ee not determined). LCMS: (M+1) m/z=472.

Synthesis of Int-97-6

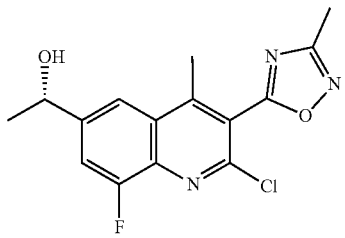 [SMILES: Cc1noc(-c2c(Cl)nc3c(F)cc([C@H](C)O)cc3c2C)n1]

Dichloro (p-cymene) ruthenium(II) dimer (1.13 mg, 1.8 µmol) and (1S,2S)-(+)-N-p-tosyl-1,2-diphenylethylenediamine (1.63 mg, 4.4 µmol) were suspended in water (0.74 mL). The mixture was degassed with nitrogen, then heated at 70° C. for 90 min under nitrogen. The resulting mixture was allowed to cool down to RT. Ketone Int-97-5 (120 mg, 0.37 mmol), sodium formate (125.8 mg, 1.85 mmol) and anhydrous THF (0.37 mL) were added, and the reaction was degassed with nitrogen. The reaction mixture was stirred at 40° C. for 2.5 h. The reaction mixture was diluted with EtOAc, and washed with brine. The aqueous phase was extracted with EtOAc. The combined organic layers were dried over $Na_2SO_4$ and evaporated under reduced pressure. The residue was purified by column chromatography (Hexanes:EtOAc=70:30) to provide the title compound as a white solid (109 mg, 91% yield, ee not determined). LCMS: (M+1) m/z=322, 324.

Synthesis of Int-97-7

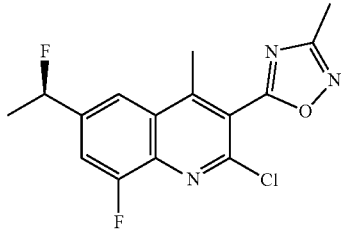 [SMILES: Cc1noc(-c2c(Cl)nc3c(F)cc([C@@H](C)F)cc3c2C)n1]

N-(Trimethylsilyl)morpholine (92 µL, 0.52 mmol) was added dropwise to a solution of DAST (67 µL, 0.508 mmol) in dry $CH_2Cl_2$ (0.2 mL) at −78° C. The resulting solution was stirred at RT for 2.5 h. The reaction mixture was cooled at −78° C. and a solution of (S)-1-(2-chloro-8-fluoro-4-methyl-3-(3-methyl-1,2,4-oxadiazol-5-yl)quinolin-6-yl)ethan-1-ol Int-97-6 (50 mg, 0.16 mmol) in dry $CH_2Cl_2$ (0.46 mL) was added dropwise. The reaction mixture was stirred at RT overnight. The reaction mixture was then slowly poured into 10 mL of saturated $NaHCO_3$ solution. The organic layer was separated and the aqueous phase extracted with additional $CH_2Cl_2$ (3×10 mL). The combined organic phase was dried over $Na_2SO_4$ and evaporated under reduced pressure. The residue was purified by preparative-TLC (Hexanes:EtOAc=80:20) to provide the desired compound as a yellow oil (20.5 mg, 41% yield) (ee not determined). LCMS: (M+1) m/z=324, 326.

Synthesis of Compound 98

A mixture of (R)-5-(2-chloro-8-fluoro-6-(1-fluoroethyl)-4-methylquinolin-3-yl)-3-methyl-1,2,4-oxadiazole Int-97-7 (8.0 mg, 0.024 mmol), N-(tetrahydro-2H-pyran-4-yl)piperidin-4-amine Int-97-4 (6.8 mg, 0.036 mmol) and DIPEA (6 µL, 0.036 mmol) in DMF (0.2 mL) was heated at 120° C. overnight. The reaction mixture was diluted with brine and EtOAc. The organic phase was separated, and washed with brine (2×5 mL). The organic phase was dried over $Na_2SO_4$ and concentrated to dryness. The residue was purified by preparative-TLC ($CH_2Cl_2$:MeOH=96:4) to provide Compound 98 as a yellow solid (2.6 mg, 23% yield) (ee not determined). LCMS: (M+1) m/z=472.

Examples 99-101

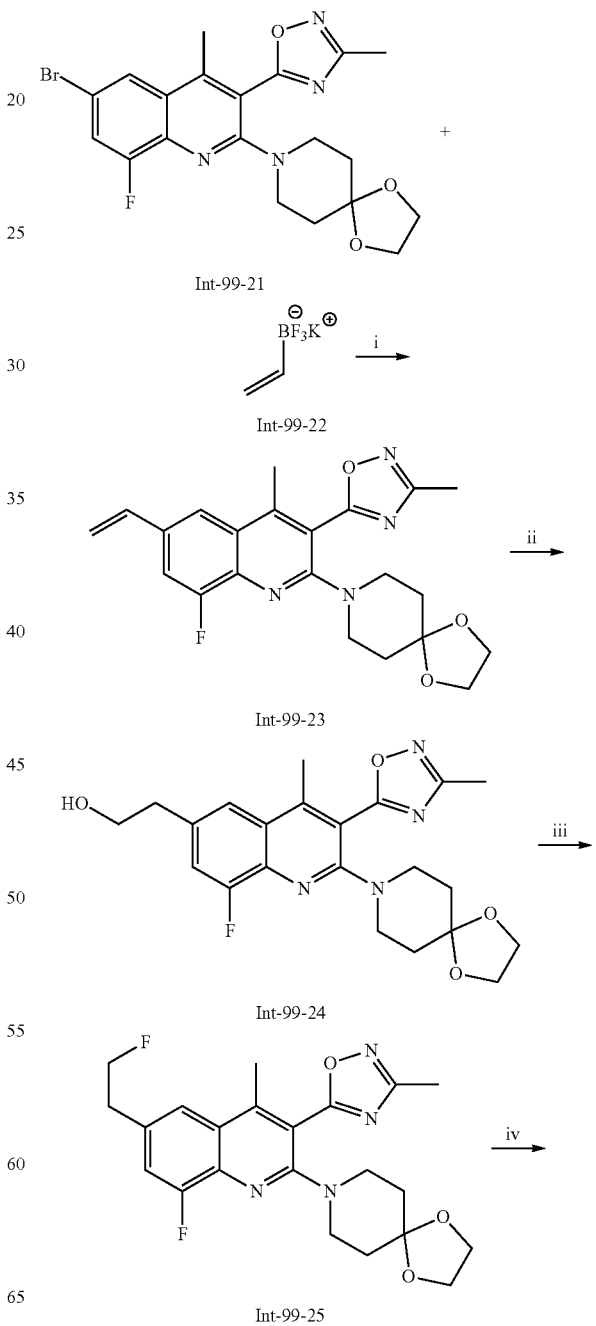

-continued

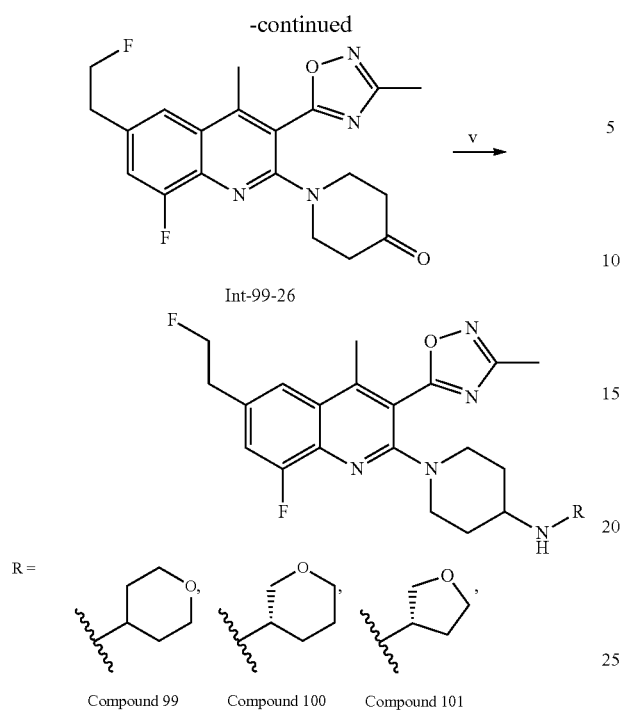

Reagents and conditions: i) Int-99-21 (1.0 equiv.), Int-99-22 (1.1 equiv.), PPh₃ (0.06 equiv.), PdCl₂ (1/12 equiv.), Cs₂CO₃ (3.0 equiv.), THF/H₂O 85° C., 24 h, 69-72%; ii) Int-99-23 (1.0 equiv.), BH₃·Me₂S (2.06 equiv.), H₂O₂, NaOH, THF, 50° C., 2 h, 44-46%; iii) Int-99-24 (1.0 equiv.), DAST (1.1 equiv.), CH₂Cl₂, 0° C., 2.5 h; iv) Int-99-25 (1.0 equiv.), 10% aq. H₂SO₄, THF, 45° C., 2 h, 54-57% (two steps); v) Int-99-26 (1.0 equiv.), Amine (2.0 equiv.), NaBH(OAc)₃ (2.0 equiv.), AcOH (2.0 equiv.), DIPEA (2.0 equiv.), 1,2-dichloroethane, rt, overnight.

Synthesis of Int-99-23

A suspension of Int-99-21 (1.0 equiv.), Potassium vinyltrifluoroborate (1.1 equiv.), PPh$_3$ (0.06 equiv.), PdCl$_2$ (1/12 equiv.) and Cs$_2$CO$_3$ (3.0 equiv.) in THF/H$_2$O (9/1) was heated at 85° C. for 24 h. After cooling to RT, the crude was filtered through celite. The filtrate was diluted with EtOAc and washed with brine, and the organic phase was concentrated under reduced pressure. The residue was purified by column chromatography (hexanes:EtOAc) to afford Int-99-23 as a pale yellow solid. LCMS: (M+1) m/z=411.

Synthesis of Int-99-24

A solution of BH$_3$·Me$_2$S (2M, 2.06 equiv.) in THF was slowly added to a solution of Int-99-23 (1.0 equiv.) in THF at 0° C. The mixture was warmed to RT. and stirred for 1 h. The solution was cooled to 0° C. and quenched with 30% aqueous H$_2$O$_2$ (7 equiv.) and NaOH (1M, 1.4 equiv.), and the mixture was heated at 50° C. for 2 h. The mixture was concentrated under reduced pressure and the product was purified by column chromatography (hexanes:EtOAc). LCMS: (M+1) m/z=429.

Synthesis of Int-99-25

To a solution of Int-99-24 (1.0 equiv.) in anhydrous CH$_2$Cl$_2$ at 0° C. was slowly added a solution of DAST (1.1 equiv.) in CH$_2$Cl$_2$ and the reaction was stirred for 2.5 h at 0-5° C. The mixture was diluted with EtOAc and washed with brine (2×). The organic phase was dried over Na$_2$SO$_4$ and concentrated under reduced pressure. The crude was used without further purification (mixture of Int-99-25 and Int-99-23). LCMS: (M+1) m/z=431.

Synthesis of Int-99-26

A solution of Int-99-25 and Int-99-23 in THF/10% aq. H$_2$SO$_4$ was stirred at 45° C. for 2 h. After cooling to RT, the mixture was neutralized with sat. aq. NaOH and the product extracted with EtOAc. The organic phase was dried over Na$_2$SO$_4$ and concentrated under reduced pressure. The product was purified by column chromatography using hexanes/EtOAc, and ketone Int-99-26 was obtained as a pale yellowish solid (54-57% yield for two steps). LCMS: (M+1) m/z=387.

Synthesis of Compound 99, Compound 100 and Compound 101

A mixture of ketone Int-99-26 (1.0 equiv.), the appropriate amine (2.0 equiv.), DIPEA (2.0 equiv.), NaBH(OAc)$_3$ (2.0 equiv.) and AcOH (2.0 equiv.) in 1,2-dichloroethane was stirred at RT overnight. The mixture was filtrated through celite, concentrated under reduced pressure and purified by HPLC to give the desired compounds. Compound 99 was obtained as off-white solid in 91-92% yield (last step). LCMS: (M+1) m/z=472. Compound 100 was obtained as pale yellow solid in 62-64% yield (last step). LCMS: (M+1) m/z=472. Compound 101 was obtained as pale yellow solid in 81-83% yield (last step). LCMS: (M+1) m/z=458.

Example 102

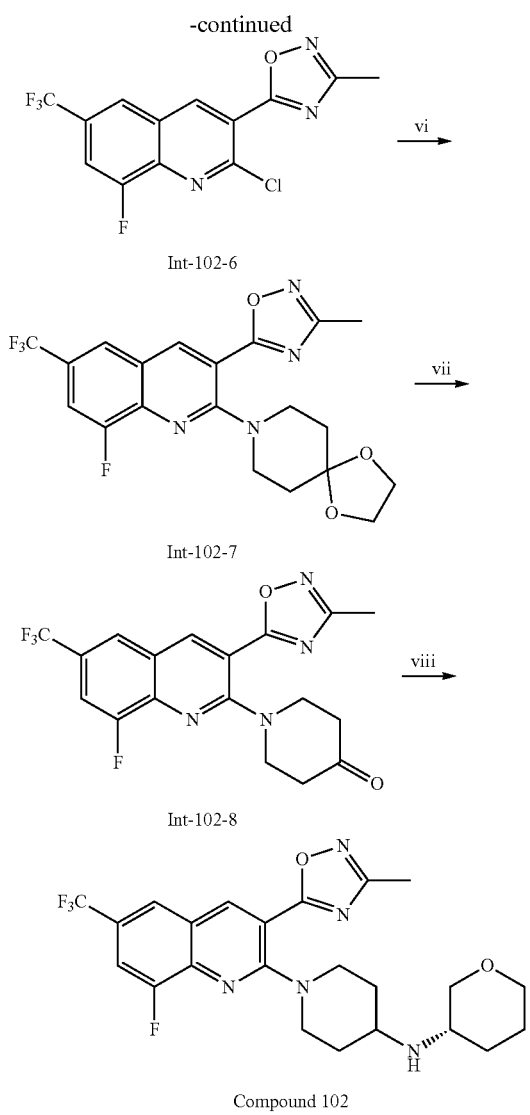

Reagents and conditions: i) Int-102-1 (1.0 equiv.), Br₂ (1.2 equiv.), Fe (15 mol %), NaHCO₃ (1.0 equiv.), CH₂Cl₂, 50° C., overnight, 88%; ii) Int-102-2 (1.0 equiv.), nBuLi (2.2 equiv.), THF, -78° C., 1 h, followed by DMF (2.0 equiv.), -78° C.~0° C., 2 h, 11%; iii) Int-102-3 (1.0 equiv.), ethyl cyanoacetate (2.0 equiv.), NH₄OAc (5.0 equiv.), 1,4-dioxane, 95° C., overnight, 90%; iv) Conc. HCl, 1,4-dioxane, 100° C, 2 h, 83%; v) 5 (1.0 equiv.), POCl₃, 110° C., 2 h, followed by N-hydroxyacetamidine (1.2 equiv.), DIPEA (3.0 equiv.), 1,4-dioxane, 110° C., 1.5 h, 35%; vi) Int-102-6 (1.0 equiv.), 1,4-dioxa-8-azaspiro[4,5]decane (2.0 equiv.), DIPEA (2.0 equiv.), iPrOH, 110° C., overnight, 62%; vii) 10% aq. H₂SO₄, THF, 45° C., 2 h, 90%; viii) Int-102-8 (1.0 equiv.), amine (2.0 equiv.), NaBH(OAc)₃ (3.0 equiv.), AcOH (3.0 equiv.), DIPEA (2.0 equiv.), 1,2-dichloroethane, RT, overnight, 73%-83%.

Synthesis of Int-102-2

To a suspension of aniline Int-102-1 (5.0 g, 27.9 mmol), iron powder (0.23 g, 4.2 mmol, 15 mol %) and NaHCO₃ (2.34 g, 27.9 mmol) in CH₂Cl₂ (100 mL) was added Br₂ (1.73 mL, 33.5 mmol) dropwise. The resulting mixture was refluxed at 50° C. overnight. The mixture was partitioned between 2N NaOH and CH₂Cl₂. The organic layer was separated, dried over Na₂SO₄ and concentrated. The residue was purified by column chromatography (Hexanes/EtOAc gradient) to give Int-102-2 as a yellow solid (6.35 g, 88% yield).

Synthesis of Int-102-3

To a solution of Int-102-2 (6.35 g, 24.6 mmol) in THF (30 mL) was added 2.5 M solution of nBuLi in hexanes dropwise at -78° C. After 1 h of stirring at -78° C., DMF (3.8 mL, 49.2 mmol) was added at the same temperature. The temperature was increased to 0° C. and the mixture was stirred at 0° C. for 2 h. The mixture was then concentrated in vacuo, and the residue was purified by column chromatography (Hexanes/EtOAc gradient) to give Int-102-3 as a yellow solid (0.56 g, 11% yield).

Synthesis of Int-102-4

The mixture of Int-102-3 (560 mg, 2.68 mmol), ethyl cyanoacetate (605 mg, 5.36 mmol) and NH₄OAc (1.03 g, 13.4 mmol) in 1,4-dioxane (5 mL) was stirred and heated at 95° C. overnight. After cooling to room temperature, the mixture was concentrated in vacuo. The residue was partitioned between H₂O and EtOAc. The organic layer was separated, dried over Na₂SO₄ and concentrated to dryness. Product Int-102-4, a pale yellow solid, was used for the next reaction without further purification (620 mg, 90% yield).

Synthesis of Int-102-5

The suspension of compound Int-102-4 (620 mg, 2.41 mmol) in conc. HCl (5 mL) and 1,4-dioxane (5 mL) was heated at 100° C. for 2 h. After cooling to room temperature, H₂O (20 mL) was added. The precipitated product was filtered and dried. Product Int-102-5, a pale yellow powder, was used for the next reaction without further purification (550 mg, 83% yield).

Synthesis of Int-102-6

The mixture of acid Int-102-5 (550 mg, 2.0 mmol) and POCl₃ (5 mL) was heated at 110° C. for 2 h. After cooling to room temperature, the excess POCl₃ was removed in vacuo. The residue was dissolved in 1,4-dioxane (5 mL), and N-hydroxyacetamidine (178 mg, 2.4 mmol) and DIPEA (1.04 mL, 6.0 mmol) were added. The resulting mixture was heated at 110° C. for 1.5 h. After cooling to room temperature, the mixture was concentrated in vacuo. The residue was purified with a short silica gel path using 15% EtOAc in Hexanes to give Int-102-6 as a pale yellow solid (232 mg, 35% yield).

Synthesis of Int-102-7

To a solution of Int-102-6 (184 mg, 0.55 mmol) and DIPEA (0.19 mL, 1.1 mmol) in iPrOH (3 mL) was added 1,4-dioxa-8-azaspiro[4,5]decane (0.14 mL, 1.1 mmol) at room temperature. The mixture was then heated at 110° C. overnight. After cooling to room temperature, the mixture was concentrated and purified by column chromatography (Hexanes/EtOAc gradient) to give Int-102-7 as a yellow solid (150 mg, 62% yield). LCMS: (M+1) m/z=439.

Synthesis of Int-102-8

To a solution of Int-102-7 (150 mg, 0.34 mmol) in THF (2 mL) was added 10% aq. H₂SO₄ (4 mL) at room temperature. The mixture was then stirred at 45° C. for 2 h. After cooling to room temperature, the mixture was neutralized with sat. aq. Na₂CO₃ and extracted with EtOAc (×2). The combined organic layers were dried over Na₂SO₄ and concentrated in vacuo. The residue was purified by column chromatography (Hexanes/EtOAc gradient) to give Int-102-8 as a yellow oil (128 mg, 90% yield). LCMS: (M+1) m/z=395.

Synthesis of Compound 102

A mixture of Int-102-8 (9.0 mg, 0.023 mmol), (S)-3-aminotetrahydropyran (6.3 mg, 0.046 mmol) and DIPEA (8 µL, 0.046 mmol) in 1,2-dichloroethane (1.5 mL) was stirred at room temperature for 10 min. To the mixture, NaBH(OAc)₃ (14.5 mg, 0.069 mmol) and AcOH (4 µL, 0.069 mmol) were added. The resulting mixture was stirred at room temperature overnight. After filtration through Celite, the filtrate was concentrated in vacuo. The reside was purified by HPLC (10-95% ACN in H₂O for 12 min) to give Compound 102 as a pale yellow solid (8.0 mg, 73% yield). LCMS: (M+1) m/z=480.

Example 103

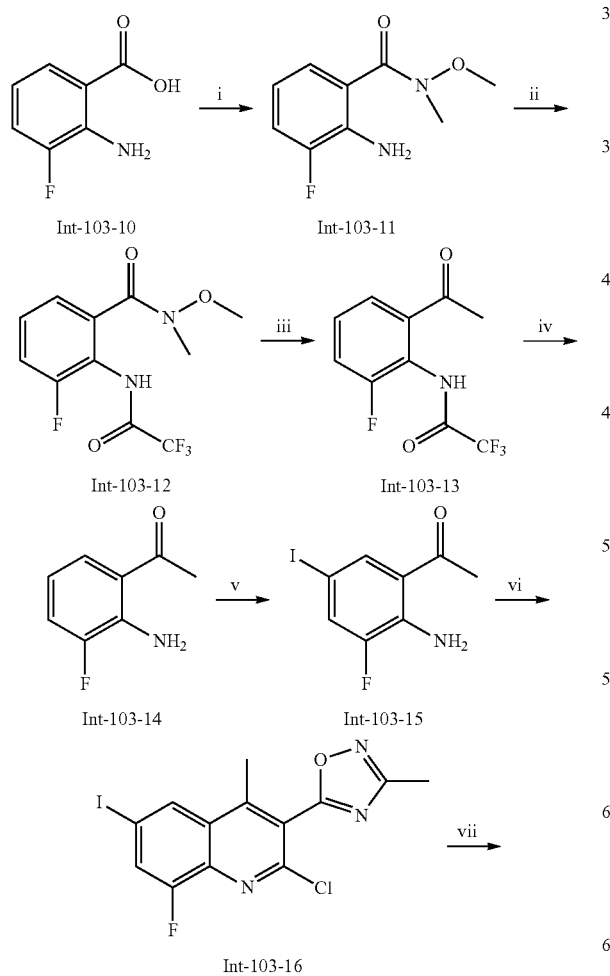

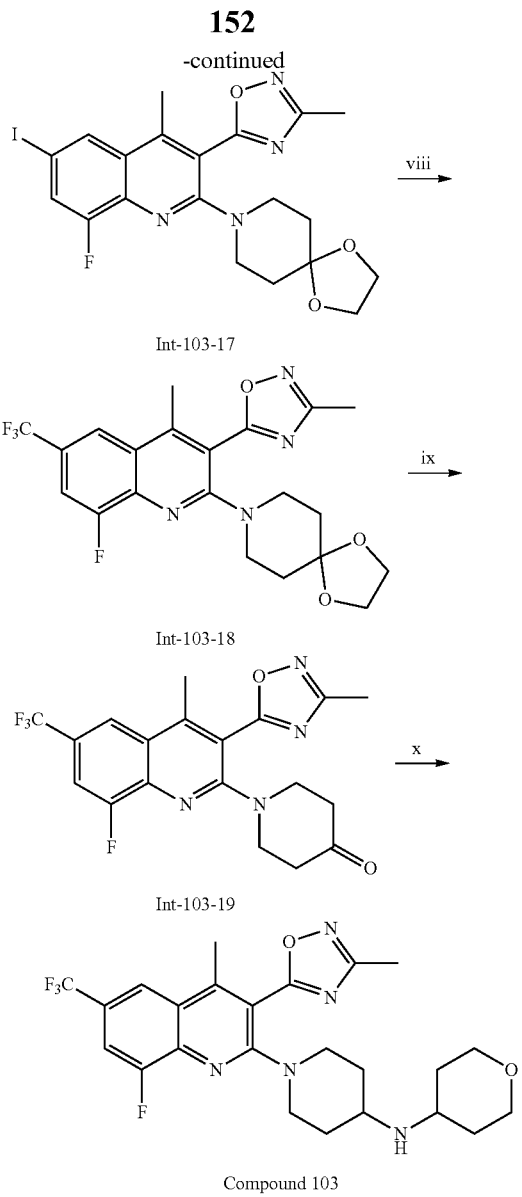

Reagents and conditions: i) Int-103-10 (1.0 equiv.), N,O-dimethylhydroxylamine HCl (1.8 equiv.), EDCI (1.2 equiv.), HOBt (1.2 equiv.), DIPEA (2.0 equiv.), DMF, RT, 18 h, 80%; ii) Int-103-11 (1.0 equiv.), (CF₃CO)₂O (1.2 equiv.), TEA (1.2 equiv.), DCM, 0° C.-RT, 5 h, 93%; iii) 12 (1.0 equiv.), MeMgBr (4.0 equiv.), THF, RT, 6 h, 76%; iv) Int-103-13 (1.0 equiv.), 2N NaOH (1.7 equiv), MeOH, 90° C., 1.5 h, 99%; v) Int-103-14 (1.0 equiv.), PyICl (1.0 equiv.), MeOH, 100° C., 18 h, 79%; vi) Int-103-15 (1.0 equiv.), oxadiazole acid (1.2 equiv.), POCl₃, 110° C., 1 h; vii) Int-103-16 (1.0 equiv.), 1,4-dioxa-8-azaspiro[4,5]decane (1.2 equiv.), DIPEA (1.2 equiv.), EtOH, 120° C., 18 h, 22% over two steps; viii) Int-103-17 (1.0 equiv.), FO₂SCF₂CO₂Me (5.0 equiv.), CuI (2.0 equiv.), DMF, 8%; ix) 10% aq. H₂SO₄, THF, 50° C., 1.5 h, qantitative yield; x) Int-103-19 (1.0 equiv.), amine (2.0 equiv.), NaBH(OAc)₃ (3.0 equiv.), AcOH (3.0 equiv.), DIPEA (2.0 equiv.), 1,2-dichloroethane, RT, 18 h, 82%.

Synthesis of Int-103-11

A mixture of 2-amino-3-fluorobenzoic acid 10 (10.3 g, 66.4 mmol), N,O-dimethylhydroxyl amine HCl (11.7 g, 119.5 mmol), EDCl (15.3 g, 79.7 mmol), HOBt (12.2 g, 79.7 mmol) and DIPEA (23 mL, 132.8 mmol) in DMF (166 mL) was stirred at room temperature overnight. The mixture was diluted with EtOAc and washed with 1N NaOH, 10% aq. HCl and brine sequentially. The organic layer was dried over Na₂SO₄ and concentrated to dryness. Product Int-103-11 as a brown oil was used for the next reaction without further purification (10.48 g, 80% yield).

Synthesis of Int-103-12

To a solution of Int-103-11 (10.48 g, 52.9 mmol) and TEA (8.8 mL, 63.4 mmol) in $CH_2Cl_2$ (200 mL) was added $(CF_3CO)_2O$ (8.8 mL, 63.4 mmol) at 0° C. The resulting mixture was stirred at room temperature for 5 h. The mixture was then washed with sat. aq. $NaHCO_3$ and brine. The organic layer was dried over $Na_2SO_4$ and concentrated to dryness. Product Int-103-12 as a brown solid was used for the next reaction without further purification (14.47 g, 93% yield). LCMS: (M+1) m/z=295.

Synthesis of Int-103-13

To a solution of Int-103-12 (14.47 g, 49.2 mmol) in anhydrous THF (200 mL) was added 3M solution of MeMgBr in diethyl ether (66 mL, 196.7 mmol) at 0° C. The mixture was stirred at room temperature for 6 h. The mixture was then poured into crushed ice to quench the reaction, and extracted with EtOAc. The organic layer was washed with 10% aq. HCl and brine, dried over $Na_2SO_4$ and concentrated to dryness. Product Int-103-13 as a brown oil was used for the next reaction without further purification (9.36 g, 76% yield).

Synthesis of Int-103-14

To a solution of Int-103-13 (9.36 g, 37.5 mmol) in MeOH (32 mL) was added 2N NaOH at room temperature. The mixture was then heated at 90° C. for 1.5 h. After cooling to room temperature, the mixture was partitioned between brine and $CH_2Cl_2$. The aqueous layer was extracted with $CH_2Cl_2$. The combined organic extracts were dried over $Na_2SO_4$ and concentrated to dryness. Product Int-103-14 as a dark brown oil was used for the next reaction without further purification (5.70 g, 99% yield).

Synthesis of Int-103-15

A mixture of Int-103-14 (5.7 g, 37.2 mmol) and PyICl (9.0 g, 37.2 mmol) in MeOH (125 mL) was heated at 100° C. overnight. After cooling to room temperature, the mixture was concentrated in vacuo. The residue was purified by column chromatography (Hexanes/EtOAc gradient) to give Int-103-15 as a yellow solid (7.91 g, 76% yield). LCMS: (M+1) m/z=280.

Synthesis of Int-103-16

A mixture of Int-103-15 (2.20 g, 7.9 mmol), oxadiazole acid (1.34 g, 9.5 mmol) and $POCl_3$ (10 mL) was stirred at 110° C. for 1 h. After cooling to room temperature, excess $POCl_3$ was removed in vacuo. The residue was partitioned between $H_2O$ and $CH_2Cl_2$. The organic layer was separated, washed with sat. aq. $NaHCO_3$, dried over $Na_2SO_4$ and concentrated. Residue Int-103-16 was used for the next reaction without further purification.

Synthesis of Int-103-17

To a slurry of crude Int-103-16 (2.70 g, 6.7 mmol) and DIPEA (1.4 mL, 8.0 mmol) in EtOH (50 mL) was added 1,4-dioxa-8-azaspiro[4,5]decane (1.0 mL, 8.0 mmol) at room temperature. The mixture was then heated at 120° C. overnight. After cooling to room temperature, the mixture was concentrated in vacuo, and the residue was purified by column chromatography (Hexanes/EtOAc gradient) to give Int-103-17 as a brown solid (0.75 g, 22% yield over two steps). LCMS: (M+1) m/z=511.

Synthesis of Int-103-18

To a slurry of 17 (200 mg, 0.39 mmol) and CuI (148 mg, 0.78 mmol) in DMF (4 mL) was added methyl fluorosulfonyldifluoroacetate (0.24 mL, 1.95 mmol) at room temperature. The mixture was then heated at 80° C. for 1 h. After filtration through Celite, the filtrate was concentrated. The residue was purified by HPLC (50-95% ACN in $H_2O$ for 15 min) to give Int-103-18 as an orange solid (14.8 mg, 8% yield). LCMS: (M+1) m/z=453.

Synthesis of Int-103-19

To a solution of Int-103-18 (14.8 g, 0.033 mmol) in THF (1 mL) was added 10% aq. $H_2SO_4$ (2 mL) at room temperature. The mixture was then stirred at 50° C. for 1.5 h. After cooling to room temperature, the mixture was neutralized with sat. aq. $Na_2CO_3$ and extracted with EtOAc (×2). The combined organic layers were dried over $Na_2SO_4$ and concentrated to dryness. The ketone Int-103-19 as a yellow solid was used for the next reaction without further purification. (13.3 mg, quantitative yield). LCMS: (M+1) m/z=409.

Synthesis of Compound 103

A mixture of Int-103-19 (13.3 mg, 0.033 mmol), 4-aminotetrahydropyran (6.6 mg, 0.066 mmol) and DIPEA (11 μL, 0.066 mmol) in 1,2-dichloroethane (1.5 mL) was stirred at RT for 10 min. To the mixture, $NaBH(OAc)_3$ (20.8 mg, 0.099 mmol) and AcOH (6 μL, 0.099 mmol) were added. The resulting mixture was stirred at room temperature overnight. After filtration through Celite, the filtrate was concentrated in vacuo. The reside was purified by HPLC (10-95% ACN in $H_2O$ for 12 min) to give Compound 103 as a pale orange solid (13.2 mg, 82% yield). LCMS: (M+1) m/z=494.

Examples 104-107

Compounds 104-107 were obtained according to the procedure disclosed above for Compound 103. Compound 104 was obtained as pale yellow solid in quantitative yield (last step). LCMS: (M+1) m/z=494. Compound 105 was obtained as pale yellow solid in quantitative yield (last step). LCMS: (M+1) m/z=494. Compound 106 was obtained as pale yellow solid in 97% yield (last step). LCMS: (M+1) m/z=480. Compound 107 was obtained as pale yellow solid in 84% yield (last step). LCMS: (M+1) m/z=480.

Examples 108-109

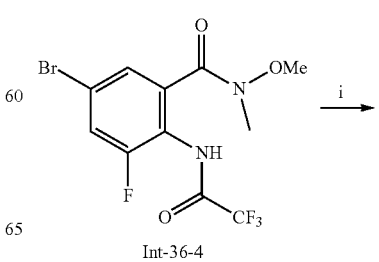

Int-36-4

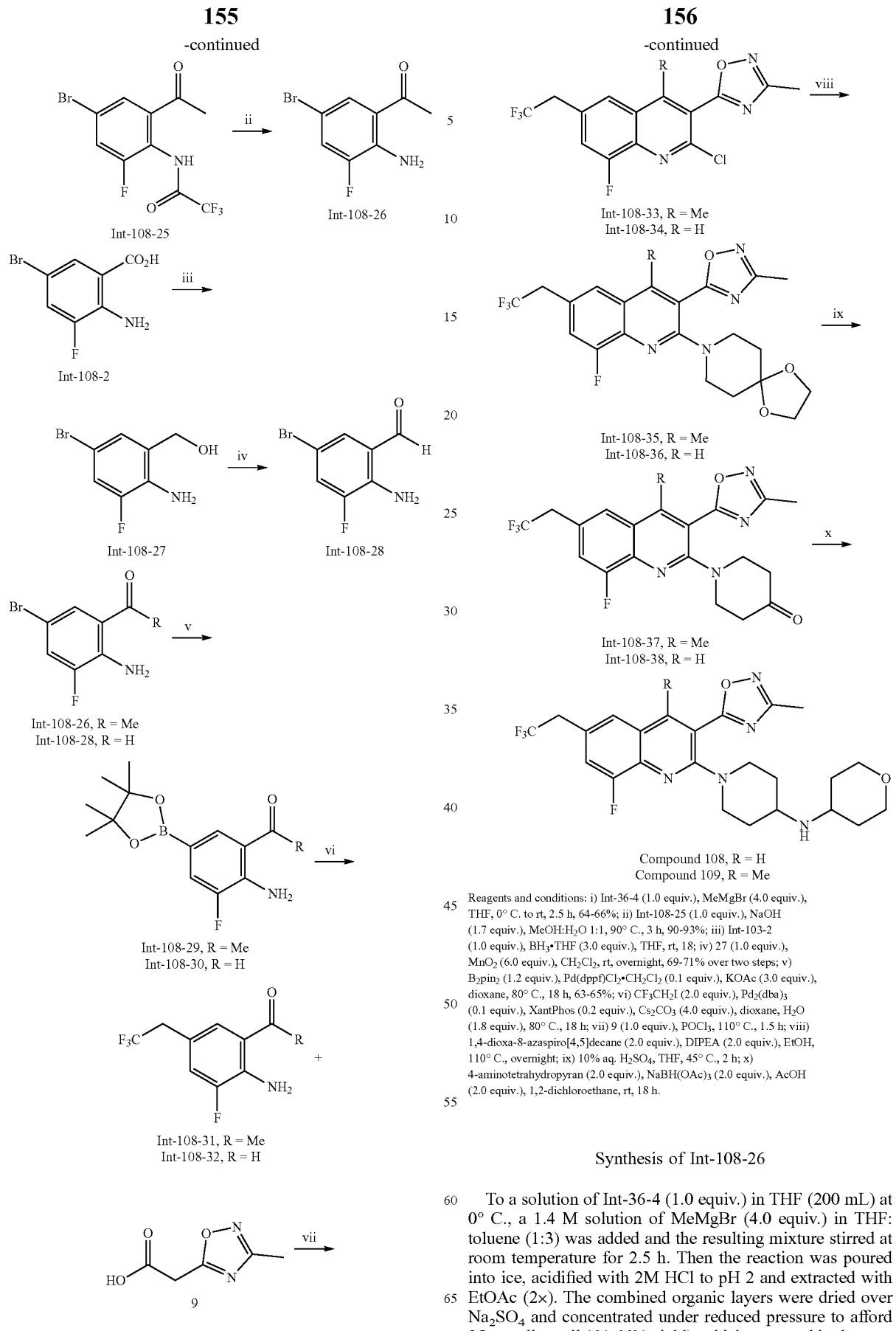

Reagents and conditions: i) Int-36-4 (1.0 equiv.), MeMgBr (4.0 equiv.), THF, 0° C. to rt, 2.5 h, 64-66%; ii) Int-108-25 (1.0 equiv.), NaOH (1.7 equiv.), MeOH:H$_2$O 1:1, 90° C., 3 h, 90-93%; iii) Int-103-2 (1.0 equiv.), BH$_3$•THF (3.0 equiv.), THF, rt, 18; iv) 27 (1.0 equiv.), MnO$_2$ (6.0 equiv.), CH$_2$Cl$_2$, rt, overnight, 69-71% over two steps; v) B$_2$pin$_2$ (1.2 equiv.), Pd(dppf)Cl$_2$•CH$_2$Cl$_2$ (0.1 equiv.), KOAc (3.0 equiv.), dioxane, 80° C., 18 h, 63-65%; vi) CF$_3$CH$_2$I (2.0 equiv.), Pd$_2$(dba)$_3$ (0.1 equiv.), XantPhos (0.2 equiv.), Cs$_2$CO$_3$ (4.0 equiv.), dioxane, H$_2$O (1.8 equiv.), 80° C., 18 h; vii) 9 (1.0 equiv.), POCl$_3$, 110° C., 1.5 h; viii) 1,4-dioxa-8-azaspiro[4,5]decane (2.0 equiv.), DIPEA (2.0 equiv.), EtOH, 110° C., overnight; ix) 10% aq. H$_2$SO$_4$, THF, 45° C., 2 h; x) 4-aminotetrahydropyran (2.0 equiv.), NaBH(OAc)$_3$ (2.0 equiv.), AcOH (2.0 equiv.), 1,2-dichloroethane, rt, 18 h.

Synthesis of Int-108-26

To a solution of Int-36-4 (1.0 equiv.) in THF (200 mL) at 0° C., a 1.4 M solution of MeMgBr (4.0 equiv.) in THF:toluene (1:3) was added and the resulting mixture stirred at room temperature for 2.5 h. Then the reaction was poured into ice, acidified with 2M HCl to pH 2 and extracted with EtOAc (2×). The combined organic layers were dried over Na$_2$SO$_4$ and concentrated under reduced pressure to afford 25 as yellow oil (64-66% yield), which was used in the next step without further purification. LCMS: (M−1) m/z=325, 327. To a solution of Int-108-25 (1.0 equiv.) in MeOH was added a 2 M aq. solution of NaOH (1.7 equiv.) and the reaction was heated at 90° C. for 3 h. The reaction mixture was diluted with water and the solid collected by filtration to obtain Int-108-26 as a yellow solid (90-93% yield), which was used in the next step without further purification LCMS: (M+1) m/z=231, 233.

Synthesis of Int-108-28

To a solution of Int-108-2 (1.0 equiv.) in THF (60 mL) was added dropwise a solution of BH$_3$·THF complex (3.0 equiv.) at 0° C. The mixture was then stirred at room temperature 18 h. The reaction was quenched with MeOH at 0° C., concentrated, resuspended in EtOAc and washed with sat. aq. NaHCO$_3$ solution. The organic phase was dried over Na$_2$SO$_4$ and concentrated to afford the alcohol Int-108-27, which was used in the next step without further purification. LCMS: (M+1) m/z=219, 221. To a solution of alcohol 27 in CH$_2$Cl$_2$ was slowly added activated MnO$_2$ (6.0 equiv.) and the mixture was stirred at room temperature overnight. The mixture was filtered through celite and the solvent removed under reduced pressure to obtain aldehyde Int-108-28 as a yellow solid (69-71% yield over two steps), which was used in the next step without further purification. LCMS: (M+23) m/z=239, 241.

Synthesis of Int-108-29 and Int-108-30

A mixture of Int-108-28 (1.0 equiv.), bis(pinacolato) diboron (1.2 equiv.), Pd(dppf)Cl$_2$·CH$_2$Cl$_2$ (0.1 equiv.) and KOAc (3.0 equiv.) in dioxane was heated at 80° C. for 18 h. The mixture was cooled to room temperature, filtered through celite, concentrated under reduced pressure and purified by column chromatography (Hexanes/EtOAc) to give boronate Int-108-30 as an off-white solid (63-65% yield). LCMS: (M+1) m/z=266.

Boronate Int-108-29 was obtained using the same reactions conditions as a grey solid in 93-95% yield. LCMS: (M+1) m/z=280.

Synthesis of Int-108-31 and Int-108-32

To a suspension of Pd$_2$(dba)$_3$ (0.1 equiv.), XantPhos (0.2 equiv.) and Cs$_2$CO$_3$ (4.0 equiv.) in dioxane in a sealed vial was added a solution of boronate Int-108-30 (1.0 equiv.) and CF$_3$CH$_2$I (2.0 equiv.) in dioxane. The reaction mixture was stirred at room temperature for 1 minute, then H$_2$O (1.8 equiv.) was added. The mixture was stirred at 80° C. for 18 h. After cooling, the reaction mixture was diluted with EtOAc and washed with water and brine. The organic layer was dried over Na$_2$SO$_4$, concentrated and purified by column chromatography (Hexanes/EtOAc) to give Int-108-32 as an orange solid (95-97% yield). LCMS: (M+1) m/z=222.

Ketone Int-108-31 was obtained in a similar manner as a pale yellow solid in 77-79% yield. LCMS: (M+1) m/z=236.

Synthesis of Int-108-33 and Int-108-34

A mixture of aldehyde Int-108-32 (1.0 equiv.), acid Int-108-9 (1.0 equiv.) and POCl$_3$ was stirred at 110° C. for 1.5 h. The excess POCl$_3$ was removed under reduced pressure. The residue was resuspended in a sat. aq. NaHCO$_3$ solution and extracted with EtOAc (2×). The combined organic layers were dried over Na$_2$SO$_4$ and concentrated to dryness. The crude product was purified by column chromatography (Hexanes/EtOAc) to yield quinoline Int-108-34 as a white solid (15-17% yield). LCMS: (M+1) m/z=346.

Quinoline Int-108-33 was obtained in a similar manner as a pale grey solid in 28-30% yield. LCMS: (M+1) m/z=360

Synthesis of Int-108-35 and Int-108-36

A mixture of Int-108-34 (1.0 equiv.), 1,4-dioxa-8-azaspiro [4,5]decane (2.0 equiv.) and DIPEA (2.0 equiv.) was heated at 110° C. overnight. After cooling to room temperature, the mixture was concentrated under reduced pressure and purified by column chromatography (Hexanes/EtOAc) to give ketal 36 as yellow solid (61-64% yield). LCMS: (M+1) m/z=453.

Ketal Int-108-35 was obtained in a similar manner as a pale yellow solid in 84-86% yield. LCMS: (M+1) m/z=467.

Synthesis of Int-108-37 and Int-108-38

To a solution of ketal Int-108-36 (1.0 equiv.) in THF was added 10% aq. H$_2$SO$_4$. The mixture was stirred at 45° C. for 2 h. After cooling to room temperature, the mixture was neutralized with sat. aq. Na$_2$CO$_3$ and extracted with EtOAc (2×). The combined organic layers were dried over Na$_2$SO$_4$, concentrated and purified by preparative-TLC (hexanes: EtOAc 7:3) to give ketone Int-108-38 as a yellow solid (54-56% yield), which was used in the next step without further purification LCMS: (M+1) m/z=409.

Ketone Int-108-37 was obtained in a similar manner as a pale yellow solid in 88-90% yield. LCMS: (M+1) m/z=423

Synthesis of Compound 108 and Compound 109

A mixture of ketone Int-108-38 (1.0 equiv.), 4-aminotetrahydropyran (2.0 equiv.), NaBH(OAc)$_3$ (2.0 equiv.) and AcOH (2.0 equiv.) in 1,2-dichloroethane was stirred at room temperature for 18 h. The mixture was concentrated under reduced pressure and purified by preparative-TLC (EtOAc: $^i$PrOH, 95:5) to give Compound 108 as a yellow solid (19-21% yield). LCMS: (M+1) m/z=494.

Compound 109 was obtained following the same procedure as a yellow solid in 22-24% yield. LCMS: (M+1) m/z=508.

Example 110

Compound 110 was obtained according to the procedure for Compound 109 starting from ketone Int-108-37 and corresponding amine, as pale yellow solid in 49-51% yield. LCMS: (M+1) m/z=508.

Examples 111-115

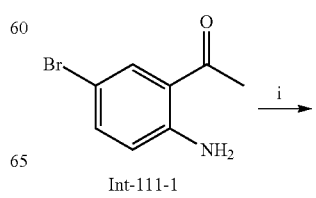

Int-111-1

-continued

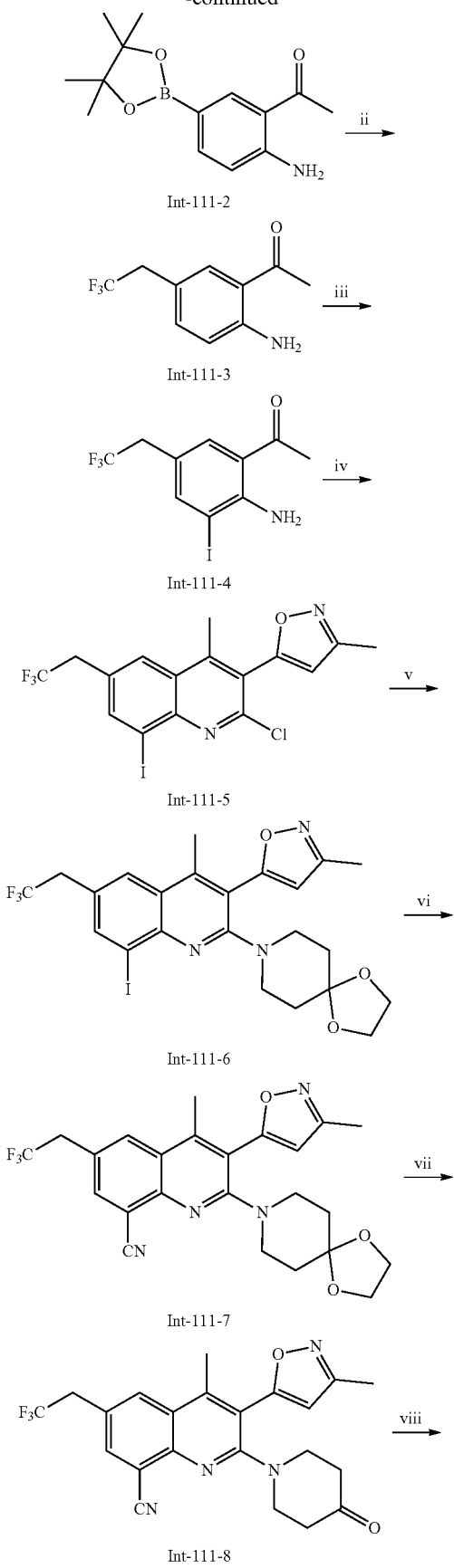

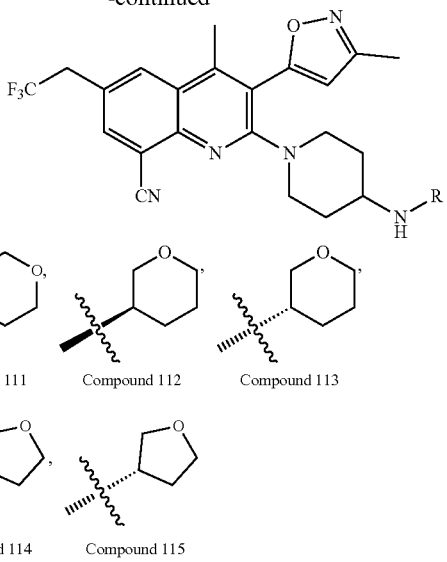

Reagents and conditions: i) Int-111-1 (1.0 equiv.), B₂pin₂ (1.2 equiv.), Pd(dppf)Cl₂—CH₂Cl₂ (0.03 equiv.), KOAc (3.0 equiv.), 1,4-dioxane, 90° C., overnight, 55% ii) Int-111-2 (1.0 equiv.), CF₃CH₂I (2.0 equiv.), Pd₂(dba)₂ (0.1 equv.), XantPhos (0.1 equiv.), Cs₂CO₃ (4 equiv.), H₂O (2.0 equiv.), 1,4-dioxane, 80° C., overnight, 78% iii) Int-111-3 (1.0 equiv.), PyICl (1.05 equiv.), MeOH, 90° C., overnight, 67%; iv) 4 (1.0 equiv.), oxadiazole acid (1.2 equiv.), POCl₃, 110° C., 1 h; v) Int-111-5 (1.0 equiv.), 1,4-dioxa-8-azaspiro[4,5]decane (1.2 equiv.), DIPEA (2.0 equiv.), EtOH, 120° C., overnight, 26% (over two steps); vi) Int-111-6 (1.0 equiv.), Zn(CN)₂ (1.0 equiv.), Zn (0.1 equiv.), Pd(PPh₃)₄ (0.1 equiv.), THF/DMF, 80° C., overnight, 84%; vii) 10% aq. H₂SO₄, THF, 50° C., 2 h, quantitative yield; viii) Int-111-8 (1.0 equiv.), amine (2.0 equiv.), NaBH(OAc)₃ (3.0 equiv.), AcOH (3.0 equiv.), DIPEA (2.0 equiv.), 1,2-dichloroethane, RT, overnight, 89%~quantitative yield.

Synthesis of Int-111-2

A mixture of Int-111-1 (6.42 g, 30.0 mmol), Bis(pinacolato)diboron (9.14 g, 36.0 mmol), [1,1'-Bis(diphenylphosphino)ferrocene]dichloropalladium(II) CH₂Cl₂ (0.73 g, 0.9 mmol) and KOAc (8.82 g, 90.0 mmol) in 1,4-dioxane (30 mL) was stirred at 90° C. overnight. After cooling to room temperature, the mixture was filtered and the filtrate was concentrated under reduced pressure. The residue was purified by column chromatography (Hexanes/EtOAc gradient) to give Int-111-2 as a pale yellow solid (4.31 g, 55% yield).

Synthesis of Int-111-3

A mixture of Int-111-2 (1.70 g, 6.51 mmol), Pd₂(dba)₂ (0.62 g, 0.65 mmol), XantPhos (0.38 g, 0.65 mmol), Cs₂CO₃ (8.50 g, 26.04 mmol) and CF₃CH₂I (1.3 mL, 13.02 mmol) in 1,4-dioxane (32 mL) was stirred at room temperature for 1 min. To this, H₂O (0.23 mL, 13.02 mmol) was added, and the resulting mixture was stirred at 80° C. overnight in a sealed vessel. After cooling to room temperature, the mixture was filtered through Celite and the filtrate was concentrated under reduced pressure. The residue was purified by column chromatography (Hexanes/EtOAc gradient) to give Int-111-3 as a yellow solid (1.11 g, 78% yield). LCMS: (M+1) m/z=218.

Synthesis of Int-111-4

A mixture of Int-111-3 (1.11 g, 5.11 mmol) and PyICl[1] (1.30 g, 5.36 mmol) in MeOH (20 mL) was stirred at 90° C.

overnight. After cooling to room temperature, the mixture was concentrated under reduced pressure. The residue was purified by column chromatography (Hexanes/EtOAc gradient) to give Int-111-4 as a yellow solid (1.17 g, 67% yield). LCMS: (M+1) m/z=344.

Synthesis of Int-111-5

A mixture of Int-111-4 (1.17 g, 3.41 mmol), oxadiazole acid (0.58 g, 4.09 mmol) and POCl₃ (7 mL) was stirred at 110° C. for 1 h. After cooling to room temperature, excess POCl₃ was removed under the reduced pressure. To the residue, H₂O was added at 0° C., and the mixture was stirred at 0° C. for 10 min. The precipitated crude chloroquinoline 5 was filtered, washed with H₂O and dried under the reduced pressure. The crude product Int-111-5 was used for the next reaction without further purification.

Synthesis of Int-111-6

To a suspension of crude chloroquinoline Int-111-5 (1.59 g, 3.41 mmol) and DIPEA (1.2 mL, 6.82 mmol) in EtOH was added 1,4-dioxa-8-azaspiro[4,5]decane (4.09 mL, 7.9 mmol) at room temperature. The mixture was then stirred at 120° C. overnight. After cooling to room temperature, the mixture was concentrated and purified by column chromatography (Hexanes/EtOAc gradient) to give Int-111-6 as a dark brown foam (513 mg, 26% yield over two steps). LCMS: (M+1) m/z=575.

Synthesis of Int-111-7

A mixture of Int-111-6 (513 mg, 0.89 mmol), Zn(CN)₂ (105 mg, 0.89 mmol), Zn (6 mg, 0.09 mmol) and Pd(PPh₃)₄ (103 mg, 0.09 mmol) in THF/DMF (12 mL, 1:1, v/v) was stirred at 80° C. overnight. After cooling to room temperature, the mixture was filtered and the filtrate was concentrated under reduced pressure. The residue was purified by column chromatography (Hexanes/EtOAc gradient) to give Int-111-7 as a yellow solid (356 mg, 84% yield). LCMS: (M+1) m/z=474.

Synthesis of Int-111-8

To a solution of Int-111-7 (356 mg, 0.75 mmol) in THF (3 mL) was added 10% aq. H₂SO₄ (6 mL) at room temperature. The mixture was then stirred at 50° C. for 2 h. After cooling to room temperature, the mixture was neutralized with sat. aq. Na₂CO₃ and extracted with EtOAc (×2). The combined organic extracts were dried over Na₂SO₄ and concentrated to dryness. The ketone Int-111-8 as a yellow solid was used for the next reaction without further purification. (322 mg, quantitative yield). LCMS: (M+1) m/z=430.

Synthesis of Compound 111, Compound 112, Compound 113, Compound 114, Compound 115

A mixture of Int-111-8 (11 mg, 0.026 mmol), the appropriate amine (0.052 mmol) and DIPEA (9 μL, 0.052 mmol) in 1,2-dichloroethane (1.5 mL) was stirred at room temperature for 10 min. To the mixture, NaBH(OAc)₃ (16.3 mg, 0.078 mmol) and AcOH (5 μL, 0.078 mmol) were added. The resulting mixture was stirred at room temperature overnight. After filtration through Celite, the filtrate was concentrated under reduced pressure. The reside was purified by HPLC (10-95% ACN in H₂O for 12 min) to give the title compounds: Compound 111, 11.8 mg, yellow solid, 89% yield. LCMS: (M+1) m/z=515; Compound 112, 13.2 mg, yellow solid, 89% yield. LCMS: (M+1) m/z=515; Compound 113, 13.2 mg, yellow solid, 89% yield. LCMS: (M+1) m/z=515; Compound 114, 12.8 mg, yellow solid, 89% yield. LCMS: (M+1) m/z=501; and Compound 115, 12.8 mg, yellow solid, 89% yield. LCMS: (M+1) m/z=501.

Examples 116-117

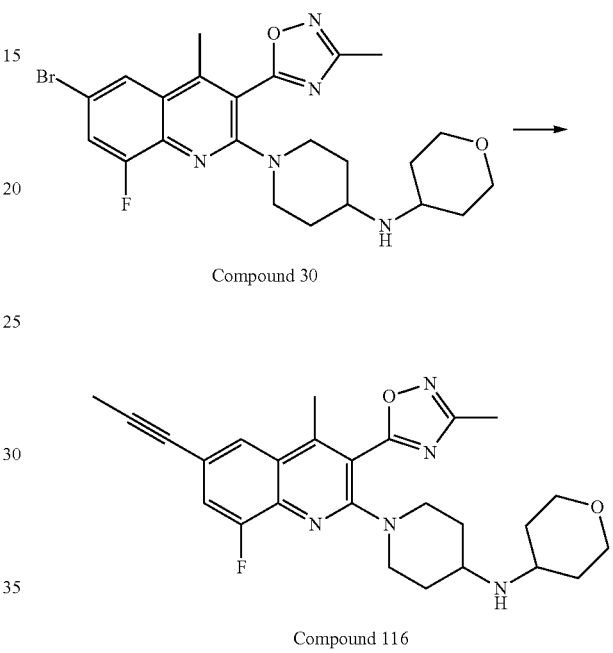

Compound 30

Compound 116

Synthesis of Compound 116

To a solution of Compound 30 (30 mg, 0.060 mmol) and tributyl(prop-1-yn-1-yl)stannane (78 mg, 0.24 mmol) in 1,4-dioxane (1.5 mL) was added bis(triphenylphosphine) palladium(II) chloride (3.3 mg, 4.8 μmol), and the reaction was microwaved under nitrogen at 100° C. for 45 min. The mixture was filtered, and the solution was concentrated under reduced pressure. The residue was purified by prep-HPLC to yield Compound 16 (5.0 mg, 18% yield) as white solid. LCMS: (M+1) m/z=464; Retention time: 2.50 min (Method 1).

Synthesis of Compound 117

Preparation of Compound 117 was the same as Compound 116 except replacing 1-(6-bromo-8-fluoro-4-methyl-3-(3-methyl-1,2,4-oxadiazol-5-yl)quinolin-2-yl)-N-(tetrahydro-2H-pyran-4-yl)piperidin-4-amine Compound 30 with (R)-1-(6-bromo-8-fluoro-4-methyl-3-(3-methyl-1,2,4-oxadiazol-5-yl)quinolin-2-yl)-N-(tetrahydro-2H-pyran-3-yl)piperidin-4-amine. LCMS: (M+1) m/z=464; Retention time: 2.55 min (Method 1).

Example 118

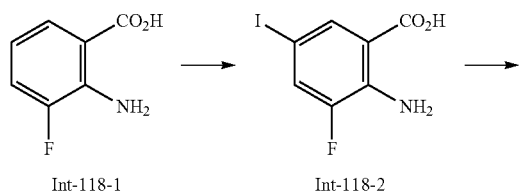

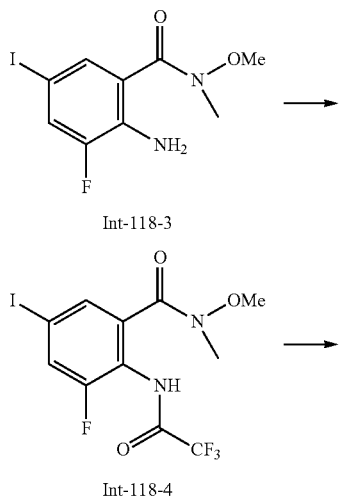

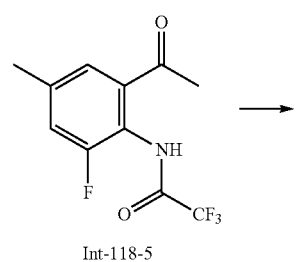

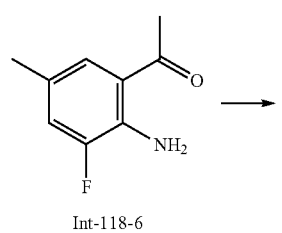

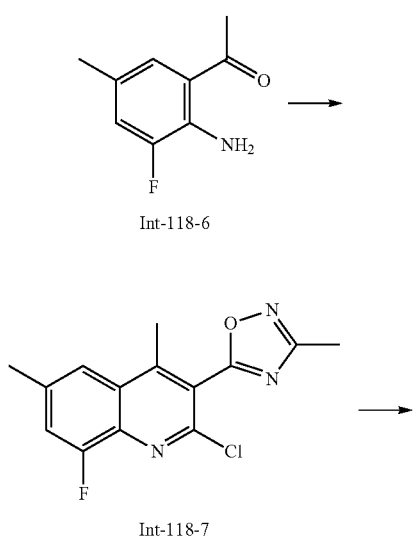

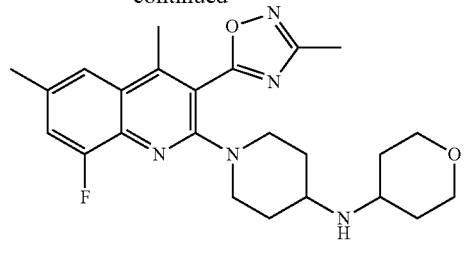

Compound 118

Reagents and conditions: i) Int-118-14 (1.0 equiv.), NBS (1.0 equiv.), CH$_2$Cl$_2$, rt, 18 h, 84-86%; ii) Int-118-15 (1.0 equiv.), (MeO)NH(Me)•HCl (1.8 equiv.), EDCI (1.2 equiv.), HOBt (1.2 equiv.), DIPEA (2.0 equiv.), DMF, rt, 4 h, 84-86%; iii) Int-118-16 (1.0 equiv.), (CF$_3$CO)$_2$O (1.3 equiv.), TEA (1.2 equiv.), CH$_2$Cl$_2$, 0° C. to rt, overnight, 90-92%; iv) Int-118-17 (1.0 equiv.), BEt$_3$ (3.0 equiv.), Cs$_2$CO$_3$ (3.0 equiv.), Pd(dppf)Cl$_2$ (0.02 equiv.), THF, 70° C., 1.5 h 45-47%; v) Int-118-18 (1.0 equiv.), MeMgBr (5.0 equiv.), THF, 0° C. to rt, 2.5 h, 85-87%; vi) Int-118-19 (1.0 equiv.), NaOH (1.7 equiv.), MeOH:H$_2$o 1:1, 90° C., 3 h, 80-82%; vii) Int-118-20 (1.0 equiv.), 8 (2.0 equiv.), p-TsOH (cat), 150° C., 2 h, 19-21%; viii) 21, POCl$_3$, 110° C., 2 h, 97-98%; ix) Int-118-22 (1.0 equiv.), 1,4-dioxa-8-azaspiro[4,5]decane (2.0 equiv.), DIPEA (2.0 equiv.), EtOH, 110° C., overnight, 73-75%; x) 10% aq. H$_2$SO$_4$, THF, 45° C., 2 h, 83-85%; xi) Int-118-24 (1.0 equiv.), 4-aminotetrahydropyran (1.5 equiv.), NaBH(OAc)$_3$ (2.0 equiv.), AcOH (2.0 equiv.), 1,2-dichloroethane, rt, overnight, 89-90%.

Synthesis of Int-118-2

To a suspension of 2-amino-3-fluorobenzoic acid Int-118-1 (15.0 g, 96.7 mmol) in CH$_2$Cl$_2$ (250 mL) was added N-iodosuccinimide (17.2 g, 96.7 mmol), and the mixture was stirred at room temperature overnight. The product was filtered, washed with CH$_2$Cl$_2$ and dried under the reduced pressure to give Int-118-2 as a pale brown solid (24.7 g, 91% yield).

Synthesis of Int-118-3

A mixture of Int-118-2 (6.2 g, 22.06 mmol), N,O-dimethylhydroxyl amine HCl (3.9 g, 39.71 mmol), EDCI (5.1 g, 26.47 mmol), HOBt (4.1 g, 26.47 mmol) and DIPEA (7.7 mL, 44.12 mmol) in DMF (110 mL) was stirred at room temperature overnight. The mixture was diluted with EtOAc and washed with 1N NaOH, 10% aq. HCl and brine sequentially. The organic layer was dried over Na$_2$SO$_4$ and concentrated to dryness. Product Int-118-3 as a brown oil was used for the next reaction without further purification (6.9 g, 96% yield).

Synthesis of Int-118-4

To a solution of Int-118-3 (6.9 g, 21.3 mmol) and TEA (3.6 mL, 25.6 mmol) in CH$_2$Cl$_2$ (70 mL) was added (CF$_3$CO)$_2$O (3.9 mL, 27.7 mmol) at 0° C. The resulting mixture was stirred at room temperature overnight. The mixture was then washed with sat. aq. NaHCO$_3$ and brine. The organic layer was dried over Na$_2$SO$_4$ and concentrated to dryness. Product Int-118-4 as dark brown oil was used for the next reaction without further purification (8.8 g, 98% yield). LCMS: (M+1) m/z=421.

Synthesis of Int-118-5

To a solution of Int-118-4 (4.47 g, 10.6 mmol) in anhydrous THF (100 mL) was added 1.4M solution of MeMgBr in diethyl ether (42 mL, 59.4 mmol) at 0° C. The mixture was stirred at room temperature for 18 h. The mixture was then poured into crushed ice to quench the reaction, and extracted with EtOAc. The organic layer was washed with 10% aq. HCl and brine, dried over $Na_2SO_4$ and concentrated to dryness. Product Int-118-5 as a dark orange oil was used for the next reaction without further purification (1.68 g, 60% yield).

Synthesis of Int-118-6

To a solution of Int-118-5 (1.22 g, 4.63 mmol) in MeOH (7 mL) was added 2N NaOH (4 mL) at room temperature. The mixture was then heated at 90° C. for 1.5 h. After cooling to room temperature, the mixture was partitioned between $CH_2Cl_2$ and brine. The aqueous layer was extracted with $CH_2Cl_2$. The combined organic extracts were dried over $Na_2SO_4$ and concentrated to dryness. Product Int-118-6 as a yellow solid was used for the next reaction without further purification (0.73 g, 94% yield).

Synthesis of Int-118-7

A mixture of Int-118-6 (371 mg, 2.22 mmol), oxadiazole acid (380 mg, 2.67 mmol) and $POCl_3$ (4.5 mL) was stirred at 110° C. for 1 h. After cooling to room temperature, excess $POCl_3$ was removed under reduced pressure. The residue was partitioned between $CH_2Cl_2$ and $H_2O$. The organic layer was separated, washed with sat. aq. $NaHCO_3$, dried over $Na_2SO_4$ and concentrated. The residue was purified by column chromatography (Hexanes/EtOAc gradient) to give compound Int-118-7 as a pale brown solid (0.25 g, 39% yield). LCMS: (M+1) m/z=292.

Synthesis of Compound 118

A mixture of Int-118-7 (30 mg, 0.103 mmol), amine (127 mg, 0.309 mmol) and 2,2,6,6-tetramethylpiperidine (18 μL, 0.103 mmol) in DMF (1 mL) was heated at 150° C. overnight. After cooling to room temperature, the mixture was concentrated. The reside was purified by preparative-TLC ($CH_2Cl_2$:MeOH=95:5) to give Compound 118 as a pale yellow solid (23 mg, 51% yield). LCMS: (M+1) m/z=440.

Examples 119-120

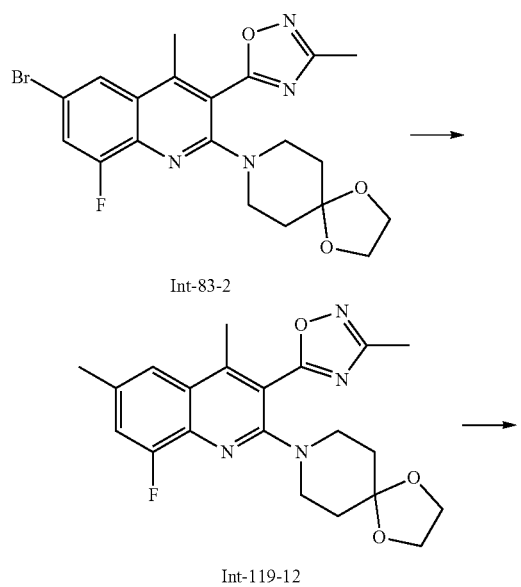

Int-83-2

Int-119-12

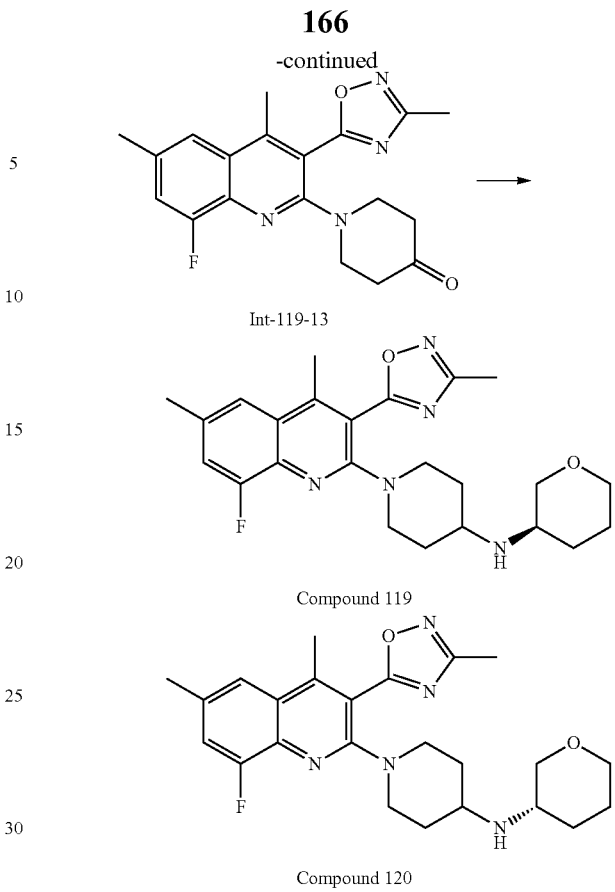

Int-119-13

Compound 119

Compound 120

Synthesis of Int-119-12

To a suspension of 8-(6-bromo-8-fluoro-4-methyl-3-(3-methyl-1,2,4-oxadiazol-5-yl)quinolin-2-yl)-1,4-dioxa-8-azaspiro[4.5]decane (Int-83-2, 100 mg, 0.22 mmol) and bis(triphenylphosphine)palladium(II) chloride (14 mg, 18 umol) in dioxane (5 mL) was added dimethylzinc (10% wt in hexanes, 0.50 mL), and the reaction was stirred at 60° C. for 1 h. The reaction was quenched by methanol and citric acid solution (5% aq.), and extracted with ethyl acetate twice. The organic layers were combined, washed with brine, dried over $Na_2SO_4$ and concentrated under reduced pressure. The residue was purified by silica gel chromatography to give 8-(8-fluoro-4,6-dimethyl-3-(3-methyl-1,2,4-oxadiazol-5-yl)quinolin-2-yl)-1,4-dioxa-8-azaspiro[4.5]decane (Int-119-12) as yellow solid (42 mg, 49% yield). LCMS (ESI): m/z 399 (M+H); Retention time: 3.05 min (Method 1).

Synthesis of Int-119-13

Int-119-13 was synthesized using the general procedure used for 1-(6-bromo-8-fluoro-4-methyl-3-(3-methyl-1,2,4-oxadiazol-5-yl)quinolin-2-yl)piperidin-4-one (Int-30-11f) replacing 8-(6-bromo-8-fluoro-4-methyl-3-(3-methyl-1,2,4-oxadiazol-5-yl)quinolin-2-yl)-1,4-dioxa-8-azaspiro[4.5]decane (Int-1-1d) with 8-(8-fluoro-4,6-dimethyl-3-(3-methyl-1,2,4-oxadiazol-5-yl)quinolin-2-yl)-1,4-dioxa-8-azaspiro[4.5]decane (Int-119-12). LCMS (ESI): m/z 355 (M+H); Retention time: 2.60 min (Method 1).

Synthesis of Compound 119

The procedure is the same as (R)-1-(6-bromo-8-fluoro-4-methyl-3-(3-methyl-1,2,4-oxadiazol-5-yl)quinolin-2-yl)-N-

(tetrahydro-2H-pyran-3-yl)piperidin-4-amine (Compound 31) by replacing 1-(6-bromo-8-fluoro-4-methyl-3-(3-methyl-1,2,4-oxadiazol-5-yl)quinolin-2-yl)piperidin-4-one (Int-30-11f) with 1-(8-fluoro-4,6-dimethyl-3-(3-methyl-1,2,4-oxadiazol-5-yl)quinolin-2-yl)piperidin-4-one (Int-119-13) to yield Compound 119. LCMS (ESI): m/z 440 (M+H); Retention time: 2.41 min (Method 1).

Synthesis of Compound 120

The procedure is the same as Compound 119 by replacing (R)-tetrahydro-2H-pyran-3-amine hydrochloride (2.0 equiv.) with (S)-tetrahydro-2H-pyran-3-amine hydrochloride (2.0 equiv.) to yield Compound 120. LCMS (ESI): m/z 440 (M+H); Retention time: 2.44 min (Method 1).

Examples 121-133

Compounds 121-128 are obtained in the manner disclosed below for Compounds 134-137 utilizing the amine with the appropriate stereochemistry and appropriate ketone.

Compounds 129-133 are obtained in the manner disclosed below for Compounds 147-152, or in the manner described above for Compounds 67-71.

Examples 134-137

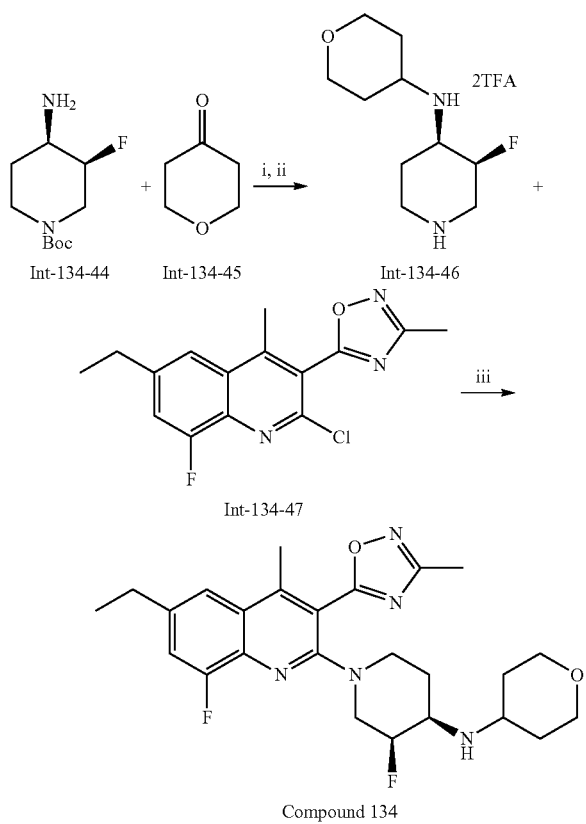

Compound 134
Reagents and conditions: i) Int-134-44 (1.0 equiv.), Int-134-45 (2.0 equiv.), NaBH(OAc)3 (2.0 equiv.), AcOH (2.0 equiv.), 1,2-dichloroethane, rt, overnight; ii) TFA (10 equiv.), CH₂Cl₂, rt, 2 h; iii) Int-134-46 (2.0 equiv.), Int-134-47 (1.0 equiv.), DIPEA (4.0 equiv.), EtOH, 110° C., overnight, 65-68% (3 steps).

Synthesis of Int-134-46

A mixture of Int-134-44 (1.0 equiv.), Int-134-45 (2.0 equiv.), NaBH(OAc)₃ (2.0 equiv.) and AcOH (2.0 equiv.) in DCE was stirred at RT overnight. The mixture was quenched with sat. aq. NaHCO₃ and the product extracted with CH₂Cl₂ (3×). The organic phase was dried over Na₂SO₄ and concentrated under reduced pressure. The product was used without further purification. LCMS: (M+1) m/z=303. A mixture of the previous product and TFA (10.0 equiv.) in CH₂Cl₂ was stirred at RT for 2 h. The mixture was concentrated under reduced pressure and the product was used without further purification. LCMS: (M+1) m/z=203.

Synthesis of Compound 134

A mixture of Int-134-46 (2.0 equiv.), Int-134-47 (1.0 equiv.) and DIPEA (4.0 equiv.) in EtOH was heated at 110° C. overnight. The mixture was concentrated under reduced pressure and the product purified by preparative-TLC (CH₂Cl₂:MeOH=96:4) to give Compound 134 in 65-68% yield (3 steps).

Synthesis of Compound 135, Compound 136 and Compound 137

Compound 135, Compound 136 and Compound 137 were prepared in the same manner as Compound 134, by replacing staring material Int-134-44 with the appropriate stereoisomers. Compound 135, a pale grey solid; Compound 136, a pale yellow solid, Compound 137, a pale grey solid.

Example 138

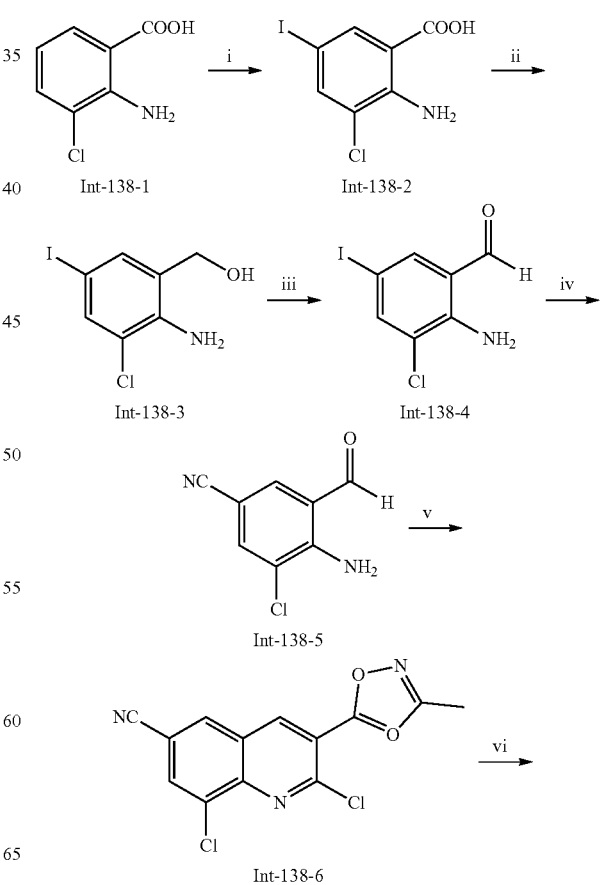

-continued

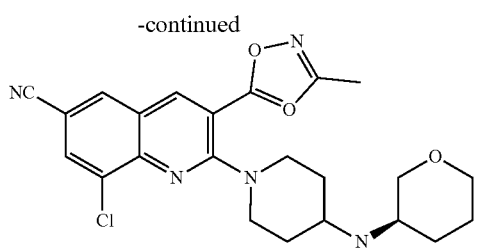

Compound 138

Reagents and conditions: i) Int-138-1 (1.0 equiv.), NIS (1.0 equiv.), CH2Cl2, RT, 6 h, 76%; ii) Int-138-2 (1.0 equiv.), BH₃—THF (5.0 equiv.), THF, RT, 6 h, quantitative yield; iii) Int-138-3 (1.0 equiv.), MnO₂ (6.0 equiv.), CH2Cl2, RT, overnight, quantitative yield; iv) Int-138-4 (1.0 equiv.), Zn(CN)2 (1.0 equiv.), Zn (0.1 equiv.), Pd(PPh3)4 (0.05 equiv.), DMF, 80° C., overnight, 42%; v) Int-138-5 (1.0 equiv.), oxadiazole acid (1.2 equiv.), POCl3, 110° C., 1 h, 92%; vi) Int-138-6 (1.0 equiv.), amine (2.0 equiv.), DIPEA (2.0 equiv.), CH3CN, 120° C., overnight, 17%.

Synthesis of Int-138-2

To a suspension of 2-amino-3-chlorobenzoic acid Int-138-1 (17.16 g, 100 mmol) in $CH_2Cl_2$ (250 mL) was added N-iodosuccinimide (17.80 g, 100 mmol). The mixture was stirred at room temperature for 6 h. The product was filtered, washed with $CH_2Cl_2$ and dried under the reduced pressure. Product Int-138-2 as an off-white solid was used for the next reaction without further purification (22.61 g, 76% yield). LCMS: (M−1) m/z=296.

Synthesis of Int-138-3

To a suspension of Int-138-2 (22.61 g, 76.0 mmol) in THF (100 mL) was added a solution of $BH_3$·THF complex (1M in THF, 380 mL, 380 mmol) dropwise at 0° C. The mixture was then stirred at room temperature for 6 h. The reaction was quenched by slow addition of MeOH at 0° C. and the mixture was concentrated to dryness. Product Int-138-3 as a pink solid was used for the next reaction without further purification (21.54 g, quantitative yield). LCMS: (M−1) m/z=282.

Synthesis of Int-138-4

A mixture of Int-138-3 (21.54 g, 76.0 mmol) and activated $MnO_2$ (40.0 g, 456.0 mmol) in $CH_2Cl_2$ (500 mL) was stirred at room temperature overnight. The reaction mixture was filtered through Celite to give Int-138-4 as a yellow solid (21.39 g, quantitative yield).

Synthesis of Int-138-5

A mixture of Int-138-4 (9.95 g, 35.35 mmol), $Zn(CN)_2$ (4.15 g, 35.35 mmol), Zn powder (0.23 g, 3.54 mmol) and $Pd(PPh_3)_4$ (2.04 g, 1.77 mmol) in DMF (70 mL) was heated at 80° C. overnight. After cooling to room temperature, the mixture was filtered through Celite and the filtrate was concentrated. The residue was purified by column chromatography (Hexanes/EtOAc gradient) to give Int-138-5 as a pale yellow solid (2.68 g, 42% yield). LCMS: (M+1) m/z=181.

Synthesis of Int-138-6

A mixture of Int-138-5 (180 mg, 1.00 mmol), oxadiazole acid (175 mg, 1.23 mmol) and $POCl_3$ (3 mL) was stirred at 110° C. for 1 h. After cooling to room temperature, excess $POCl_3$ was removed under the reduced pressure. To the residue, $H_2O$ was added at 0° C. The mixture was partitioned between EtOAc and brine. The aqueous layer was separated and extracted with EtOAc (×2). The combined organic layers were dried over $Na_2SO_4$ and concentrated to dryness. Product Int-138-6 as a brown solid was used for the next reaction without further purification (281 mg, 92% yield).

Synthesis of Compound 138

A mixture of Int-138-6 (17 mg, 0.056 mmol), amine (33 mg, 0.112 mmol) and DIPEA (19 µL, 0.112 mmol) in $CH_3CN$ (1 mL) was heated at 120° C. overnight. After cooling to room temperature, the mixture was concentrated. The reside was purified by preparative-TLC ($CH_2Cl_2$: MeOH=95:5 to 90:10) to give Compound 138 as a yellow oil (4.3 mg, 17% yield). LCMS: (M+1) m/z=453.

Example 139

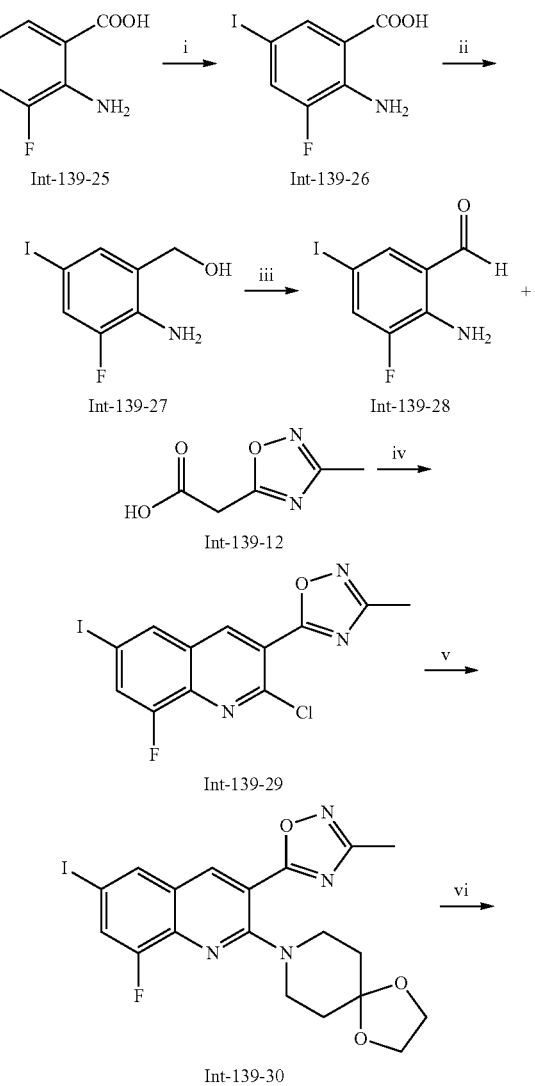

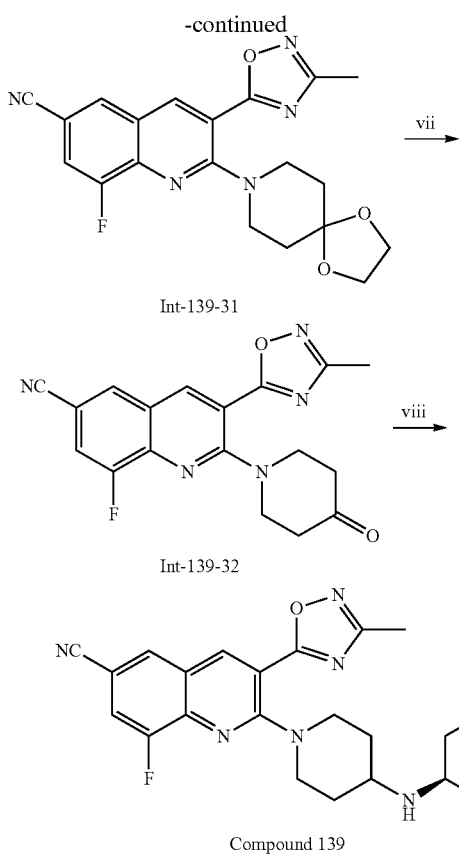

Int-139-31

Int-139-32

Compound 139

Synthesis of Int-139-28

To a suspension of 2-amino-3-fluorobenzoic acid 25 (15.0 g, 96.7 mmol) in $CH_2Cl_2$ (250 mL) was added N-iodosuccinimide (17.2 g, 96.7 mmol). The mixture was stirred at room temperature overnight. The product was filtered, washed with $CH_2Cl_2$ and dried under reduced pressure to give iodobenzoic acid 26 as an off white solid. To a solution of Int-139-Int-139-26 (22.48 g, 80.0 mmol) in THF (200 mL) was added dropwise a solution of $BH_3 \cdot THF$ complex (1M in THF, 400 mL, 400 mmol) at 0° C. The mixture was then stirred at room temperature overnight. The reaction was quenched by MeOH at 0° C. slowly. After removing the solvent to dryness, the crude alcohol Int-139-Int-139-27 was dissolved in $CH_2Cl_2$ (500 mL), and activated $MnO_2$ (41.7 g, 480 mmol) was added. The mixture was stirred at room temperature overnight. The crude product was purified by short silica gel path (Hexanes:EtOAc, 1:1) to give aldehyde Int-139-Int-139-28 as a yellow solid (11.4 g, 45% yield over three steps). LCMS: (M−1) m/z=264.

Synthesis of Int-139-Int-139-30

A mixture of aldehyde Int-139-Int-139-28 (5.74 g, 21.6 mmol), oxadiazole acid Int-139-Int-139-12 (3.69 g, 26.0 mmol) and $POCl_3$ (22 mL) was stirred at 110° C. for 1 h. After cooling to room temperature, excess $POCl_3$ was removed under reduced pressure. To this residue, $H_2O$ was added at 0° C. and the mixture was stirred at 0° C. for 10 min. The crude chloride 29 was filtered, washed with $H_2O$ and dried under reduced pressure. To a suspension of 29 in EtOH (100 mL) were added 1,4-dioxa-8-azaspiro[4,5]decane (5.5 mL, 43.2 mmol) and DIPEA (7.5 mL, 43.2 mmol) at room temperature. The mixture was then heated at 120° C. overnight. After cooling to room temperature, the mixture was concentrated and purified by column chromatography (hexanes/EtOAc gradient) to give quinoline Int-139-Int-139-30 as yellow oil (2.50 g, 23% yield over two steps). LCMS: (M+1) m/z=497.

Synthesis of Int-139-31

A mixture of Int-139-30 (2.50 g, 5.04 mmol), $Zn(CN)_2$ (0.59 g, 5.04 mmol), Zn powder (33 mg, 0.50 mmol) and $Pd(PPh_3)_4$ (0.58 g, 0.50 mmol) in THF/DMF (50 mL, 1:1 (v/v)) was heated at 80° C. for 5 h. After cooling to room temperature, the mixture was filtered through Celite and the filtrate was concentrated. The residue was purified by column chromatography (hexanes/EtOAc gradient) to give cyanoquinoline Int-139-31 as yellow oil (0.93 g, 47% yield). LCMS: (M+1) m/z=396.

Synthesis of Int-139-32

To a solution of Int-139-31 (0.47 g, 1.19 mmol) in THF (5 mL) was added 10% aq. $H_2SO_4$ (12 mL, v/v). The mixture was stirred at 45° C. for 4 h. After cooling to room temperature, the mixture was neutralized with sat. aq. $Na_2CO_3$ and extracted with EtOAc (2×40 mL). The combined organic layers were dried over $Na_2SO_4$ and concentrated to dryness. The residue was purified by column chromatography (hexanes/EtOAc gradient) to give ketone Int-139-Int-139-32 as a yellow solid (308 mg, 74% yield). LCMS: (M+1) m/z=352.

Synthesis of Compound 139

A mixture of ketone Int-139-32 (15.8 mg, 0.045 mmol), (S)-3-aminotetrahydropyran hydrochloride (12.4 mg, 0.09 mmol) and DIPEA (16 µL, 0.08 mmol) in 1,2-dichloroethane (1.5 mL) was stirred at room temperature for 10 min. To the mixture were added $NaBH(OAc)_3$ (28.6 mg, 0.135 mmol) and AcOH (8 µL, 0.135 mmol). The resulting mixture was stirred at room temperature overnight. After filtration through Celite, the filtrate was concentrated under reduced pressure. The reside was purified by preparative-TLC ($CH_2Cl_2$:MeOH=95:5) to give Compound 139 as yellow oil (18.1 mg, 92% yield). LCMS: (M+1) m/z=437.

Example 140

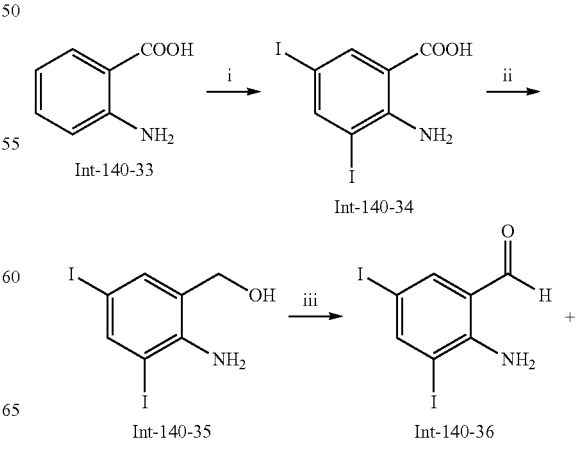

Int-140-33

Int-140-34

Int-140-35

Int-140-36

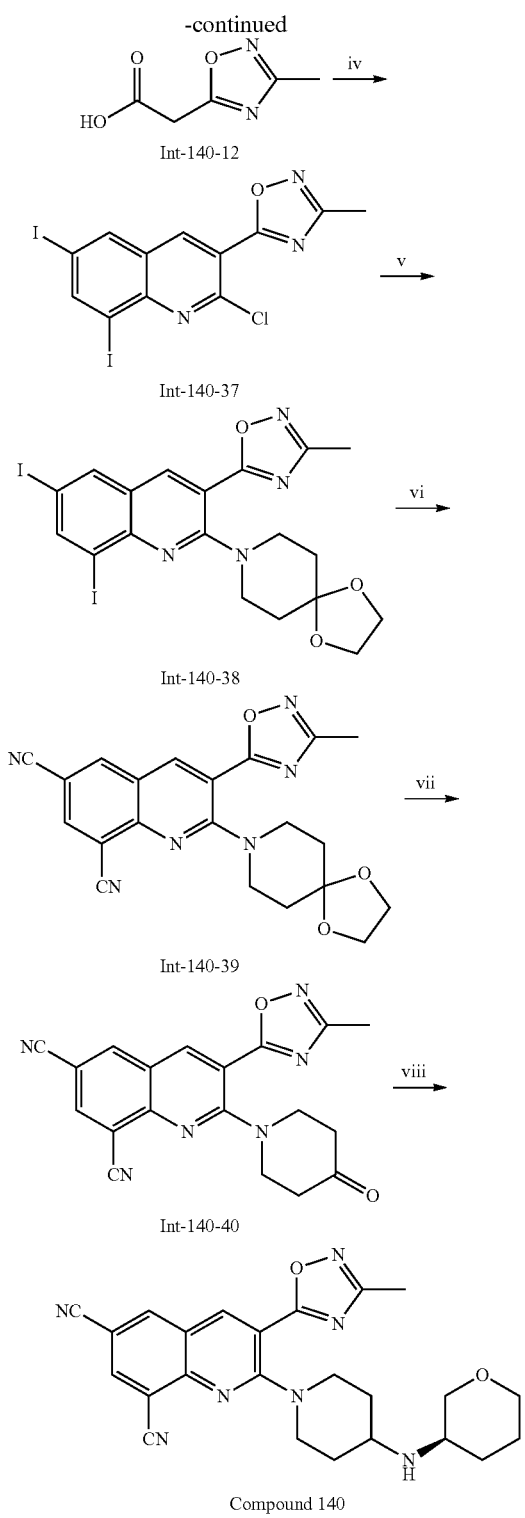

solution of Int-140-34 (12.53 g, 32.2 mmol) in THF (100 mL) was added dropwise a solution of $BH_3 \cdot THF$ complex (1M in THF, 161 mL, 161 mmol) at 0° C. The mixture was then stirred at room temperature overnight. The reaction was quenched by MeOH at 0° C. slowly. After removing the solvent to dryness, the crude alcohol Int-140-35 was dissolved in $CH_2Cl_2$ (200 mL), and activated $MnO_2$ (16.8 g, 193.2 mmol) was added. The mixture was stirred at room temperature overnight. The crude product was purified with a short silica gel path to give aldehyde Int-140-36 as a yellow solid (5.83 g, 32% yield over three steps). LCMS: (M+1) m/z=374.

Synthesis of Int-140-38

A mixture of aldehyde Int-140-36 (4.81 g, 12.9 mmol), oxadiazole acid 12 (3.69 g, 15.5 mmol) and $POCl_3$ (13 mL) was stirred at 110° C. for 1 h. After cooling to room temperature, excess $POCl_3$ was removed under reduced pressure. To this residue, $H_2O$ was added at 0° C. The mixture was stirred at 0° C. for 10 min. The crude chloride Int-140-37 was filtered, washed with $H_2O$ and dried under reduced pressure. To a suspension of Int-140-37 in EtOH (65 mL) were added 1,4-dioxa-8-azaspiro[4,5]decane (3.3 mL, 25.8 mmol) and DIPEA (4.5 mL, 25.8 mmol) at room temperature. The mixture was then heated at 120° C. overnight. After cooling to room temperature, the mixture was concentrated and purified by column chromatography (hexanes/EtOAc gradient) to give quinoline Int-140-38 as yellow oil (1.56 g, 20% yield over two steps). LCMS: (M+1) m/z=605.

Synthesis of Int-140-39

A mixture of Int-140-38 (1.56 g, 2.58 mmol), $Zn(CN)_2$ (0.61 g, 5.16 mmol), Zn powder (34 mg, 0.52 mmol) and $Pd(PPh_3)_4$ (0.60 g, 0.52 mmol) in THF/DMF (30 mL, 1:1 (v/v)) was heated at 80° C. for 5 h. After cooling to room temperature, the mixture was filtered through Celite and the filtrate was concentrated. The residue was purified by column chromatography (hexanes/EtOAc gradient) to give cyanoquinoline Int-140-39 as yellow oil (0.62 g, 60% yield). LCMS: (M+1) m/z=403.

Synthesis of Int-140-40

To a solution of Int-140-39 (0.57 g, 1.42 mmol) in THF (5 mL) was added 10% aq. $H_2SO_4$ (12 mL, v/v). The mixture was stirred at 45° C. for 4 h. After cooling to room temperature, the mixture was neutralized with sat. aq. $Na_2CO_3$ and extracted with EtOAc (2×40 mL). The combined organic layers were dried over $Na_2SO_4$ and concentrated to dryness. The ketone Int-140-40 as an orange solid was used for the next reaction without further purification. (513 mg, quantitative yield). LCMS: (M+1) m/z=359.

Synthesis of Compound 140

A mixture of ketone Int-140-40 (13.0 mg, 0.036 mmol), (S)-3-aminotetrahydropyran hydrochloride (10.0 mg, 0.072 mmol) and DIPEA (13 µL, 0.072 mmol) in 1,2-dichloroethane (1.5 mL) was stirred at room temperature for 10 min. To the mixture were added $NaBH(OAc)_3$ (23.0 mg, 0.108 mmol) and AcOH (6 µL, 0.108 mmol). The resulting mixture was stirred at room temperature overnight. After filtration through Celite, the filtrate was concentrated under reduced pressure. The reside was purified by preparative-TLC Synthesis of Int-140-36

To a suspension of 2-aminobenzoic acid 33 (6.6 g, 48.1 mmol) in $CH_2Cl_2$ (150 mL) was added N-iodosuccinimide (17.1 g, 96.2 mmol). The mixture was stirred at room temperature overnight. The product was filtered, washed with $CH_2Cl_2$ and dried under reduced pressure to give iodobenzoic acid Int-140-34 as an off white solid. To a ($CH_2Cl_2$:MeOH=95:5) to give Compound 140 as yellow oil (14.1 mg, 88% yield). LCMS: (M+1) m/z=444.

Example 141

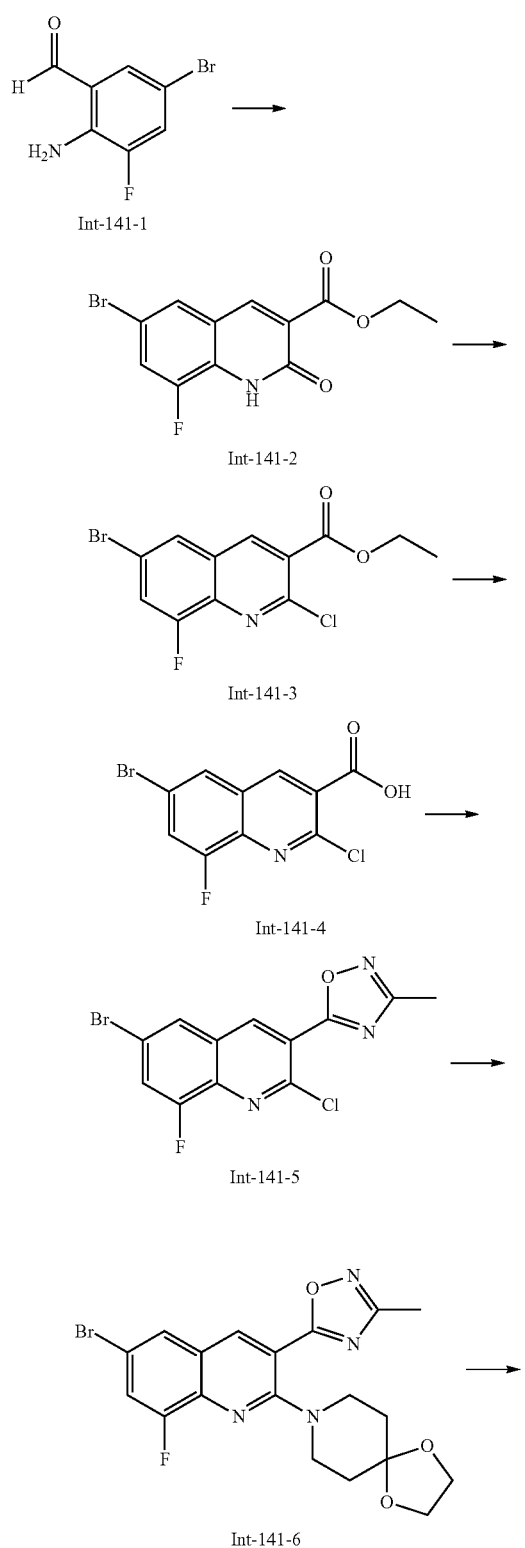

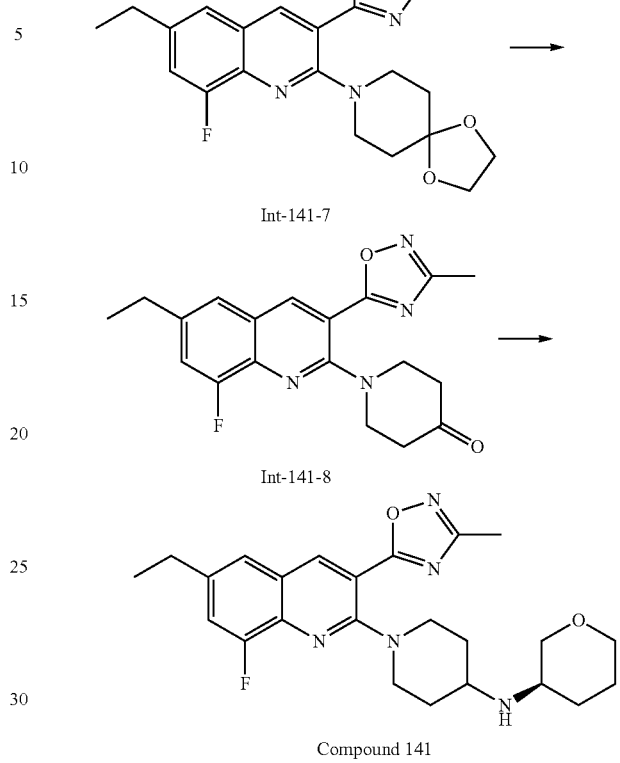

Synthesis of Int-141-2

To a solution of Int-141-1 (2.04 g, 9.38 mmol) in EtOH (14 mL) were added diethyl malonate (1.99 mL, 13.1 mmol) and catalytic amount of piperidine. The reaction mixture was refluxed for 24 h. The reaction mixture was cooled to RT, and the resulting solid was collected by vacuum filtration rinsing with EtOH to provide Int-141-2 as a white solid (2.6 g, 88% yield). LCMS: (M−1) m/z=313.

Synthesis of Int-141-3

A mixture of Int-141-2 (806 mg, 2.56 mmol) and phosphorus(V) oxychloride (5 mL) was heated at 110° C. for 1 h. Phosphorus(V) oxychloride was removed under reduced pressure. Water was added to the residue, and the precipitate was collected by vacuum filtration to provide Int-141-3 as a white solid (850 mg, quantitative yield).

Synthesis of Int-141-4

To a solution of Int-141-3 (720 mg, 2.16 mmol) in THF (3.5 mL) were added NaOH (519 mg, 13.0 mmol) and water (7 mL). The reaction was stirred at RT for 2 h. The solvent was evaporated under reduced pressure, then resin Amberlite IRN77 and MeOH (15 mL) were added. The resulting mixture was stirred at RT for 15 min, then the resin was filtered off. The filtrate was concentrated to dryness to provide Int-141-4 as an off-white solid (660 mg, quantitative yield). LCMS: (M−1) m/z=303.

Synthesis of Int-141-5

A mixture of Int-141-4 (660 mg, 2.16 mmol) in dichloromethane (4 mL) and N,N-dimethylformamide (0.2 mL)

was treated with oxalyl chloride (2M in dichloromethane, 4 mL). The reaction mixture was stirred at RT for 2 h. The reaction mixture was evaporated under reduced pressure. The residue was dissolved in dichloromethane (4 mL) and N,N-dimethylformamide (4 mL), then treated with N-hydroxyacetamide (160 mg, 2.16 mmol) and DIPEA (1.13 mL, 6.48 mmol). The reaction mixture was heated at 120° C. for 2 h, then cooled to RT. Dichloromethane was removed in vacuo. EtOAc and water were added to the residue. The organic phase was separated, and washed with brine (3×20 mL). The organic phase was dried over $Na_2SO_4$ and concentrated to dryness, followed by column chromatography (Hexanes:EtOAc=92:8) to afford Int-141-5 as a yellow solid (178 mg, 24% yield). LCMS: (M+1) m/z=342, 344.

Synthesis of Int-141-6

A mixture of Int-141-5 (150 mg, 0.44 mmol), 1,4-dioxa-8-azaspiro[4,5]decane (0.11 mL, 0.88 mmol) and DIPEA (0.15 mL, 0.88 mmol) in EtOH (3 mL) was heated with microwave at 120° C. for 50 min. The reaction mixture was concentrated and purified by column chromatography (Hexanes:EtOAc=92:8) to provide Int-141-6 as a yellow solid (190 mg, 96% yield). LCMS: (M+1) m/z=449, 451.

Synthesis of Int-141-7

A mixture of Int-141-6 (190 mg, 0.42 mmol), triethylborane (1M in THF, 0.85 mL), $K_2CO_3$ (117 mg, 0.85 mmol) and Pd(dppf)$Cl_2$—$CH_2Cl_2$ (34 mg, 0.041 mmol) in DMF (2 mL) was degassed with nitrogen, and heated at 70° C. for 2 h. The reaction mixture was cooled to RT, filtered on celite, and the product was partitioned between EtOAc and water. The organic phase was washed with brine (3×20 mL), dried over $Na_2SO_4$ and concentrated to dryness. The product was purified by column chromatography to provide Int-141-7 as a yellow solid (45 mg, 27% yield). LCMS: (M+1) m/z=399.

Synthesis of Int-141-8

To compound Int-141-7 (34 mg, 0.084 mmol) was added 10% aq. $H_2SO_4$ (0.28 mL) at RT. The mixture was then stirred at 45° C. for 2 h. After cooling to RT, the mixture was neutralized with saturated aq. $Na_2CO_3$ and extracted with EtOAc (2×10 mL). The combined organic layers were dried over $Na_2SO_4$ and concentrated to dryness to provide Int-141-8 as a yellow solid (29 mg, quantitative yield). LCMS: (M+1) m/z=355.

Synthesis of Compound 141

A mixture of Int-141-8 (30 mg, 0.084 mmol), (R)-tetrahydro-2H-pyran-3-amine hydrochloride (15 mg, 0.11 mmol) and DIPEA (20 µl, 0.11 mmol) in 1,2-dichloroethane (0.4 mL) was stirred at RT for 10 min. To the mixture NaBH(OAc)$_3$ (27 mg, 0.13 mmol) and AcOH (7 µl, 0.13 mmol) were added. The resulting mixture was stirred at RT for 3 h. The reaction mixture was directly purified by preparative-TLC ($CH_2Cl_2$:MeOH=95:5) to give Compound 141 as a yellow solid (32 mg, 87% yield). LCMS: (M+1) m/z=440.

Examples 142-146

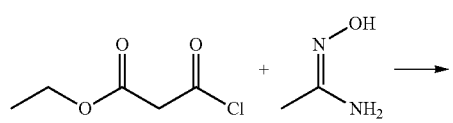

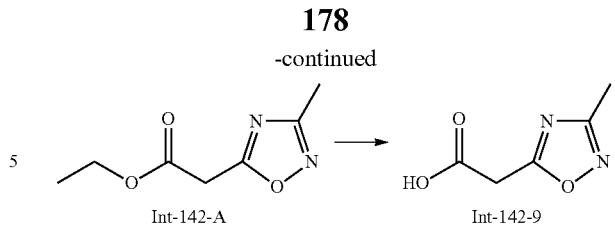

Synthesis of Int-142-A

To a suspension of N-hydroxyacetamidine (29 g, 0.39 mol) and DIPEA (102 mL, 0.58 mol) in 1,4-dioxane (200 mL) was added dropwisely ethyl malonyl chloride (50 mL, 0.39 mol) at 0° C. The mixture was stirred at RT for 20 min, then heated at 100° C. for 3 h. After cooling to RT, the mixture was concentrated under the reduced pressure. The residue was partitioned between brine and ether. The organic layer was washed with saturated aq. NaHCO$_3$, dried over $Na_2SO_4$ and concentrated. The residue was purified with a short silica gel path eluting with 20% EtOAc in Hexane to give Int-142-A as light brown liquid (40.28 g, 61% yield).

Synthesis of Int-142-9

To a solution of oxadiazole ester Int-142-A (10.0 g, 58.9 mmol) in THF (50 mL) was added 2M aq. NaOH (59 mL) at 0° C. The mixture was then stirred at RT for 1 h. To this, Amberlite IR 120 (H$^+$) resin was added to adjust pH to pH 4. The resin was removed by filtration and washed with H$_2$O. The filtrate was concentrated under the reduced pressure. The residue was dried over $P_2O_5$ under vacuum to provide Int-142-9 and used for the next step without purification.

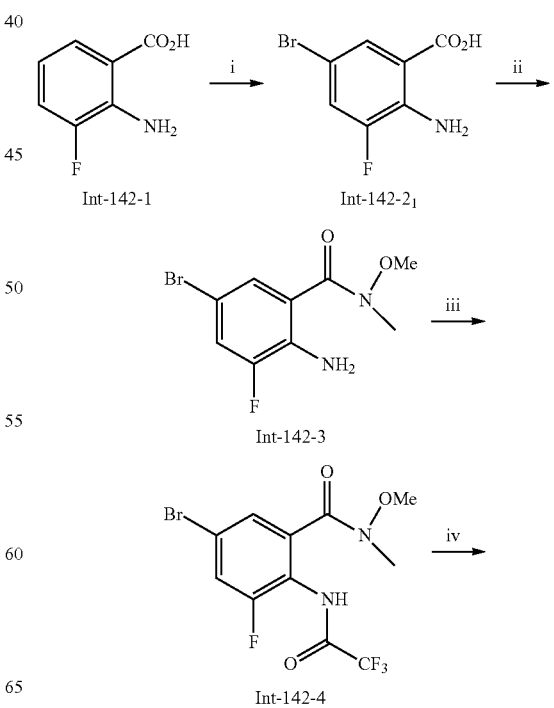

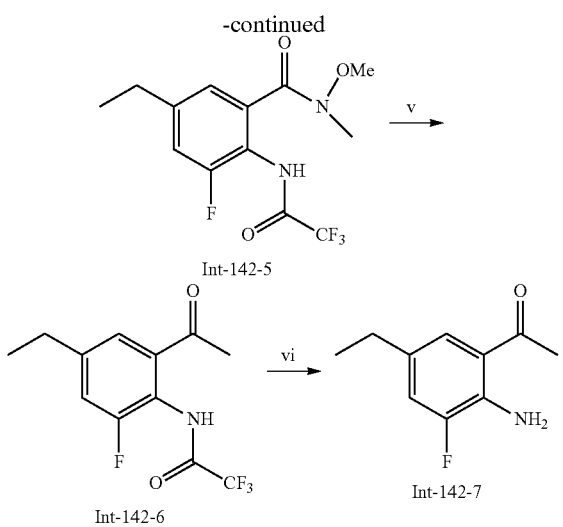

Synthesis of Int-142-2

To a suspension of 2-amino-3-fluorobenzoic acid 1 (20.0 g, 129 mmol) in $CH_2Cl_2$ (300 mL) was added N-bromosuccinimide (22.9 g, 129 mmol). The mixture was stirred at room temperature overnight. The product was collected by vacuum filtration to give 2-amino-5-bromo-3-fluorobenzoic acid Int-142-2 as an off-white solid (27 g, 90% yield), which was used in the next step without further purification. LCMS: (M−1) m/z=232, 234.

Synthesis of Int-142-3

A mixture of Int-142-2 (8.5 g, 36.3 mmol), N,O-dimethylhydroxylamine hydrochloride (6.4 g, 65.3 mmol), DIPEA (12.6 mL), EDCI (8.4 g, 43.6 mmol) and HOBt (6.7 g, 43.6 mmol) in DMF (90 mL) was stirred at room temperature during 4 h. Then, the reaction was diluted with 100 mL of EtOAc and washed sequentially with 1M NaOH, 1M HCl and brine to obtain Int-142-3 as a brown oil (8.6 g, 85% yield), which was used in the next step without further purification. LCMS: (M+1) m/z=277, 279.

Synthesis of Int-142-4

To a solution of Int-142-3 (8.6 g, 31 mmol) in $CH_2Cl_2$ (100 mL) at 0° C., TEA (5.2 mL, 37 mmol) was added, followed by dropwise addition of trifluoroacetic anhydride (5.6 mL, 40 mmol). The reaction was stirred at room temperature overnight. Sat. aq. $NaHCO_3$ solution was then added and the organic phase was separated and washed with water. The organic layer was dried over $Na_2SO_4$ and concentrated to dryness to afford Int-142-4 as a yellow solid (9.4 g, 80% yield), which was used in the next step without further purification. LCMS: (M+1) m/z=373, 375.

Synthesis of Int-142-5

To a suspension of Int-142-4 (4.3 g, 11.5 mmol), $Cs_2CO_3$ (11.0 g, 34.6 mmol) and Pd(dppf)$Cl_2$ (170 mg, 0.23 mmol) in THF (25 mL), 1M solution of $BEt_3$ in THF (34.6 mL, 34.6 mmol) was added, and the reaction was heated at 70° C. for 1.5 h. After cooling to room temperature, the crude was filtered through celite and purified by column chromatography (hexanes:EtOAc) to afford Int-142-5 as a yellow solid (2.5 g, 54% yield). LCMS: (M+1) m/z=323.

Synthesis of Int-142-6

To a solution of Int-142-5 (2.0 g, 6.2 mmol) in THF (40 mL) at 0° C., 1.4 M solution of MeMgBr in THF:toluene (22 mL, 31 mmol) was added, and the reaction was stirred at room temperature for 2.5 h. The reaction was poured into ice, acidified to pH=2 with 2M HCl and extracted with EtOAc. The combined organic layers were dried over $Na_2SO_4$ and concentrated to dryness to afford Int-142-6 as a yellow oil, which was used in the next step without further purification. LCMS: (M−1) m/z=276.

Synthesis of Int-142-7

To a solution of Int-142-6 (2.0 g, 7.2 mmol) in MeOH (6 mL), 2 M aq. solution of NaOH (6 mL) was added, the reaction was heated at 90° C. for 1.5 h. Water was added and the solid collected by filtration to obtain Int-142-7 as a yellow solid (1.2 g, 92% yield), which was used in the next step without further purification. LCMS: (M+1) m/z=182.

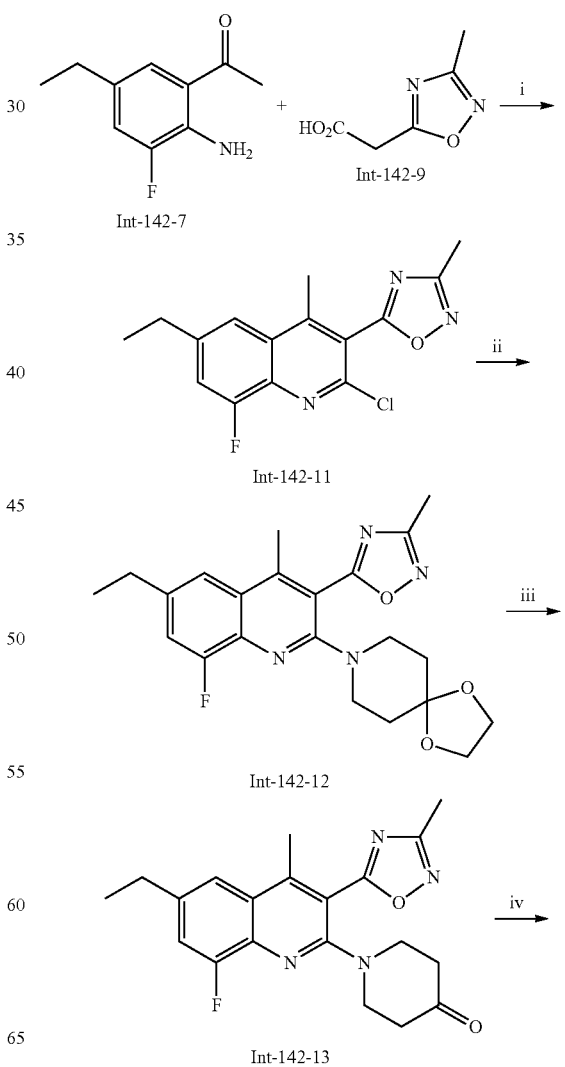

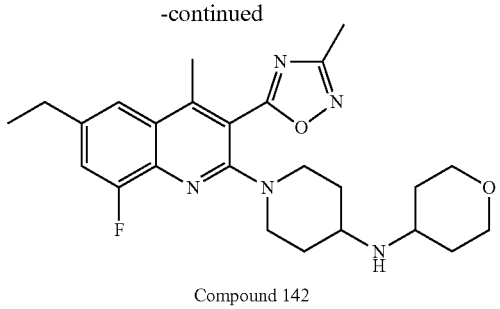

Compound 142

Synthesis of Int-142-11

A mixture of ketone Int-142-7 (250 mg, 1.38 mmol), 2-(3-methyl-1,2,4-oxadiazol-5-yl)acetic acid 9 (235 mg, 1.65 mmol) and $POCl_3$ (2.5 mL) was stirred at 110° C. for 1 h. The excess $POCl_3$ was removed under vacuum. To the residue was added a sat. aq. solution of $NaHCO_3$, and the product was extracted with EtOAc. The combined organic layers were dried over $Na_2SO_4$ and concentrated to dryness. The crude product was purified by column chromatography (hexanes/EtOAc) to give 2-chloroquinoline Int-142-11 as a white solid (176 mg, 42% yield). LCMS: (M+1) m/z=306, 308.

Synthesis of Int-142-12

To a suspension of Int-142-11 (220 mg, 0.72 mmol) in EtOH (5 mL), 1,4-dioxa-8-azaspiro[4,5]decane (184 µL, 1.44 mmol) and DIPEA (250 µL, 1.44 mmol) were added. The mixture was heated at 110° C. overnight. After cooling to room temperature, the mixture was concentrated under reduced pressure and purified by column chromatography (hexanes/EtOAc) to give ketal Int-142-12 as yellow oil (278 mg, 93% yield). LCMS: (M+1) m/z=413.

Synthesis of Int-142-13

To a solution of ketal Int-142-12 (278 mg, 0.67 mmol) in THF (1 mL), 10% aq. $H_2SO_4$ (5 mL) was added. The mixture was stirred at 45° C. for 2 h. After cooling to room temperature, the mixture was neutralized with sat. aq. $Na_2CO_3$ and extracted with EtOAc, dried over $Na_2SO_4$ and concentrated to dryness to give ketone Int-142-13 as a yellowish oil (224 mg, 90% yield), which was used in the next step without further purification LCMS: (M+1) m/z=369.

Synthesis of Compound 142

A mixture of ketone Int-142-13 (160 mg, 0.43 mmol), 4-aminotetrahydropyran (66 mg, 0.65 mmol), $NaBH(OAc)_3$ (182 mg, 0.86 mmol) and AcOH (50 µL, 1.05 mmol) in 1,2-dichloroethane (5.0 mL) was stirred at room temperature overnight. The mixture was concentrated under reduced pressure and purified by preparative-TLC ($CH_2Cl_2$:MeOH, 95:5) to give Compound 142 as a yellow solid (178 mg, 91% yield). LCMS: (M+1) m/z=454.

Synthesis of Compound 143, Compound 144, Compound 145, Compound 146

Synthesis of Compound Nos. 143-146 was in a similar manner to Compound 142 via reductive amination of intermediate 13 and the appropriate amine. Compound 143, a pale yellow solid, for the last step (red. amin.): 89% yield. LCMS: (M+1) m/z=424; Compound 144, a pale yellow solid, for the last step (red. amin.): 59% yield. LCMS: (M+1) m/z=454; Compound 145, a pale yellow solid, for the last step (red. amin.): 59% yield. LCMS: (M+1) m/z=440; Compound 146, a pale yellow solid, for the last step (red. amin.): 75% yield. LCMS: (M+1) m/z=440.

Example 147

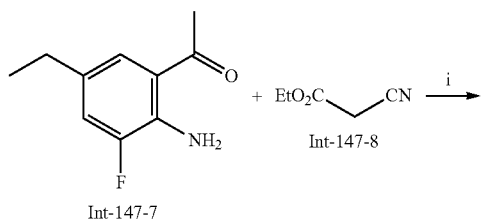

Int-147-7     Int-147-8

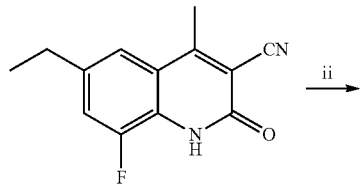

Int-147-10

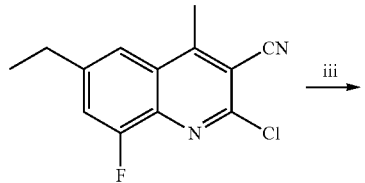

Int-147-11

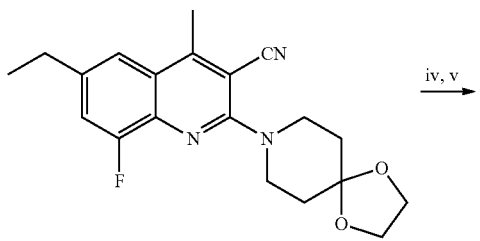

Int-147-12

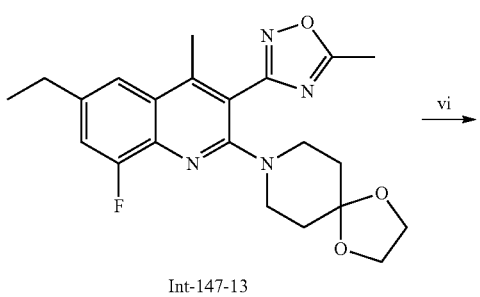

Int-147-13

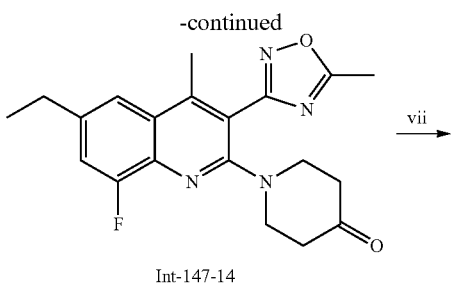

Int-147-14

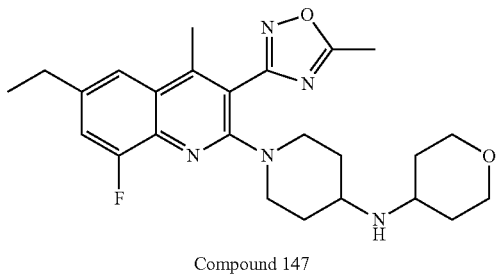

Compound 147

Synthesis of Int-147-11

A mixture of ketone Int-147-7 (1.0 equiv.), ethyl 2-cyanoacetate Int-147-8 (2.0 equiv.) and NH₄OAc (5.0 equiv.) in dioxane was stirred at 90° C. for 8 h. The mixture was concentrated under reduced pressure and the solid was washed sequentially with water and EtOAc/hexanes (1:9) (2×). The pale yellow solid was used without further purification (83-85% yield). LCMS: (M+1) m/z=231. A suspension of Int-147-10 (1.0 equiv.) in POCl₃ was stirred at 110° C. for 1.5 h. The excess POCl₃ was removed under reduced pressure. The crude was quenched with ice and the mixture was stirred at room temperature for 15 min. The crude was collected by filtration and washed with water (3×). Product Int-147-11 was obtained as a pale yellow solid in quantitative yield. LCMS: (M+1) m/z=249.

Synthesis of Int-147-12

A mixture of Int-147-11 (1.0 equiv.), 1,4-dioxa-8-azaspiro[4,5]decane (1.5 equiv.) and DIPEA (1.5 equiv.) in EtOH was heated at 110° C. overnight. The mixture was concentrated under reduced pressure and the product purified by column chromatography using hexanes/EtOAc. Product Int-147-12 was obtained as a pale brown solid in 97-98%. LCMS: (M+1) m/z=356.

Synthesis of Int-147-13

A mixture of Int-147-12 (1.0 equiv.), NH₂OH·HCl (5.0 equiv.) and Na₂CO₃ (5.0 equiv.) in anhydrous isopropanol was heated at 100° C. overnight. The mixture was cooled to room temperature and filtrated. The organic phase was concentrated under reduced pressure and the product used without further purification. LCMS: (M+1) m/z=389. A mixture of amidoxime (1.0 equiv.), acetic anhydride (1.2 equiv.) and DIPEA (1.2 equiv.) in dioxane was stirred at room temperature for 40 min, then the mixture was heated at 100° C. for 8 h. The mixture was concentrated under reduced pressure and the product purified by column chromatography using hexanes/EtOAc, the pale brown solid was obtained in 64-66% yield (two steps). LCMS: (M+1) m/z=413. To a solution of ketal Int-147-13 (1.0 equiv.) in THF (1 mL) was added 10% aq. H₂SO₄ and the mixture was stirred at 45° C. for 2 h. After cooling to room temperature, the mixture was neutralized with sat. aq. Na₂CO₃ and extracted with EtOAc (4×), dried over Na₂SO₄ and concentrated to dryness to give the pale brown ketone Int-147-14 in quantitative yield, which was used in the next step without further purification LCMS: (M+1) m/z=369.

Synthesis of Compound 147

A mixture of ketone Int-147-14 (1.0 equiv.), 4-aminotetrahydropyran (1.2 equiv.), NaBH(OAc)₃ (1.5 equiv.) and AcOH (1.5 equiv.) in 1,2-dichloroethane was stirred at room temperature overnight. The mixture was concentrated under reduced pressure and purified by preparative-TLC (CH₂Cl₂: MeOH, 95:5) to give Compound 147 as an off-white solid in 90-92% yield. LCMS: (M+1) m/z=454.

Example 148

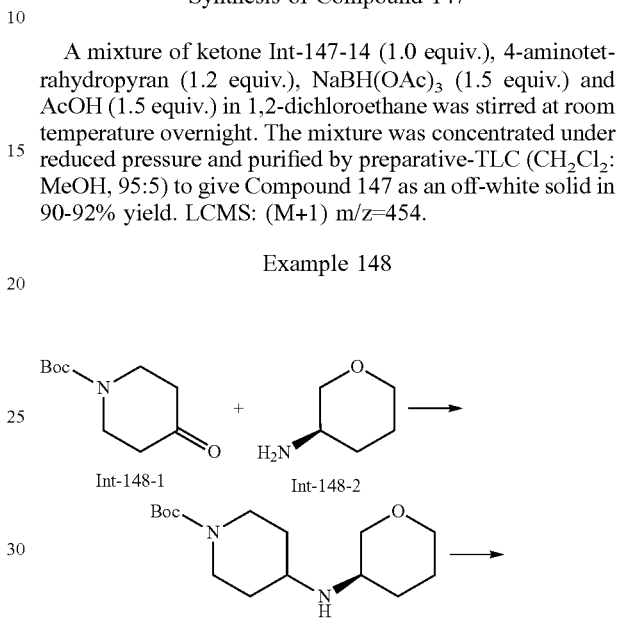

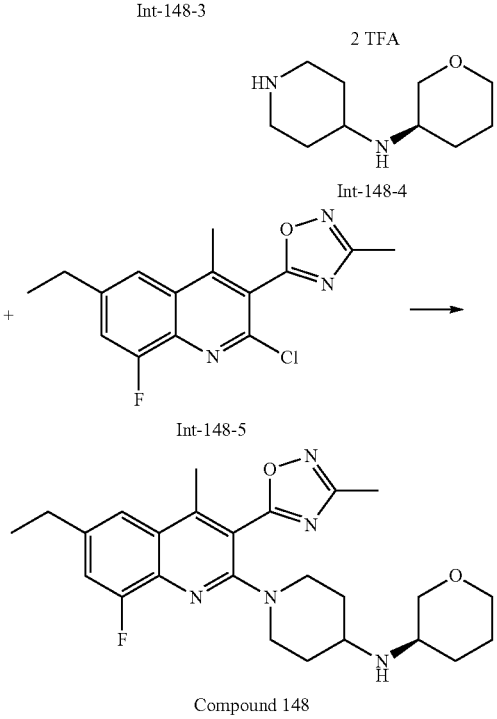

Compound 148

Synthesis of 3

A mixture of Int-148-1 (500 mg, 2.53 mmol), (R)-tetrahydro-2H-pyran-3-amine hydrochloride 2 (384 mg, 2.79 mmol) and DIPEA (0.485 mL, 2.78 mmol) in 1,2-dichloroethane (10 mL) was stirred at RT for 10 min. To the mixture NaBH(OAc)$_3$ (803 mg, 3.79 mmol) and AcOH (0.22 mL, 3.79 mmol) were added. The reaction mixture was stirred at RT overnight. The solvent was evaporated under reduced pressure, and the residue was partitioned between saturated aqueous solution of Na$_2$CO$_3$ and EtOAc. The organic phase was separated, and the aqueous layer was extracted with EtOAc (2×20 mL). The combined organic phase was dried over Na$_2$SO$_4$ and evaporated under reduced pressure. The product was purified by column chromatography (EtOAc: iPrOH=80:20) to afford Int-148-13 as an amber oil (705 mg, 98% yield). LC-MS: (M+1) m/z=285.

Synthesis of Int-148-14

To Int-148-13 (703 mg, 2.47 mmol) in CH$_2$Cl$_2$ (5 mL) was added dropwise trifluoroacetic acid (3.78 mL, 49 mmol). The reaction mixture was stirred at RT for 1 h, then the solvent and the excess of trifluoroacetic acid were evaporated under reduced pressure to provide Int-148-14 as a yellow oil which was used in the next step without further purification (1.01 g, quantitative yield). LCMS: (M+1) m/z=185.

Synthesis of Compound 148

To a solution of Int-148-15 (24.4 mg, 0.08 mmol) in EtOH (0.4 mL) and 2-propanol (0.2 mL) were added Int-148-14 (R)—N-(tetrahydro-2H-pyran-3-yl)piperidin-4-amine bis trifluoroacetate (33 mg, 0.08 mmol) and DIPEA (55 µl, 0.32 mmol). The reaction mixture was heated with microwave at 140° C. for 140 min, then cooled to RT, and purified by preparative-TLC (CH$_2$Cl$_2$:MeOH=96:4) (2.6 g, 88% yield) to afford Compound 148 as a yellow solid (10.0 mg, 27% yield) LCMS: (M+1) m/z=454.

Examples 149-152

Compounds 149-152 were obtained according to the procedure for Compound 147 starting from ketone Int-147-14 and corresponding amine. Compound 149 was obtained as a pale yellow solid in 88-90% yield. LCMS: (M+1) m/z=440. Compound 150 was obtained as a pale brown solid in 89-90% yield. LCMS: (M+1) m/z=440. Compound 151 was obtained as a pale brown solid in 82-83% yield. LCMS: (M+1) m/z=454. Compound 152 was obtained as a pale yellow solid in 71-75% yield. LCMS: (M+1) m/z=454.

Examples 153-155

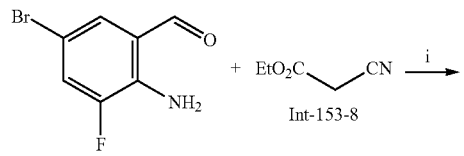

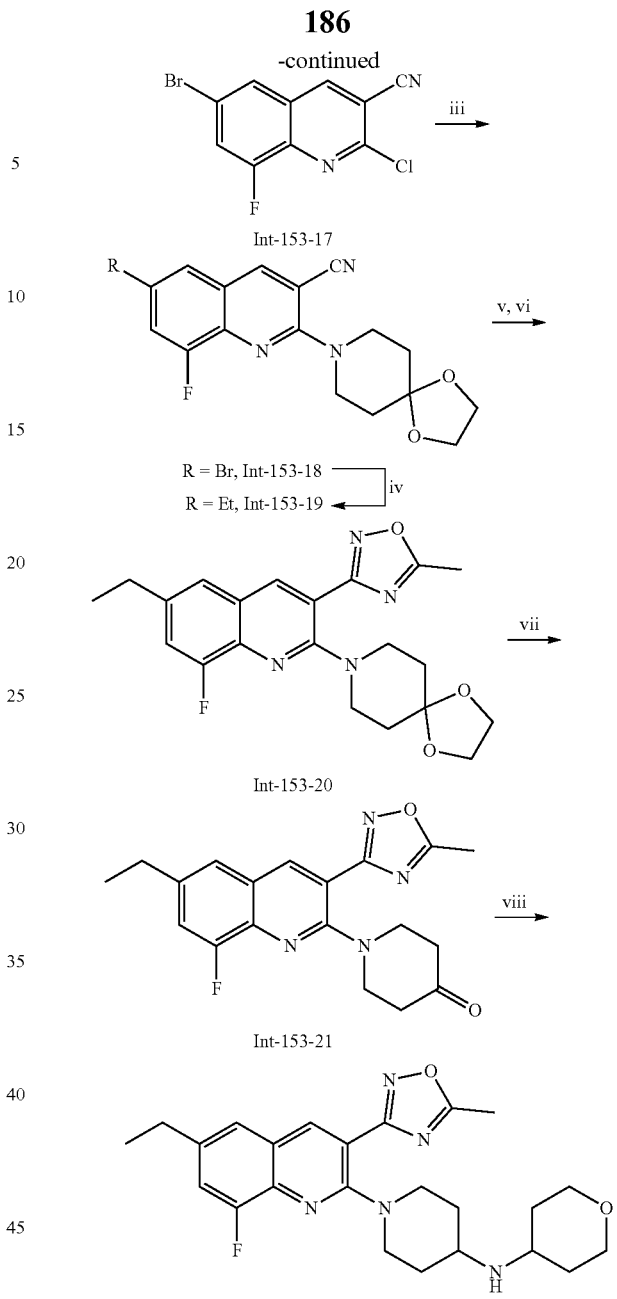

Compound 153

Reagents and conditions: i) Int-153-15 (1.0 equiv.), Int-153-8 (2.0 equiv.), NH4OAc (5.0 equiv.), 90° C., 8 h, 95-97%; ii) POCl3, 110° C., 1.5 h, quantitative; iii) Int-153-17 (1.0 equiv.), 1,4-dioxa-8-azaspiro[4,5]decane (1.1 equiv.), DIPEA (1.1 equiv.), iPrOH, 120° C., overnight, 96-98%; iv) Int-153-18 (1.0 equiv.), BEt3 (2.0 equiv.), Cs2CO3 (2.0 equiv.), Pd(dppf)Cl2•CH2Cl2 (0.05 equiv.), THF, 70° C., 1.5 h, 96-98%; v) Int-153-19 (1.0 equiv.), NH2OH•HCl (5.0 equiv.), Na2CO3 (5.0 equiv.), iPrOH, 90° C., overnight; vi) (AcO)2O (1.2 equiv.), DIPEA (1.2 equiv.), dioxane, rt to 90° C., 8 h, 28-30% two steps; vii) 10% aq. H2SO4, THF, 45° C., 2 h, 52-54%; viiii) 4-aminotetrahydropiran (1.2 equiv.), NaBH(OAc)3 (1.5 equiv.), AcOH (1.5 equiv.), 1,2-dichloroethane, rt, overnight, 78-80%.

Synthesis of Int-153-16

A mixture of aldehyde Int-153-15 (1.0 equiv.), ethyl 2-cyanoacetate Int-153-8 (2.0 equiv.) and NH$_4$OAc (5.0 equiv.) in dioxane was stirred at 90° C. for 8 h. The mixture was concentrated under reduced pressure and the solid was washed sequentially with water and EtOAc/hexanes (1:9)

(2x). Yellow solid Int-153-16 was used without further purification (95-97% yield). LCMS: (M+1) m/z=266, 268.

Synthesis of Int-153-17

A suspension of Int-153-16 (1.0 equiv.) in POCl$_3$ was stirred at 110° C. for 1.5 h. The excess POCl$_3$ was removed under reduced pressure. The crude was quenched with ice and the mixture was stirred at room temperature for 15 min. The crude was collected by filtration and washed with water (3x) to give Int-153-17 as a pale yellow solid in quantitative yield. LCMS: (M+1) m/z=284, 286.

Synthesis of Int-153-18

A mixture of 17 (1.0 equiv.), 1,4-dioxa-8-azaspiro[4,5]decane (1.1 equiv.) and DIPEA (1.1 equiv.) in iPrOH was heated at 120° C. overnight. The mixture was concentrated under reduced pressure and the product purified by column chromatography using hexanes/EtOAc. Product Int-153-18 was obtained as a pale brown solid in 96-98%. LCMS: (M+1) m/z=392, 394.

Synthesis of Int-153-19

To a suspension of Int-153-18 (1.0 equiv.), Cs$_2$CO$_3$ (2.0 equiv.) and Pd(dppf)Cl$_2$·CH$_2$Cl$_2$ (0.05 equiv.) in THF was added 1M solution of BEt$_3$ in THF (2.0 equiv.) and the reaction was heated at 70° C. for 1.5 h. After cooling to room temperature, the crude was filtered through celite and purified by column chromatography (hexanes:EtOAc) to afford Int-153-19 as a yellow solid (96-98% yield). LCMS: (M+1) m/z=342.

Synthesis of Int-153-20

A mixture of Int-153-19 (1.0 equiv.), NH$_2$OH·HCl (5.0 equiv.) and Na$_2$CO$_3$ (5.0 equiv.) in anhydrous isopropanol was heated at 90° C. overnight. The mixture was cooled to room temperature and filtrated. The organic phase was concentrated under reduced pressure and the product used without further purification. LCMS: (M+1) m/z=375. A mixture of the amidoxime (1.0 equiv.), acetic anhydride (1.2 equiv.) and DIPEA (1.2 equiv.) in dioxane was stirred at room temperature for 40 min, then the mixture was heated at 90° C. for 8 h. The mixture was concentrated under reduced pressure and the product purified by column chromatography using hexanes/EtOAc, a pale yellow solid Int-153-20 was obtained in 28-30% yield. LCMS: (M+1) m/z=399.

Synthesis of Int-153-21

To a solution of ketal Int-153-20 (1.0 equiv.) in THF was added 10% aq. H$_2$SO$_4$ and the mixture was stirred at 45° C. for 2 h. After cooling to room temperature, the mixture was neutralized with sat. aq. Na$_2$CO$_3$ and extracted with EtOAc (4x), dried over Na$_2$SO$_4$ and concentrated to dryness. The product was purified by column chromatography using hexanes:EtOAc to give the pale-yellow ketone Int-153-21 in 52-54% yield. LCMS: (M+1) m/z=355.

Synthesis of Compound 153

A mixture of ketone Int-153-21 (1.0 equiv.), 4-aminotetrahydropyran (1.2 equiv.), NaBH(OAc)$_3$ (1.5 equiv.) and AcOH (1.5 equiv.) in 1,2-dichloroethane was stirred at room temperature overnight. The mixture was concentrated under reduced pressure and purified by preparative-TLC (CH$_2$Cl$_2$:MeOH, 95:5) to give Compound 153 as an off-white solid in 78-80% yield. LCMS: (M+1) m/z=440.

Synthesis of Compound 154 and Compound 155

Compounds 154-155 were prepared in the same manner from ketone Int-153-21. Compound 155 was obtained as a pale-yellow oil in 85-86% yield. LCMS: (M+1) m/z=426. Compound 154 was obtained as a pale-yellow oil in 89-90% yield. LCMS: (M+1) m/z=426.

Examples 156-158

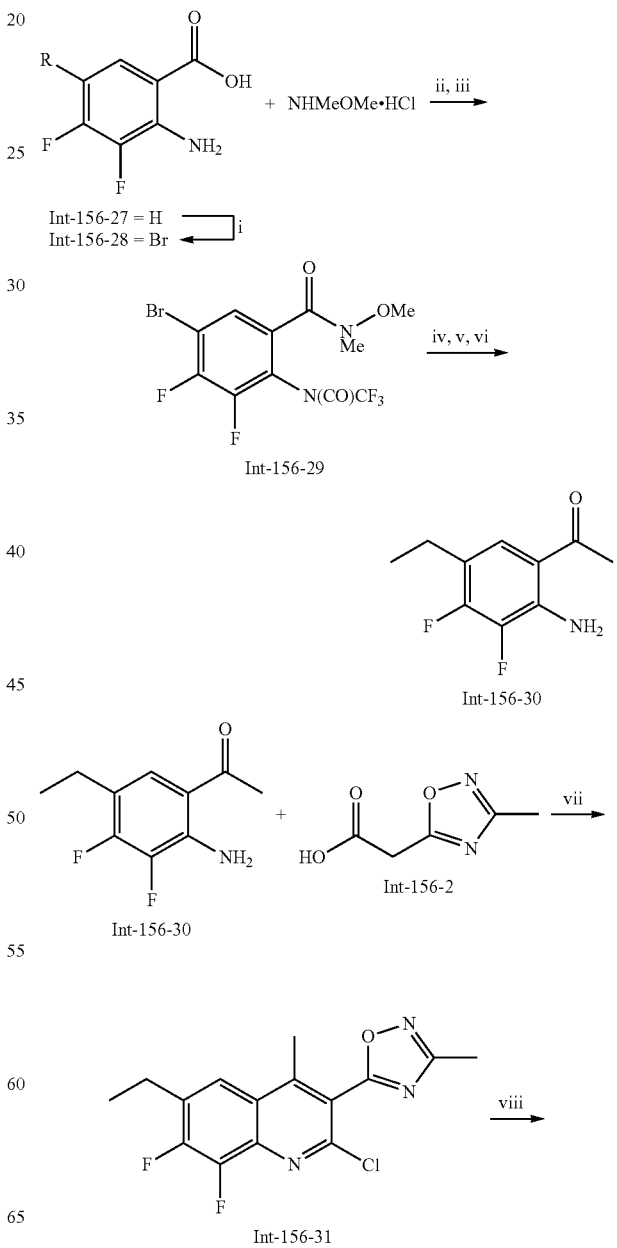

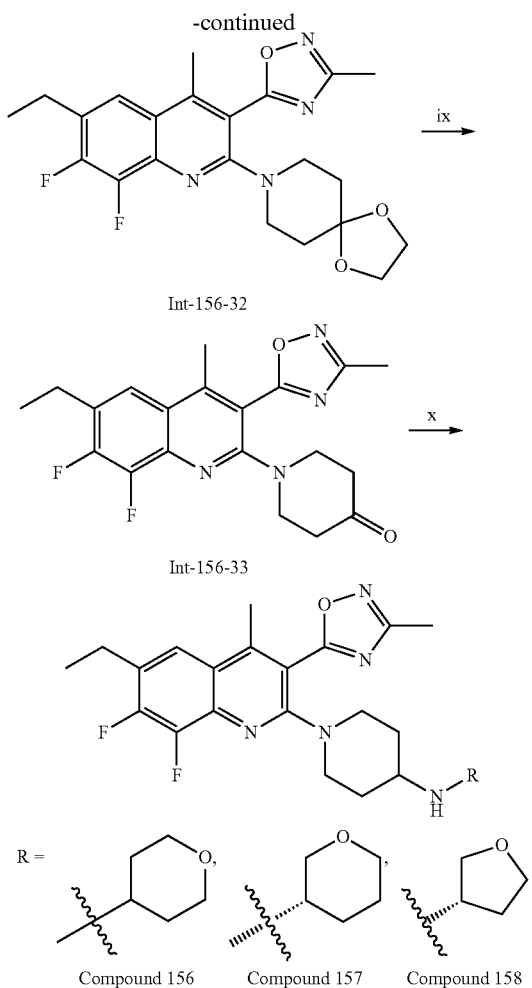

Compound 156   Compound 157   Compound 158

Synthesis of Int-156-28

To a suspension of 2-amino-3,4-difluorobenzoic acid 27 (1.0 equiv.) in $CH_2Cl_2$ was added N-bromosuccinimide (1.01 equiv.) and the mixture was stirred at RT for 48 h. The product was collected by filtration to give acid Int-156-28 as a white solid (92-95% yield), which was used in the next step without further purification. LCMS: (M−1) m/z=251, 253.

Synthesis of Int-156-29

A mixture of Int-156-28 (1.0 equiv.), N,O-dimethylhydroxylamine hydrochloride (1.2 equiv.), DIPEA (1.2 equiv.), EDCI (1.5 equiv.) and HOBt (1.5 equiv.) in DMF was stirred at RT for 4 h. The reaction mixture was diluted with water and the product was collected by filtration as a white solid, which was used in the next step without further purification. LCMS: (M+1) m/z=294, 296. To a solution of the Weinreb amide (1.0 equiv.) and TEA (1.2 equiv.) in $CH_2Cl_2$ at 0° C. was added dropwise trifluoroacetic anhydride (1.2 equiv.). The reaction was stirred at r.t. overnight. The mixture was concentrated under reduced pressure and the crude diluted with water. The solid was collected by filtration and was used in the next step without further purification. LCMS: (M−1) m/z=388, 390.

Synthesis of Int-156-30

A 1M solution of $Et_3B$ (3.0 equiv.) in THF was added to a suspension of Int-156-29 (1.0 equiv.), $Cs_2CO_3$ (3.0 equiv.) and $Pd(dppf)Cl_2$ (0.1 equiv.) in THF and the reaction was heated at 50° C. overnight. After cooling to RT the crude was filtered through celite and purified by column chromatography (hexanes:EtOAc) to afford the appropriate product in 9-11% yield. LCMS: (M+1) m/z=341. To a solution of the above product (1.0 equiv.) in THF at 0° C. was added MeMgBr (1.4 M) in THF:toluene (4.0 equiv.) and the reaction was stirred at room temperature for 2.5 h. The reaction was poured into ice, acidified to pH 2 with 2M HCl and the product extracted with EtOAc (2×). The combined organic layers were dried over $Na_2SO_4$ and concentrated to afford the corresponding ketone which was used in the next step without further purification. LCMS: (M−1) m/z=294. To a solution of ketone (1.0 equiv.) in MeOH was added 2 M aq. solution of NaOH (2.0 equiv.), and the reaction was heated at 90° C. for 1.5 h. The reaction mixture was concentrated and acidified with 1M HCl. The product was extracted with EtOAc (3×) and the organic phase was concentrated under reduced pressure. The crude was purified by column chromatography using hexanes:EtOAc to give Int-156-30 as a pale yellow solid (50-54% yield, two steeps). LCMS: (M+1) m/z=200.

Synthesis of Int-156-31

A mixture of ketone Int-156-30 (1.0 equiv.), 2-(3-methyl-1,2,4-oxadiazol-5-yl)acetic acid 2 (1.0 equiv.) and $POCl_3$ (2.5 mL) was stirred at 80° C. for 1 h. The excess $POCl_3$ was removed under reduced pressure. Ice/water was added to the residue and the solid was collected by filtration. The crude was used without further purification. LCMS: (M+1) m/z=324, 326.

Synthesis of Int-156-32

A suspension of Int-156-31 (1.0 equiv.), 1,4-dioxa-8-azaspiro[4,5]decane (1.2 equiv.) and DIPEA (1.2 equiv.) in iPrOH was heated at 125° C. overnight. After cooling to room temperature, the mixture was concentrated under reduced pressure and purified by column chromatography (Hexanes:EtOAc) to give ketal Int-156-32 as yellow solid (47-49% yield, two steps). LCMS: (M+1) m/z=431.

Synthesis of Int-156-33

A suspension of ketal Int-156-32 (1.0 equiv.) in 10% aq. $H_2SO_4$ was stirred at 45° C. for 2 h. After cooling to RT, the mixture was neutralized with $Na_2CO_3$ and the product extracted with EtOAc (3×). The organic phase was dried over $Na_2SO_4$ and concentrated to give ketone Int-156-33 as a yellowish solid which was used in the next step without further purification. LCMS: (M+1) m/z=387.

Synthesis of Compound 156, Compound 157 and Compound 158

A mixture of ketone Int-156-33 (1.0 equiv.), the appropriate amine (2.0 equiv.), $NaBH(OAc)_3$ (2.0 equiv.) and AcOH (2.0 equiv.) in 1,2-dichloroethane was stirred at RT overnight. The mixture was concentrated under reduced pressure and purified by HPLC to give the titled compounds. Compound 156 was obtained as pale brown solid in 96-97% yield (last step). LCMS: (M+1) m/z=472. Compound 157 was obtained as pale brown solid in 79-81% yield (last step). LCMS: (M+1) m/z=472. Compound 158 was obtained as pale yellow oil in 94-96% yield (last step). LCMS: (M+1) m/z=458.

Examples 159-160

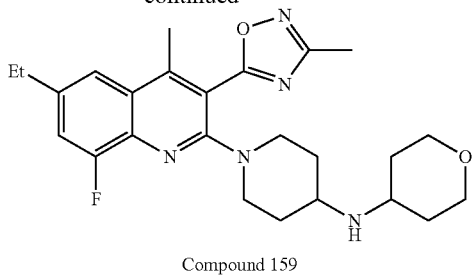

Compound 159

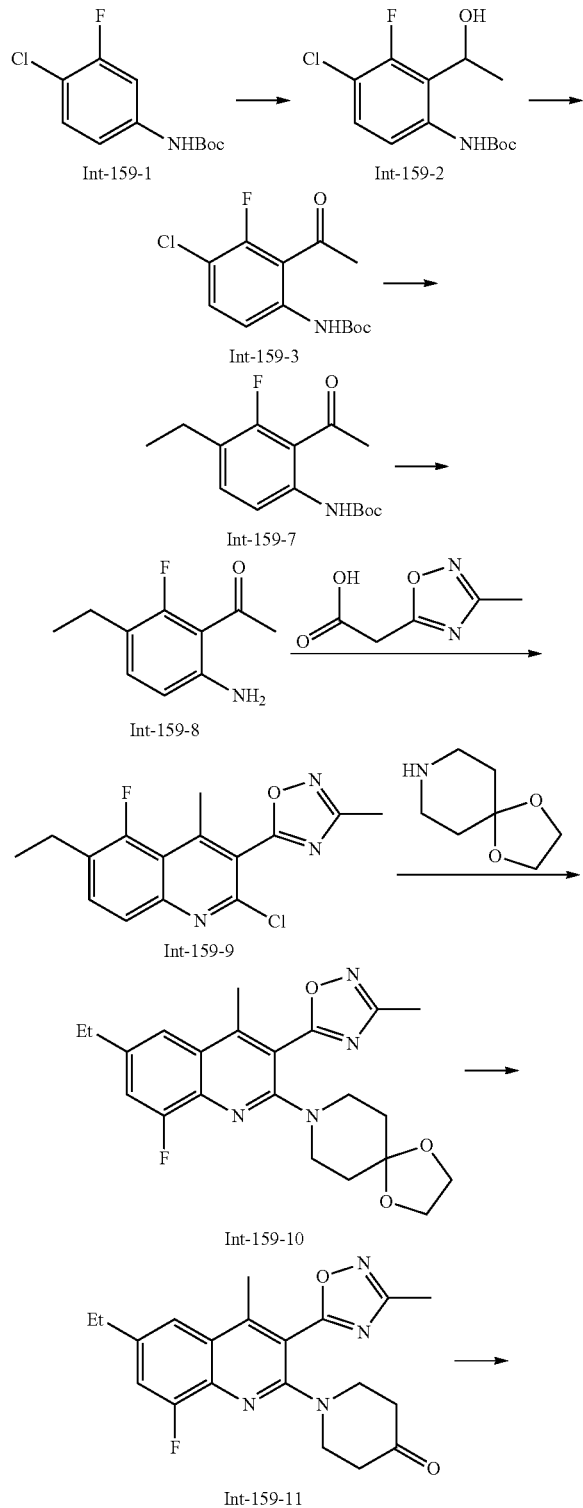

Synthesis of Int-159-2

To a solution of Int-159-1 (1.23 g, 5 mmol) in THF (25 mL) was added n-BuLi solution (2.5 M in Hexane, 6 mL, 15 mmol) at −78° C. and the mixture was stirred at −78° C. for 1 h. Acetaldehyde (1.1 mL, 20 mmol) was added at −78° C. and the mixture was stirred at −78° C. for 0.5 hour. The reaction was quenched with sat. aq. NH$_4$Cl solution and the product extracted with EtOAc (3×). The organic layer was dried over Na$_2$SO$_4$ and concentrated to dryness to afford Int-159-2 as a yellow liquid, which was used in the next step without further purification. LCMS: (M+1) m/z=290.

Synthesis of Int-159-3

To a solution of Int-159-2 in CH$_2$Cl$_2$ (30 mL) was added DMP (3.18 g, 7.5 mmol) and NaHCO$_3$ (0.84 g, 10 mmol) at room temperature and the mixture was stirred for 2 hour. Hexanes (30 mL) were added to the mixture and the combined suspension filtered through a short silica-gel column. The column was washed with hexanes/EtOAc (4:1, 50 mL×3). The combined organic solution was concentrated to afford Int-159-3 as a yellow solid (1.34 g, 93% yield for 2 steps), which was used in the next step without further purification. LCMS: (M+23) m/z=312.

Synthesis of Int-159-7

To a solution of Int-159-3 (288 mg, 1 mmol) in THF (4 mL) was added Pd(OAc)$_2$ (6.7 mg, 0.03 mmol), XPhos (28.6 mg, 0.06 mmol), Et$_3$B (1.0 M in THF, 3 mL, 3 mmol) and Cs$_2$CO$_3$ (975 mg, 3 mmol). The reaction mixture was stirred at 80° C. overnight. After cooling to room temperature, the crude was filtered through celite and purified by column chromatography (Hexanes:EtOAc) to afford Int-159-7 as a yellow liquid (176 mg, 51% yield). LCMS: (M+23) m/z=304.

Synthesis of Int-159-8

A mixture of Int-159-7 (150 mg, 0.53 mmol) and TFA (1 mL) in CH$_2$Cl$_2$ (4 mL) was stirred at room temperature for 4 hour. The reaction was quenched with sat. aq. Na$_2$CO$_3$ solution and the product extracted with CH$_2$Cl$_2$. The combined organic layer was dried over Na$_2$SO$_4$ and concentrated to afford Int-159-8 as a yellow liquid, which was used in the next step without further purification. LCMS: (M+1) m/z=182.

Synthesis of Int-159-9

A mixture of Int-159-8, 2-(3-methyl-1,2,4-oxadiazol-5-yl)acetic acid (110 mg, 0.77 mmol) and POCl$_3$ (1.5 mL) was stirred at 110° C. overnight. The excess POCl₃ was removed under vacuum. To the residue was added sat. aq. solution of NaHCO₃, and the product was extracted with EtOAc. The combined organic layers were dried over Na₂SO₄ and concentrated to dryness. The crude product was purified by column chromatography (Hexanes/EtOAc) to give Int-159-9 as a yellow solid (60 mg, 39% yield for 2 steps). LCMS: (M+1) m/z=306.

Synthesis of Int-159-10

To a suspension of Int-159-9 (50 mg, 0.16 mmol) in EtOH (1.6 mL), 1,4-dioxa-8-azaspiro[4,5]decane (41 µL, 0.32 mmol) and DIPEA (56 µL, 0.32 mmol) were added. The mixture was heated at 110° C. overnight. After cooling to room temperature, the mixture was concentrated under reduced pressure and purified by column chromatography (Hexanes/EtOAc) to give ketal Int-159-10 as yellow solid (60 mg, 91% yield). LCMS: (M+1) m/z=413.

Synthesis of Int-159-11

To a solution of Int-159-10 (1.0 equiv.) in the acetone was added aq. 2M HCl solution and the mixture was stirred at RT for 5 h. The reaction was diluted with EtOAc and washed sequentially with aq. Na₂CO₃ solution and brine to give Int-159-11 as a pale-brown solid in 91-93% yield, which was used in the next step without further purification. LCMS: (M+1) m/z=369.

Synthesis of Compound 159

A mixture of ketone Int-159-11 (1.0 equiv.), 4-aminotetrahydropyran (1.2 equiv.), NaBH(OAc)₃ (1.5 equiv.) and AcOH (1.5 equiv.) in 1,2-dichloroethane was stirred at room temperature overnight. The mixture was concentrated under reduced pressure and purified by HPLC to give Compound 159 as an off-white solid in 91-93% yield. LCMS: (M+1) m/z=454.

Synthesis of Compound 160

Compound 160 was obtained in the same manner as Compound 159, using intermediate ketone Int-159-11 and corresponding amine, as pale yellow oil; 81% yield. LCMS: (M+1) m/z=454.

Examples 161-165

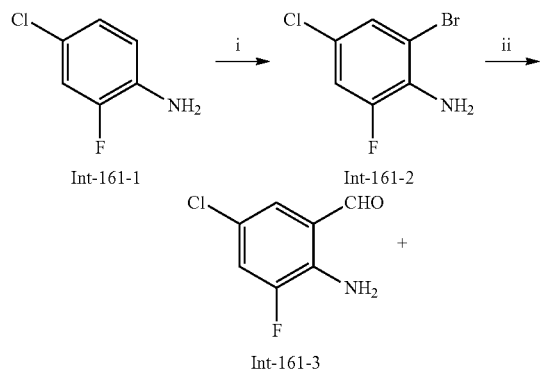

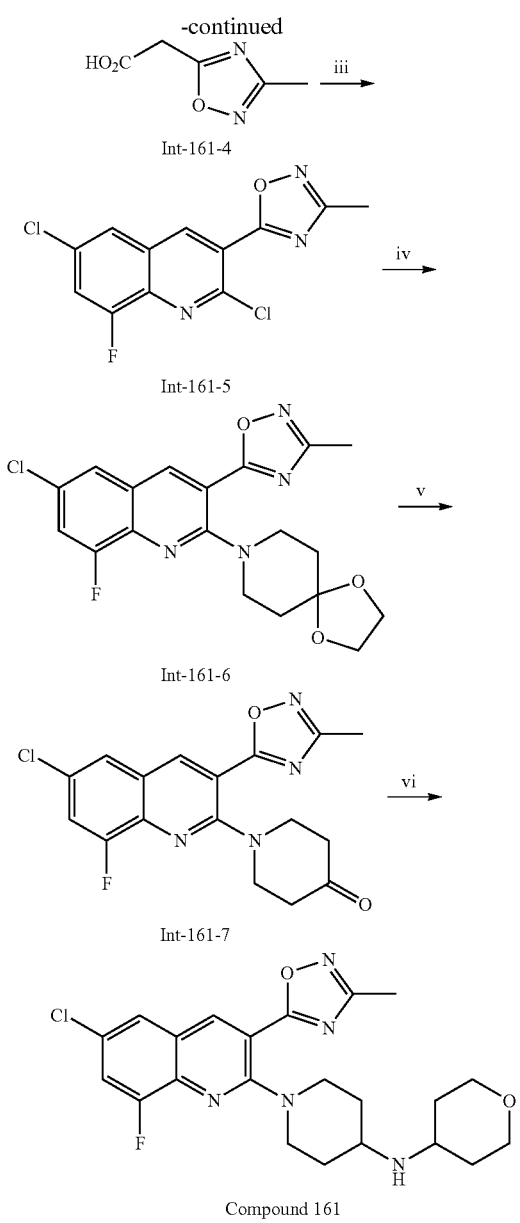

Synthesis of Int-161-2

To a suspension of aniline Int-161-1 (1.0 equiv.) in CH₂Cl₂ (100 mL) was added NBS (1.05 equiv.) and the reaction mixture was stirred at room temperature overnight. The mixture was partitioned between sat. aq. NaHCO₃ and CH₂Cl₂. The organic layer was separated, dried over Na₂SO₄ and concentrated. The residue was purified by column chromatography (hexanes/EtOAc) to give Int-161-2 as a yellow solid (57-59% yield). LCMS: (M+1) m/z=223, 225.

Synthesis of Int-161-3

To a solution of Int-161-2 (1.0 equiv.) in THF at −78° C. was added 2.0 M solution of nBuLi (2.2 equiv.) in hexanes dropwise. After stirring at −78° C. for 1 h, DMF (1.4 equiv.) was added at the same temperature. The temperature was increased to 0° C. and the mixture was stirred at 0° C. for 2 h. The mixture was quenched with sat. aq. NH4Cl and the product extracted with EtOAc (2×). The organic phase was washed with brine (3×), dried over sodium sulfate and concentrated under reduced pressure. The residue was purified by column chromatography (Hexanes/EtOAc gradient) to give Int-161-3 as a yellow solid (53-55% yield). LCMS: (M+1) m/z=174.

Synthesis of Int-161-5

The mixture of Int-161-3 (1.0 equiv.) and 4 (1.2 equiv.) in POCl3 was stirred 110° C. for 1.5 h. The excess of POCl3 was concentrated under reduced pressure. The crude was quenched with ice and stirred for 15 min at room temperature. The solid was collected by vacuum filtration and washed with water (2×). The solid was purified with a short-path silica gel using hexanes/EtOAc to give compound Int-161-5 in 17-19% yield as a yellow solid. LCMS: (M+1) m/z=397, 399.

Synthesis of Int-161-6

To a solution of Int-161-5 (1.0 equiv.), 1,4-dioxa-8-azaspiro[4,5]decane (2.0 equiv.) and DIPEA (2.0 equiv.) in iPrOH was heated at 110° C. overnight. After cooling to room temperature, the mixture was concentrated and purified by column chromatography (hexanes/EtOAc) to give Int-161-6 as a yellow solid (82-84% yield). LCMS: (M+1) m/z=405.

Synthesis of Int-161-7

To a solution of Int-161-6 (1.0 equiv.) in THF was added 10% aq. H2SO4 at room temperature. The mixture was then stirred at 45° C. for 2 h. After cooling to room temperature, the mixture was neutralized with sat. aq. Na2CO3 and extracted with EtOAc (×3). The combined organic layers were dried over Na2SO4 and concentrated under reduced pressure. The residue was purified by column chromatography (Hexanes/EtOAc gradient) to give Int-161-7 as pale yellow solid (63-65% yield). LCMS: (M+1) m/z=361.

Synthesis of Compound 161

A mixture of Int-161-7 (1.0 equiv.), amine (2.0 equiv.), NaBH(OAc)3 (2.0 equiv.) and AcOH (2.0 equiv.) in 1,2-dichloroethane was stirred at room temperature overnight. After filtration through Celite, the filtrate was concentrated under reduced pressure. The residue was purified by preparative-TLC using CH2Cl2/MeOH. Compound 161 was obtained as a pale yellow solid in 71-73% yield. LCMS: (M+1) m/z=446.

Synthesis of Compound 162, Compound 163, Compound 164, Compound 165

The titled compounds were obtained according to the procedure for Compound 160 starting from ketone Int-161-14 and corresponding amine. Compound 162 was obtained as a pale yellow solid 65-67% yield. LCMS: (M+1) m/z=446. Compound 163 was obtained as a pale yellow solid 66-68% yield. LCMS: (M+1) m/z=446. Compound 164 was obtained as a pale yellow solid 59-61% yield. LCMS: (M+1) m/z=432. Compound 165 was obtained as a pale yellow solid 72-74% yield. LCMS: (M+1) m/z=432.

Example 166

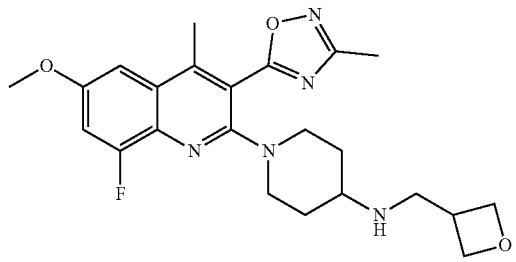 [SMILES: COc1cc(F)c2nc(N3CCC(NCC4COC4)CC3)c(-c3nc(C)no3)c(C)c2c1]

Compound 166 was prepared using ketone Int-33-14k described above for the synthesis of Compounds 33-35. A mixture of ketone Int-33-14k (15 mg, 0.040 mmol), oxetan-3-ylmethanamine (5.3 mg, 0.060 mmol), and AcOH (5 μL, 0.081 mmol) in 1,2-dichloroethane (0.1 mL) was stirred at room temperature for 30 minutes before NaBH(OAc)3 (17.2 mg, 0.081 mmol) was added. The mixture was stirred at room temperature overnight. The mixture was concentrated under reduced pressure and purified by preparative-TLC (CH2Cl2:MeOH, 95:5) to give Compound 166 as a yellow solid (2.3 mg, 12.9% yield). LCMS: (M+1) m/z=442.

Examples 167-169

Compound 167

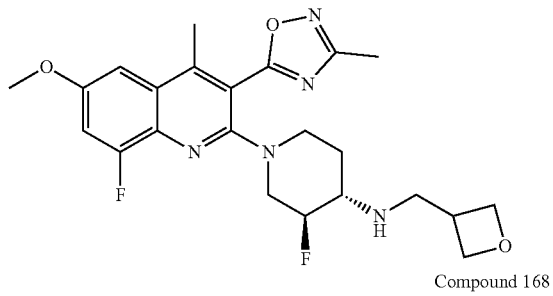

Compound 168

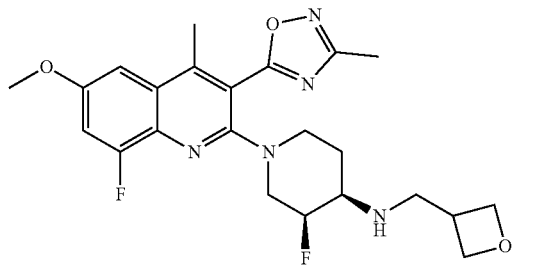

Compound 169

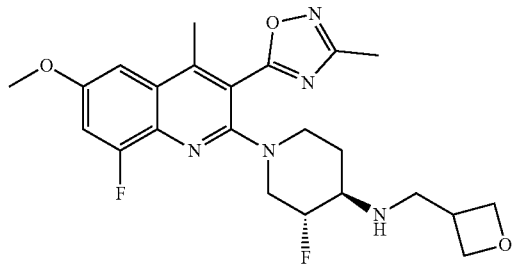

Compounds 167-169 are obtained as disclosed above for Compounds 40-59 and Compounds 134-137 using the appropriate amines with the appropriate stereochemistry, and Int-36-14h described above for the preparation of Compounds 36-39.

Examples 170-171

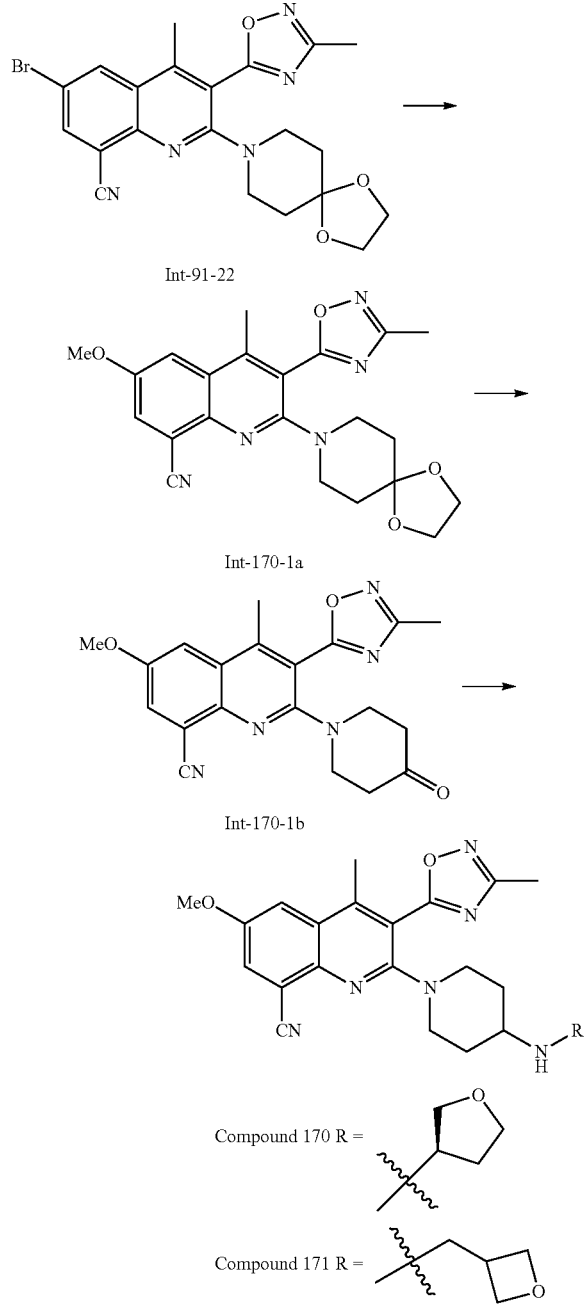

Synthesis of Int-170-1a

Intermediate Int-170-1a is obtained starting from Int-91-22 described above for the synthesis of Compound 91, and as disclosed for Int-33-14j described above for the synthesis of Compounds 33-35.

Synthesis of 1b

Intermediate Int-170-1b is obtained as disclosed for Int-33-14k described above for the synthesis of Compounds 33-35.

Synthesis of Compound 170 and Compound 171

Compound 170 and Compound 171 are obtained from Int-170-1b and the opportune amine, as disclosed above for the synthesis of Compounds 33-35

Example 172

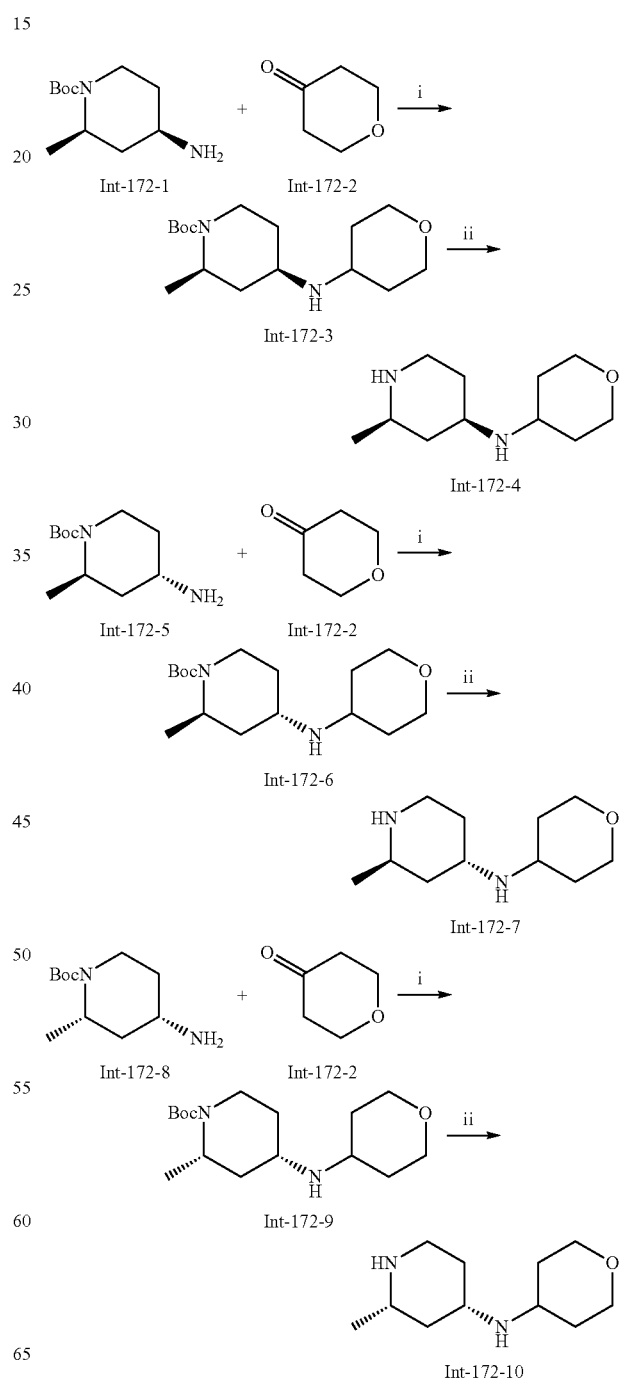

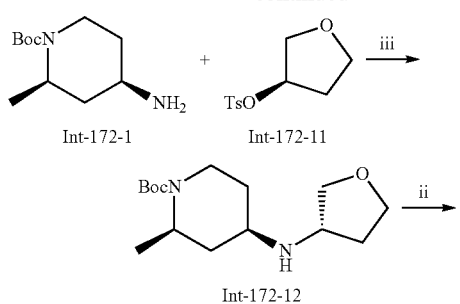

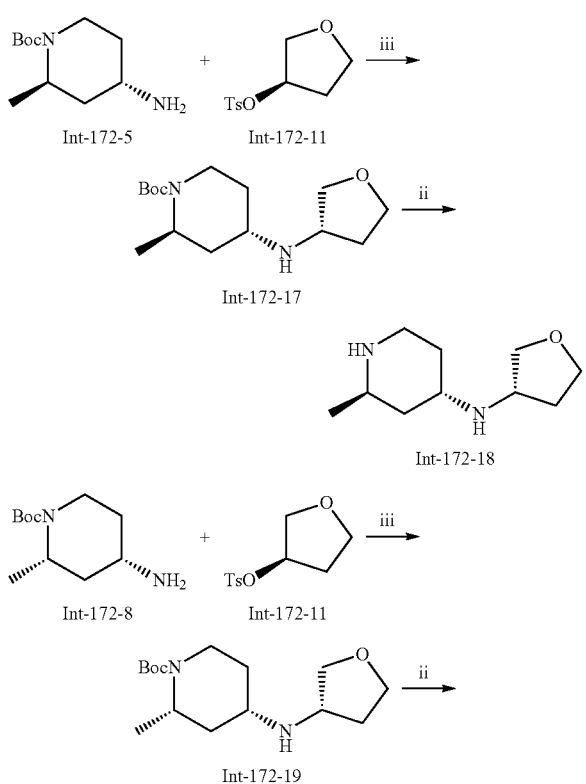

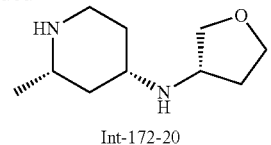

Reagents and conditions (Int-172-4 and Int-172-13 as examples):
i) Int-172-1 (1.0 eq.), amine (Int-172-2, 1.2 eq.), NaBH(OAc)$_3$ (1.5 eq.), AcOH (1.5 eq.), 1,2-dichloroethane, r.t., 18 h, 87-97%; ii) Int-172-3 (1.0 eq.), TFA (20 eq.), CH$_2$Cl$_2$, r.t., 40 min; iii) Int-172-1 (1.0 eq.), Int-172-11 (2.0 eq.), DIPEA (3.0 eq.), CH$_3$CN, 95° C., 48 h, 68-95%.

Synthesis of (2R,4R)-tert-butyl 2-methyl-4-((tetrahydro-2H-pyran-4-yl)amino)piperidine-1-carboxylate Int-172-3

To a solution of amine Int-172-1 (40 mg, 0.187 mmol) and ketone Int-172-2 (20.8 µL, 0.22 mmol) in DCE (300 µL) was added NaBH(OAc)$_3$ (59 mg, 0.28 mmol) and AcOH (15.5 µL, 0.28 mmol). The resulting mixture was stirred at room temperature overnight. The mixture was quenched with 1M NaOH and extracted with EtOAc (4×). The organic layer was dried over Na$_2$SO$_4$ and concentrated. The residue was purified by column chromatography (CH$_2$Cl$_2$/MeOH gradient) to give compound Int-172-3 as a pale grey solid (54 mg, 97% yield). LCMS: (M+1) m/z=299.

Synthesis of (2R,4R)-2-methyl-N-(tetrahydro-2H-pyran-4-yl)piperidin-4-amine Int-172-4

A mixture of Int-172-3 (54 mg, 0.18 mmol) and TFA (277 µL, 3.61 mmol) in CH$_2$Cl$_2$ (2 mL) was stirred at room temperature for 40 min. The mixture was concentrated under reduced pressure. The crude was re-dissolved in EtOAc and drops of concentrated aq. NaOH were slowly added. The H$_2$O was removed by addition of anhydrous MgSO$_4$ and the solid was filtrated off and rinsed with EtOAc (3×). The filtrate was concentrated and the product was used without further purification (quantitative yield). Int-172-4 was obtained as a pale-yellow oil. LCMS: (M+1) m/z=199.

Synthesis of tert-butyl (2R,4S)-2-methyl-4-((tetrahydro-2H-pyran-4-yl)amino)piperidine-1-carboxylate Int-172-6

To a solution of amine Int-172-5 (40 mg, 0.187 mmol) and ketone Int-172-2 (20.8 µL, 0.22 mmol) in DCE (300 µL) was added NaBH(OAc)$_3$ (59 mg, 0.28 mmol) and AcOH (15.5 µL, 0.28 mmol). The resulting mixture was stirred at room temperature overnight. The mixture was quenched with 1M NaOH and extracted with EtOAc (4×). The organic layer was dried over Na$_2$SO$_4$ and concentrated. The residue was purified by column chromatography (CH$_2$Cl$_2$/MeOH gradient) to give compound Int-172-6 as a pale grey solid (53 mg, 97% yield). LCMS: (M+1) m/z=299.

Synthesis of (2R,4S)-2-methyl-N-(tetrahydro-2H-pyran-4-yl)piperidin-4-amine Int-172-7

A mixture of Int-172-6 (53 mg, 0.18 mmol) and TFA (277 µL, 3.61 mmol) in CH$_2$Cl$_2$ (2 mL) was stirred at room temperature for 40 min. The mixture was concentrated under reduced pressure. The crude was re-dissolved in EtOAc and drops of concentrated aq. NaOH were slowly added. The H$_2$O was removed by addition of anhydrous MgSO$_4$ and the solid was filtrated off and rinsed with EtOAc (3×). The filtrate was concentrated and the product was used without further purification (quantitative yield). Int-172-7 was obtained as a pale-yellow oil. LCMS: (M+1) m/z=199.

Synthesis of (2S,4S)-2-methyl-N-(tetrahydro-2H-pyran-4-yl)piperidin-4-amine Int-172-10

Compound (2S,4S)-2-methyl-N-(tetrahydro-2H-pyran-4-yl)piperidin-4-amine Int-172-10 was synthesized in a similar fashion in 94% yield (over two steps) and obtained as pale yellow oil. LCMS: (M+1) m/z=199.

Synthesis of (2R,4R)-2-methyl-N—((S)-tetrahydrofuran-3-yl)piperidin-4-amine Int-172-13

A mixture of Int-172-1 (1.0 g, 4.6 mmol), Int-172-11 (3.3 g, 14 mmol) and DIPEA (2.44 mL, 14 mmol) in acetonitrile (10 mL) was heated 95° C. for 48 h. The mixture was concentrated under reduced pressure and purified by column chromatography using CH$_2$Cl$_2$/MeOH as mobile phase to give 1.0 g of pale grey solid (76% yield). LCMS: (M+1) m/z=285.

A mixture of Int-172-12 (1 g, 3.51 mmol) and TFA (5.38 mL, 70.3 mmol) in CH$_2$Cl$_2$ was stirred at room temperature for 40 min. The mixture was concentrated under reduced pressure. The crude was re-dissolved in EtOAc and drops of concentrated aq. NaOH were slowly added. The H$_2$O was removed by addition of anhydrous MgSO$_4$ and the solid was filtrated off and rinsed with EtOAc (3×). The filtrate was concentrated and the product was used without further purification (640 mg, quantitative yield). LCMS: (M+1) m/z=185.

Synthesis of (2R,4R)-2-methyl-N—((R)-tetrahydrofuran-3-yl)piperidin-4-amine Int-172-16

A mixture of Int-172-1 (1.0 g, 4.6 mmol), Int-172-14 (3.3 g, 14 mmol) and DIPEA (2.44 mL, 14 mmol) in acetonitrile (10 mL) was heated 95° C. for 48 h. The mixture was concentrated under reduced pressure and purified by column chromatography using CH$_2$Cl$_2$/MeOH as mobile phase. 1.26 g of a pale grey solid was obtained (95% yield). LCMS: (M+1) m/z=285.

A mixture of Int-172-15 (1260 mg, 4.43 mmol) and TFA (6.78 mL, 88.6 mmol) in CH$_2$Cl$_2$ (20 mL) was stirred at room temperature for 40 min. The mixture was concentrated under reduced pressure. The crude was re-dissolved in EtOAc and drops of concentrated aq. NaOH were slowly added. The H$_2$O was removed by addition of anhydrous MgSO$_4$ and the solid was filtrated off and rinsed with EtOAc (3×). The filtrate was concentrated and the product was used without further purification (810 mg, quantitative yield). LCMS: (M+1) m/z=185.

Synthesis of (2R,4S)-2-methyl-N—((S)-tetrahydrofuran-3-yl)piperidin-4-amine Int-172-18

Compound (2R,4S)-2-methyl-N—((S)-tetrahydrofuran-3-yl)piperidin-4-amine Int-172-18 was synthesized in a similar fashion. The product was obtained as pale yellow oil in 46% yield (two steps). LCMS: (M+1) m/z=185.

Synthesis of (2S,4S)-2-methyl-N—((S)-tetrahydrofuran-3-yl)piperidin-4-amine Int-172-20

Compound (2S,4S)-2-methyl-N—((S)-tetrahydrofuran-3-yl)piperidin-4-amine Int-172-20 was synthesized in a similar fashion. The product was obtained as pale yellow oil in 33% yield (two steps). LCMS: (M+1) m/z=185.

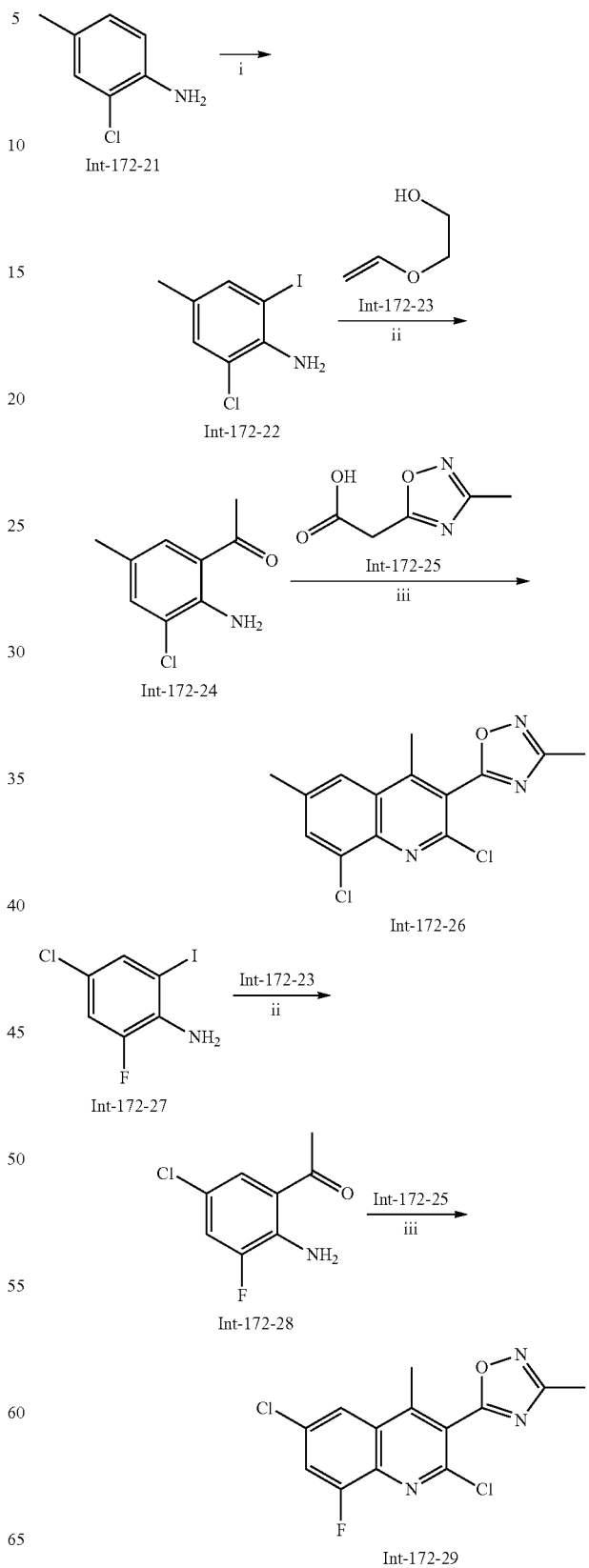

203
-continued

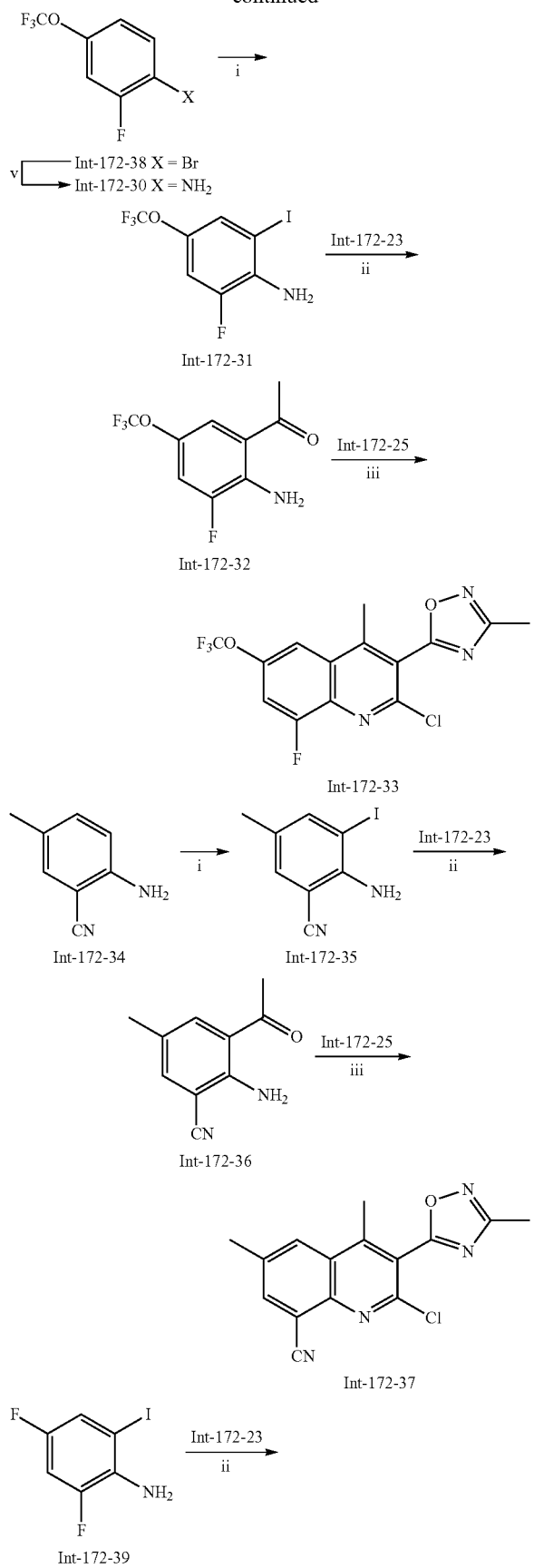

204
-continued

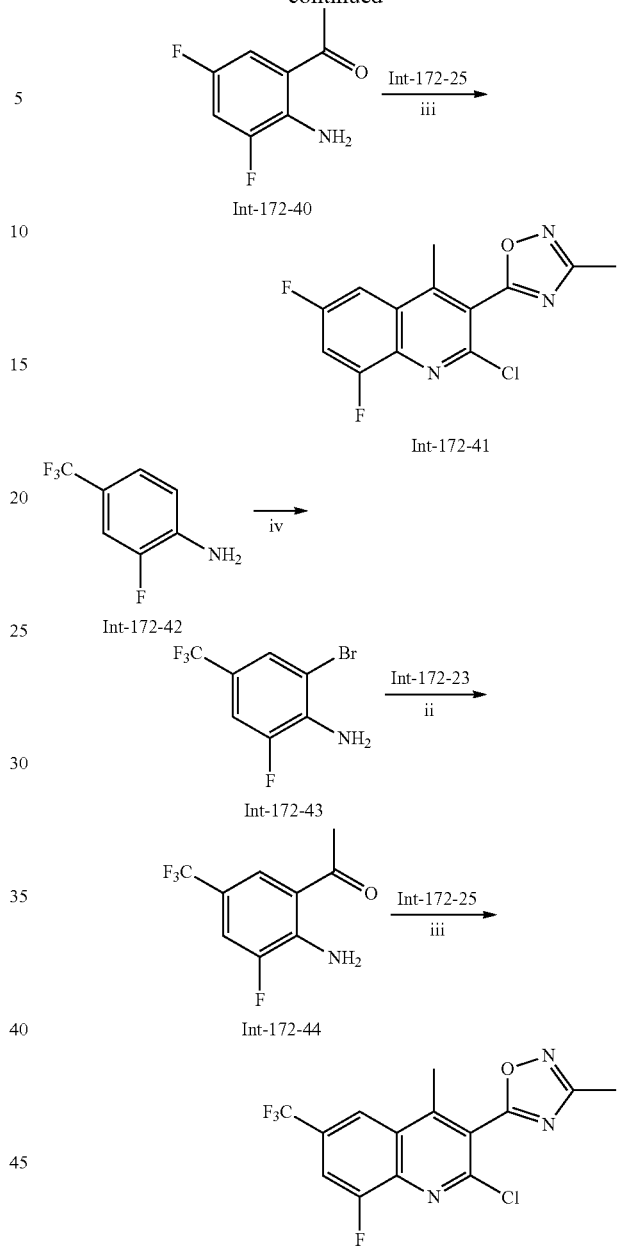

Reagents and conditions (Int-172-26 as example): i) Int-172-21 (1.0 eq.), NIS (1.05 eq.), AcOH, r.t., 67-74%; ii) Int-172-22 (1.0 eq.), Int-172-23 (6.0 eq.), K₂CO₃ (1.2 eq.), DPPP (0.05 eq.), Pd(OAc)₂ (0.01 eq.), toluene/H₂O (1:9) 90° C., 24-40 h, 10-37%; iii) Int-172-24 (1.0 eq.), Int-172-25 (1.2 eq.), POCl₃, 80° C., 1 h, 17-95%; iv) Int-172-42 (1.0 eq.), NBS (1.05 eq.), CH₂Cl₂, r.t., 18 h, 56%; v) Int-172-38 (1.0 eq.), benzophenone imine (1.2 eq.), Pd₂(dba)₃ (0.025 eq.), XantPhos (0.1 eq.), NaOtBu (1.2 eq.), 1,4-dioxane, 100° C., 18 h; followed by HCl (1M aq.), THF, r.t., 1 h, 30%.

Synthesis of 5-(2,8-dichloro-4,6-dimethylquinolin-3-yl)-3-methyl-1,2,4-oxadiazole Int-172-26

Synthesis of 2-chloro-6-iodo-4-methylaniline Int-172-22

To a mixture of Int-172-21 (5.0 g, 35.3 mmol) in acetic acid (50 mL) was added in a single portion NIS (8.34 g, 37.1 mmol) and the mixture was stirred at room temperature for 1 h. The mixture was diluted with EtOAc (500 mL) and washed with brine (3×) and sat. aq. NaHCO₃ solution (2×). The organic phase was dried over Na₂SO₄ and concentrated under reduced pressure. The product was purified by column chromatography using hexanes/EtOAc (0 to 30% EtOAc in hexanes) as mobile phase. The product was obtained as a pale red solid in 74% yield (7 g). LCMS: (M+1) m/z=267.

Synthesis of 1-(2-amino-3-chloro-5-methylphenyl)ethanone Int-172-24

A mixture of Int-172-22 (7 g, 26.17 mmol), 23 (14.09 mL, 157 mmol), K₂CO₃ (4.34 g, 31.4 mmol), DPPP (521 mg, 1.3 mmol) and Pd(OAc)₂ (59 mg, 0.26 mmol) in 60 mL H₂O/toluene (9:1) was heated at 90° C. for 24 h. After the mixture was cooled to room temperature, concentrated HCl (15 mL) was slowly added and the mixture was stirred at room temperature for 1 h. The product was extracted with EtOAc (3×). The organic phase was dried over anhydrous Na₂SO₄ and concentrated under reduced pressure. The product was purified by column chromatography using hexanes/EtOAc (0 to 20% EtOAc in hexanes) and obtained as a pale yellow solid (1.3 g) in 27% yield. LCMS: (M+1) m/z=184.

Synthesis of 5-(2,8-dichloro-4,6-dimethylquinolin-3-yl)-3-methyl-1,2,4-oxadiazole Int-172-26

A mixture of Int-172-24 (1.3 g, 7.08 mmol) and 25 (1.2 g, 8.5 mmol) in POCl₃ (5 mL) was stirred at 80° C. for 1 h. The mixture was concentrated under reduced pressure and quenched with ice/H₂O. The mixture was stirred at room temperature for 30 min and the product was filtered. The solid was purified by column chromatography using hexanes/EtOAc (0 to 30% EtOAc in hexanes) and the product was obtained as a pale yellow solid in 19% yield (430 mg). LCMS: (M+1) m/z=308.

Synthesis of 5-(2,6-dichloro-8-fluoro-4-methylquinolin-3-yl)-3-methyl-1,2,4-oxadiazole 29

Synthesis of 1-(2-amino-5-chloro-3-fluorophenyl)ethan-1-one Int-172-28

A mixture of Int-172-27 (5 g, 18.4 mmol), 23 (9.9 mL, 110.5 mmol), K₂CO₃ (3.05 g, 22.1 mmol), DPPP (366 mg, 0.92 mmol) and Pd(OAc)₂ (41 mg, 0.18 mmol) in 60 mL H₂O/toluene (9:1) was heated at 90° C. for 24 h. After the mixture was cooled to room temperature, concentrated HCl (14 mL) was slowly added and the mixture was stirred at room temperature for 1 h. The product was extracted with EtOAc (3×). The organic phase was dried over anhydrous Na₂SO₄ and concentrated under reduced pressure. The product was purified by column chromatography using hexanes/EtOAc (0 to 20% EtOAc in hexanes) and obtained as a pale brown solid (1.3 g) in 37% yield. LCMS: (M+1) m/z=188.

Synthesis of 5-(2,6-dichloro-8-fluoro-4-methylquinolin-3-yl)-3-methyl-1,2,4-oxadiazole Int-172-29

A mixture of Int-172-28 (1.25 g, 6.66 mmol) and 25 (1.04 g, 7.33 mmol) in POCl₃ (5 mL) was stirred at 80° C. for 1 h. The mixture was concentrated under reduced pressure and quenched with ice/H₂O. The mixture was stirred at room temperature for 30 min and the product was filtered. The solid was purified by column chromatography using hexanes/EtOAc (0 to 30% EtOAc in hexanes) and the product was obtained as a pale brown solid in 17% yield (350 mg). LCMS: (M+1) m/z=312.

Synthesis of 5-(2-chloro-8-fluoro-4-methyl-6-(trifluoromethoxy)quinolin-3-yl)-3-methyl-1,2,4-oxadiazole Int-172-33

Synthesis of 2-fluoro-6-iodo-4-(trifluoromethoxy)aniline Int-172-31

A mixture of 1-bromo-2-fluoro-4-(trifluoromethoxy)benzene Int-172-38 (12.8 g, 49.4 mmol), benzophenone imine (10 mL, 59.3 mmol), Pd₂(dba)₃ (1.1 g, 1.23 mmol), Xant-Phos (2.8 g, 4.9 mmol) and NaOtBu (5.7 g, 59.3 mmol) in 1,4-dioxane (100 mL) was stirred and heated at 100° C. overnight. After cooling to room temperature, the mixture was concentrated. The residue was then partitioned between EtOAc and H₂O, and the organic layer was separated, dried over Na₂SO₄ and concentrated. The residue was purified by column chromatography using hexanes/EtOAc (0 to 5% EtOAc in hexanes). The product was dissolved in THF (100 mL), and 1M aqueous HCl (50 mL) was added. After being stirred at room temperature for 1 h, the mixture was partitioned between EtOAc and H₂O. The organic layer was separated, washed with brine, dried over Na₂SO₄ and concentrated. The residue was purified by column chromatography using hexanes/EtOAc (0 to 20% EtOAc in hexanes). The product 30 was obtained as pale brown oil in 30% yield (5.4 mg). LCMS: (M+1) m/z=196.

To a mixture of Int-172-30 (310 mg, 1.58 mmol) in acetic acid (5 mL) was added in a single portion NIS (373 mg, 1.66 mmol) and the mixture was stirred at room temperature for 2.5 h. The mixture was diluted with EtOAc and washed with brine (3×) and sat. aq. Na₂CO₃ (2×). The organic layer was dried over Na₂SO₄ and concentrated in vacuo. The product was purified by column chromatography using hexanes/EtOAc (0 to 20% EtOAc in hexanes) as mobile phase. The product was obtained as a red oil in 67% yield (340 mg).

Synthesis of 1-(2-amino-3-fluoro-5-(trifluoromethoxy)phenyl)ethanone Int-172-32

A mixture of Int-172-31 (340 mg, 1.06 mmol), Int-172-23 (0.5 mL, 5.30 mmol), K₂CO₃ (176 mg, 1.27 mmol), DPPP (22 mg, 0.053 mmol) and Pd(OAc)₂ (2.4 mg, 0.0106 mmol) in 1,4-dioxane/H₂O (2 mL, 9:1 v/v) was heated at 90° C. overnight. After the mixture was cooled to room temperature, concentrated HCl (1 mL) was slowly added and the mixture was stirred at room temperature for 1 h. The product was extracted with EtOAc (3×). The combined organic layers were dried over Na₂SO₄ and concentrated in vacuo. The product was purified by column chromatography using hexanes/EtOAc (0 to 20% EtOAc in hexanes) as mobile phase. The product was obtained as a pale yellow solid (128 mg) in 51% yield. LCMS: (M+1) m/z=238.

Synthesis of 5-(2-chloro-8-fluoro-4-methyl-6-(trifluoromethoxy)quinolin-3-yl)-3-methyl-1,2,4-oxadiazole Int-172-33

A mixture of Int-172-32 (128 mg, 0.54 mmol) and Int-172-25 (92 mg, 0.65 mmol) in POCl₃ (2 mL) was stirred at 100° C. for 1 h. After cooling to room temperature, excess POCl₃ was removed in vacuo. To the residue, H₂O was added at 0° C., and the mixture was stirred at 0° C. for 10 min. The precipitated crude chloroquinoline Int-172-33 was filtered, washed with H$_2$O, and dried under the reduced pressure. The residue as dark brown solid was used without further purification (185 mg, 95% yield). LCMS: (M+1) m/z=362.

Synthesis of 2-chloro-4,6-dimethyl-3-(3-methyl-1,2,4-oxadiazol-5-yl)quinoline-8-carbonitrile Int-172-37

Synthesis of 2-amino-3-iodo-5-methylbenzonitrile Int-172-35

To a mixture of Int-172-34 (5.0 g, 37.8 mmol) in acetic acid (50 mL) was added in a single portion NIS (8.9 g, 39.7 mmol) and the mixture was stirred at room temperature for 1 h. The mixture was diluted with EtOAc (500 mL) and washed with brine (3×) and sat NaHCO$_3$ solution (2×). The organic phase was dried over Na$_2$CO$_3$ and concentrated under reduced pressure. The product was purified by column chromatography using hexanes/EtOAc (0 to 30% EtOAc in hexanes) as mobile phase. 35 was obtained as a pale brown solid in 71% yield (6.9 g). LCMS: (M+1) m/z=258.

Synthesis of 3-acetyl-2-amino-5-methylbenzonitrile Int-172-36

A mixture of Int-172-35 (2 g, 7.75 mmol), Int-172-23 (4.17 mL, 46.5 mmol), K$_2$CO$_3$ (1.28 g, 9.3 mmol), DPPP (154 mg, 0.39 mmol) and Pd(OAc)$_2$ (17 mg, 0.08 mmol) in 40 mL H$_2$O/toluene (9:1) was heated at 90° C. for 24 h. After the mixture was cooled to room temperature, concentrated HCl (8 mL) was slowly added and the mixture was stirred at room temperature for 1 h. The product was extracted with EtOAc (3×). The organic phase was dried over anhydrous Na$_2$SO$_4$ and concentrated under reduced pressure. The product was purified by column chromatography using hexanes/EtOAc (0 to 30% EtOAc in hexanes) and obtained as a pale yellow solid (203 mg) in 15% yield. LCMS: (M+1) m/z=175.

Synthesis of 2-chloro-4,6-dimethyl-3-(3-methyl-1,2,4-oxadiazol-5-yl)quinoline-8-carbonitrile Int-172-37

A mixture of Int-172-36 (408 mg, 2.3 mmol) and Int-172-25 (400 mg, 2.8 mmol) in POCl$_3$ (4 mL) was stirred at 80° C. for 1 h. The mixture was concentrated under reduced pressure and quenched with ice/H$_2$O. The mixture was stirred at room temperature for 30 min and the product filtered. The solid was purified by column chromatography using hexanes/EtOAc (0 to 40% EtOAc in hexanes) and the product was obtained as a pale yellow solid in 28% yield (190 mg). LCMS: (M+1) m/z=299.

Synthesis of 5-(2-chloro-6,8-difluoro-4-methylquinolin-3-yl)-3-methyl-1,2,4-oxadiazole Int-172-41

Synthesis of 1-(2-amino-3,5-difluorophenyl)ethanone Int-172-40

A mixture of Int-172-39 (3.02 g, 11.84 mmol), 23 (5.3 mL, 59.20 mmol), K$_2$CO$_3$ (2.0 g, 14.20 mmol), DPPP (0.24 g, 0.59 mmol) and Pd(OAc)$_2$ (27 mg, 0.12 mmol) in 1,4-dioxane/H$_2$O (25 mL, 9:1, v/v) was heated at 90° C. for 2 days. After the mixture was cooled to room temperature, concentrated HCl (6 mL) was slowly added and the mixture was stirred at room temperature for 1 h. The product was extracted with EtOAc (3×). The combined organic layers were dried over Na$_2$SO$_4$ and concentrated in vacuo. The product was purified by column chromatography using hexanes/EtOAc (0 to 20% EtOAc in hexanes) as mobile phase. The product was obtained as a yellow solid in 28% yield (0.56 g). LCMS: (M+1) m/z=172.

Synthesis of 5-(2-chloro-6,8-difluoro-4-methylquinolin-3-yl)-3-methyl-1,2,4-oxadiazole Int-172-41

A mixture of Int-172-40 (0.56 g, 3.28 mmol) and Int-172-25 (0.56 g, 3.94 mmol) in POCl$_3$ (10 mL) was stirred at 100° C. for 1 h. After cooling to room temperature, excess POCl$_3$ was removed in vacuo. To the residue, H$_2$O was added at 0° C., and the mixture was stirred at 0° C. for 10 min. The precipitated crude chloroquinoline Int-172-41 was filtered, washed with H$_2$O, and dried under the reduced pressure. The solid was purified by column chromatography using hexanes/EtOAc (0 to 20% EtOAc in hexanes) as mobile phase. The product was obtained as a pale brown solid in 25% yield (0.25 g). LCMS: (M+1) m/z=296.

Synthesis of 5-(2-chloro-8-fluoro-4-methyl-6-(trifluoromethyl)quinolin-3-yl)-3-methyl-1,2,4-oxadiazole Int-172-45

Synthesis of 2-bromo-6-fluoro-4-(trifluoromethyl)aniline Int-172-43

To a solution of Int-172-42 (8.5 g, 47.45 mmol) in CH$_2$Cl$_2$ (100 mL) was added in a single portion NBS (8.9 g, 49.83 mmol) and the mixture was stirred at room temperature overnight. After concentration in vacuo, the mixture was purified by column chromatography using hexanes/EtOAc (0 to 20% EtOAc in hexanes) as mobile phase. The product was obtained as red oil in 56% yield (6.8 g).

Synthesis of 1-(2-amino-3-fluoro-5-(trifluoromethyl)phenyl)ethanone Int-172-44

A mixture of Int-172-43 (6.8 g, 26.35 mmol), Int-172-23 (12 mL, 131.75 mmol), K$_2$CO$_3$ (4.4 g, 31.62 mmol), DPPP (0.55 g, 1.32 mmol) and Pd(OAc)$_2$ (59 mg, 0.26 mmol) in 1,4-dioxane/H$_2$O (60 mL, 9:1, v/v) was heated at 95° C. for 40 h. After the mixture was cooled to room temperature, concentrated HCl (14 mL) was slowly added and the mixture was stirred at room temperature for 1 h. The product was extracted with EtOAc (3×). The combined organic layers were dried over Na$_2$SO$_4$ and concentrated in vacuo. The product was purified by column chromatography using hexanes/EtOAc (0 to 20% EtOAc in hexanes) as mobile phase. The product was obtained as a yellow solid in 10% yield (0.58 g). LCMS: (M+1) m/z=222.

Synthesis of 5-(2-chloro-8-fluoro-4-methyl-6-(trifluoromethyl)quinolin-3-yl)-3-methyl-1,2,4-oxadiazole Int-172-45

A mixture of Int-172-44 (0.58 g, 2.64 mmol) and Int-172-25 (0.45 g, 3.17 mmol) in POCl$_3$ (5 mL) was stirred at 100° C. for 1 h. After cooling to room temperature, excess POCl$_3$ was removed in vacuo. To the residue, H$_2$O was added at 0° C., and the mixture was stirred at 0° C. for 10 min. The precipitated crude chloroquinoline Int-172-45 was filtered, washed with H$_2$O, and dried under reduced pressure. The solid was purified by column chromatography using hexanes/EtOAc (0 to 20% EtOAc in hexanes) as mobile phase. The product was obtained as a pale brown solid in 26% yield (0.24 g). LCMS: (M+1) m/z=346, 348.

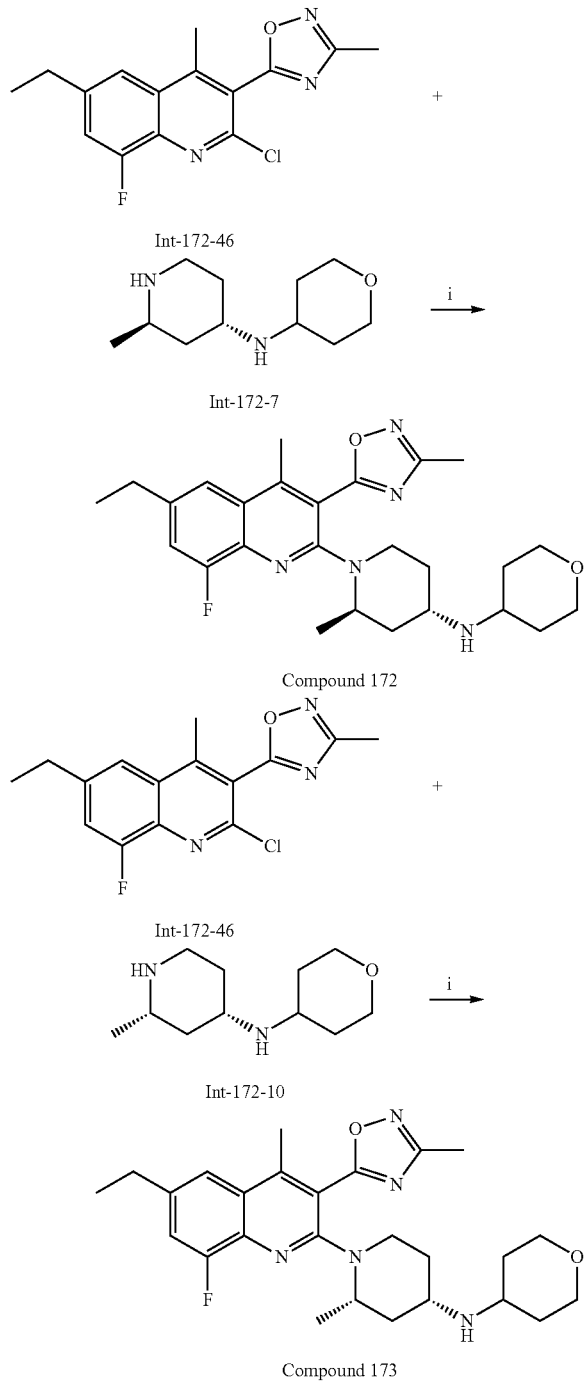

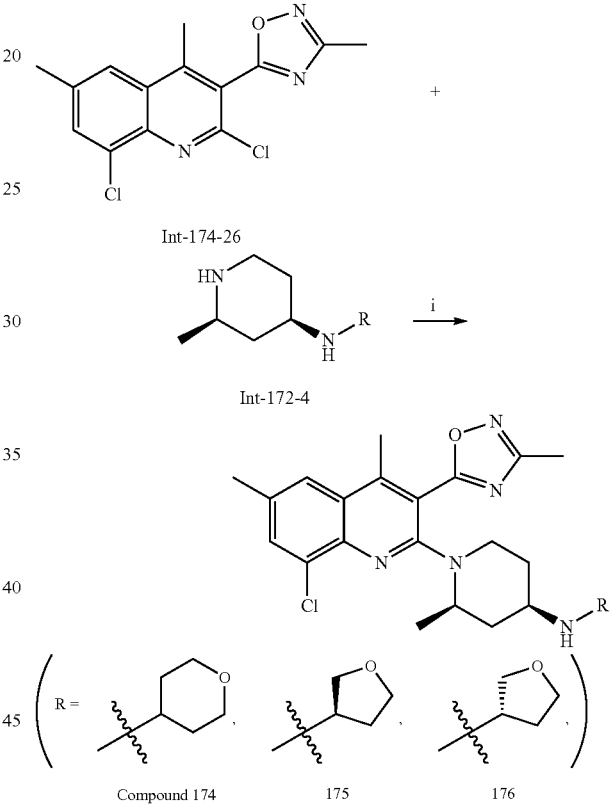

Reagents and conditions: i) Int-172-46 (1.0 eq.), amine (1.5 eq.), KF (2.5 eq.), DMF, 125° C., 18 h, 10-21%.

Synthesis of (2R,4S)-1-(6-ethyl-8-fluoro-4-methyl-3-(3-methyl-1,2,4-oxadiazol-5-yl)quinolin-2-yl)-2-methyl-N-(tetrahydro-2H-pyran-4-yl)piperidin-4-amine (Compound 172)

A mixture of Int-172-46 (10 mg, 0.033 mmol), 7 (9.7 mg, 0.049 mmol) and KF (4.7 mg, 0.08 mmol) in DMF (150 μL) was heated at 125° C. overnight. The mixture was cooled to room temperature, diluted with EtOAc (100 mL) and washed with 1M NaOH solution (3×). The organic phase was dried over $Na_2SO_4$, concentrated under reduced pressure and the product was purified by prep-TLC using $CH_2Cl_2$/MeOH (95:5). Compound 172 was obtained as pale brown oil in 21% yield (3.2 mg). LCMS: (M+1) m/z=468.

(2S,4S)-1-(6-ethyl-8-fluoro-4-methyl-3-(3-methyl-1,2,4-oxadiazol-5-yl)quinolin-2-yl)-2-methyl-N-(tetrahydro-2H-pyran-4-yl)piperidin-4-amine Compound 173 was obtained as pale yellow oil in 10% yield (4.1 mg).). LCMS: (M+1) m/z=468.

Examples 174-176

Reagents and conditions: i) Int-174-26 (1.0 eq.), amine (1.5 eq.), KF (2.5 eq.), DMSO, 125° C., 14 h, 17-20%.

Synthesis of (2R,4S)-1-(8-chloro-4,6-dimethyl-3-(3-methyl-1,2,4-oxadiazol-5-yl)quinolin-2-yl)-2-methyl-N-(tetrahydro-2H-pyran-4-yl)piperidin-4-amine (Compound 174)

A mixture of Int-174-26 (20 mg, 0.062 mmol), Int-174-4 (19 mg, 0.097 mmol) and KF (9.4 mg, 0.163 mmol) in DMSO (200 μL) was heated at 125° C. for 14 h. The mixture was cooled to room temperature, diluted with EtOAc (100 mL) and washed with 1M NaOH solution (3×). The organic phase was dried over $Na_2SO_4$, concentrated under reduced pressure and the product was purified by prep-TLC using $CH_2Cl_2$/MeOH (95:5). Compound 174 was obtained as pale yellow oil in 17% yield (5.3 mg). LCMS: (M+1) m/z=470.

(2R,4S)-1-(8-chloro-4,6-dimethyl-3-(3-methyl-1,2,4-oxadiazol-5-yl)quinolin-2-yl)-2-methyl-N—((R)-tetrahydrofuran-3-yl)piperidin-4-amine (Compound 175) was obtained as pale yellow oil in 20% yield (5.8 mg). LCMS: (M+1) m/z=456.

(2R,4S)-1-(8-chloro-4,6-dimethyl-3-(3-methyl-1,2,4-oxadiazol-5-yl)quinolin-2-yl)-2-methyl-N—((S)-tetrahydrofuran-3-yl)piperidin-4-amine Compound 176 was obtained as pale yellow oil in 20% yield (5.8 mg). LCMS: (M+1) m/z=456.

drofuran-3-yl)piperidin-4-amine (Compound 178) was obtained as pale brown oil in 33% yield (9.7 mg). LCMS: (M+1) m/z=460.

(2R,4R)-1-(6-chloro-8-fluoro-4-methyl-3-(3-methyl-1,2,4-oxadiazol-5-yl)quinolin-2-yl)-2-methyl-N—((R)-tetrahydrofuran-3-yl)piperidin-4-amine (Compound 179) was obtained as pale brown oil in 30% yield (8.7 mg). LCMS: (M+1) m/z=460.

Examples 177-179

Example 180

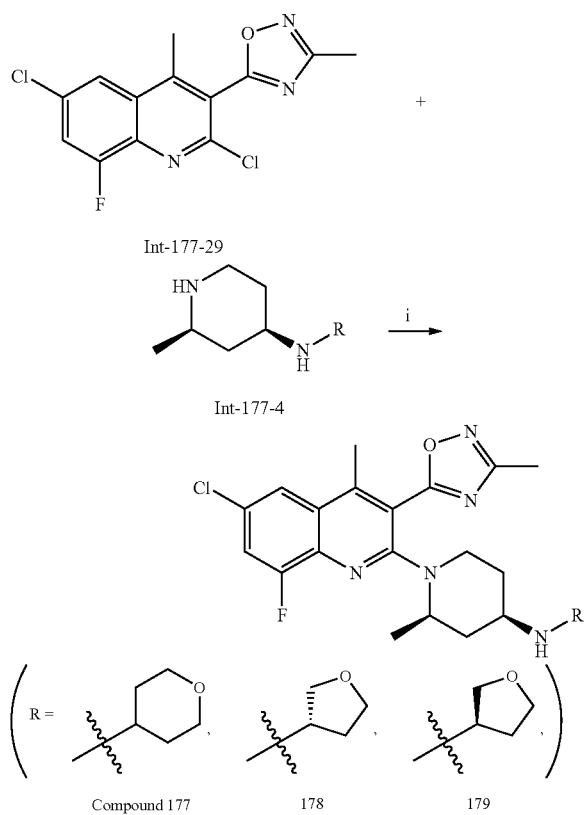

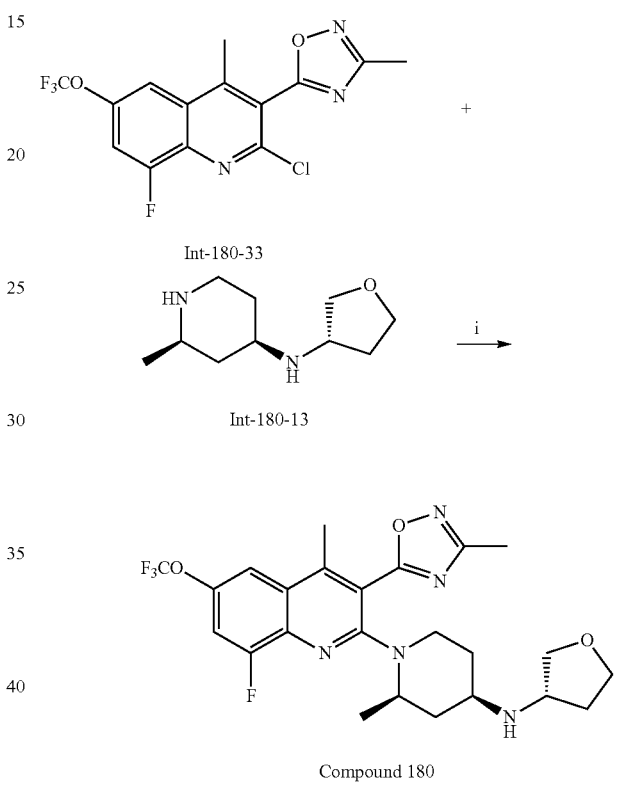

Reagents and conditions: i) Int-180-33 (1.0 eq.), Int-180-13 (1.5 eq.), KF (2.0 eq.), DIPEA (3.0 eq.), DMSO, 140° C., 18 h, 10%.

Reagents and conditions: i) Int-177-29 (1.0 eq.), amine (2.0 eq.), KF (2.5 eq.), DMSO, 125° C., 14 h, 14-33%.

Synthesis of (2R,4R)-1-(6-chloro-8-fluoro-4-methyl-3-(3-methyl-1,2,4-oxadiazol-5-yl)quinolin-2-yl)-2-methyl-N-(tetrahydro-2H-pyran-4-yl)piperidin-4-amine (Compound 177)

A mixture of Int-177-29 (20 mg, 0.064 mmol), Int-177-4 (25 mg, 0.127 mmol) and KF (9.3 mg, 0.159 mmol) in DMSO (200 μL) was heated at 125° C. overnight. The mixture was cooled to room temperature, diluted with EtOAc (100 mL) and washed with 1M NaOH solution (3×). The organic phase was dried over $Na_2SO_4$, concentrated under reduced pressure and the product was purified by prep-TLC using $CH_2Cl_2$/MeOH (95:5). Compound 177 was obtained as pale brown oil in 14% yield (4.3 mg). LCMS: (M+1) m/z=474.

(2R,4R)-1-(6-chloro-8-fluoro-4-methyl-3-(3-methyl-1,2,4-oxadiazol-5-yl)quinolin-2-yl)-2-methyl-N—((S)-tetrahy- Synthesis of (2R,4R)-1-(8-fluoro-4-methyl-3-(3-methyl-1,2,4-oxadiazol-5-yl)-6-(trifluoromethoxy)quinolin-2-yl)-2-methyl-N—((S)-tetrahydrofuran-3-yl)piperidin-4-amine (Compound 180)

A mixture of Int-180-33 (15 mg, 0.041 mmol), Int-180-13 (11 mg, 0.062 mmol), KF (4.7 mg, 0.082 mmol) and DIPEA (21 μL, 0.123 mmol) in DMSO (1 mL) was heated at 140° C. overnight. The mixture was cooled to room temperature, diluted with $CH_2Cl_2$ and washed with brine. The organic phase was dried over $Na_2SO_4$ and concentrated in vacuo. The crude was purified by prep-TLC using $CH_2Cl_2$/MeOH (96:4) then EtOAc:iPrOH (95:5). Compound 180 was obtained as a yellow solid in 10% yield (2.0 mg). LCMS: (M+1) m/z=510.

Examples 181-183

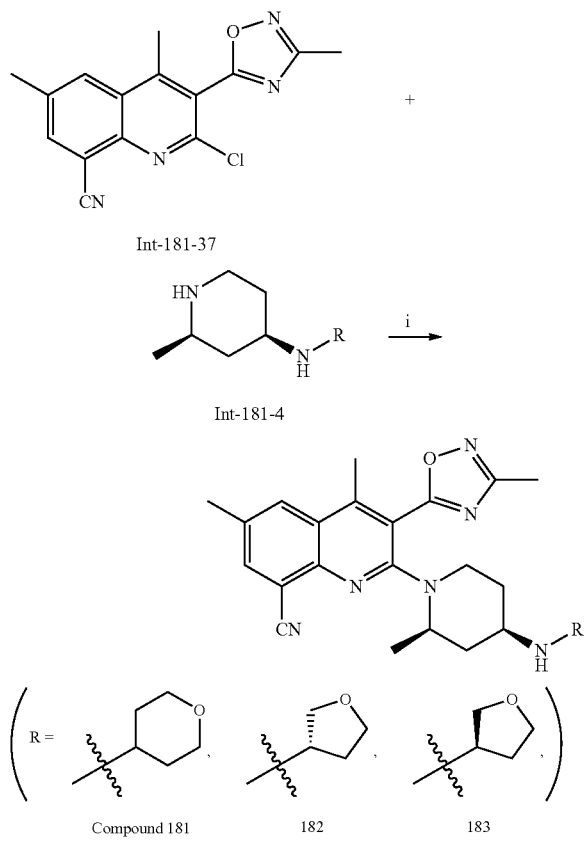

Reagents and conditions: i) Int-181-37 (1.0 eq.), amine (2.0 eq.), KF (2.5 eq.), DMSO, 125° C., 14 h, 14-17%.

Synthesis of 4,6-dimethyl-3-(3-methyl-1,2,4-oxadiazol-5-yl)-2-((2R,4R)-2-methyl-4-((tetrahydro-2H-pyran-4-yl)amino)piperidin-1-yl)quinoline-8-carbonitrile (Compound 181)

A mixture of Int-181-37 (20 mg, 0.066 mmol), Int-181-4 (18.4 mg, 0.1 mmol) and KF (9.6 mg, 0.165 mmol) in DMSO (200 µL) was heated at 125° C. for 14 h. The mixture was cooled to room temperature, diluted with EtOAc (100 mL) and washed with 1M NaOH solution (3×). The organic phase was dried over $Na_2SO_4$, concentrated under reduced pressure and the product was purified by prep-TLC using $CH_2Cl_2$/MeOH (95:5). Compound 181 was obtained as pale yellow oil in 14% yield (4.3 mg). LCMS: (M+1) m/z=461.

4,6-dimethyl-3-(3-methyl-1,2,4-oxadiazol-5-yl)-2-((2R,4R)-2-methyl-4-(((S)-tetrahydrofuran-3-yl)amino)piperidin-1-yl)quinoline-8-carbonitrile (Compound 182) was obtained as pale brown oil in 17% yield (5.1 mg). LCMS: (M+1) m/z=447.

4,6-dimethyl-3-(3-methyl-1,2,4-oxadiazol-5-yl)-2-((2R,4R)-2-methyl-4-(((R)-tetrahydrofuran-3-yl)amino)piperidin-1-yl)quinoline-8-carbonitrile (Compound 183) was obtained as pale brown oil in 15% yield (4.3 mg). LCMS: (M+1) m/z=447.

Examples 184-186

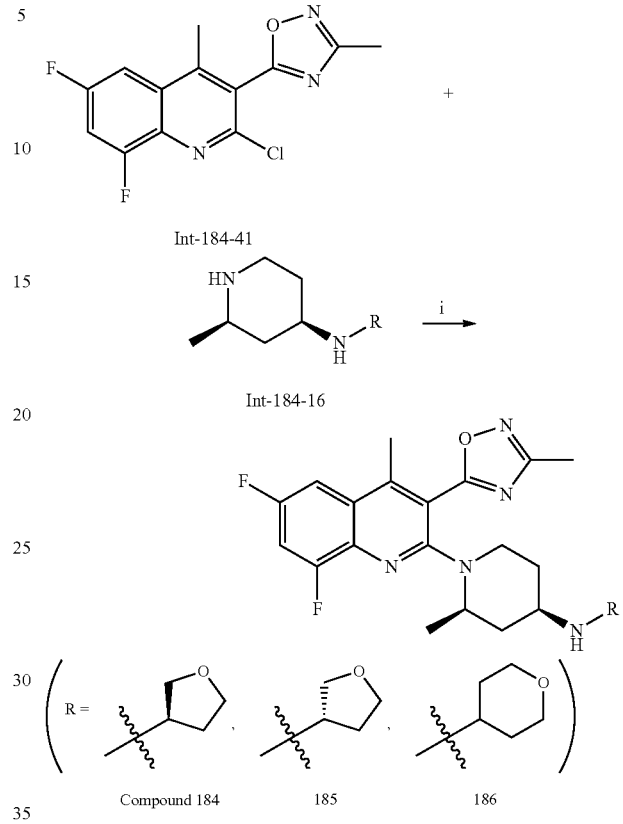

Reagents and conditions: i) Int-184-41 (1.0 eq.), amine (1.5 eq.), KF (2.0 eq.), DIPEA (3.0 eq.), DMSO, 125° C., 18 h, 6-22%.

Synthesis of (2R,4R)-1-(6,8-difluoro-4-methyl-3-(3-methyl-1,2,4-oxadiazol-5-yl)quinolin-2-yl)-2-methyl-N—((R)-tetrahydrofuran-3-yl)piperidin-4-amine (Compound 184)

A mixture of Int-184-41 (25 mg, 0.084 mmol), Int-184-16 (23 mg, 0.126 mmol), KF (10 mg, 0.168 mmol) and DIPEA (44 µL, 0.252 mmol) in DMSO (1 mL) was heated at 125° C. overnight. The mixture was cooled to room temperature, diluted with $CH_2Cl_2$ and washed with brine. The organic phase was dried over $Na_2SO_4$ and concentrated in vacuo. The crude was purified by prep-TLC using EtOAc:iPrOH (97:3) then $CH_2Cl_2$/MeOH (95:5). Compound 184 was obtained as a pale yellow solid in 6% yield (2.1 mg). LCMS: (M+1) m/z=444.

(2R,4R)-1-(6,8-difluoro-4-methyl-3-(3-methyl-1,2,4-oxadiazol-5-yl)quinolin-2-yl)-2-methyl-N—((S)-tetrahydrofuran-3-yl)piperidin-4-amine (Compound 185) was obtained as pale yellow solid in 12% yield (4.5 mg). LCMS: (M+1) m/z=444.

(2R,4R)-1-(6,8-difluoro-4-methyl-3-(3-methyl-1,2,4-oxadiazol-5-yl)quinolin-2-yl)-2-methyl-N-(tetrahydro-2H-pyran-4-yl)piperidin-4-amine (Compound 186) was obtained as pale yellow solid in 22% yield (7.5 mg). LCMS: (M+1) m/z=458.

Examples 187-189

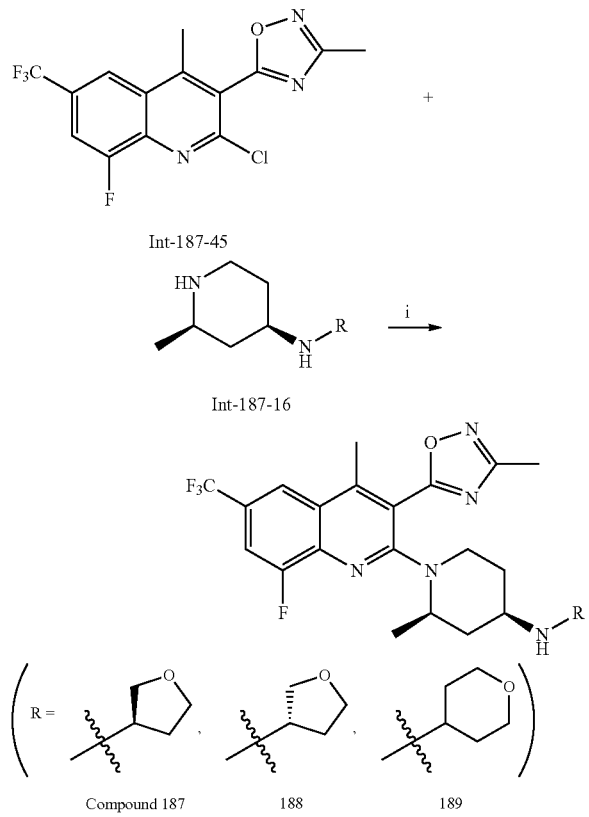

Reagents and conditions: i) Int-187-45 (1.0 eq.), amine (1.5 eq.), KF (2.0 eq.), DIPEA (3.0 eq.), DMSO, 125° C., 18 h, 14-33%.

Examples 190-192

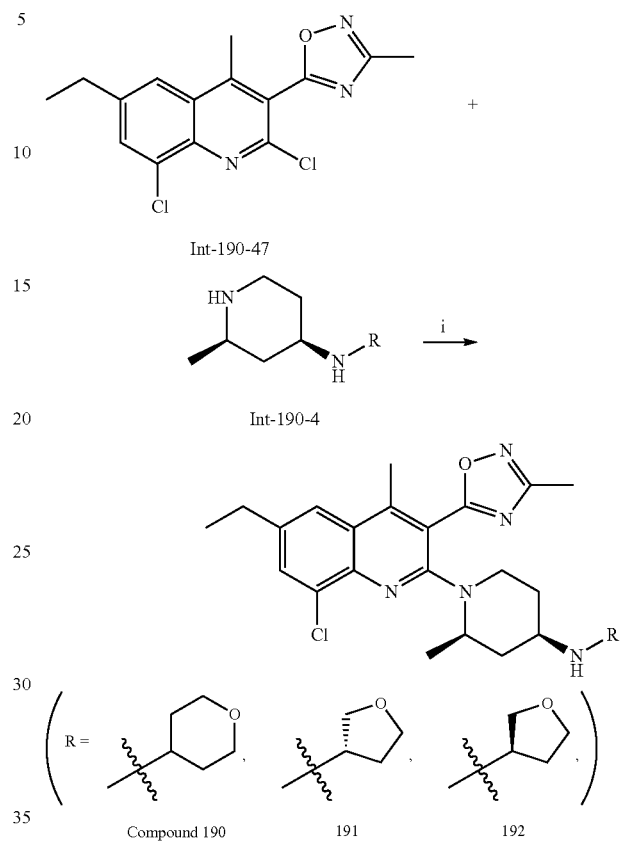

Reagents and conditions: i) Int-190-47 (1.0 eq.), amine (2.0 eq.), KF (2.5 eq.), DMSO, 125° C., 14 h, 23-24%.

Synthesis of (2R,4R)-1-(8-fluoro-4-methyl-3-(3-methyl-1,2,4-oxadiazol-5-yl)-6-(trifluoromethyl)guinolin-2-yl)-2-methyl-N—((R)-tetrahydrofuran-3-yl)piperidin-4-amine (Compound 187)

A mixture of Int-187-45 (25 mg, 0.072 mmol), Int-187-16 (20 mg, 0.108 mmol), KF (8.4 mg, 0.144 mmol) and DIPEA (38 µL, 0.216 mmol) in DMSO (1 mL) was heated at 125° C. overnight. The mixture was cooled to room temperature, diluted with CH$_2$Cl$_2$ and washed with brine. The organic phase was dried over Na$_2$SO$_4$ and concentrated in vacuo. The crude was purified by prep-TLC using EtOAc:iPrOH (98:2) then CH$_2$Cl$_2$/MeOH (97:3). Compound 187 was obtained as a pale orange solid in 14% yield (4.8 mg). LCMS: (M+1) m/z=494.

(2R,4R)-1-(8-fluoro-4-methyl-3-(3-methyl-1,2,4-oxadiazol-5-yl)-6-(trifluoromethyl)quinolin-2-yl)-2-methyl-N—((S)-tetrahydrofuran-3-yl)piperidin-4-amine (Compound 188) was obtained as pale orange solid in 31% yield (11.1 mg). LCMS: (M+1) m/z=494.

(2R,4R)-1-(8-fluoro-4-methyl-3-(3-methyl-1,2,4-oxadiazol-5-yl)-6-(trifluoromethyl)quinolin-2-yl)-2-methyl-N-(tetrahydro-2H-pyran-4-yl)piperidin-4-amine (Compound 189) was obtained as pale orange solid in 33% yield (12.2 mg). LCMS: (M+1) m/z=508.

Synthesis of (2R,4R)-1-(8-chloro-6-ethyl-4-methyl-3-(3-methyl-1,2,4-oxadiazol-5-yl)quinolin-2-yl)-2-methyl-N-(tetrahydro-2H-pyran-4-yl)piperidin-4-amine (Compound 190)

A mixture of Int-190-47 (20 mg, 0.062 mmol), Int-190-4 (15 mg, 0.074 mmol) and KF (9 mg, 0.155 mmol) in DMSO (200 µL) was heated at 125° C. overnight. The mixture was cooled to room temperature, diluted with EtOAc (100 mL) and washed with 1M NaOH solution (3×). The organic phase was dried over Na$_2$SO$_4$, concentrated under reduced pressure and the product was purified by prep-TLC using CH$_2$Cl$_2$/MeOH (95:5). Compound 190 was obtained as pale orange oil in 23% yield (7 mg). LCMS: (M+1) m/z=484.

(2R,4R)-1-(8-chloro-6-ethyl-4-methyl-3-(3-methyl-1,2,4-oxadiazol-5-yl)quinolin-2-yl)-2-methyl-N—((S)-tetrahydrofuran-3-yl)piperidin-4-amine (Compound 191) was obtained as pale brown oil in 23% yield (6.8 mg). LCMS: (M+1) m/z=470.

(2R,4R)-1-(8-chloro-6-ethyl-4-methyl-3-(3-methyl-1,2,4-oxadiazol-5-yl)quinolin-2-yl)-2-methyl-N—((R)-tetrahydrofuran-3-yl)piperidin-4-amine (Compound 192) was obtained as pale orange oil in 24% yield (7.1 mg). LCMS: (M+1) m/z=470.

Examples 193-194

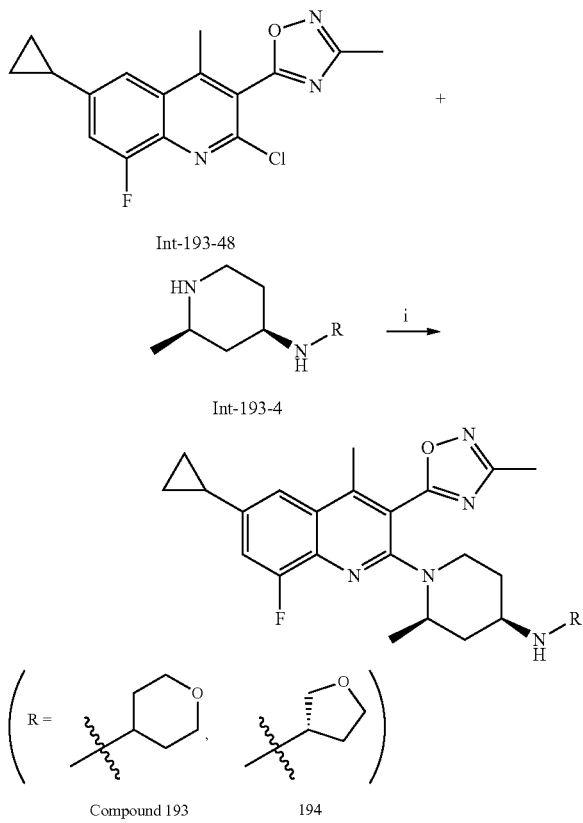

Reagents and conditions: i) Int-193-48 (1.0 eq.), amine (2.0 eq.), KF (2.5 eq.), DMSO, 125° C., 14 h, 18-21%.

Synthesis of (2R,4R)-1-(6-cyclopropyl-8-fluoro-4-methyl-3-(3-methyl-1,2,4-oxadiazol-5-yl)quinolin-2-yl)-2-methyl-N-(tetrahydro-2H-pyran-4-yl)piperidin-4-amine (Compound 193)

A mixture of Int-193-48 (10 mg, 0.031 mmol), Int-193-4 (7.4 mg, 0.037 mmol) and KF (4.5 mg, 0.078 mmol) in DMSO (200 μL) was heated at 125° C. overnight. The mixture was cooled to room temperature, diluted with EtOAc (100 mL) and washed with 1M NaOH solution (3×). The organic phase was dried over Na$_2$SO$_4$, concentrated under reduced pressure and the product was purified by prep-TLC using CH$_2$Cl$_2$/MeOH (95:5). Compound 193 was obtained as pale orange oil in 21% yield (3.2 mg). LCMS: (M+1) m/z=480.

(2R,4R)-1-(6-cyclopropyl-8-fluoro-4-methyl-3-(3-methyl-1,2,4-oxadiazol-5-yl)quinolin-2-yl)-2-methyl-N—((S)-tetrahydrofuran-3-yl)piperidin-4-amine (Compound 194) was obtained as pale yellow oil in 18% yield (3.9 mg). LCMS: (M+1) m/z=466.

Examples 195-197

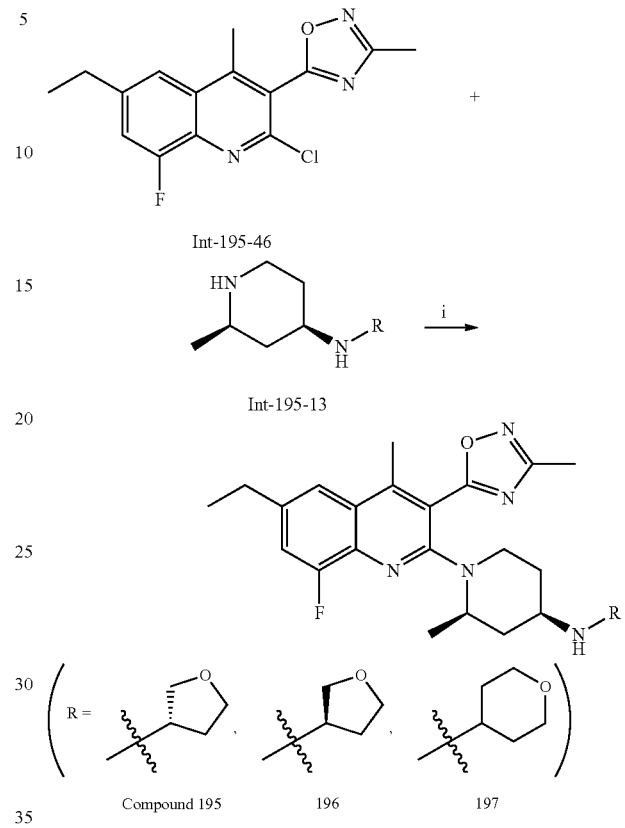

Reagents and conditions: i) Int-195-46 (1.0 eq.), amine (1.5 eq.), KF (2.5 eq.), DMF, 125° C., 18 h, 10-22%.

Synthesis of (2R,4R)-1-(6-ethyl-8-fluoro-4-methyl-3-(3-methyl-1,2,4-oxadiazol-5-yl)quinolin-2-yl)-2-methyl-N—((S)-tetrahydrofuran-3-yl)piperidin-4-amine (Compound 195)

A mixture of Int-195-46 (15 mg, 0.049 mmol), Int-195-13 (15.6 mg, 0.074 mmol) and KF (7 mg, 0.123 mmol) in DMSO (200 μL) was heated at 125° C. overnight. The mixture was cooled to room temperature, diluted with EtOAc (100 mL) and washed with 1M NaOH solution (3×). The organic phase was dried over Na$_2$SO$_4$, concentrated under reduced pressure and the product was purified by prep-TLC using CH$_2$Cl$_2$/MeOH (95:5). Compound 195 was obtained as pale brown oil in 22% yield (4.9 mg). LCMS: (M+1) m/z=454.

(2R,4R)-1-(6-ethyl-8-fluoro-4-methyl-3-(3-methyl-1,2,4-oxadiazol-5-yl)quinolin-2-yl)-2-methyl-N—((R)-tetrahydrofuran-3-yl)piperidin-4-amine (Compound 196) was obtained as pale brown oil in 12% yield (2.6 mg). LCMS: (M+1) m/z=454.

(2R,4R)-1-(6-ethyl-8-fluoro-4-methyl-3-(3-methyl-1,2,4-oxadiazol-5-yl)quinolin-2-yl)-2-methyl-N-(tetrahydro-2H-pyran-4-yl)piperidin-4-amine (Compound 197) was obtained as pale yellow oil in 10% yield (3.2 mg). LCMS: (M+1) m/z=468.

Examples 198-203

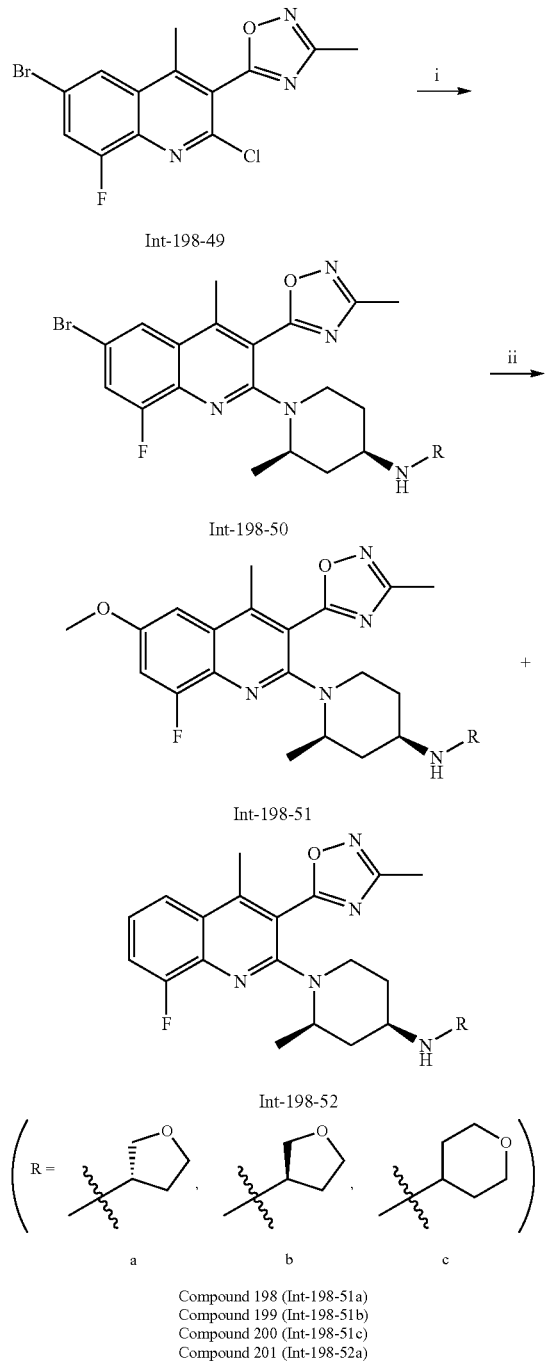

Compound 198 (Int-198-51a)
Compound 199 (Int-198-51b)
Compound 200 (Int-198-51c)
Compound 201 (Int-198-52a)
Compound 202 (Int-198-52b)
Compound 203 (Int-198-52c)

Reagents and conditions:
i) Int-198-49 (1.0 eq.), amine (1.5 eq.), KF (2.0 eq.), DIPEA (3.0 eq.), DMSO, 125° C., 18 h, 50-56%;
ii) Int-198-50 (1.0 eq.), NaB(OCH$_3$)$_4$ (4.0 eq.), Pd$_2$(dba)$_3$ (2.5% eq.), tBuXPhos (5.5% eq.), 1,4-dioxane, 125° C., 2 h, 6-10%.

Synthesis of Int-198-50

A mixture of Int-198-49 (100 mg, 0.28 mmol), amine Int-195-13 in example 195-197 (77 mg, 0.42 mmol), KF (33 mg, 0.56 mmol) and DIPEA (150 μL, 0.84 mmol) in DMSO (1 mL) was heated at 125° C. overnight. After cooling to room temperature, the mixture was diluted with CH$_2$Cl$_2$ and washed with brine. The organic phase was separated, dried over Na$_2$SO$_4$ and concentrated in vacuo. The crude was purified by column chromatography (0~50% EtOAc in hexanes, then 0~10% MeOH in CH$_2$Cl$_2$). The product was obtained as green oil in 54% yield (77 mg). LCMS: (M+1) m/z=504, 506.

Reaction with Int-187-16 in Example 187-189; 79 mg, green oil, 56% yield. LCMS: (M+1) m/z=504, 506.

Reaction with Int-187-4 in Example 193-194; 73 mg, green solid, 50% yield. LCMS: (M+1) m/z=518, 520.

Preparation of NaB(OMe)4 Prior to Synthesis of Int-198-51

A solution of NaBH$_4$ (0.5 g) in MeOH (25 mL) was refluxed for 30 min. After cooling to room temperature, the mixture was concentrated in vacuo to dryness and used without further purification.

Synthesis of Int-198-51 (a: Compound 198, b: Compound 199, c: Compound 200) and 52 (a: Compound 201, b: Compound 202, c: Compound 203)

A mixture of Int-198-50 (77 mg, 0.15 mmol), NaB(OMe)$_4$ (96 mg, 0.61 mmol), Pd$_2$(dba)$_3$ (3.5 mg, 2.5 mol %) and tBuXPhos (3.6 mg, 5.5 mol %) in 1,4-dioxane (1.5 mL) was stirred at 125° C. for 2 h. After cooling to room temperature, the mixture was partitioned between CH$_2$Cl$_2$ and brine. The organic layer was dried over Na$_2$SO$_4$ and concentrated in vacuo. The residue was purified by prep-TLC using EtOAc:iPrOH (97:3). (2R,4R)-1-(8-fluoro-6-methoxy-4-methyl-3-(3-methyl-1,2,4-oxadiazol-5-yl)quinolin-2-yl)-2-methyl-N—((S)-tetrahydrofuran-3-yl)piperidin-4-amine (Compound 198) was obtained as a yellow solid in 6% yield (4.2 mg). LCMS: (M+1) m/z=456; the byproduct, (2R,4R)-1-(8-fluoro-4-methyl-3-(3-methyl-1,2,4-oxadiazol-5-yl)quinolin-2-yl)-2-methyl-N—((S)-tetrahydrofuran-3-yl)piperidin-4-amine (Compound 201), was obtained as yellow oil in 3% (2.4 mg). LCMS: (M+1) m/z=426.

(2R,4R)-1-(8-fluoro-6-methoxy-4-methyl-3-(3-methyl-1,2,4-oxadiazol-5-yl)quinolin-2-yl)-2-methyl-N—((R)-tetrahydrofuran-3-yl)piperidin-4-amine (Compound 199) was obtained as yellow solid in 10% yield (7.1 mg). LCMS: (M+1) m/z=456.

(2R,4R)-1-(8-fluoro-6-methoxy-4-methyl-3-(3-methyl-1,2,4-oxadiazol-5-yl)quinolin-2-yl)-2-methyl-N-(tetrahydro-2H-pyran-4-yl)piperidin-4-amine (Compound 200) was obtained as yellow solid in 6% yield (4.2 mg). LCMS: (M+1) m/z=470.

(2R,4R)-1-(8-fluoro-4-methyl-3-(3-methyl-1,2,4-oxadiazol-5-yl)quinolin-2-yl)-2-methyl-N—((R)-tetrahydrofuran-3-yl)piperidin-4-amine (Compound 202) was obtained as yellow oil in 5% yield (3.2 mg). LCMS: (M+1) m/z=426.

(2R,4R)-1-(8-fluoro-4-methyl-3-(3-methyl-1,2,4-oxadiazol-5-yl)quinolin-2-yl)-2-methyl-N-(tetrahydro-2H-pyran-4-yl)piperidin-4-amine (Compound 203) was obtained as yellow oil in 0.8% yield (0.5 mg). LCMS: (M+1) m/z=440.

Example 204

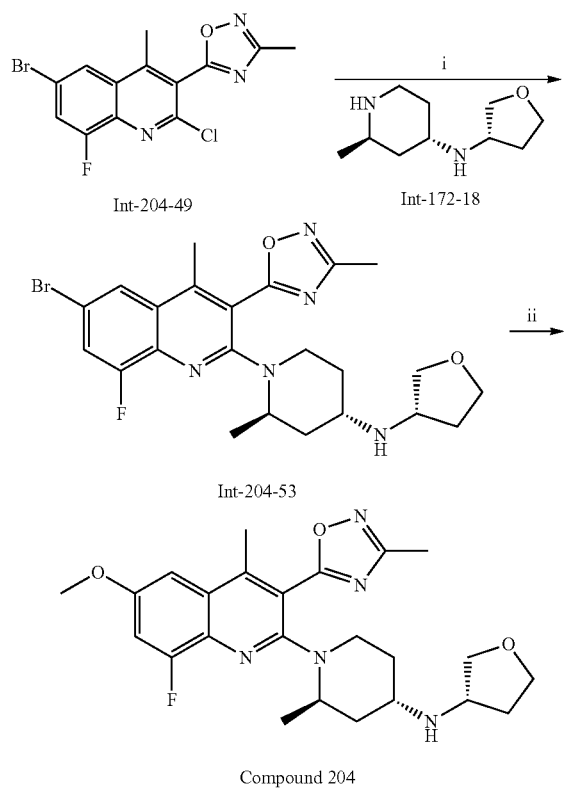

Compound 204

Reagents and conditions:
i) Int-204-49 (1.0 eq.), Int-172-18 (1.0 eq.), KF (2.0 eq.), DIPEA (2.0 eq.), DMSO, 125° C., 18 h, 38%;
ii) Int-204-53 (1.0 eq.), NaB(OCH₃)₄ (4.0 eq.), Pd₂(dba)₃ (2.5% eq.), tBuXPhos (5.5% eq.), 1,4-dioxane, 125° C., 2 h, 8%.

Synthesis of (2R,4S)-1-(6-bromo-8-fluoro-4-methyl-3-(3-methyl-1,2,4-oxadiazol-5-yl)quinolin-2-yl)-2-methyl-N—((S)-tetrahydrofuran-3-yl)piperidin-4-amine Int-204-53

A mixture of Int-204-49 (45.2 mg, 0.127 mmol), amine Int-172-18 in example 172 (23.4 mg, 0.127 mmol), KF (15 mg, 0.254 mmol) and DIPEA (44 µL, 0.254 mmol) in DMSO (1 mL) was heated at 125° C. overnight. After cooling to room temperature, the mixture was diluted with $CH_2Cl_2$ and washed with brine. The organic phase was separated, dried over $Na_2SO_4$ and concentrated in vacuo. The crude was purified by column chromatography using hexanes/EtOAc (0 to 50% EtOAc in hexanes) and then $CH_2Cl_2$/MeOH (0 to 10% MeOH in $CH_2Cl_2$) as mobile phase. The product Int-204-53 was obtained as green oil in 38% yield (24 mg). LCMS: (M+1) m/z=505.

Synthesis of (2R,4S)-1-(8-fluoro-6-methoxy-4-methyl-3-(3-methyl-1,2,4-oxadiazol-5-yl)quinolin-2-yl)-2-methyl-N—((S)-tetrahydrofuran-3-yl)piperidin-4-amine (Compound 204)

A mixture of Int-204-53 (24 mg, 0.047 mmol), NaB(OMe)₄ (30 mg, 0.19 mmol), Pd₂(dba)₃ (1 mg, 2.5 mol %) and tBuXPhos (1 mg, 5.5 mol %) in 1,4-dioxane (1 mL) was stirred at 125° C. for 2 h. After cooling to room temperature, the mixture was partitioned between $CH_2Cl_2$ and brine. The organic layer was dried over $Na_2SO_4$ and concentrated in vacuo. The residue was purified by prep-TLC using EtOAc:iPrOH (97:3). Compound 204 was obtained as a yellow solid in 8% yield (1.7 mg). LCMS: (M+1) m/z=456.

Example 205

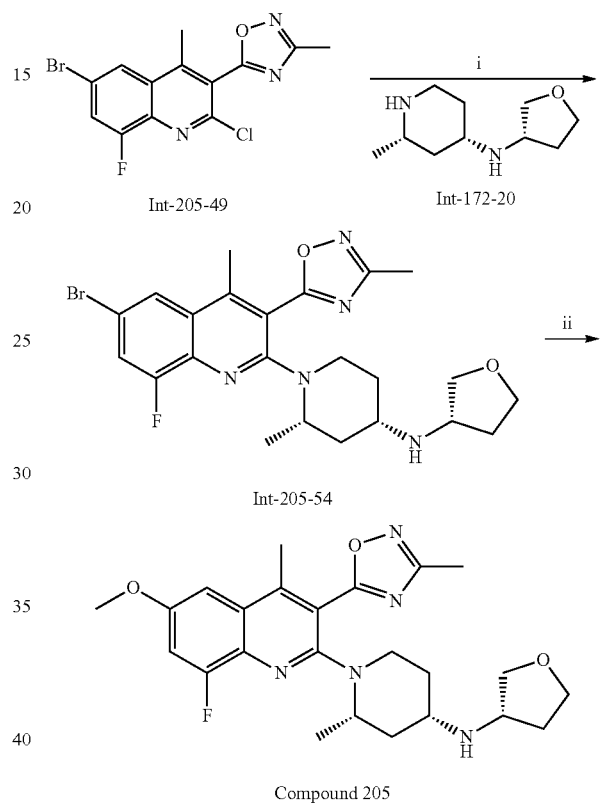

Compound 205

Reagents and conditions:
i) Int-205-49 (1.0 eq.), Int-172-20 (1.0 eq.), KF (2.0 eq.), DIPEA (2.0 eq.), DMSO, 125° C., 18 h, 51%;
ii) Int-205-54 (1.0 eq.), NaB(OCH₃)₄ (4.0 eq.), Pd₂(dba)₃ (2.5% eq.), tBuXPhos (5.5% eq.), 1,4-dioxane, 125° C., 2 h, 4%.

Synthesis of (2S,4S)-1-(6-bromo-8-fluoro-4-methyl-3-(3-methyl-1,2,4-oxadiazol-5-yl)quinolin-2-yl)-2-methyl-N—((S)-tetrahydrofuran-3-yl)piperidin-4-amine Int-205-54

A mixture of Int-205-49 (33.2 mg, 0.093 mmol), amine Int-172-20 in example 172 (17.2 mg, 0.093 mmol), KF (11 mg, 0.186 mmol) and DIPEA (32 µL, 0.186 mmol) in DMSO (1 mL) was heated at 125° C. overnight. After cooling to room temperature, the mixture was diluted with $CH_2Cl_2$ and washed with brine. The organic phase was separated, dried over $Na_2SO_4$ and concentrated in vacuo. The crude was purified by column chromatography (0~50% EtOAc in hexanes, and then 0~10% MeOH in $CH_2Cl_2$). The product Int-205-54 was obtained as green oil in 51% yield (24 mg). LCMS: (M+1) m/z=504, 506.

Synthesis of (2S,4S)-1-(8-fluoro-6-methoxy-4-methyl-3-(3-methyl-1,2,4-oxadiazol-5-yl)quinolin-2-yl)-2-methyl-N—((S)-tetrahydrofuran-3-yl)piperidin-4-amine (Compound 205)

A mixture of Int-205-54 (24 mg, 0.047 mmol), NaB(OMe)$_4$ (30 mg, 0.19 mmol), Pd$_2$(dba)$_3$ (1 mg, 2.5 mol %) and tBuXPhos (1 mg, 5.5 mol %) in 1,4-dioxane (1 mL) was stirred at 125° C. for 2 h. After cooling to room temperature, the mixture was partitioned between CH$_2$Cl$_2$ and brine. The organic layer was dried over Na$_2$SO$_4$ and concentrated in vacuo. The residue was purified by prep-TLC using EtOAc:iPrOH (97:3). Compound 205 was obtained as a yellow solid in 4% yield (0.9 mg). LCMS: (M+1) m/z=456.

Examples 206-208

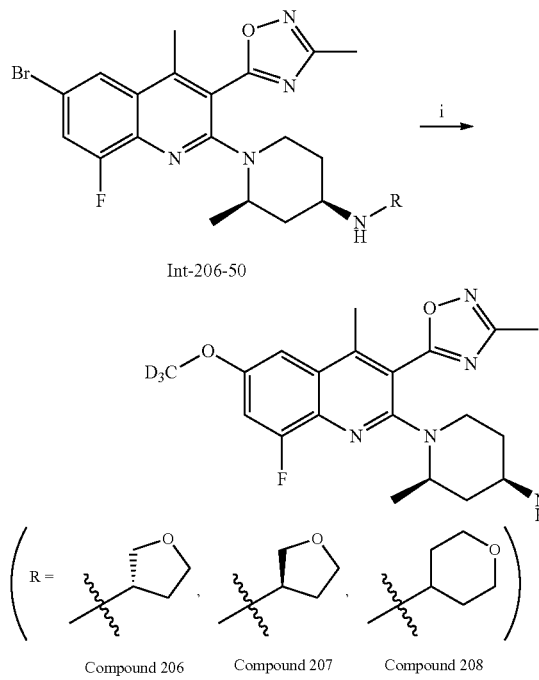

Compound 206    Compound 207    Compound 208

Reagents and conditions: i) Int-206-50 (1.0 eq.), NaB(OCD$_3$)$_4$ (4.0 eq.), Pd$_2$(dba)$_3$ (2.5% eq.), tBuXPhos (5.5% eq.), 1,4-dioxane, 125° C., 18 h, 1-11%.

Synthesis of (2R,4R)-1-(8-fluoro-6-(methoxy-d3)-4-methyl-3-(3-methyl-1,2,4-oxadiazol-5-yl)quinolin-2-yl)-2-methyl-N—((S)-tetrahydrofuran-3-yl)piperidin-4-amine (Compound 206)

A solution of NaBH$_4$ (0.1 g) in CD$_3$OD (5 mL) was refluxed for 30 min. After cooling to room temperature, the mixture was concentrated in vacuo to dryness and used without purification. A mixture of Int-206-50 (70.5 mg, 0.14 mmol), NaB(OCD$_3$)$_4$ (95 mg, 0.56 mmol), Pd$_2$(dba)$_3$ (3.2 mg, 2.5 mol %) and tBuXPhos (3.2 mg, 5.0 mol %) in 1,4-dioxane (1.5 mL) was stirred at 125° C. overnight. After cooling to room temperature, the mixture was partitioned between CH$_2$Cl$_2$ and brine. The organic layer was dried over Na$_2$SO$_4$ and concentrated in vacuo. The residue was purified by prep-TLC using EtOAc:iPrOH (97:3). Compound 206 was obtained as yellow oil in 4% yield (2.7 mg). LCMS: (M+1) m/z=459.

(2R,4R)-1-(8-fluoro-6-(methoxy-d3)-4-methyl-3-(3-methyl-1,2,4-oxadiazol-5-yl)quinolin-2-yl)-2-methyl-N—((R)-tetrahydrofuran-3-yl)piperidin-4-amine (Compound 207) was obtained as yellow oil in 1% yield (0.6 mg). LCMS: (M+1) m/z=459.

(2R,4R)-1-(8-fluoro-6-(methoxy-d3)-4-methyl-3-(3-methyl-1,2,4-oxadiazol-5-yl)quinolin-2-yl)-2-methyl-N-(tetrahydro-2H-pyran-4-yl)piperidin-4-amine (Compound 208) was obtained as yellow oil in 11% yield (6 mg). LCMS: (M+1) m/z=473.

Examples 209-211

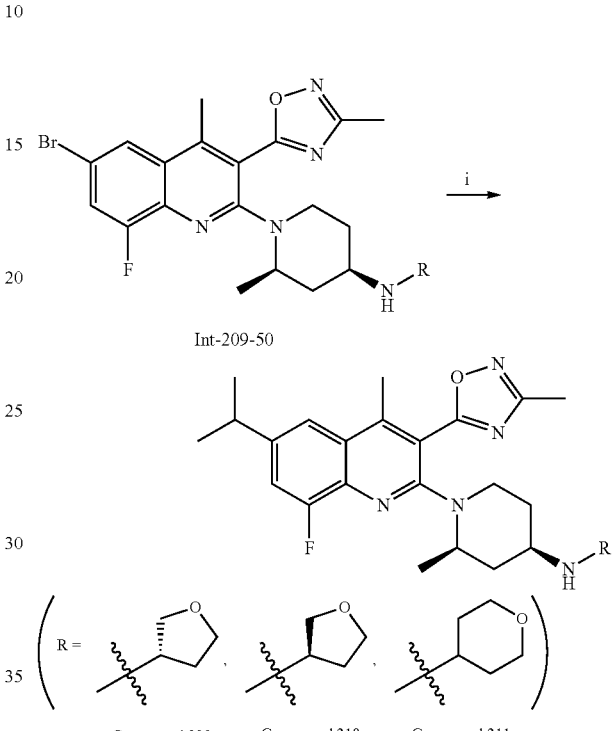

Compound 209    Compound 210    Compound 211

Reagents and conditions: i) Int-209-50 (1.0 eq.), iPrMgCl (3.0 eq.), Pd(OAc)$_2$ (0.1 eq.), P(tBu)$_3$ HBF$_4$ (0.12 eq.), ZnBr$_2$ (0.5 eq.), THF, 25° C., 2 h, 8-13%.

Synthesis of (2R,4R)-1-(8-fluoro-6-isopropyl-4-methyl-3-(3-methyl-1,2,4-oxadiazol-5-yl)quinolin-2-yl)-2-methyl-N—((S)-tetrahydrofuran-3-yl)piperidin-4-amine (Compound 209)

To a suspension of Int-209-50 (70.5 mg, 0.14 mmol), Pd(OAc)$_2$ (3.1 mg, 0.014 mmol), P(tBu)$_3$·HBF$_4$ (4.9 mg, 0.017 mmol), ZnBr$_2$ (70 µL, 1M in THF) in THF (1.5 mL) was added 2M solution of iPrMgCl (0.21 mL, 0.42 mmol) and the mixture was stirred at room temperature for 2 h. The mixture was then poured into ice-water, and the product was extracted with EtOAc (3×). The combined organic layers were washed with 1% aq. HCl and brine, dried over Na$_2$SO$_4$ and concentrated in vacuo. The residue was purified by prep-TLC using EtOAc:iPrOH (97:3) and CH$_2$Cl$_2$:MeOH (96:4). Compound 209 was obtained as a yellow solid in 8% yield (5.4 mg). LCMS: (M+1) m/z=468.

(2R,4R)-1-(8-fluoro-6-isopropyl-4-methyl-3-(3-methyl-1,2,4-oxadiazol-5-yl)quinolin-2-yl)-2-methyl-N—((R)-tetrahydrofuran-3-yl)piperidin-4-amine (Compound 210) was obtained as a yellow solid, 8% yield (5.2 mg). LCMS: (M+1) m/z=468.

(2R,4R)-1-(8-fluoro-6-isopropyl-4-methyl-3-(3-methyl-1,2,4-oxadiazol-5-yl)quinolin-2-yl)-2-methyl-N-(tetrahydro-2H-pyran-4-yl)piperidin-4-amine (Compound 211) was obtained as yellow oil, 13% yield (7.4 mg). LCMS: (M+1) m/z=482.

Examples 212-213

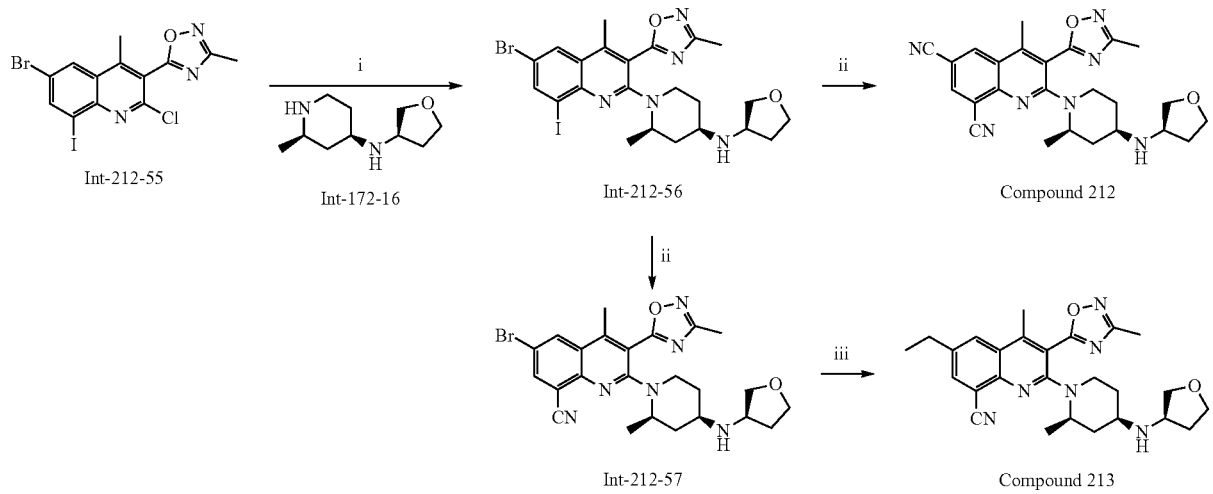

Reagents and conditions: i) Int-212-55 (1.0 eq.), Int-172-16 (1.5 eq.), KF (2.0 eq.) DIPEA (3.0 eq.), DMSO, 125° C., 18 h, 48%; ii) Int-212-56 (1.0 eq.), Zn(CN)₂ (1.0 eq.), Zn (0.1 eq.), Pd(PPh₃)₄ (0.1 eq), THF/DMF (1:1, v/v), 80° C., 18 h, 2% (for Compound 212) and 58% (for Int-212-57); iii) Int-21-57 (1.0 eq.), EtB(OH)₂ (1.4 eq.), PCy₃ (0.1 eq.), K₃PO₄ (3.6 eq.), Pd(OAc)₂ (5% eq.), Toluene, H₂O, 100° C., 18 h, 18%.

Synthesis of (2R,4R)-1-(6-bromo-8-iodo-4-methyl-3-(3-methyl-1,2,4-oxadiazol-5-yl)quinolin-2-yl)-2-methyl-N—((R)-tetrahydrofuran-3-yl)piperidin-4-amine Int-212-56

A mixture of Int-212-55 (150 mg, 0.32 mmol), amine Int-172-16 Example 172 (89 mg, 0.48 mmol), KF (37 mg, 0.64 mmol) and DIPEA (0.17 mL, 0.96 mmol) in DMSO (2 mL) was heated at 125° C. overnight. After cooling to room temperature, the mixture was diluted with CH₂Cl₂ and washed with brine. The organic phase was separated, dried over Na₂SO₄ and concentrated in vacuo. The crude was purified by column chromatography using hexanes/EtOAc (0 to 50% EtOAc in hexanes) and then CH₂Cl₂/MeOH (0 to 10% MeOH in CH₂Cl₂) as mobile phase. The product was obtained as dark green oil in 48% yield (94.3 mg). LCMS: (M+1) m/z=612, 614.

Synthesis of 4-methyl-3-(3-methyl-1,2,4-oxadiazol-5-yl)-2-((2R,4R)-2-methyl-4-(((R)-tetrahydrofuran-3-yl)amino)piperidin-1-yl)quinoline-6,8-dicarbonitrile (Compound 212) and 57

A mixture of Int-212-56 (94.3 mg, 0.154 mmol), Zn(CN)₂ (18.0 mg, 0.154 mmol), Zn powder (1.0 mg, 0.0154 mmol) and Pd(PPh₃)₄ (17.8 mg, 0.0154 mmol) in THF/DMF (2 mL, 1:1, v/v) was stirred at 80° C. overnight. After cooling to room temperature, the mixture was filtered through Celite, and the filtrate was concentrated in vacuo. The residue was purified by prep-TLC using EtOAc:iPrOH (98:2) to produce Compound 212 as a yellow solid (1.4 mg, 2% yield) and 57 as a yellow solid in 58% (45.6 mg). LCMS: (M+1) m/z=511, 513.

Synthesis of 6-ethyl-4-methyl-3-(3-methyl-1,2,4-oxadiazol-5-yl)-2-((2R,4R)-2-methyl-4-(((R)-tetrahydrofuran-3-yl)amino)piperidin-1-yl)quinoline-8-carbonitrile (Compound 213)

A mixture of Int-212-57 (45.6 mg, 0.089 mmol), EtB(OH)₂ (9.2 g, 0.125 mmol), P(Cy)₃ (2.5 mg, 0.0089 mmol), Pd(OAc)₂ (1.0 mg, 0.0045 mmol) and K₃PO₄ (68 mg, 0.32 mmol) in toluene (2 mL) and H₂O (40 μL) was stirred and heated at 100° C. overnight. After cooling to room temperature, the mixture was filtered through Celite. The filtrated was concentrated in vacuo and purified by prep-TLC using EtOAc:iPrOH (98:2) then CH₂Cl₂/MeOH (97:3). The product Compound 213 was obtained as a yellow solid in 18% yield (7.4 mg). LCMS: (M+1) m/z=461.

Examples 214-215

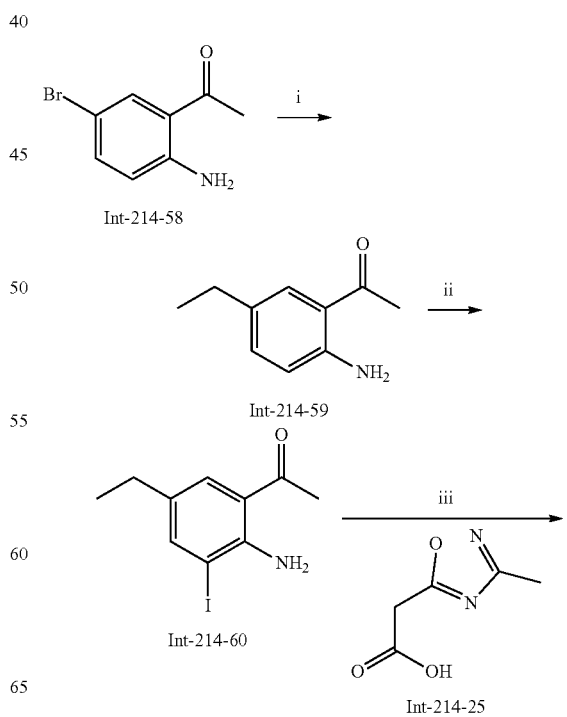

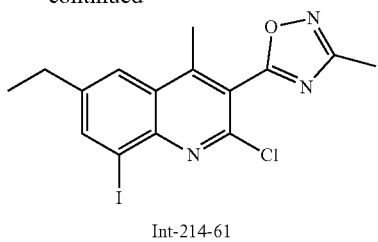

Int-214-61

Int-214-61 + 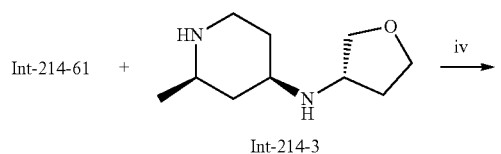 →ⁱᵛ

Int-214-3

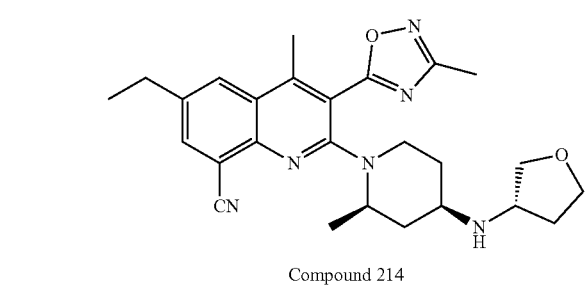

Int-214-62a

Compound 214

Int-214-61 + 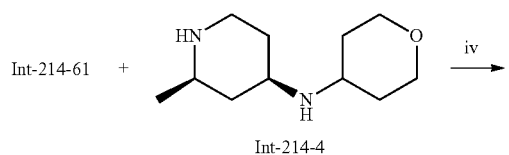 →ⁱᵛ

Int-214-4

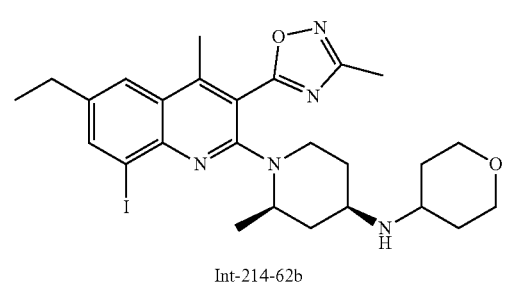

Int-214-62b

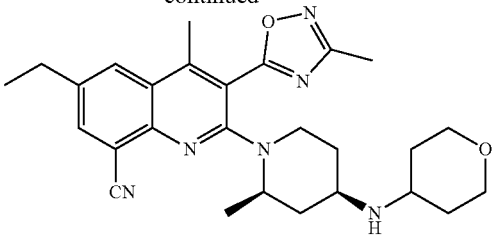

Compound 215

Reagents and conditions: i) Int-214-58 (1.0 eq.), Et₃B (1.5 eq.), K₂CO₃ (2.0 eq.), Pd(PPh₃)₄ (5% eq.), THF/DMF (1:1, v/v), 80° C., 1.5 h, 66%; ii) Int-214-59 (1.0 eq.), NIS (1.05 eq.), AcOH, RT, 1.5 h, 88%; iii) Int-214-60 (1.0 eq.), POCl₃, 100° C., 1 h, 44%; iv) Int-214-61 (1.0 eq.), amine (1.5 eq.), KF (2.0 eq.) DIPEA (3.0 eq.), DMSO, 125° C., 18 h, 32-41%; v) Int-214-62 (1.0 eq.) Zn(CN)₂ (1.5 eq.), Zn (0.1 eq.), Pd(PPh₃)₄ (0.1 eq), DMF, 80° C., 18 h, 13-17%.

Synthesis of Int-214-59

To a mixture of Int-214-58 (6.0 g, 28.0 mmol), K₂CO₃ (7.7 g, 56.0 mmol), and Pd(PPh₃)₄ (1.6 g, 1.4 mmol) in THF/DMF (60 mL, 1:1 v/v) was added 1M solution of Et₃B in THF (42 mL, 42.0 mmol) at room temperature. The mixture was then heated at 80° C. for 1.5 h. After cooling to room temperature, the mixture was filtered through Celite. The filtrated was concentrated in vacuo and purified by column chromatography using hexanes/EtOAc (0 to 20% EtOAc in hexanes) as mobile phase. The product Int-214-59 was obtained as a yellow solid in 66% yield (3.0 g). LCMS: (M+1) m/z=164.

Synthesis of Int-214-60

To a mixture of Int-214-59 (2.5 g, 15.6 mmol) in acetic acid (50 mL) was added in a single portion NIS (3.7 g, 16.4 mmol) and the mixture was stirred at room temperature for 1.5 h. The mixture was diluted with EtOAc (500 mL) and washed with brine (3×) and sat NaHCO₃ solution (2×). The organic phase was dried over Na₂SO₄ and concentrated in vacuo. The product was purified by column chromatography using hexanes/EtOAc (0 to 30% EtOAc in hexanes) as mobile phase. The product was obtained as red oil in 88% yield (4.0 g). LCMS: (M+1) m/z=290.

Synthesis of Int-214-61

A mixture of Int-214-60 (2.09 g, 7.23 mmol) and Int-214-25 (1.13 g, 7.95 mmol) in POCl₃ (14 mL) was stirred at 100° C. for 1 h. After cooling to room temperature, excess POCl₃ was removed in vacuo. To the residue, H₂O was added at 0° C., and the mixture was stirred at 0° C. for 10 min. The precipitated crude chloroquinoline Int-214-61 was filtered, washed with H₂O, and dried under the reduced pressure. The solid was purified by column chromatography (0 to 20% EtOAc in hexanes) as mobile phase. The product was obtained as a yellow solid in 44% yield (1.33 g).

Synthesis of Int-214-62

A mixture of Int-214-61 (75 mg, 0.18 mmol), Int-214-13 (50 mg, 0.27 mmol), KF (21 mg, 0.36 mmol) and DIPEA (94 µL, 0.54 mmol) in DMSO (2 mL) was heated at 125° C. overnight. After cooling to room temperature, the mixture was diluted with CH₂Cl₂ and washed with brine. The organic phase was dried over Na₂SO₄ and concentrated in vacuo. The crude was purified by column chromatography using hexanes/EtOAc (0 to 50% EtOAc in hexanes) and then CH₂Cl₂/MeOH (0 to 10% MeOH in CH₂Cl₂) as mobile phase. The product Int-214-62a was obtained as dark brown oil in 41% yield (41.4 mg). LCMS: (M+1) m/z=562.

Reaction with amine Int-214-4 afforded Int-214-62b (33.1 mg, 32% yield) as dark brown oil. LCMS: (M+1) m/z=576.

Synthesis of 6-ethyl-4-methyl-3-(3-methyl-1,2,4-oxadiazol-5-yl)-2-((2R,4R)-2-methyl-4-(((S)-tetrahydrofuran-3-yl)amino)piperidin-1-yl)quinoline-8-carbonitrile (Compound 214)

A mixture of Int-214-62 (41.4 mg, 0.074 mmol), Zn(CN)₂ (13.0 mg, 0.111 mmol), Zn powder (0.5 mg, 0.0074 mmol) and Pd(PPh₃)₄ (8.6 mg, 0.0074 mmol) in DMF (2 mL) was stirred at 80° C. overnight. After cooling to room temperature, the mixture was filtered through Celite, and the filtrate was concentrated in vacuo. The residue was purified by prep-TLC using EtOAc:iPrOH (98:2) then CH₂Cl₂/MeOH (97:3). The product Compound 214 was obtained as a yellow solid in 17% yield (6.0 mg). LCMS: (M+1) m/z=461.

6-ethyl-4-methyl-3-(3-methyl-1,2,4-oxadiazol-5-yl)-2-((2R,4R)-2-methyl-4-((tetrahydro-2H-pyran-4-yl)amino)piperidin-1-yl)quinoline-8-carbonitrile (Compound 215) was obtained as a yellow solid in 29% yield (7.9 mg). LCMS: (M+1) m/z=475.

Example 216

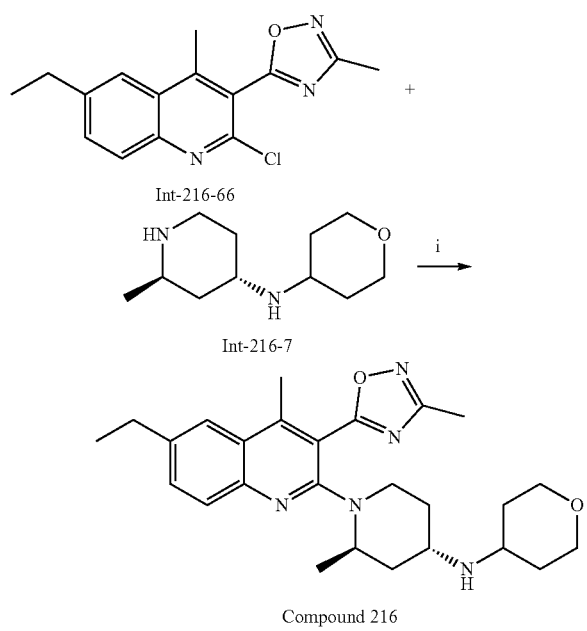

Compound 216

Reagents and conditions: i) Int-216-66 (1.0 eq.), amine (1.2 eq.), TMP/DMSO (1:1, v/v), 150° C., 18 h, 8%.

Synthesis of (2R,4S)-1-(6-ethyl-4-methyl-3-(3-methyl-1,2,4-oxadiazol-5-yl)quinolin-2-yl)-2-methyl-N-(tetrahydro-2H-pyran-4-yl)piperidin-4-amine (Compound 216)

A mixture of Int-216-66 (30 mg, 0.104 mmol) and 7 (23 mg, 0.125 mmol) in 2,2,6,6-tetramethylpiperidine/DMSO (1.5 mL, 1:1 v/v) was heated at 150° C. overnight. After cooling to room temperature, the mixture was partitioned between CH₂Cl₂ and brine. The organic layer was dried over Na₂SO₄ and concentrated in vacuo. The residue was purified by prep-TLC using CH₂Cl₂/MeOH (96:4). The product Compound 216 was obtained as brown oil in 8% yield (3.7 mg). LCMS: (M+1) m/z=450.

Example 217

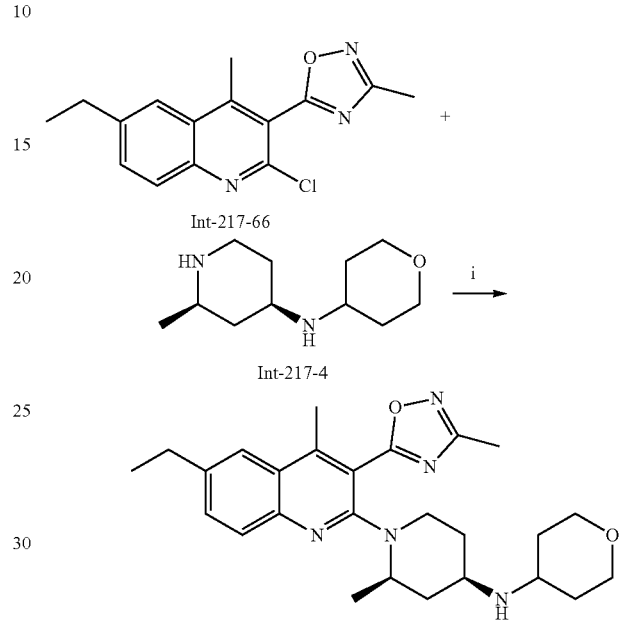

Compound 217

Reagents and conditions: i) Int-217-66 (1.0 eq.), amine (1.2 eq.), TMP/DMSO (1:1, v/v), 150° C., 18 h, 6%.

Synthesis of (2R,4R)-1-(6-ethyl-4-methyl-3-(3-methyl-1,2,4-oxadiazol-5-yl)quinolin-2-yl)-2-methyl-N-(tetrahydro-2H-pyran-4-yl)piperidin-4-amine (Compound 217)

A mixture of Int-217-66 (30 mg, 0.104 mmol) and Int-217-4 (23 mg, 0.125 mmol) in 2,2,6,6-tetramethylpiperidine/DMSO (1.5 mL, 1:1 v/v) was heated at 150° C. overnight. After cooling to room temperature, the mixture was partitioned between CH₂Cl₂ and brine. The organic layer was dried over Na₂SO₄ and concentrated in vacuo. The residue was purified by prep-TLC using CH₂Cl₂/MeOH (96:4). The product Compound 217 was obtained as brown oil in 6% yield (2.7 mg). LCMS: (M+1) m/z=450.

Examples 218-220

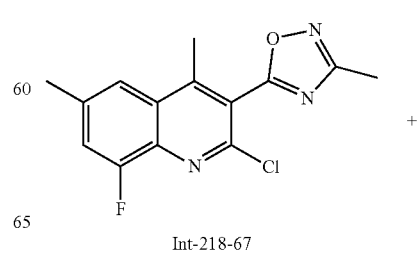

Int-218-67

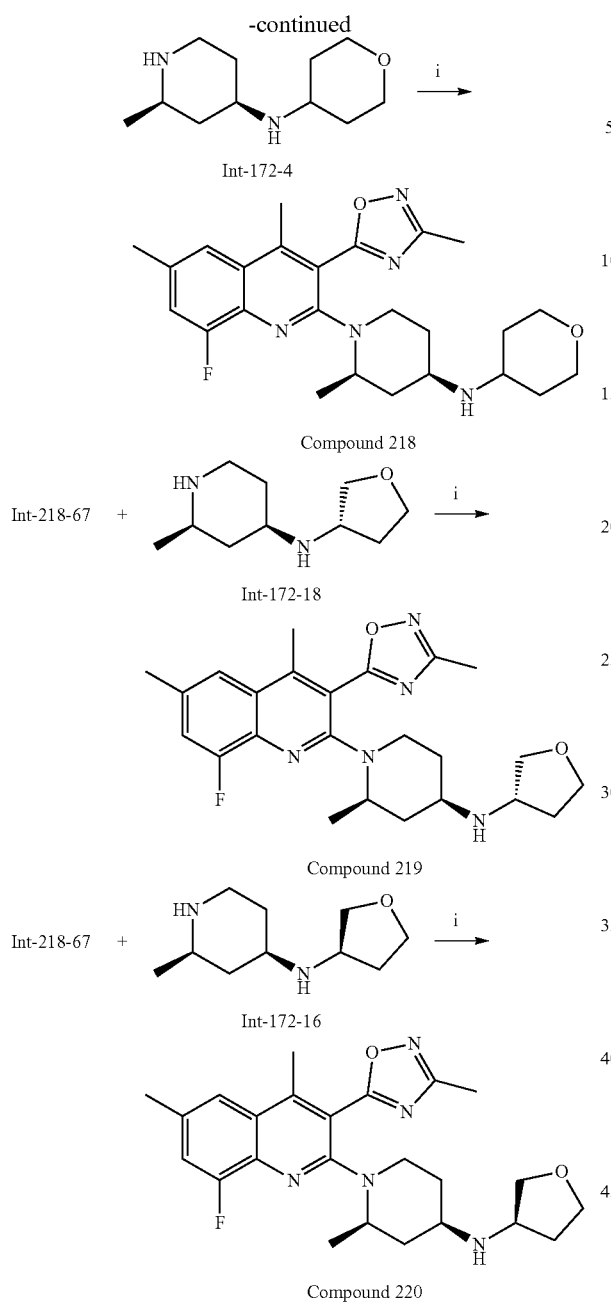

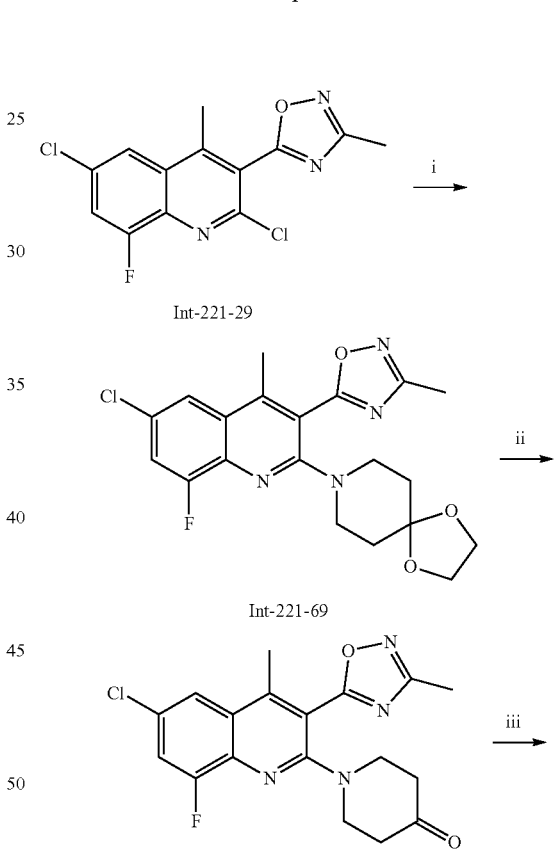

Reagents and conditions: i) Int-218-67 (1.0 eq.), amine (1.2 eq.), KF (2.5 eq.), DIPEA (2.0 eq.), DMF, 125° C., 18 h, 13%.

Synthesis of (2R,4R)-1-(8-fluoro-4,6-dimethyl-3-(3-methyl-1,2,4-oxadiazol-5-yl)quinolin-2-yl)-2-methyl-N-(tetrahydro-2H-pyran-4-yl)piperidin-4-amine (Compound 218)

A mixture of Int-218-67 (15 mg, 0.051 mmol) and Int-172-4 (12.3 mg, 0.062 mmol), KF (7.4 mg, 0.128 mmol) and DIPEA (18 μL, 0.102 mmol) in DMF (200 μL) was heated at 125° C. overnight. The mixture was cooled to room temperature, diluted with EtOAc (60 mL) and washed with 1M NaOH solution (3×). The organic phase was dried over $Na_2SO_4$, concentrated under reduced pressure and the product was purified by prep-TLC using $CH_2Cl_2$/MeOH (95:5).

Compound 218 was obtained as pale yellow oil in 13% yield (3.1 mg). LCMS: (M+1) m/z=454.

(2R)-1-(8-fluoro-4,6-dimethyl-3-(3-methyl-1,2,4-oxadiazol-5-yl)quinolin-2-yl)-2-methyl-N—((S)-tetrahydrofuran-3-yl)piperidin-4-amine (Compound 219) was obtained as pale yellow oil in 15% yield (3.3 mg). LCMS: (M+1) m/z=440.

(2R)-1-(8-fluoro-4,6-dimethyl-3-(3-methyl-1,2,4-oxadiazol-5-yl)quinolin-2-yl)-2-methyl-N—((R)-tetrahydrofuran-3-yl)piperidin-4-amine (Compound 220) was obtained as pale yellow oil in 13% yield (3.0 mg). LCMS: (M+1) m/z=440.

Compounds 219a and 220a are obtained according to the procedure described for Compounds 219-220, replacing the amine Int-218-4 with one of appropriate stereochemistry and functionality.

Examples 221-223

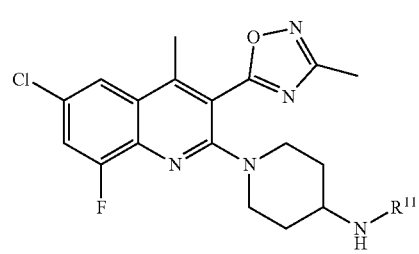

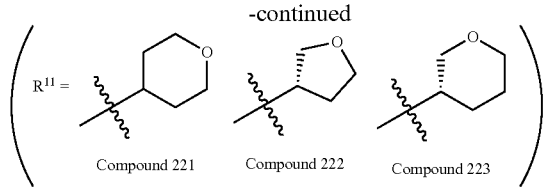

Reagents and conditions: i) Int-221-29 (1.0 eq.), 1,4-dioxa-8-azaspiro[4,5]decane (2.0 eq.), DIPEA (2.0 eq.), iPrOH, 120° C., overnight, 23%; ii) Int-221-69 (1.0 eq.), $H_2SO_4$ (10% aq.), THF, 40° C., 2 h, 62%; iii) Int-221-70 (1.0 eq.), amine (2.0 eq.), NaBH(OAc)$_3$ (2.0 eq.), AcOH (2.0 eq.), DIPEA (2.0 eq.), 1,2-dichloroethane, RT, overnight, 76-95%.

Synthesis of Int-221-69

A suspension of Int-221-29 (210 mg, 0.669 mmol), 1,4-dioxa-8-azaspiro[4,5]decane (190 mg, 1.33 mmol) and DIPEA (233 µL, 1.33 mmol) in iPrOH (4 mL) was heated at 120° C. overnight. After cooling to room temperature, the mixture was concentrated under reduced pressure and purified by column chromatography (Hexanes/EtOAc) to give ketal Int-221-69 as yellow solid in 23% yield (65 mg). LCMS: (M+1) m/z=419.

Synthesis of Int-221-70

A solution of ketal Int-221-69 (60 mg, 0.143 mmol) in THF/10% aq. $H_2SO_4$ (1:1, 1.5 mL) was stirred at 40° C. for 2 h. After cooling to room temperature, the mixture was neutralized with sat. aq. NaOH and extracted with EtOAc (2×). The organic layer was dried over $Na_2SO_4$ and concentrated under reduced pressure to give ketone Int-221-70 as a yellow solid in 62% yield (33 mg), which was used in the next step without further purification LCMS: (M+1) m/z=367.

Synthesis of Compounds 221-223

A mixture of ketone Int-221-70 (8 mg, 0.021 mmol), 4-aminotetrahydropyran (4.3 mg, 0.043 mmol), DIPEA (7.4 µL, 0.043 mmol), NaBH(OAc)$_3$ (9 mg, 0.043 mmol) and AcOH (2.4 µL, 0.043 mmol) in 1,2-dichloroethane was stirred at room temperature overnight. The mixture was filtrated through celite, concentrated under reduced pressure and purified by prep-TLC using $CH_2Cl_2$/MeOH (95:5) to give 1-(6-chloro-8-fluoro-4-methyl-3-(3-methyl-1,2,4-oxadiazol-5-yl)quinolin-2-yl)-N-(tetrahydro-2H-pyran-4-yl)piperidin-4-amine (Compound 221) as a pale yellow solid in 91% yield (8.9 mg). LCMS: (M+1) m/z=460.

(S)-1-(6-chloro-8-fluoro-4-methyl-3-(3-methyl-1,2,4-oxadiazol-5-yl)quinolin-2-yl)-N-(tetrahydrofuran-3-yl)piperidin-4-amine (Compound 222) was obtained as pale yellow solid in 95% yield (9.0 mg). LCMS: (M+1) m/z=446.

(S)-1-(6-chloro-8-fluoro-4-methyl-3-(3-methyl-1,2,4-oxadiazol-5-yl)quinolin-2-yl)-N-(tetrahydro-2H-pyran-3-yl)piperidin-4-amine (Compound 223) was obtained as pale yellow oil in 76% yield (7.4 mg). LCMS: (M+1) m/z=460.

Examples 224-225

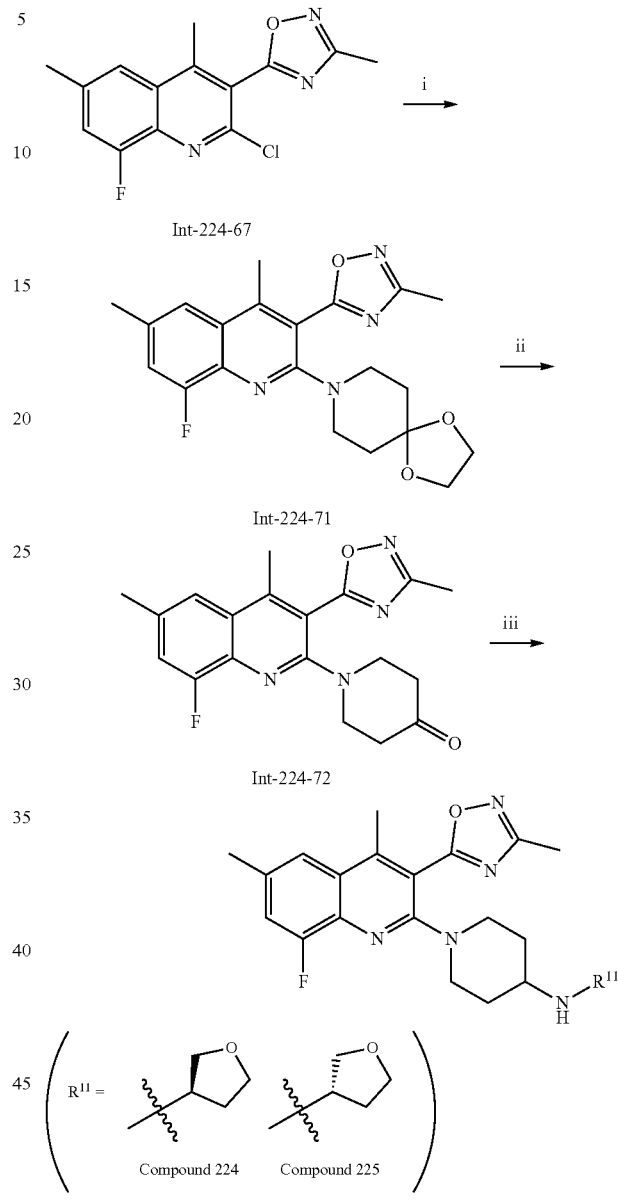

Reagents and conditions: i) Int-224-67 (1.0 eq.), 1,4-dioxa-8-azaspiro[4,5]decane (2.0 eq.), DIPEA (2.0 eq.), EtOH, 120° C., overnight, 84%; ii) Int-224-71 (1.0 eq.), $H_2SO_4$ (10% aq.), THF, 50° C., 2 h, 87%; iii) Int-224-72 (1.0 eq.), amine (1.2 eq.), NaBH(OAc)$_3$ (2.0 eq.), AcOH (2.0 eq.), DIPEA (2.0 eq.), 1,2-dichloroethane, RT, overnight, 50-62%.

Synthesis of Int-224-71

To a suspension of chloroquinoline Int-224-67 (210 mg, 0.75 mmol) and DIPEA (0.26 mL, 1.50 mmol) in EtOH (5 mL) was added 1,4-dioxa-8-azaspiro[4,5]decane (0.20 mL, 1.50 mmol) at room temperature. The mixture was then heated at 120° C. overnight. After cooling to room temperature, the mixture was concentrated and purified by column chromatography (0 to 20% EtOAc in hexanes) as mobile phase. The product Int-224-71 was obtained as a pale yellow solid in 84% yield (251 mg). LCMS: (M+1) m/z=399.

Synthesis of Int-224-72

To a solution of Int-224-71 (246 mg, 0.62 mmol) in THF (2.5 mL) was added 10% aq. $H_2SO_4$ (5 mL) at room temperature. The mixture was then stirred at 50° C. for 1 h. After cooling to room temperature, the mixture was neutralized with sat. aq. $Na_2CO_3$ and extracted with EtOAc (2×20 mL). The combined organic layers were dried over $Na_2SO_4$ and concentrated in vacuo. The product was purified by column chromatography (0 to 66% EtOAc in hexanes) as mobile phase. The product Int-224-72 was obtained as a yellow solid in 87% yield (189 mg). LCMS: (M+1) m/z=355.

Synthesis of (R)-1-(8-fluoro-4,6-dimethyl-3-(3-methyl-1,2,4-oxadiazol-5-yl)quinolin-2-yl)-N-(tetrahydrofuran-3-yl)piperidin-4-amine (Compound 224)

A mixture of Int-224-72 (10.0 mg, 0.028 mmol), (R)-3-aminotetrahydrofuran hydrochloride (4.2 mg, 0.034 mmol) and DIPEA (10 μL, 0.056 mmol) in 1,2-dichloroethane (1 mL) was stirred at room temperature for 10 min. To the mixture, NaBH(OAc)$_3$ (12.0 mg, 0.056 mmol) and AcOH (3 μL, 0.056 mmol) were added. The resulting mixture was stirred at room temperature overnight. The mixture was then filtered through Celite, and the filtrate was concentrated in vacuo. The residue was purified by prep-TLC using $CH_2Cl_2$/MeOH (96:4). The product Compound 224 was obtained as a yellow solid in 62% yield (7.4 mg). LCMS: (M+1) m/z=426.

(S)-1-(8-fluoro-4,6-dimethyl-3-(3-methyl-1,2,4-oxadiazol-5-yl)quinolin-2-yl)-N-(tetrahydrofuran-3-yl)piperidin-4-amine (Compound 225) was obtained as a yellow solid in 50% yield (5.9 mg). LCMS: (M+1) m/z=426.

Examples 226-227

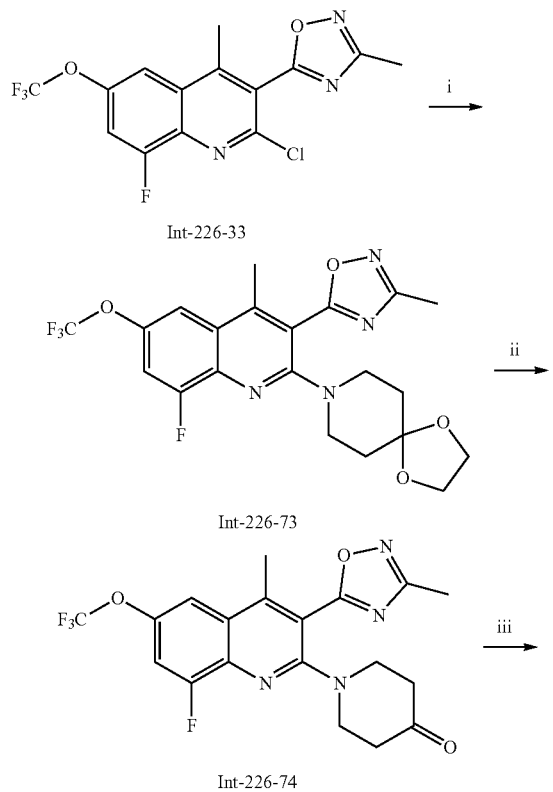

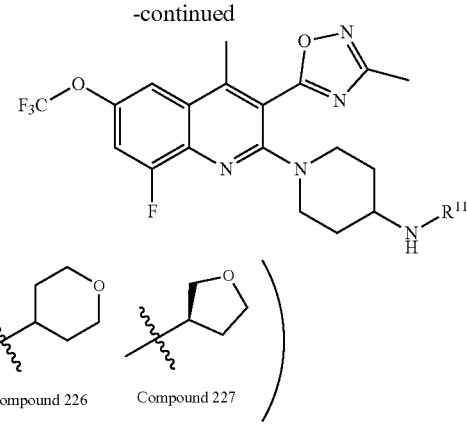

Reagents and conditions: i) Int-226-33 (1.0 eq.), 1,4-dioxa-8-azaspiro[4,5]decane (2.0 eq.), DIPEA (2.0 eq.), EtOH, 120° C., overnight, 77%; ii) Int-226-73 (1.0 eq.), $H_2SO_4$ (10% aq.), THF, 50° C., 2 h, 59%; iii) Int-226-74 (1.0 eq.), amine (1.2 eq.), NaBH(OAc)$_3$ (2.0 eq.), AcOH (2.0 eq.), DIPEA (2.0 eq.), 1,2-dichloroethane, RT, overnight, 67-79%.

Synthesis of Int-226-73

To a suspension of chloroquinoline Int-226-33 (170 mg, 0.47 mmol) and DIPEA (0.16 mL, 0.94 mmol) in EtOH (5 mL) was added 1,4-dioxa-8-azaspiro[4,5]decane (0.12 mL, 0.94 mmol) at room temperature. The mixture was then heated at 120° C. overnight. After cooling to room temperature, the mixture was concentrated and purified by column chromatography (0 to 20% EtOAc in hexanes) as mobile phase. The product Int-226-73 was obtained as red oil in 77% yield (170 mg). LCMS: (M+1) m/z=469.

Synthesis of Int-226-74

To a solution of Int-226-73 (170 mg, 0.36 mmol) in THF (2 mL) was added 10% aq. $H_2SO_4$ (3 mL) at room temperature. The mixture was then stirred at 50° C. for 2 h. After cooling to room temperature, the mixture was neutralized with sat. aq. $Na_2CO_3$ and extracted with EtOAc (2×20 mL). The combined organic layers were dried over $Na_2SO_4$ and concentrated in vacuo. The product was purified by column chromatography (0 to 66% EtOAc in hexanes) as mobile phase. The product Int-226-74 was obtained as red oil in 59% yield (91 mg). LCMS: (M+1) m/z=425.

Synthesis of 1-(8-fluoro-4-methyl-3-(3-methyl-1,2,4-oxadiazol-5-yl)-6-(trifluoromethoxy) quinolin-2-yl)-N-(tetrahydro-2H-pyran-4-yl)piperidin-4-amine (Compound 226)

A mixture of Int-226-74 (15.0 mg, 0.035 mmol), 4-aminotetrahydropyran (4.2 mg, 0.042 mmol) and DIPEA (12 μL, 0.070 mmol) in 1,2-dichloroethane (1 mL) was stirred at room temperature for 10 min. To the mixture, NaBH(OAc)$_3$ (14.8 mg, 0.070 mmol) and AcOH (4 μL, 0.070 mmol) were added. The resulting mixture was stirred at room temperature overnight. The mixture was then filtered through Celite, and the filtrate was concentrated in vacuo. The residue was purified by prep-TLC using $CH_2Cl_2$/MeOH (96:4). The product Compound 226 was obtained as a brown solid in 67% yield (11.9 mg). LCMS: (M+1) m/z=510.

(R)-1-(8-fluoro-4-methyl-3-(3-methyl-1,2,4-oxadiazol-5-yl)-6-(trifluoromethoxy) quinolin-2-yl)-N-(tetrahydrofuran- 3-yl)piperidin-4-amine (Compound 227) was obtained as a yellow solid in 79% yield (13.9 mg). LCMS: (M+1) m/z=496.

Examples 228

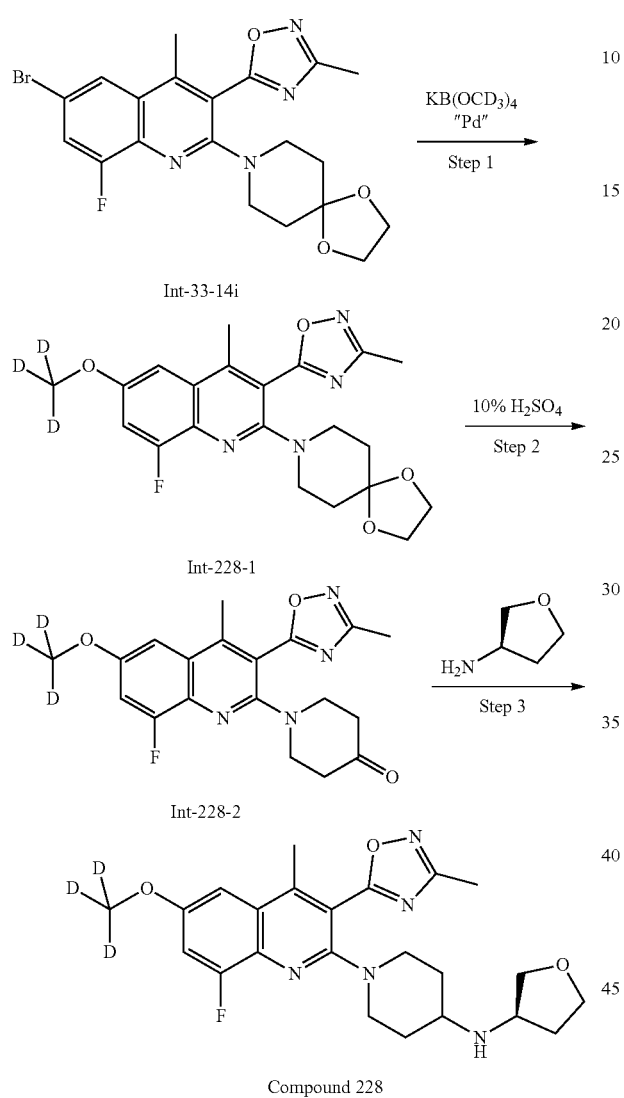

Synthesis of (R)-1-(8-fluoro-6-(methoxy-d3)-4-methyl-3-(3-methyl-1,2,4-oxadiazol-5-yl)quinolin-2-yl)-N-(tetrahydrofuran-3-yl)piperidin-4-amine (Compound 228)

Step 1: Following the preparation of Int-33-14j, in which KB(OCH$_3$)$_4$ was replaced by KB(OCD$_3$)$_4$, Int-228-1 was obtained as white solid after silica-gel chromatography purification (0-60% EtOAc/Hexanes). LCMS: m/z 418 (M+H).

Step 2-3: According to the procedure disclosed above for Compound 34 and using the corresponding deuterium-substituted intermediate(s), Compound 228 was obtained as a white solid. LCMS: m/z 445 (M+H); Retention time: 3.55 min (Method 2).

Example 229

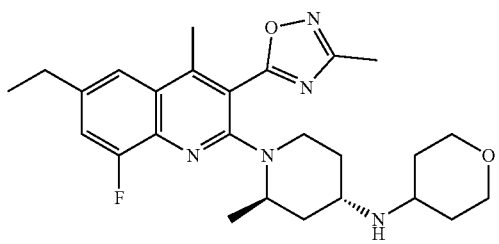 [SMILES: CCc1cc(F)c2nc(N3CC[C@H](NC4CCOCC4)C[C@H]3C)c(-c3nc(C)no3)c(C)c2c1]

Following the general procedure for synthesis of Compound 197, using the appropriate chiral amine, Compound 229 was obtained as white solid; LCMS: m/z 468 (M+H).

Examples 230-235

Compounds 230-235 are obtained using methods as disclosed in examples 195-197 or 236-237, using amines and alkylating agents of the appropriate stereochemistry.

Examples 236-237

Compound 236a

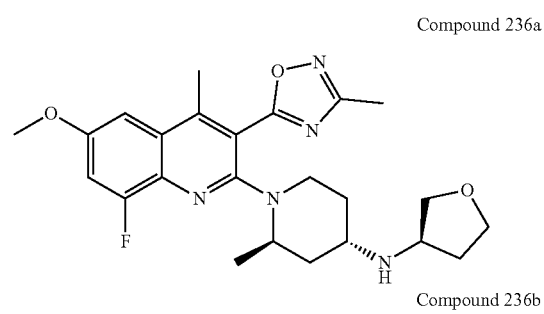

Compound 236b

Compound 237a

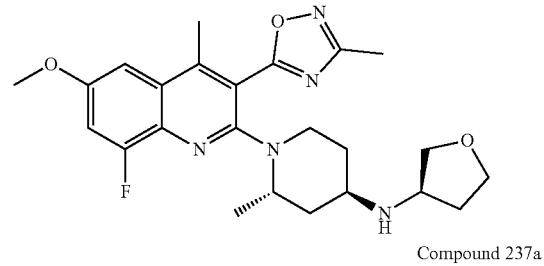

Compound 237b

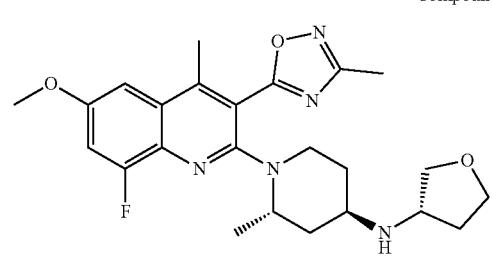

236a and 236b: A mixture of (2R,4S)-1-(8-fluoro-6-methoxy-4-methyl-3-(3-methyl-1,2,4-oxadiazol-5-yl)quinolin-2-yl)-2-methyl-N—((R)-tetrahydrofuran-3-yl)piperidin-4-amine and (2R,4S)-1-(8-fluoro-6-methoxy-4-methyl-3-(3-methyl-1,2,4-oxadiazol-5-yl)quinolin-2-yl)-2-methyl-N—((R)-tetrahydrofuran-3-yl)piperidin-4-amine, and 237a and 237b: A mixture of (2R,4S)-1-(8-fluoro-6-methoxy-4-methyl-3-(3-methyl-1,2,4-oxadiazol-5-yl)quinolin-2-yl)-2-methyl-N—((S)-tetrahydrofuran-3-yl)piperidin-4-amine and (2R,4S)-1-(8-fluoro-6-methoxy-4-methyl-3-(3-methyl-1,2,4-oxadiazol-5-yl)quinolin-2-yl)-2-methyl-N—((S)-tetrahydrofuran-3-yl)piperidin-4-amine

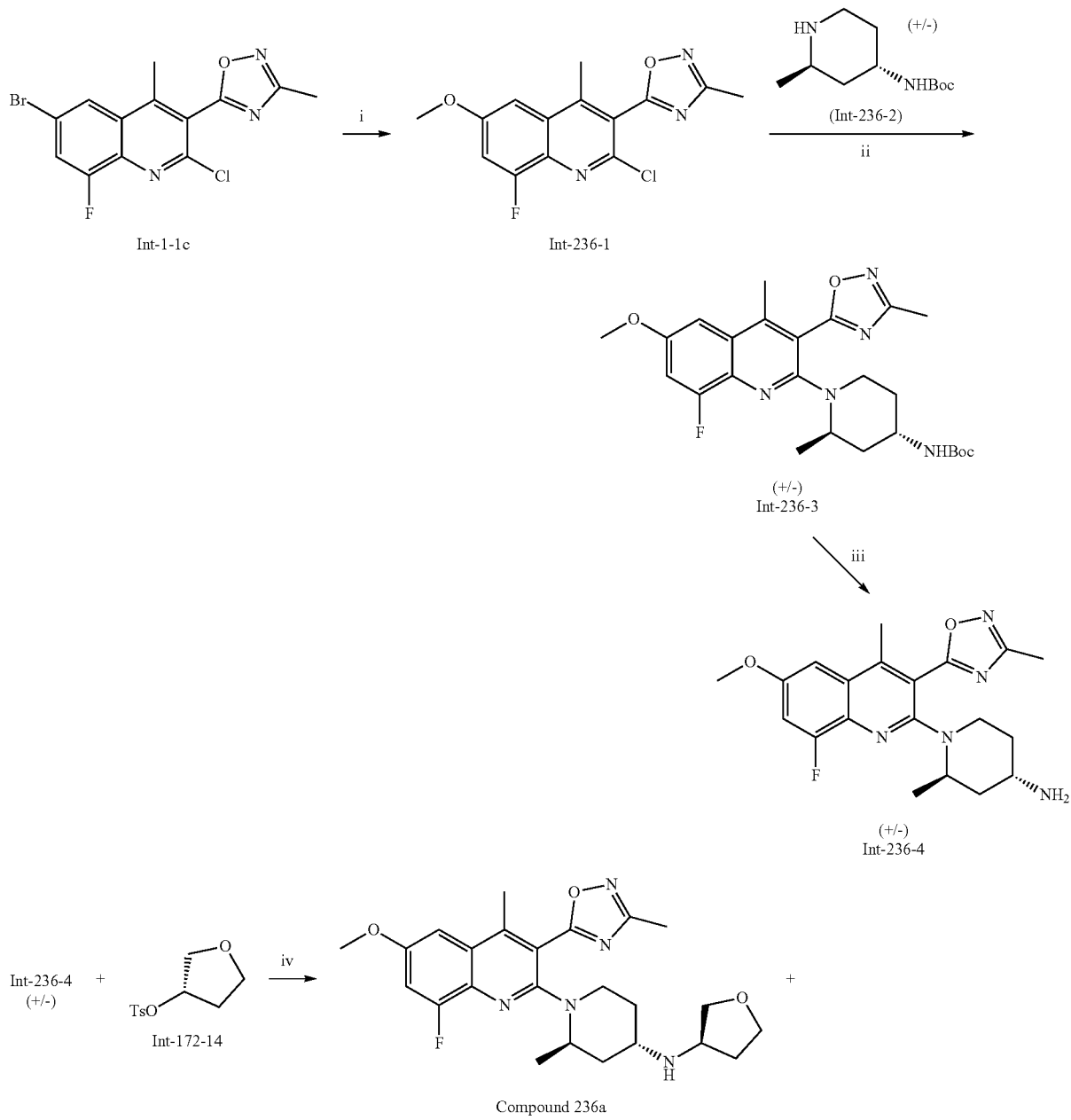

-continued

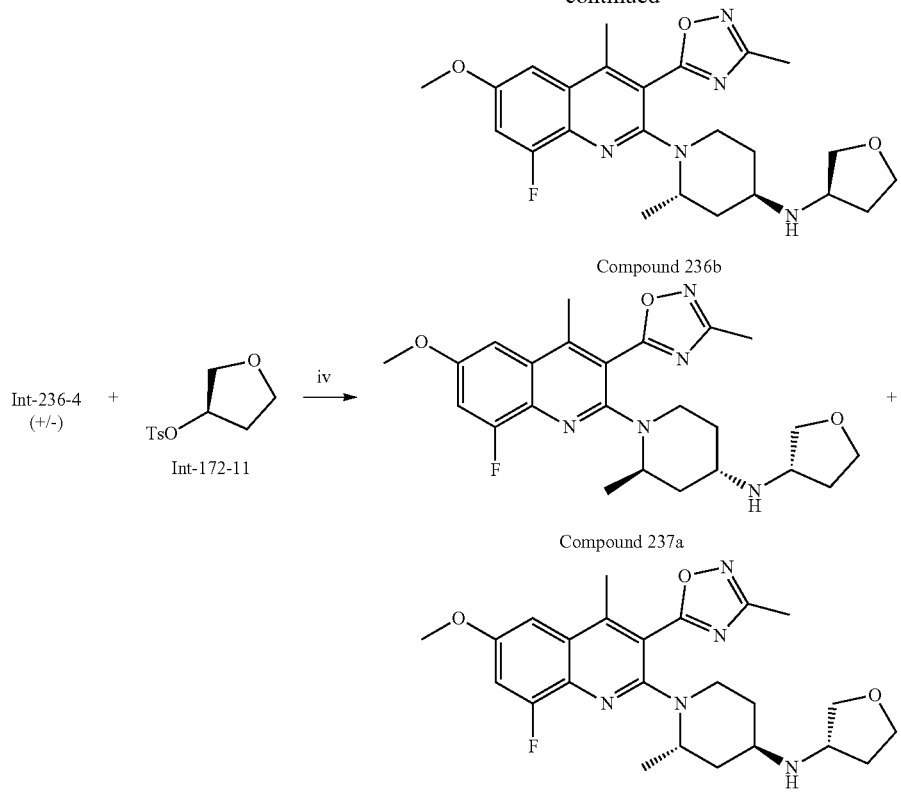

Compound 236b

Compound 237a

Compound 237b

Reagents and conditions: i) KB(OMe)4 (3 equiv.), Pd2(dba)3 (0.05 equiv.), tBuXphos (0.1 equiv.), dioxane, 100° C., 2 h; ii) KF (2.5 equiv.), DMSO, 130° C., iii) TFA, DCM; iv) DIPEA (4 equiv.), CH3CN, uW, 120° C.; iv) DIPEA (4 equiv.), CH3CN, uW, 120° C.

Int-236-1 was synthesized from Int-1-1c according to the general procedure for Int-33-14j.

Synthesis of tert-butyl 1-(8-fluoro-6-methoxy-4-methyl-3-(3-methyl-1,2,4-oxadiazol-5-yl)quinolin-2-yl)-trans-2-methylpiperidin-4-yl)carbamate (Int-236-3)

A microwave vial was charged with 5-(2-chloro-8-fluoro-6-methoxy-4-methylquinolin-3-yl)-3-methyl-1,2,4-oxadiazole (Int-236-1) (0.143 mg, 0.45 mmol), racemic tert-butyl N-[(trans)-2-methylpiperidin-4-yl]carbamate (Int-236-2, 0.199 g, 0.929 mmol), potassium fluoride (67.5 mg, 1.16 mmol), anhydrous DMSO (1.2 mL), and diisoproplyethyl-amine (0.21 mL, 1.16 mmol). The mixture was placed under a nitrogen atmosphere and heated at 130° C. for 15 hours. After cooling to room temperature, the mixture was partitioned between ethyl acetate and saturated sodium bicarbonate solution. The organic extract was successively washed with sodium bicarbonate and brine solutions, dried over sodium sulfate, and concentrated to 300 mg. The crude product was purified by column chromatography, eluting from 12 g silica gel with a gradient of 0-40% EA/hexanes to give the desired product as a yellow oil (140 mg, 61% yield) LCMS: (M+1) m/z=486.1

Synthesis of 1-(8-fluoro-6-methoxy-4-methyl-3-(3-methyl-1,2,4-oxadiazol-5-yl)quinolin-2-yl)-trans-2-methylpiperidin-4-amine (Int-236-4)

To a cooled 0° C. solution of tert-butyl 1-(8-fluoro-6-methoxy-4-methyl-3-(3-methyl-1,2,4-oxadiazol-5-yl)quino-lin-2-yl)-trans-2-methylpiperidin-4-yl)carbamate (Int-236-3, 135 mg, 0.278 mmol) in 5 mL of DCM was added 2.5 mL of TFA. The mixture was stirred for 1.5 hr at room temperature, concentrated to an orange foam, and partitioned between equal volumes of half-saturated Na2CO3 solution and EtOAc. The organic solution was washed with Na2CO3 solution twice, dried over sodium sulfate, and concentrated to give Int-236-4 as a yellow solid (99 mg, 94% yield). LCMS: (M+1) m/z=386.2

Synthesis of Compounds 236a (2R,4S)-1-(8-fluoro-6-methoxy-4-methyl-3-(3-methyl-1,2,4-oxadiazol-5-yl)quinolin-2-yl)-2-methyl-N—((R)-tetrahydrofuran-3-yl)piperidin-4-amine and 236b (2S,4R)-1-(8-fluoro-6-methoxy-4-methyl-3-(3-methyl-1,2,4-oxadiazol-5-yl)quinolin-2-yl)-2-methyl-N—((R)-tetrahydrofuran-3-yl)piperidin-4-amine A microwave vessel was charged with 1-(8-fluoro-6-methoxy-4-methyl-3-(3-methyl-1,2,4-oxadiazol-5-yl)quinolin-2-yl)-trans-2-methylpiperidin-4-amine (Int-236-4, 55 mg, 0.14 mmol), (3S)-oxolan-3-yl 4-methylbenzene-1-sulfonate (Int-172-14, 140 mg, 0.56 mmol), diisopropyleth-ylamine (97 µL, 0.56 mmol) and CH3CN (0.9 mL). The mixture was heated at 120° C. in a microwave reactor for 12 hours. The mixture was partitioned between EtOAc and aqueous Na2CO3, drying the organic fraction over sodium sulfate and concentrating to 225 mg of an orange oil. The crude product was purified by column chromatography, eluting from silica gel with a gradient of 0-60% EtOAc/ hexanes, followed by a gradient of 0-10% MeOH/DCM to give the mixture of diastereomers as a yellow solid (40 mg, 63% yield). The mixture can be separated to give the individual diasteromers using a phenomenex Lux 5μ cellulose-2 column (250 mm×4.6 mm, hexane:ethanol:DEA (80: 20:1), 1 mL/min, retention time: 15.7 min, 17.5 min. LCMS: (M+1) m/z=356.1.

Synthesis of Compound 237a (2R,4S)-1-(8-fluoro-6-methoxy-4-methyl-3-(3-methyl-1,2,4-oxadiazol-5-yl)quinolin-2-yl)-2-methyl-N—((S)-tetrahydrofuran-3-yl)piperidin-4-amine and Compound 237b (2S, 4R)-1-(8-fluoro-6-methoxy-4-methyl-3-(3-methyl-1, 2,4-oxadiazol-5-yl)quinolin-2-yl)-2-methyl-N—((S)-tetrahydrofuran-3-yl)piperidin-4-amine A microwave vessel was charged with 1-[8-fluoro-6-methoxy-4-methyl-3-(3-methyl-1,2,4-oxadiazol-5-yl)quinolin-2-yl]-trans-2-methylpiperidin-4-amine (Int-236-4, 58 mg, 0.15 mmol), (3R)-oxolan-3-yl 4-methylbenzene-1-sulfonate (Int-172-11, 146 mg, 0.56 mmol), DIPEA (0.105 mL, 0.56 mmol) and CH$_3$CN (0.9 mL). The mixture was heated for 12 hours at 120° C. in a microwave reactor. The mixture was partitioned between EtOAc and an aqueous Na$_2$CO$_3$ solution, drying the organic fraction over sodium sulfate, and concentrating to 170 mg of an orange oil. The crude product was purified by column chromatography eluting with a gradient of 0-60% EtOAc/hexanes, followed by a gradient of 0-10% MeOH/DCM to give the mixture of diastereomers as a yellow solid (38 mg, 56% yield). The mixture can be separated to give the individual diasteromers using a phenomenex Lux 5p cellulose-4 column (250 mm×4.6 mm, hexane:ethanol:DEA (73:27:0.1), 1 mL/min, retention time: 7.2 min, 8.9 min. LCMS: (M+1) m/z=356.1.

Example 238-239

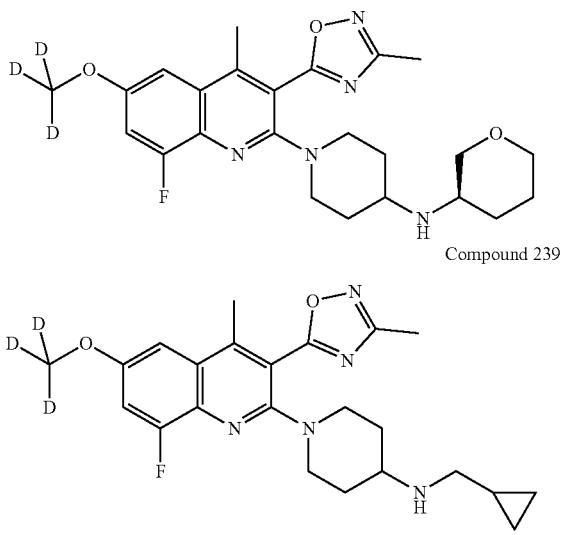

Compound 238

Compound 239

Compound 238 and 239 were prepared according to the procedure disclosed above for Compound 228, and the appropriate amines were applied in Step 3. Compound 238: yellow solid; LCMS: m/z 459 (M+H); Retention time: 3.71 min (Method 2). Compound 239: white solid; LCMS: m/z 429 (M+H); Retention time: 3.90 min (Method 2).

Example 240

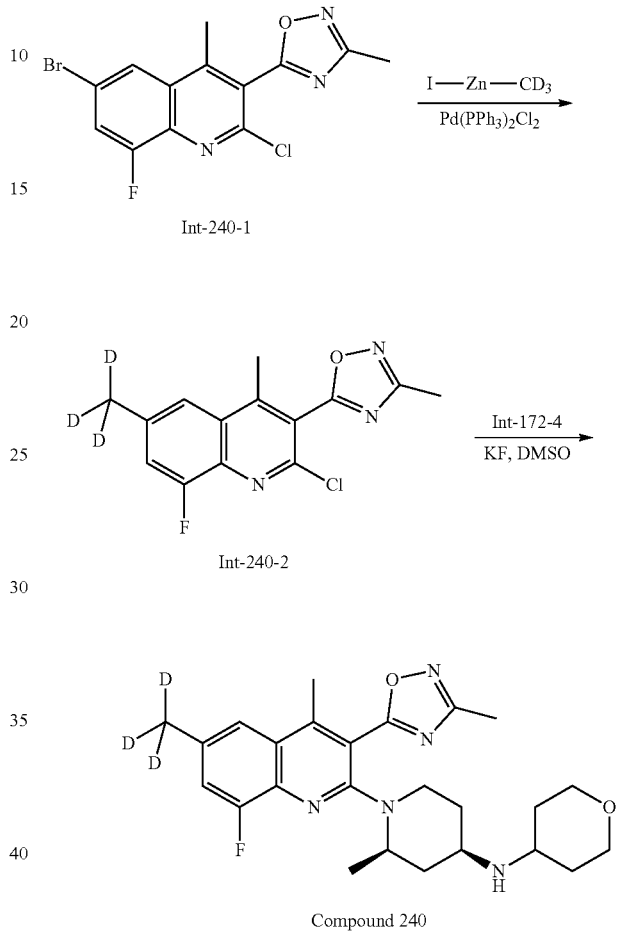

Compound 240

Step 1: To a suspension of 5-(6-bromo-2-chloro-8-fluoro-4-methylquinolin-3-yl)-3-methyl-1,2,4-oxadiazole (357 mg, 1.00 mmol) and bis(triphenylphosphine)palladium(II) chloride (68 mg, 88 umol) in THF (2 mL) was added (methyl-d3)zinc(II) iodide suspension (7.0 mL, ref: DOI: 10.1039/c7cc06106d), and the reaction was stirred at 60° C. for 4 h. The reaction was quenched by citric acid solution (5% aq.), and extracted with ethyl acetate twice. The organic layers were combined, washed with brine, dried over Na$_2$SO$_4$ and concentrated under reduced pressure. The residue was purified by silica gel chromatography (EtOAc/Hex) to give the desired product as white solid (153 mg, 52% yield). LCMS (ESI): m/z 295 (M+H).

Step 2: Similar to Compound 174 by replacing 5-(2,8-dichloro-4,6-dimethylquinolin-3-yl)-3-methyl-1,2,4-oxadiazole with 5-(2-chloro-8-fluoro-4-methyl-6-(methyl-d3)quinolin-3-yl)-3-methyl-1,2,4-oxadiazole, Compound 240 was obtained as white solid. LCMS: m/z 457 (M+H).

Example 241-242

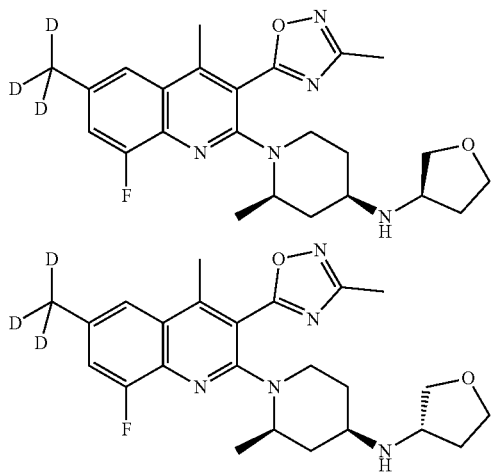

Following the procedure for Compound 240, Compound 241 was obtained as white solid; LCMS: m/z 443 (M+H); Retention time: 3.62 min (Method 2). Compound 242 was obtained as white solid; LCMS: m/z 443 (M+H); Retention time: 3.74 min (Method 2).

Example 243

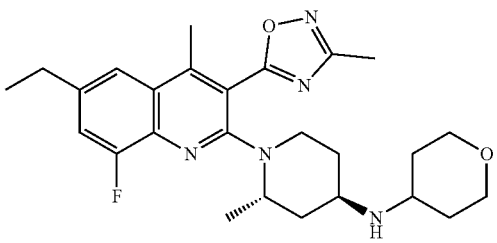 [SMILES: CCc1cc(F)c2nc(N3CC[C@@H](NC4CCOCC4)C[C@@H]3C)c(-c3nc(C)no3)c(C)c2c1]

Following the general synthetic procedure for Compound 197, using the appropriate chiral amine, Compound 243 was obtained as white solid; LCMS: m/z 468 (M+H).

Example 244

Compound 244

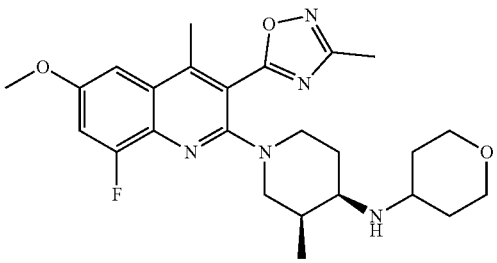

Compound 244 is obtained using methods as disclosed in examples 259-260, using the appropriate chiral amine Int-259-13 and Int-36-14h.

Examples 245-248

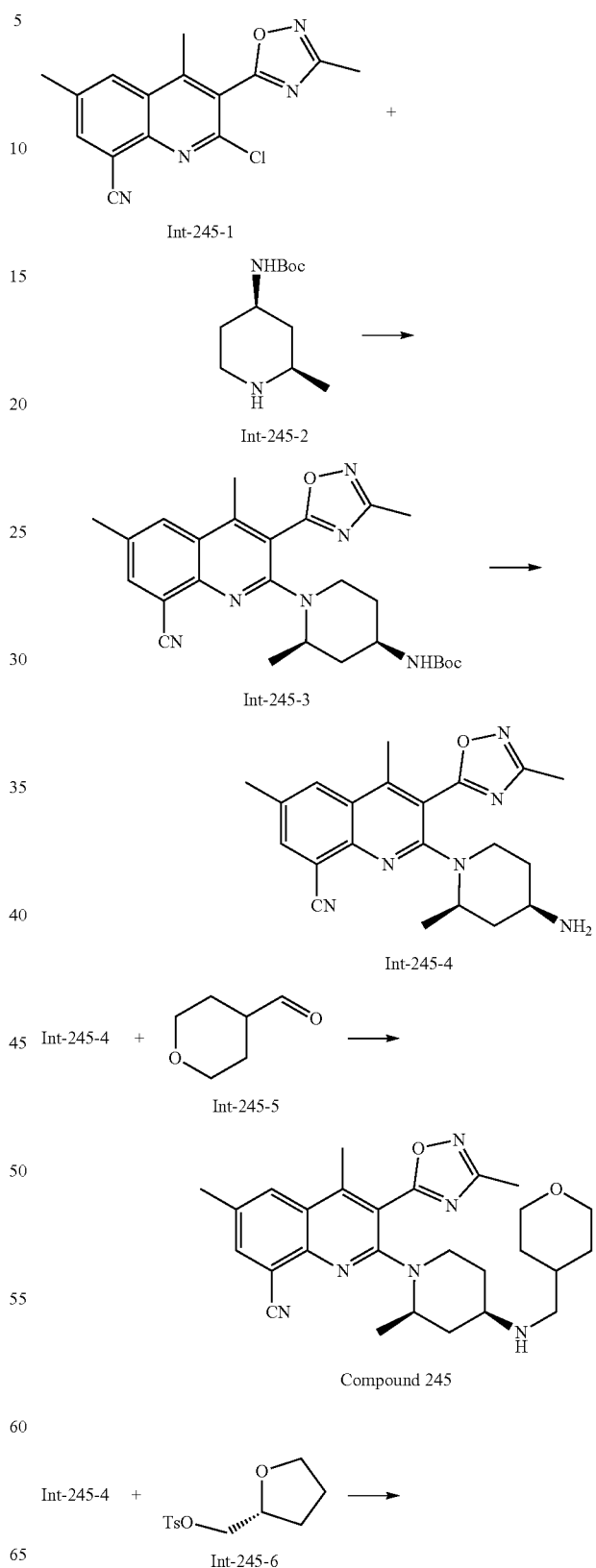

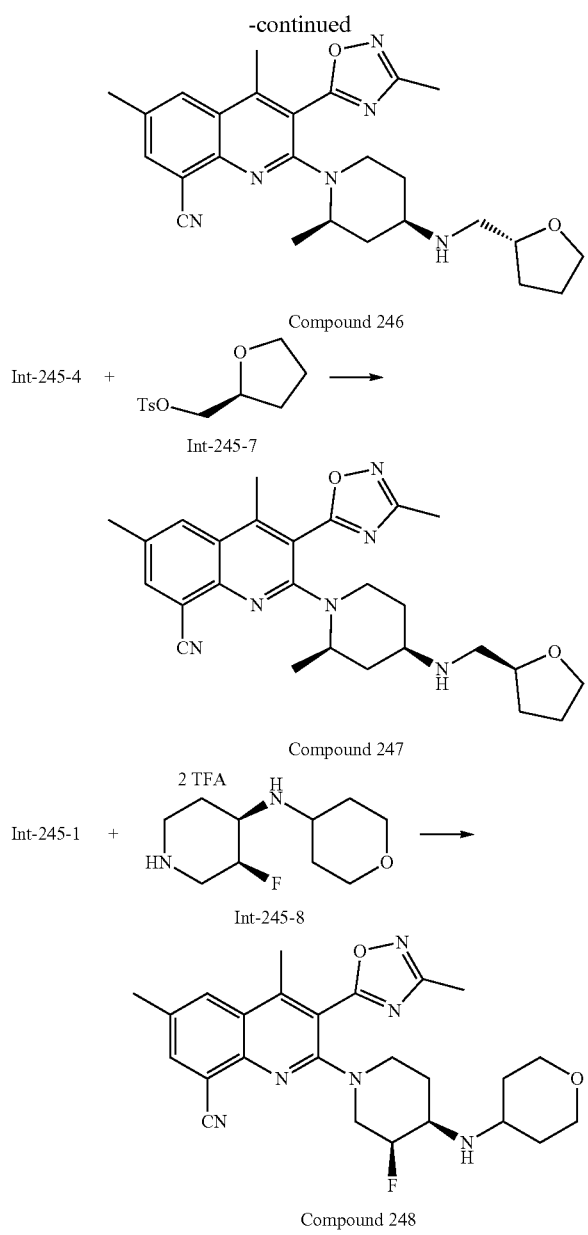

reduced pressure. The crude was re-dissolved in EtOAc and washed with 2M NaOH (2×). The aqueous phase was extracted with EtOAc (2×). The combined organic phase was dried over $Na_2SO_4$, concentrated under reduced pressure and the product was used without further purification. Int-245-4 was obtained as a yellow solid in 95% yield. LCMS: (M+1) m/z=377.

A mixture of amine Int-245-4 (10 mg, 0.026 mmol) and Int-245-5 (3 mg, 0.026 mmol) in DCE (200 μL) was stirred at room temperature for 1 h followed by addition of NaBH(OAc)$_3$ (11 mg, 0.052 mmol) and AcOH (2.9 μL, 0.052 mmol). The resulting mixture was stirred at room temperature overnight. The mixture was diluted with EtOAc (50 mL) and washed with 2M NaOH (1×). The organic layer was dried over $Na_2SO_4$ and concentrated. The residue was purified by prep-TLC using $CH_2Cl_2$/MeOH (95:5). Compound 245 was obtained as a yellow solid in 49% yield (6.1 mg). LCMS: (M+1) m/z=475.

Synthesis of 4,6-dimethyl-3-(3-methyl-1,2,4-oxadiazol-5-yl)-2-((2R,4R)-2-methyl-4-((((R)-tetrahydrofuran-2-yl)methyl)amino)piperidin-1-yl)quinoline-8-carbonitrile (Compound 246)

A mixture of Int-245-4 (10 mg, 0.026 mmol), Int-245-6 (13.3 mg, 0.052 mmol) and DIPEA (9.1 μL, 0.052 mmol) in acetonitrile (150 μL) was heated 80° C. overnight. The mixture was concentrated under reduced pressure and purified by prep-TLC using $CH_2Cl_2$/MeOH (95:5). Compound 246 was obtained as yellow oil in 53% yield (6.3 mg). LCMS: (M+1) m/z=461.

Synthesis of 4,6-dimethyl-3-(3-methyl-1,2,4-oxadiazol-5-yl)-2-((2R,4R)-2-methyl-4-((((S)-tetrahydrofuran-2-yl)methyl)amino)piperidin-1-yl)quinoline-8-carbonitrile (Compound 247)

Compound 247 was synthesized in a similar fashion and was obtained as yellow oil in 50% yield (6.0 mg). LCMS: (M+1) m/z=461.

Synthesis of 2-((3S,4R)-3-fluoro-4-((tetrahydro-2H-pyran-4-yl)amino)piperidin-1-yl)-4,6-dimethyl-3-(3-methyl-1,2,4-oxadiazol-5-yl)quinoline-8-carbonitrile (Compound 248)

A mixture of Int-245-1 (20 mg, 0.067 mmol), Int-245-8 (34.4 mg, 0.08 mmol) and DIPEA (47 μL, 0.268 mmol) in EtOH (250 μL) was heated at 125° C. overnight. The mixture was concentrated under reduced pressure and purified by prep-TLC using $CH_2Cl_2$/MeOH (95:5). Compound 248 was obtained as a yellow solid in 46% yield (14.3 mg). LCMS: (M+1) m/z=465.

Example 249

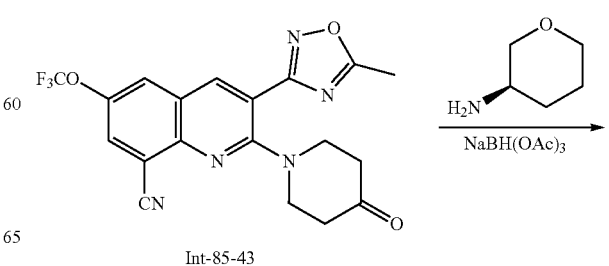

Synthesis of 4,6-dimethyl-3-(3-methyl-1,2,4-oxadiazol-5-yl)-2-((2R,4R)-2-methyl-4-(((tetrahydro-2H-pyran-4-yl)methyl)amino)piperidin-1-yl)quinoline-8-carbonitrile (Compound 245)

A mixture of Int-245-1 (200 mg, 0.67 mmol), Int-245-2 (172 mg, 0.804 mmol) and KF (97 mg, 1.67 mmol) in DMSO (2 mL) was heated at 125° C. overnight. The mixture was cooled to room temperature, diluted with EtOAc (150 mL) and washed with brine (3×). The organic phase was dried over $Na_2SO_4$, concentrated under reduced pressure, and the product was purified by column chromatography using hexanes/EtOAc (7:3). The product was obtained as yellow solid in 56% yield (180 mg). LCMS: (M+1) m/z=477.

A mixture of Int-245-3 (170 mg, 0.356 mmol) and TFA (550 μL, 7.13 mmol) in $CH_2Cl_2$ (5 mL) was stirred at room temperature for 1 h. The mixture was concentrated under

249

-continued

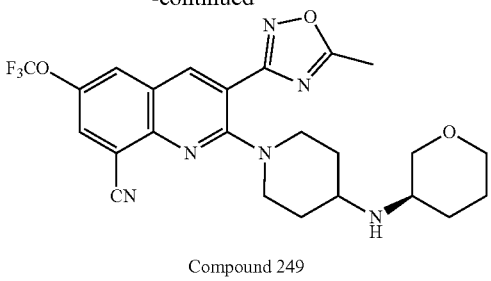

Compound 249

Synthesis of (R)-3-(5-methyl-1,2,4-oxadiazol-3-yl)-2-(4-((tetrahydro-2H-pyran-3-yl)amino) piperidin-1-yl)-6-(trifluoromethoxy)quinoline-8-carbonitrile (Compound 249)

A mixture of ketone Int-85-43 (5 mg, 0.012 mmol), 3-(R)-aminotetrahydropyran HCl (3.3 mg, 0.024 mmol), DIPEA (4.2 µL, 0.024 mmol), NaBH(OAc)$_3$ (5 mg, 0.024 mmol) and AcOH (1.3 µL, 0.024 mmol) in 1,2-dichloroethane was stirred at room temperature overnight. The mixture was filtrated through celite, concentrated under reduced pressure and purified by prep-TLC (CH$_2$Cl$_2$:MeOH=95:5) to give Compound 249 (4.1 mg, 69% yield) as a yellow solid. LCMS: (M+1) m/z=503.

Example 250

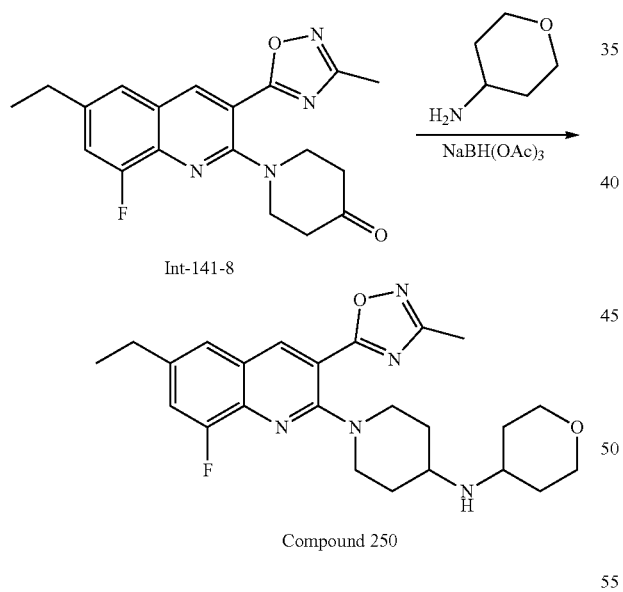

Compound 250

Synthesis of 1-(6-ethyl-8-fluoro-3-(3-methyl-1,2,4-oxadiazol-5-yl)quinolin-2-yl)-N-(tetrahydro-2H-pyran-4-yl)piperidin-4-amine (Compound 250)

A mixture of Int-141-8 (8 mg, 0.022 mmol), 4-aminotetrahydropyran (3.4 mg, 0.034 mmol), NaBH(OAc)$_3$ (7.2 mg, 0.034 mmol) and AcOH (1.9 µl, 0.13 mmol) in 1,2-dichloroethane (0.4 mL) was stirred at RT for 3 h. The reaction mixture was directly purified by preparative-TLC (CH$_2$Cl$_2$:MeOH=95:5) to give Compound 250 as a yellow solid (8.1 mg, 82% yield). LCMS: (M+1) m/z=440.

250

Example 251

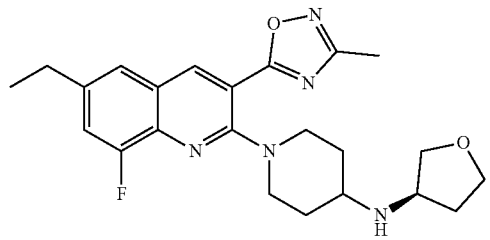 [SMILES: CCc1cc(F)c2nc(N3CCC(N[C@@H]4CCOC4)CC3)c(-c3nc(C)no3)cc2c1]

Synthesis of (R)-1-(6-ethyl-8-fluoro-3-(3-methyl-1,2,4-oxadiazol-5-yl)quinolin-2-yl)-N-(tetrahydrofuran-3-yl)piperidin-4-amine (Compound 251)

A mixture of Int-141-8 (10 mg, 0.028 mmol), (R)-tetrahydrofuran-3-amine hydrochloride (4.2 mg, 0.034 mmol) and DIPEA (5.9 µl, 0.11 mmol) in 1,2-dichloroethane (0.4 mL) was stirred at RT for 10 min. To the mixture NaBH(OAc)$_3$ (8.9 mg, 0.042 mmol) and AcOH (2.3 µl, 0.042 mmol) were added. The resulting mixture was stirred at RT for 3 h. The reaction mixture was directly purified by preparative-TLC (CH$_2$Cl$_2$:MeOH=95:5) to give Compound 251 as a yellow solid (8.1 mg, 68% yield). LCMS: (M+1) m/z=426.

Example 252-253

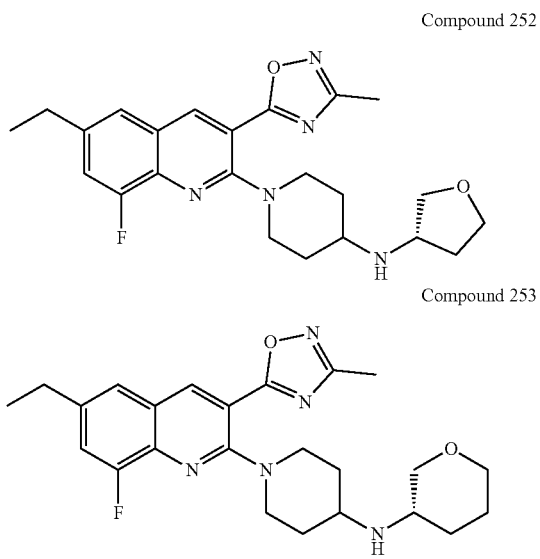

Compound 252

Compound 253

(S)-1-(6-ethyl-8-fluoro-3-(3-methyl-1,2,4-oxadiazol-5-yl)quinolin-2-yl)-N-(tetrahydrofuran-3-yl)piperidin-4-amine (Compound 252) was synthesized in a similar fashion as Compound 251 and was obtained as yellow solid in 82% yield (9.8 mg). LCMS: (M+1) m/z=426.

Synthesis of (S)-1-(6-ethyl-8-fluoro-3-(3-methyl-1,2,4-oxadiazol-5-yl)quinolin-2-yl)-N-(tetrahydro-2H-pyran-3-yl)piperidin-4-amine (Compound 253) was synthesized in a similar fashion as Compound 251 and was obtained as yellow solid in 84% yield (10.4 mg). LCMS: (M+1) m/z=440.

Example 254

Synthesis of Compounds 254

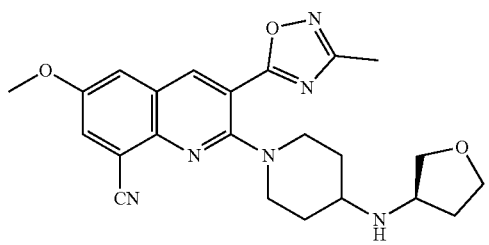
Compound 254

Compound 254 (7.6 mg, 40% yield at the final step) was obtained as white solid, following the procedure to synthesize Compound 170 by replacing 6-bromo-4-methyl-3-(5-methyl-1,2,4-oxadiazol-3-yl)-2-(1,4-dioxa-8-azaspiro[4.5]decan-8-yl)quinoline-8-carbonitrile with 6-bromo-3-(3-methyl-1,2,4-oxadiazol-5-yl)-2-(1,4-dioxa-8-azaspiro[4.5]decan-8-yl)quinoline-8-carbonitrile. LCMS (ESI): m/z 435 (M+H); Retention time: 1.86 min (Method 1).

Example 255

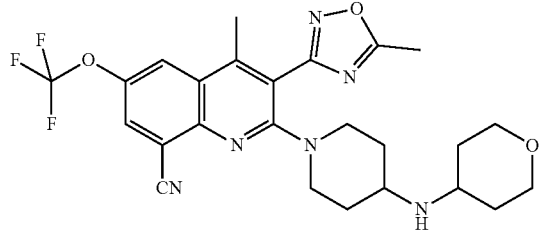
Compound 255

Compound 255 is obtained according to the procedure described for Compound 85, replacing the starting aldehyde Int-85-38 with the appropriate methyl ketone.

Example 256-258

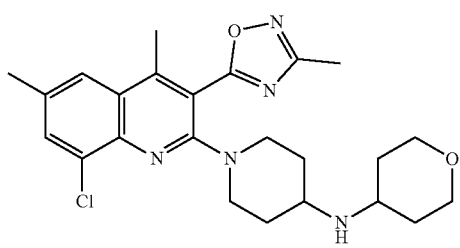
Compound 256

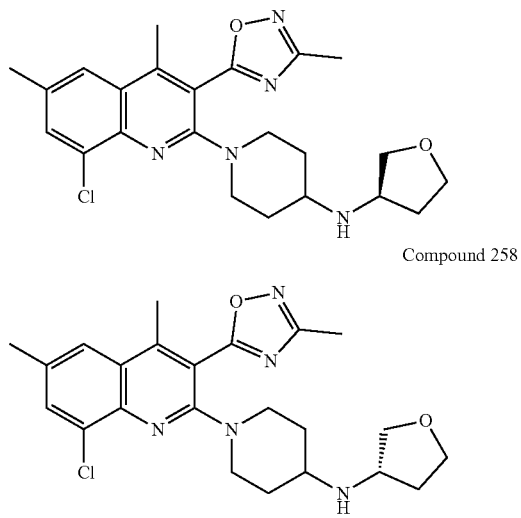
Compound 257

Compound 258

Compounds 256-258 are obtained according to the procedure described for Compounds 174-176, replacingcing the amine Int-174-4 with an amine of the appropriate stereochemistry.

Example 259 and 260

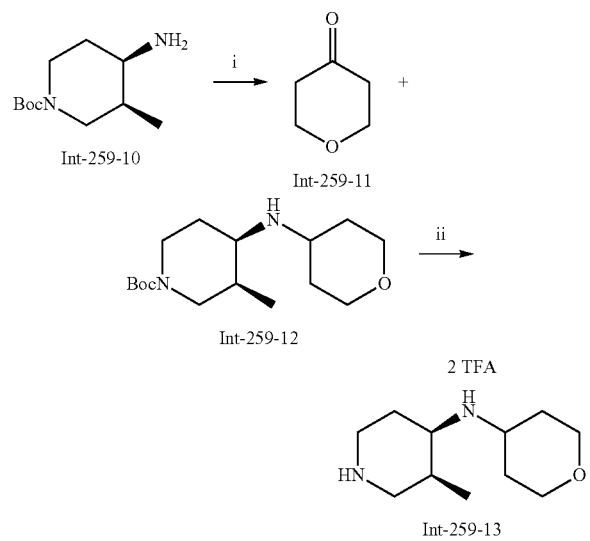

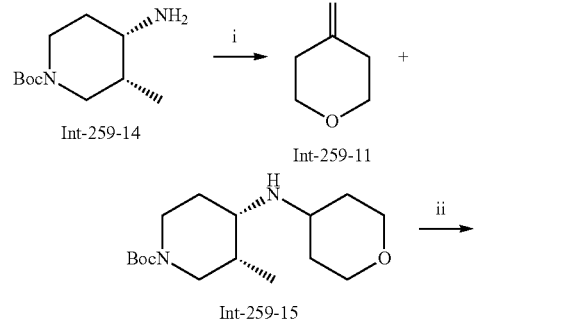

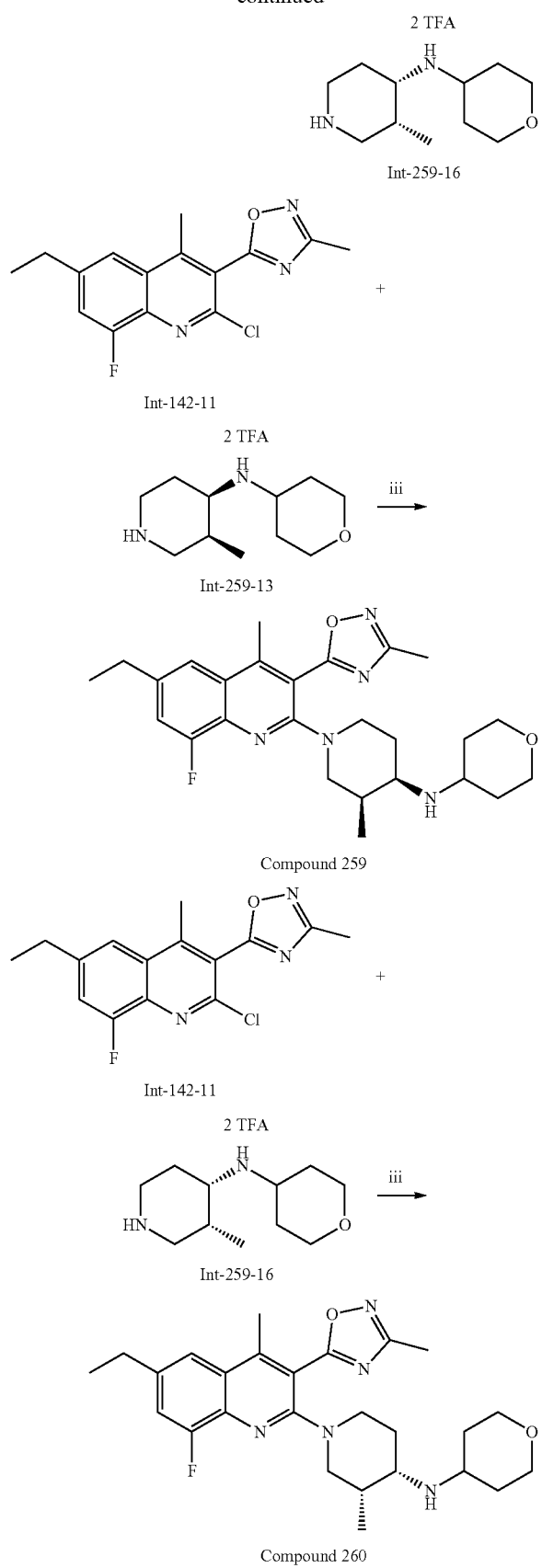

Synthesis of (3S,4R)-3-methyl-N-(tetrahydro-2H-pyran-4-yl)piperidin-4-amine Int-259-13

A mixture of Int-259-10 (100 mg, 0.46 mmol), Int-259-11 (86 μL, 0.93 mmol), NaBH(OAc)₃ (197 mg, 0.93 mmol) and AcOH (51.6 μL, 0.93 mmol) in DCE (2 mL) was stirred at room temperature overnight. The mixture was quenched with 1M NaOH and extracted with EtOAc (4×). The organic layer was dried over Na₂SO₄ and concentrated. The residue was purified by column chromatography eluting with a gradient of CH₂Cl₂/MeOH to give compound Int-259-12 as a white solid (122 mg, 89% yield). LCMS: (M+1) m/z=299.

A mixture of Int-259-12 (120 mg, 0.402 mmol) and TFA (615 μL, 3.61 mmol) in CH₂Cl₂ (2 mL) was stirred at room temperature for 1 h. The mixture was concentrated under reduced pressure. The product, Int-259-13, was used without further purification (white solid). LCMS: (M+1) m/z=199.

Synthesis of (3R,4S)-3-methyl-N-(tetrahydro-2H-pyran-4-yl)piperidin-4-amine, Int-259-16

Int-259-16 was synthesized in an analogous fashion to Int-259-13, replacing Int-259-10 with Int-259-14, and was obtained as white solid (87% yield, two steps). LCMS: (M+1) m/z=199.

Synthesis of (3S,4R)-1-(6-ethyl-8-fluoro-4-methyl-3-(3-methyl-1,2,4-oxadiazol-5-yl)quinolin-2-yl)-3-methyl-N-(tetrahydro-2H-pyran-4-yl)piperidin-4-amine, Compound 259

A mixture of Int-142-11 (15 mg, 0.049 mmol), Int-259-13 (31 mg, 0.074 mmol) and DIPEA (42 μL, 0.245 mmol) in iPrOH (250 μL) was heated at 125° C. overnight. The mixture was concentrated under reduced pressure and purified by prep-TLC using CH₂Cl₂/MeOH (95:5) as an eluent. Compound 259 was obtained as a yellow solid in 31% yield (7.1 mg). (M+1) m/z=468.

Synthesis of (3R,4S)-1-(6-ethyl-8-fluoro-4-methyl-3-(3-methyl-1,2,4-oxadiazol-5-yl)quinolin-2-yl)-3-methyl-N-(tetrahydro-2H-pyran-4-yl)piperidin-4-amine, Compound 260

Compound 260 was synthesized from Int-142-11 and Int-259-16 using the same conditions as utilized for Compound 259 and was obtained as yellow solid in 36% yield (8.3 mg). LCMS: (M+1) m/z=468.

Examples 261-265

Compounds 261-265 are obtained following the general procedures detailed for compounds 33-39 and 198-203 using cyclopropanol to replace KB(OMe)₄ in the etherification step and the appropriate amine to produce the desired products.

Example B-1

In Vitro Activity

In the experimental data below, 1-(6-ethyl-3-(3-methyl-1,2,4-oxadiazol-5-yl)quinolin-2-yl)-N-((3-methyloxetan-3-yl)methyl)piperidin-4-amine (Compound A), PF-04455242, and LY2456302 are used as reference compounds. Compound A was prepared by the synthetic procedure described in U.S. Pat. No. 9,682,966. PF-04455242 is a known KOR antagonist disclosed in WO 2009/156889. LY2456302 is a known KOR antagonist disclosed in WO 2009/094260.

KOR Antagonist Assay

The cell line for the OPRK1 antagonist assay stably expresses the following elements: The carboxy terminus of the OPRK1 receptor has a 7-amino acid linker, followed by the TEV protease cleavage site and a GAL4-VP16 fusion protein. The cell line also expresses a b-arrestin-2-TEV protease fusion protein and contains a reporter construct consisting of the UAS response element and the b-lactamase (bla) reporter gene. Upon activation of the receptor, g-protein receptor kinase (GRK) phosphorylates specific intracellular residues and this induces recruitment of B-arrestin2-TEV protease. The TEV protease recognizes and cleaves the TEV site, releasing the GAL4-VP16 fusion protein, which then translocates to the nucleus. The GAL4-V16 binds to the UAS element, driving expressing of the b-lactamase gene. B-lactamase expression is detected with the cell permeable, fluorescent substrate, CCF4-AM. This substrate consists of coumarin tethered to fluorescein via a b-lactam ring. In the absence of b-lactamase, excitation of the dye with 405 nm light results in FRET from the coumarin to fluorescein and emission of green (525 nm maximum) light. B-lactamase cleavage of the substrate separates the coumarin fluorophore from the fluorescein, and 405 nm excitation results in blue (460 nm maximum) emission. The assay is monitored by the blue/green emission ratio.

OPRK1 TANGO U2OS cells are cultured in growth media (McCoy's 5A medium, 10% Dialyzed FBS, Non-essential amino acids, 25 mM HEPES, 1 mM sodium pyruvate, penicillin/streptomycin). Two million cells are added to a T175 flask in 30 mL of growth medium and incubated at 37° C./5% $CO_2$ for four days at which point they are ~70-90% confluent. Growth medium is removed by aspiration, 5 mL of 0.25% Trypsin/EDTA is added to the flask and gently washed over the cells. The trypsin is then removed by aspiration. Cells are allowed to round up and are detached by tapping the flask. Cells are suspended in assay medium (DMEM high glucose with 1% charcoal dextran stripped FBS, Non-essential amino acids, 25 mM HEPES, 1 mM sodium pyruvate, penicillin/streptomycin) triturated, counted and pelleted by centrifugation. Cells are resuspended at 1.6 million cells per mL and 10 ul added to each well of a black, clear-bottom 384-well assay plate (Greiner part number 788092). Assay plates are placed in a humidified box and incubated 16-24 hours at 37° C./5% $CO_2$. Compounds dissolved in DMSO are serially diluted in DMSO in a 384-well polypropylene plate. 50 nl of each compound dilution is added to the wells of the assay plate using pintools. Control wells receive 50 nl DMSO. The plates are returned to the incubator for 30 minutes. After the preincubation with compound, 50 nl of 600 nM (−)-U-50, 488 (agonist challenge) is added to the compound wells of the assay plate. Control wells receive 50 nl of 5.6 uM (−)-U-50,488 (100% response control), 50 nl of 600 nM (−)-U-50,488 (EC80 control) or 50 nl of DMSO (0% response control). Assay plates are returned to the incubator for 4 hours at 37° C./5% $CO_2$. Assay plates are then removed from the incubator and 2.5 ul of LiveBlazer CCF4-AM substrate dye (Invitrogen) is added to each well. The assay plates are then placed on the benchtop for two hours at room temperature covered in foil to avoid light.

The plates are then read on a fluorescence plate reader with an excitation wavelength of 405 nm and emission wavelengths of 460 nm and 525 nm. Results are calculated using the blue/green emission ratio. Percent inhibition is calculated by the following equation, with $IC_{50}$ being the concentration of compound required to achieve 50% inhibition:

$$\% \text{ Inhibition} = 100 - \left(100\left(\frac{\text{Compound Well} - 0\% \text{ Response Well}}{EC80 \text{ Control Well} - 0\% \text{ Response Well}}\right)\right)$$

For a peripheral kappa antagonist to be effective with minimal side effects it is desirable that it not interact to any substantial degree with other opioid receptors. Thus, delta and mu opioid receptor antagonist assays were employed to assess activation at mu or delta receptors.

OPR Delta Antagonist Assay

The cell line for the OPR DELTA antagonist assay stably expresses the following elements: The carboxy terminus of the OPR DELTA receptor has a 7 amino acid linker, followed by the TEV protease cleavage site and a GAL4-VP16 fusion protein. The cell line also expresses a b-arrestin-2-TEV protease fusion protein and contains a reporter construct consisting of the UAS response element and the b-lactamase (bla) reporter gene. Upon activation of the receptor, g-protein receptor kinase (GRK) phosphorylates specific intracellular residues and this induces recruitment of B-arrestin2-TEV protease. The TEV protease recognizes and cleaves the TEV site, releasing the GAL4-VP16 fusion protein, which then translocates to the nucleus. The GAL4-V16 binds to the UAS element, driving expressing of the b-lactamase gene. B-lactamase expression is detected with the cell permeable, fluorescent substrate, CCF4-AM. This substrate consists of coumarin tethered to fluorescein via a b-lactam ring. In the absence of b-lactamase, excitation of the dye with 405 nm light results in FRET from the coumarin to fluorescein and emission of green (525 nm maximum) light. B-lactamase cleavage of the substrate separates the coumarin fluorophore from the fluorescein, and 405 nm excitation results in blue (460 nm maximum) emission. The assay is monitored by the blue/green emission ratio.

OPR DELTA TANGO U2OS cells are cultured in growth media (McCoy's 5A medium, 10% Dialyzed FBS, Non-essential amino acids, 25 mM HEPES, 1 mM sodium pyruvate, penicillin/streptomycin). Two million cells are added to a T175 flask in 30 mL of growth medium and incubated at 37° C./5% $CO_2$ for four days at which point they are ~70-90% confluent. Growth medium is removed by aspiration, 5 mL of 0.25% Trypsin/EDTA is added to the flask and gently washed over the cells. The trypsin is then removed by aspiration. Cells are allowed to round up and are detached by tapping the flask. Cells are suspended in assay medium (DMEM high glucose with 1% charcoal dextran stripped FBS, Non-essential amino acids, 25 mM HEPES, 1 mM sodium pyruvate, penicillin/streptomycin) triturated, counted and pelleted by centrifugation. Cells are resuspended at 1.6 million cells per mL and 10 ul added to each well of a black, clear-bottom 384-well assay plate (Greiner part number 788092). Assay plates are placed in a humidified box and incubated 16-24 hours at 37° C./5% $CO_2$. Compounds dissolved in DMSO are serially diluted in DMSO in a 384-well polypropylene plate. 50 nl of each compound dilution is added to the wells of the assay plate using pintools. Control wells receive 50 nl DMSO. The plates are returned to the incubator for 30 minutes. After the preincubation with compound, 50 nl of 35 uM SNC80 (agonist challenge) is added to the compound wells of the assay plate. Control wells receive 50 nl of 2 mM (100% response control), 50 nl of 35 uM SNC80 (EC80 control) or 50 nl of DMSO (0% response control). Assay plates are returned to the incubator for 4 hours at 37° C./5% $CO_2$. Assay plates are then removed from the incubator and 2.5 ul of LiveBlazer CCF4-AM substrate dye (Invitrogen) is added to each well.

The assay plates are then placed on the benchtop for two hours at room temperature covered in foil to avoid light. The plates are then read on a fluorescence plate reader with an excitation wavelength of 405 nm and emission wavelengths of 460 nm and 525 nm. Results are calculated using the blue/green emission ratio. Percent inhibition is calculated by the equation noted above, with $IC_{50}$ being the concentration of compound required to achieve 50% inhibition.

Representative compounds listed in Table 2 below all displayed an $IC_{50}$ value greater than 3,000 nM at DOR MU.

OPR Mu Antagonist Assay

The purpose of this assay is to confirm the potency and selectivity of compounds synthesized to be OPRK1 Antagonists. This assay monitors the OPRMu1 activation, in membrane recruitment of β-arrestin. The assay monitors GPCR-β-arrestin proximity using low affinity fragment complementation of beta-galactosidase (beta-gal). It employs U20S cells which express OPRMu1 fused to the complementary beta-gal fragment (enzyme acceptor). As designed, compounds that act as antagonists will prevent receptor activation resulting in reduce well luminescence. Compounds were tested in triplicate using a 10-point, 1:3 dilution series starting at a nominal concentration of 10 micromolar.

The Discover X OPRMu1-U20S cell line was routinely cultured in T175 flasks at 37° C., 5% $CO_2$ and 95% relative humidity (RH). The growth media consisted of DMEM/F12 1:1 Media supplemented with 10% v/v heat inactivated fetal bovine serum, 25 mM HEPES, Non-essential amino acids, 1 mM Sodium Pyruvate, 1× antibiotic mix (penicillin streptomycin) plus 500 ug/mL Geneticin and 300 ug/mL Hygromycin (selection antibiotics).

On Day 1 of the assay, 5000 cells in 20 ul of assay buffer (Discover X's Cell Plating Reagent 5) were seeded into each well of a 384 Corning 3570 standard white plate, and incubated 16-24 hours at 37° C., 5% $CO_2$ and 95% (RH). On Day 2, 100 nl of test compound in DMSO was added to the appropriate wells, 100 nl of DMSO added to control wells and plates were incubated for 30 min at 37° C., 5% $CO_2$ and 95% (RH). Next 100 nl of DAMGO OPRMu1 or DMSO in assay media (EC80 Challenge consists of 100 nl of 50 uM DAMGO, final assay concentration=250 nM, 100% Response wells receive 100 nl 200 uM DAMGO). After incubation for 3 hours at 37° C., 5% $CO_2$ and 95% (RH), 10 ul of Path Hunter Detection Mix is added to each well, plate placed on a plate rotator/mixer for ~10 minutes and then incubated at room temperature, in the dark for 1 hour. Well luminescence was measured on Perkin Elmer's Envision.

The Percent Inhibition was calculated from the median ratio as follows:

$$\% \text{ Inhibition} = 100 - \left(100\left(\frac{\text{Compound Well} - 0\% \text{ Response Well}}{EC80 \text{ Control Well} - 0\% \text{ Response Well}}\right)\right)$$

where:
COMPOUND WELL is defined as the well containing test compound;
EC80 CONTROL WELL is defined as wells containing DAMGO challenge (250 nM final)=0% inhibition; and
0% RESPONSE WELL is defined as wells containing DMSO=100% inhibition.

$IC_{50}$ is defined as the concentration of compound required to achieve 50% inhibition.

Activity expressed as $IC_{50}$ of representative compounds against the kappa opioid receptor (KOR) and mu opioid receptor (MOR) is provided in Table 2 below. With respect to KOR activity: "++++" denotes an $IC_{50}$ of less than 1 nM; "+++" denotes an $IC_{50}$ of from 1 nM to less than 10 nM; "++" denotes an $IC_{50}$ of from 10 nM to less than 100 nM; and "+" denotes an $IC_{50}$ of 100 nM or more. With respect to MOR activity: "++++" denotes an $IC_{50}$ of less than 1 nM; "+++" denotes an $IC_{50}$ of from 1 nM to less than 10 nM; "++" denotes an $IC_{50}$ of from 10 nM to less than 100 nM; "+" denotes an $IC_{50}$ of from 100 nM to less than 1,000 nM; and "−" denotes an $IC_{50}$ of more than 1,000 nM.

Kappa specificity of representative compounds is also displayed in Table 2 (i.e., MOR $IC_{50}$/KOR $IC_{50}$). Selectivity range is denoted as follows: ++++ denotes selectivity greater than 1,000-fold over the mu opioid receptor (MOR), +++ denotes selectivity between 100- and 1000-fold, ++ denotes selectivity between 10- and 100-fold, and + denotes selectivity less than 10 fold.

TABLE 2

Activity of Representative Compounds

| Cpd. No. | KOR $IC_{50}$ (nM) | MOR $IC_{50}$ (nM) | Selectivity |
|---|---|---|---|
| 1 | ++ | − | +++ |
| 2 | +++ | − | +++ |
| 3 | +++ | − | +++ |
| 4 | +++ | − | +++ |
| 5 | ++ | − | +++ |
| 6 | ++ | − | +++ |
| 7 | ++ | − | +++ |
| 8 | ++ | + | ++ |
| 9 | ++ | + | ++ |
| 10 | +++ | − | +++ |
| 11 | +++ | + | +++ |
| 12 | ++ | + | ++ |
| 13 | ++ | − | +++ |
| 14 | ++ | − | +++ |
| 15 | ++ | − | ++ |
| 16 | + | − | ++ |
| 17 | + | − | ++ |
| 18 | ++ | − | ++ |
| 19 | + | − | ++ |
| 20 | +++ | + | ++ |
| 21 | +++ | + | +++ |
| 22 | +++ | + | +++ |
| 23 | +++ | − | +++ |
| 24 | +++ | − | +++ |
| 25 | ++ | + | ++ |
| 26 | +++ | + | ++ |
| 27 | ++ | − | ++ |
| 28 | ++ | − | +++ |
| 29 | ++ | − | ++ |
| 30 | ++ | + | ++ |
| 31 | +++ | + | +++ |
| 32 | +++ | + | +++ |
| 33 | +++ | + | +++ |
| 34 | +++ | − | +++ |
| 35 | + | − | ++ |
| 36 | ++ | + | ++ |
| 37 | +++ | − | +++ |
| 38 | +++ | − | +++ |
| 39 | +++ | − | ++ |
| 83 | ++ | − | ++ |
| 84 | + | − | ++ |
| 85 | + | − | ++ |
| 86 | ++++ | + | +++ |
| 87 | ++ | − | +++ |
| 88 | +++ | + | ++ |

TABLE 2-continued

Activity of Representative Compounds

| Cpd. No. | KOR IC$_{50}$ (nM) | MOR IC$_{50}$ (nM) | Selectivity |
|---|---|---|---|
| 89 | ++++ | + | +++ |
| 90 | ++++ | + | ++++ |
| 91 | ++++ | ++ | +++ |
| 92 | +++ | + | +++ |
| 93 | +++ | − | ++++ |
| 94 | ++ | − | ++ |
| 95 | ++ | − | +++ |
| 96 | ++ | − | +++ |
| 97 | +++ | + | +++ |
| 98 | +++ | + | +++ |
| 99 | ++++ | + | +++ |
| 100 | ++++ | + | +++ |
| 101 | ++++ | − | ++++ |
| 102 | ++ | − | +++ |
| 103 | + | − | ++ |
| 104 | ++ | − | +++ |
| 105 | ++ | − | +++ |
| 106 | ++ | − | ++ |
| 107 | + | − | ++ |
| 108 | ++ | − | +++ |
| 109 | +++ | − | +++ |
| 110 | +++ | − | ++++ |
| 111 | +++ | + | +++ |
| 112 | ++++ | + | ++++ |
| 113 | ++++ | + | ++++ |
| 114 | +++ | − | ++++ |
| 115 | +++ | − | ++++ |
| 116 | + | − | ++ |
| 117 | + | − | ++ |
| 118 | +++ | ++ | ++ |
| 119 | ++++ | ++ | +++ |
| 120 | ++++ | + | +++ |
| 134 | +++ | + | +++ |
| 135 | +++ | + | +++ |
| 136 | +++ | + | +++ |
| 137 | +++ | + | ++ |
| 138 | ++ | − | +++ |
| 139 | + | − | ++ |
| 140 | ++ | − | +++ |
| 141 | +++ | − | ++++ |
| 142 | ++++ | + | +++ |
| 143 | +++ | + | +++ |
| 144 | ++++ | + | +++ |
| 145 | ++++ | − | ++++ |
| 146 | ++++ | − | ++++ |
| 147 | +++ | + | +++ |
| 148 | ++++ | + | +++ |
| 149 | +++ | − | +++ |
| 150 | +++ | − | +++ |
| 151 | +++ | − | ++++ |
| 152 | +++ | + | +++ |
| 153 | ++ | − | +++ |
| 154 | ++ | − | +++ |
| 155 | ++ | − | +++ |
| 156 | +++ | + | ++ |
| 157 | ++++ | + | +++ |
| 158 | +++ | + | +++ |
| 159 | ++ | − | +++ |
| 160 | +++ | − | +++ |
| 161 | + | − | ++ |
| 162 | ++ | − | +++ |
| 163 | ++ | − | +++ |
| 164 | + | − | ++ |
| 165 | + | − | ++ |
| 177 | +++ | + | ++ |
| 178 | ++ | − | +++ |
| 179 | ++ | − | +++ |
| 180 | ++ | − | +++ |
| 193 | ++ | − | +++ |
| 194 | ++ | − | +++ |
| 195 | ++++ | − | ++++ |
| 196 | +++ | − | ++++ |
| 197 | +++ | − | +++ |
| 198 | ++ | − | +++ |
| 199 | ++ | − | +++ |
| 200 | ++ | − | +++ |
| 201 | ++ | − | +++ |
| 202 | ++ | − | +++ |
| 203 | + | − | ++ |
| 206 | ++ | − | +++ |
| 207 | ++ | − | +++ |
| 208 | ++ | − | +++ |
| 209 | +++ | − | ++++ |
| 210 | ++ | − | ++++ |
| 218 | +++ | − | +++ |
| 219 | +++ | + | +++ |
| 220 | +++ | + | +++ |
| 221 | +++ | − | +++ |
| 222 | +++ | − | ++++ |
| 223 | ++ | + | ++ |
| 223 | ++ | − | ++ |
| 224 | ++ | + | ++ |
| 226 | +++ | − | +++ |
| 227 | +++ | − | +++ |
| 40 | ++ | − | +++ |
| 41 | + | − | ++ |
| 43 | ++ | − | +++ |
| 55 | ++ | − | +++ |
| 58 | ++ | − | +++ |
| 78 | ++ | − | +++ |
| 80 | ++ | + | ++ |
| 166 | +++ | − | +++ |
| 172 | +++ | ++ | ++ |
| 173 | ++ | − | ++ |
| 174 | ++++ | ++ | ++ |
| 175 | +++ | + | +++ |
| 176 | ++++ | ++ | +++ |
| 181 | ++++ | +++ | ++ |
| 182 | ++++ | + | ++ |
| 183 | ++++ | + | ++ |
| 184 | ++ | − | +++ |
| 185 | ++ | − | +++ |
| 186 | ++ | − | +++ |
| 187 | ++ | − | ++ |
| 188 | ++ | − | +++ |
| 189 | ++ | − | +++ |
| 190 | ++++ | ++ | +++ |
| 191 | ++++ | + | +++ |
| 210 | +++ | − | ++++ |
| 211 | +++ | − | ++++ |
| 212 | ++ | − | +++ |
| 213 | ++++ | + | ++++ |
| 214 | +++ | + | +++ |
| 215 | ++++ | ++ | ++ |
| 228 | +++ | − | +++ |
| 236a/236b | +++ | + | +++ |
| 237a/237b | +++ | + | +++ |
| 229/243 | ++++ | ++ | ++ |
| 241 | +++ | + | +++ |
| 240 | +++ | + | +++ |
| 248 | +++ | ++ | ++ |
| 242 | +++ | − | +++ |
| 246 | ++++ | ++ | ++ |
| 247 | ++++ | ++ | ++ |
| 245 | +++ | ++ | ++ |
| 249 | − | − | − |
| 250 | +++ | | |
| 251 | +++ | − | ++++ |
| 252 | +++ | − | ++++ |
| 253 | +++ | − | ++++ |
| 254 | + | − | ++ |
| 259 | +++ | + | +++ |
| 260 | +++ | + | +++ |
| A | +++ | − | +++ |

Dynorphin A-Induced Activation of the β-Arrestin Pathway

Compound 142 was also assessed for biased signaling at OPRK1 using the PathHunter® β-Arrestin assay (DiscoverX, Fremont CA). In this assay, cells were pre-incubated with Compound 142 (5.1 µM followed by agonist challenge using Dynorphin A (0.0498 µM) at the $EC_{80}$ concentration (run in quintuplicate). Compound 142 blocked dynorphin A-induced activation of the β-arrestin pathway ($IC_{50}$=3.1 nM), suggestive of balanced antagonist properties, and antagonized dynorphin A-induced receptor internalization ($IC_{50}$=6.1 nM). FIG. 7.

Radioligand Binding Assay

Figure 8:
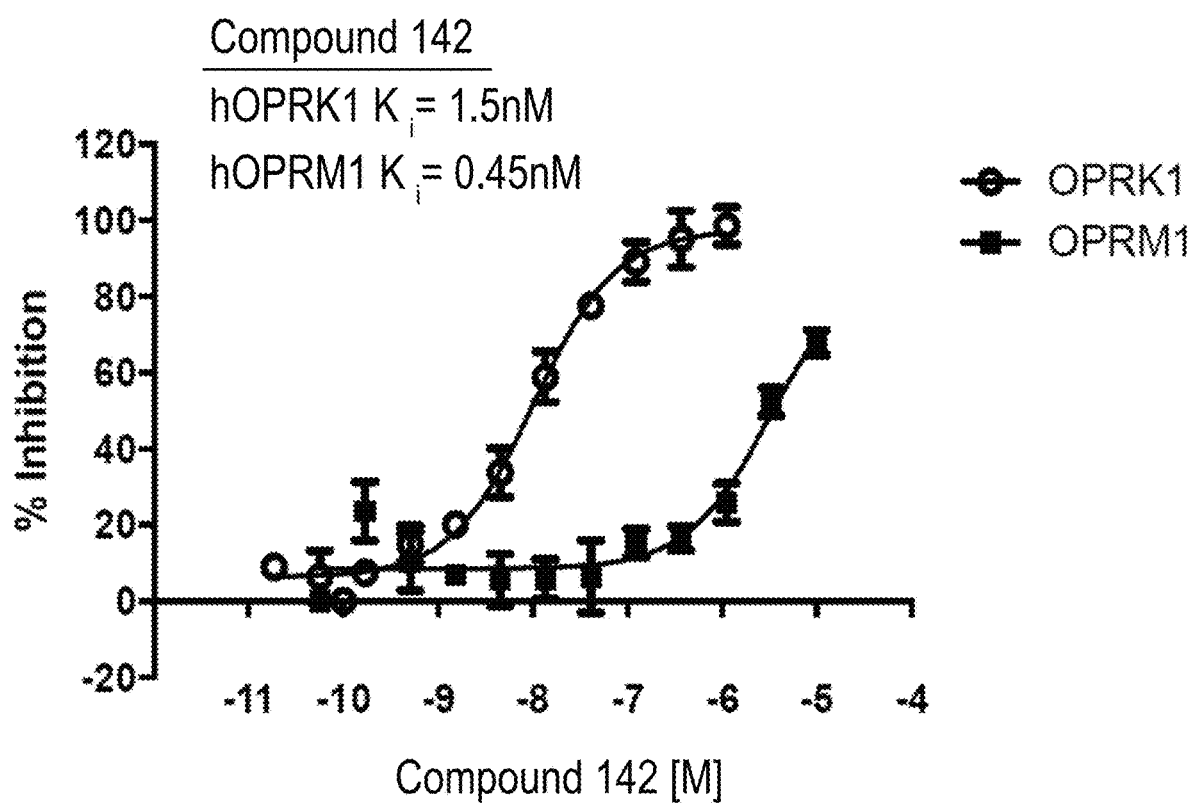
FIG. 8 illustrates the activity of a representative compound, Compound 142, as a potent and selective ligand at human OPRK1 over OPRM1 in a radioligand binding assay using [$^{3}H$]diprenorphine.

Compound 142 demonstrated potent inhibition at human opioid receptor kappa 1 (hOPRK1; Ki=1.5 nM) and showed >300-fold selectivity over human opioid receptor mu 1 (hOPRM1; Ki=0.45 µM) in radioligand binding assays using $[^{3}H]$diprenorphine (600 µM) (tested in triplicate, N=3). Mean±SEM. FIG. 8

Example B-2

In Vivo Activity

Mouse Tail Flick Study

The efficacy of systemic administration of Compound 142 in blocking (−)-U-50,488-induced acute antinociception was tested in naïveICR mice using tail flick test. Briefly, mice were tested for baseline responding to determine their tail flick latencies to 50° C. hot water submersion (with a cutoff at 15 sec to prevent tissue damage). Administration of the OPRK1 agonist (−)-U-50,488 (15 mg/kg, i.p.), test compound (1 mg/kg, i.p.), or vehicle (10% DMSO/10% Tween 80/80% saline, 5 mL/kg, i.p.) was injected 1 or 24 h later, (−)-U-50,488 (15 mg/kg, i.p.) was administered to all mice. Separate groups of mice were treated at different pretreatment time points. The tail flick latencies were assessed again at 30 min after (−)-U-50,488 administration. In this study, (−)-U-50,488 produced strong analgesia in naïve mice which was blocked by Compound 142 given at 1 h but not 24 h prior to (−)-U-50,488. Compound 142 had no effect when administered in the absence of (−)-U-50,488.

Figure 9A:
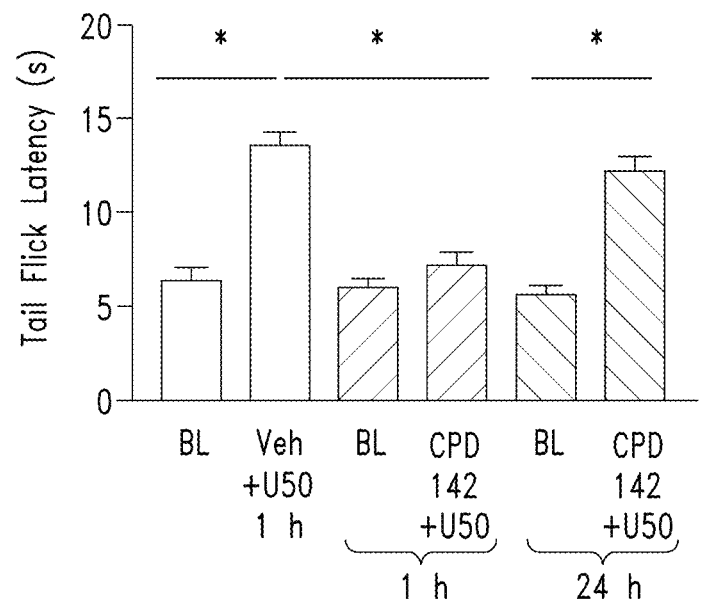
FIGS. 9A and 9B illustrate that Compound 142 (30 mg/kg, p.o.) administered at 1 h, but not 24 h, prior to (−)-U-50,488 (20 mg/kg, i.p.) blocked the analgesic effect induced by (−)-U-50,488 in the mouse tail flick assay, shown for Latency (FIG. 9A) % MPR (maximal possible effect= [post dose latency−baseline)/(15−baseline)*100](FIG. 9B).
Figure 9B:
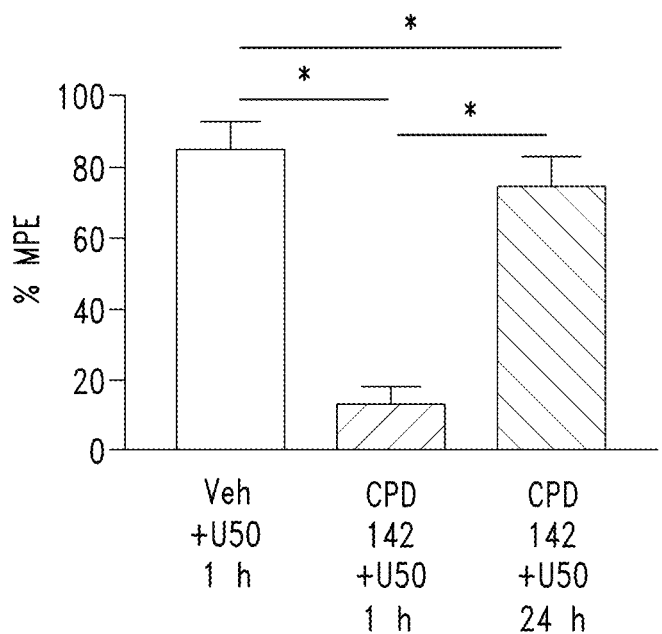

Adult, male, CD-1 mice were administered Compound 142 (30 mg/kg, p.o.) or vehicle (10% DMSO/10% Tween 80/80% saline was administered followed by (−)-U-50,488 (20 mg/kg, i.p., in saline) 1 or 24 h later in separate cohorts of mice. Latency to withdraw their tail from a 50° C. water bath was measured. In this study, Compound 142 (30 mg/kg, p.o.) administered at 1 h, but not 24 h, prior to (−)-U-50,488 blocked the analgesic effect induced by (−)-U-50,488 in the mouse tail flick assay demonstrating the reversible action of this OPRK1 antagonist in vivo. FIG. 9.

Mouse Prolactin Study

Kappa opioid antagonists were solubilized in water at a concentration of 0.5 mg/mL. 8-10 week old male C57BL/6J mice were treated intraperitoneal with 10 mpk kappa opioid antagonist, or the vehicle water, for one hour. U-69593 kappa opioid agonist (Sigma) was solubilized in 45% 2-hydroxypropyl-cyclodextrin at a concentration of 10 mg/mL.

One hour post antagonist treatment, 0.3 mg/kg U-69593, or vehicle 0.3% 2-hydroxypropyl-cyclodextrin, was administered subcutaneously at the nape of the neck. 30 minutes post agonist treatment mice were euthanized by $CO_2$, and cardiac puncture was performed. Blood was collected and placed into a microtainer coated with $K_2EDTA$ and kept cold. Blood was spun at 4° C., 1,000×g for 10 minutes. Plasma was removed and 10 ul was used to determine prolactin levels using the Milliplex Mouse Pituitary Magnetic Bead Panel (MPTMAG-49K). 50 prolactin analytes were collected from each duplicate sample using the Milliplex Analyzer Luminex 200, and pg/mL of prolactin was quantitatively determined using Milliplex Analyst 5.1 software.

Figure 1B:
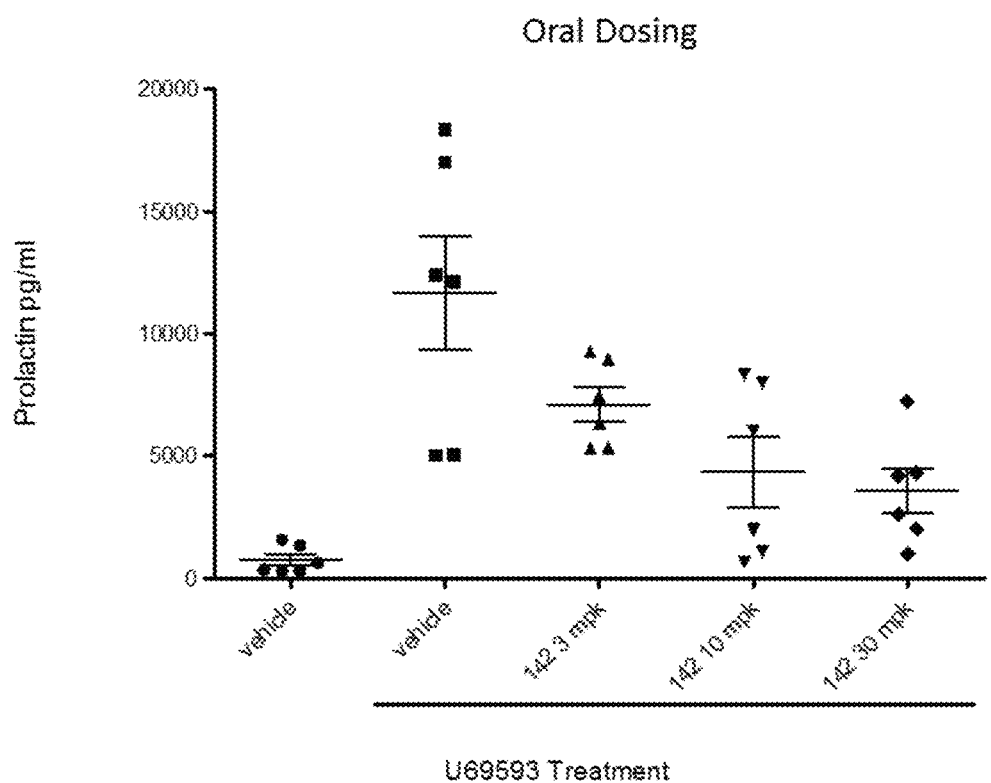

Compound 142 was tested for antagonist properties in vivo using a OPRK1 agonist-induced prolactin challenge approach in 8-10 week old male C57BL/6J mice (n=3-4/group). Specifically, administration of Compound 142 (0.01-3.0 mg/kg, IP; water [vehicle]; 1 h PTT) or Compound 142 (3, 10 or 30 mg/kg, PO; water [vehicle]; 2 h PTT) to mice was followed by injection of the OPRK1-agonist, U69593 (0.3 mg/kg, sc; 5% cyclodextran [vehicle]; 0.5 h PTT) and plasma samples were collected via cardiac puncture in a terminal procedure 0.5 h later. In these studies, U69593 significantly increased plasma prolactin concentration (p≤0.05 vs vehicle) and Compound 142 suppressed the increase in prolactin in a dose-related manner (p≤0.05 vs U69593 alone). As shown in FIG. 1, following intraperitoneal (IP) injection, Compound 142 effectively blocked the U69593-induced increase in prolactin with a minimally effective dose (MED)≤0.01 mg/kg (see FIG. 1A); and following oral (PO) administration, Compound 142 significantly suppressed the agonist-induced increase in prolactin at 10 mg/kg (see FIG. 1B).

Figure 2A:
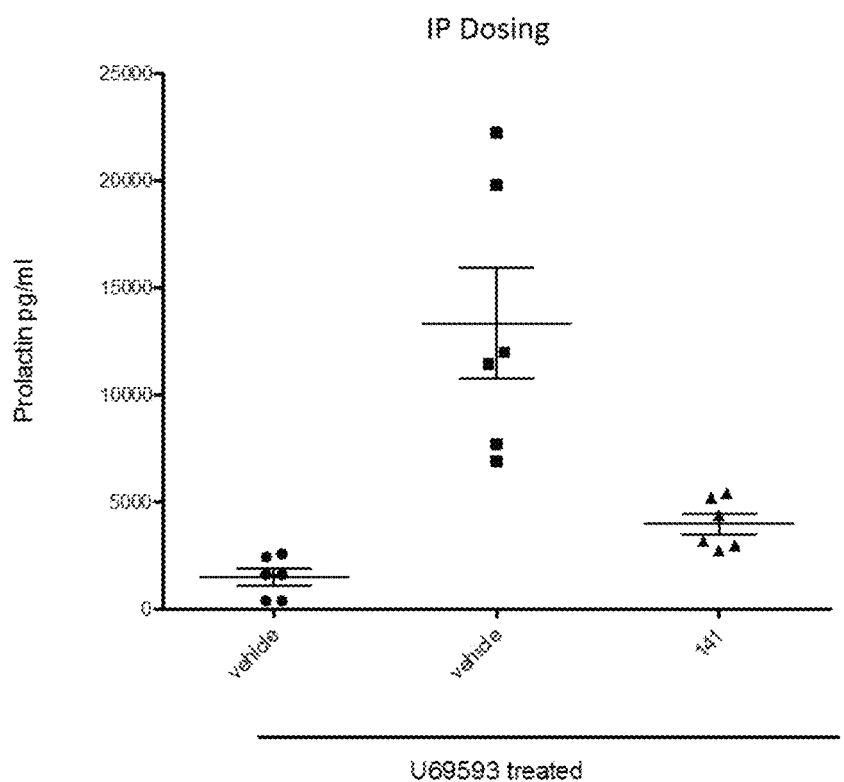
FIGS. 2A and 2B illustrate the activity of a representative compound, Compound 141, to serve as an antagonist in an OPRK1 agonist-induced prolactin challenge to 8-10-week-old male C57BL/6J mice following IP dosing (FIG. 2A) and PO dosing (FIG. 2B).
Figure 2B:
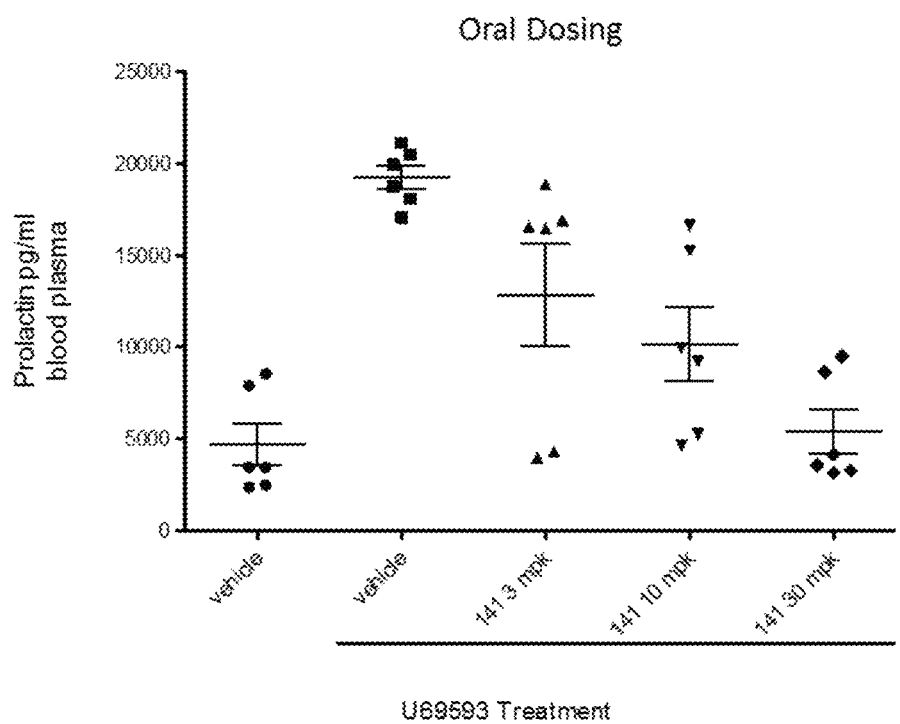
Figure 3A:
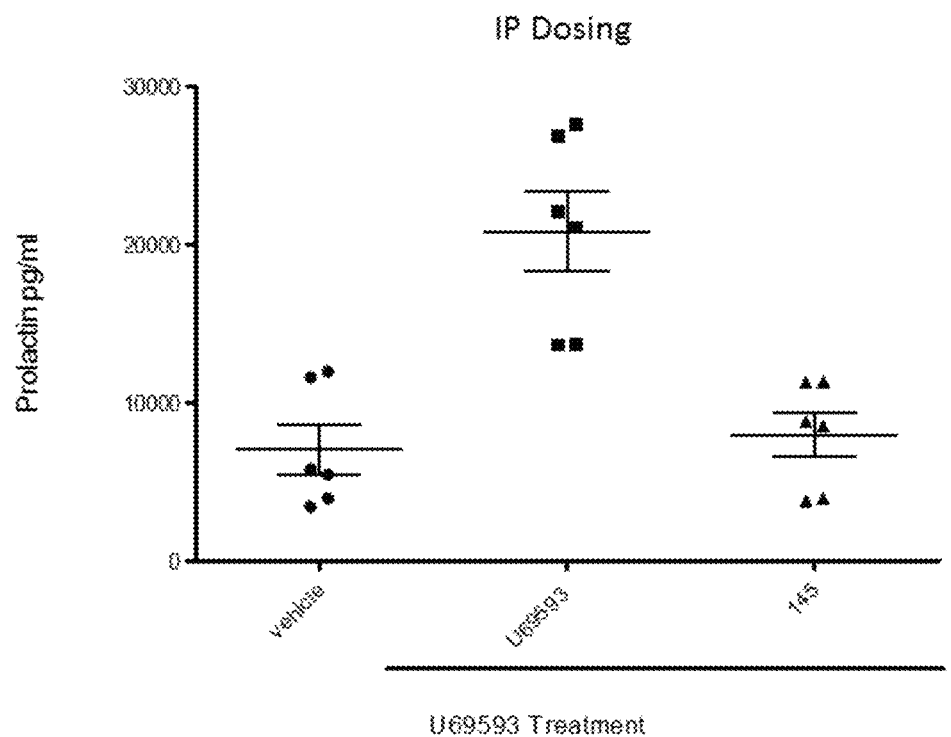
FIGS. 3A and 3B illustrate the activity of a representative compound, Compound 145, to serve as an antagonist in an OPRK1 agonist-induced prolactin challenge to 8-10-week-old male C57BL/6J mice following IP dosing (FIG. 3A) and PO dosing (FIG. 3B).
Figure 3B:
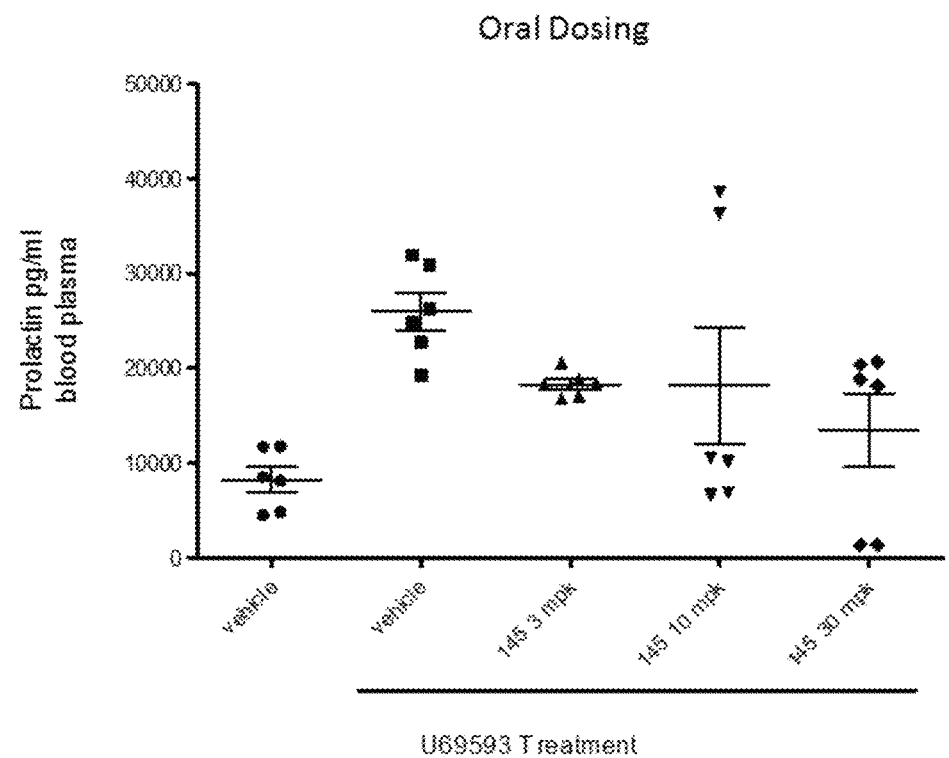
Figure 4A:
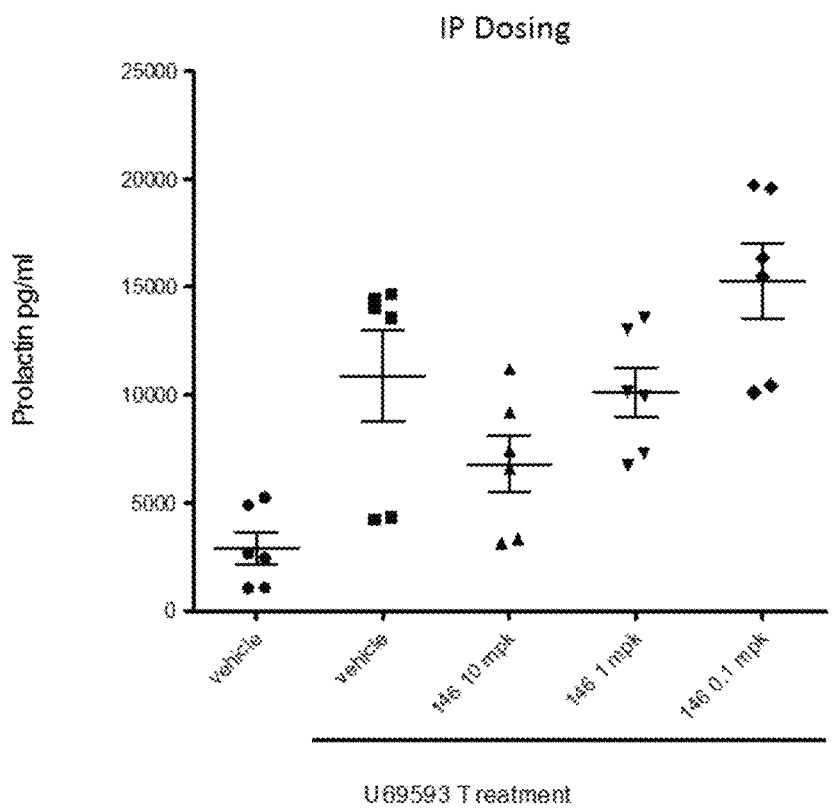
FIGS. 4A and 4B illustrate the activity of a representative compound, Compound 146, to serve as an antagonist in an OPRK1 agonist-induced prolactin challenge to 8-10-week-old male C57BL/6J mice following IP dosing (FIG. 4A) and PO dosing (FIG. 4B).
Figure 4B:
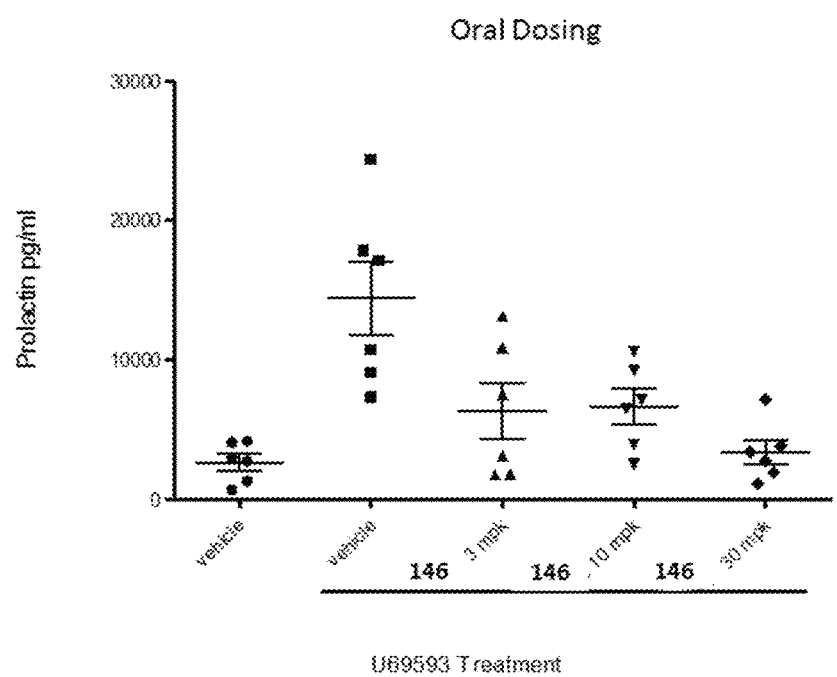
Figure 5A:
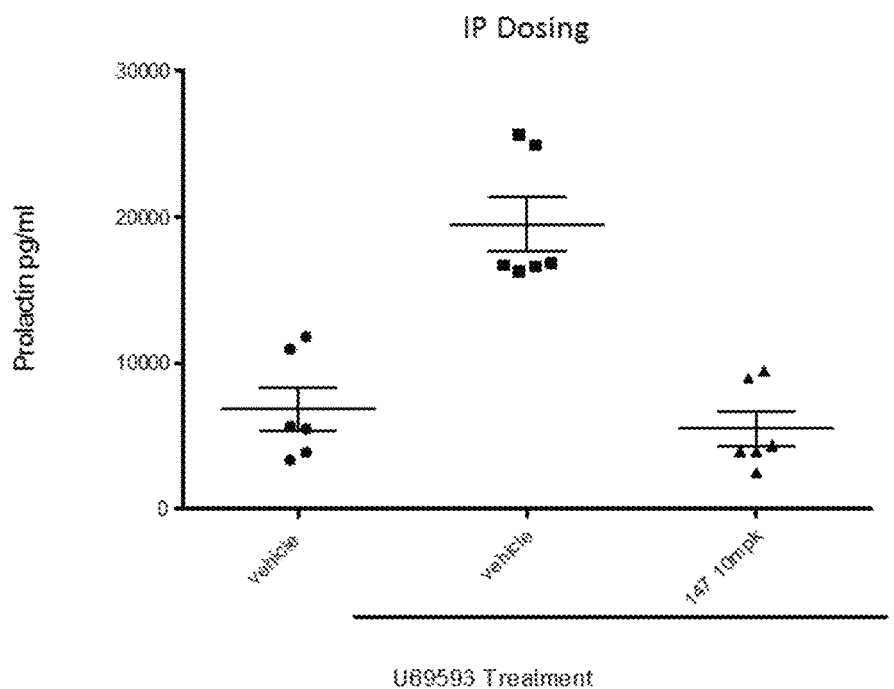
FIGS. 5A and 5B illustrate the activity of a representative compound, Compound 147, to serve as an antagonist in an OPRK1 agonist-induced prolactin challenge to 8-10-week-old male C57BL/6J mice following IP dosing (FIG. 5A) and PO dosing (FIG. 5B).
Figure 5B:
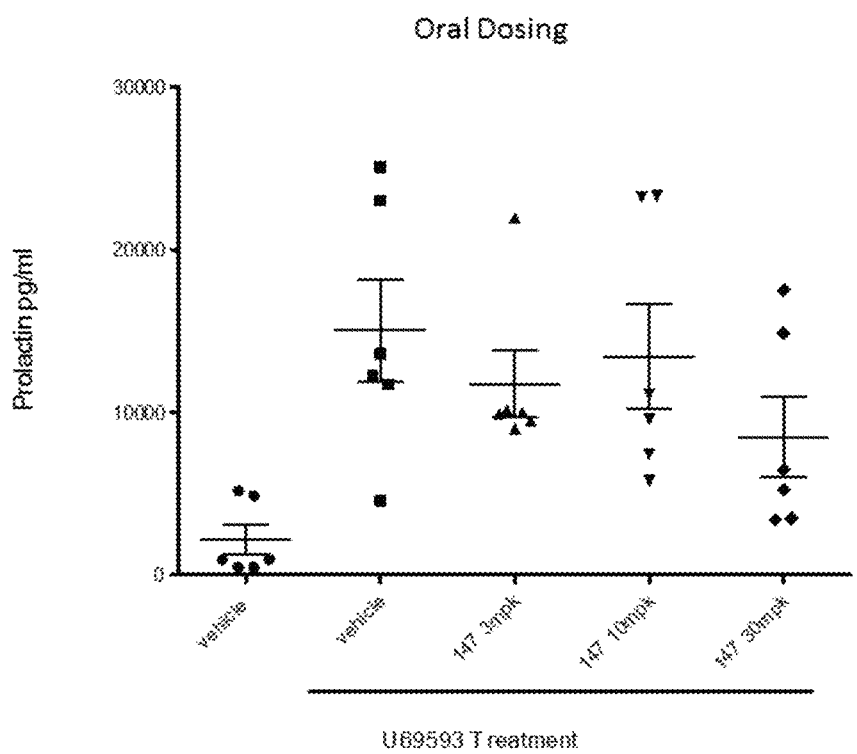
Figure 6:
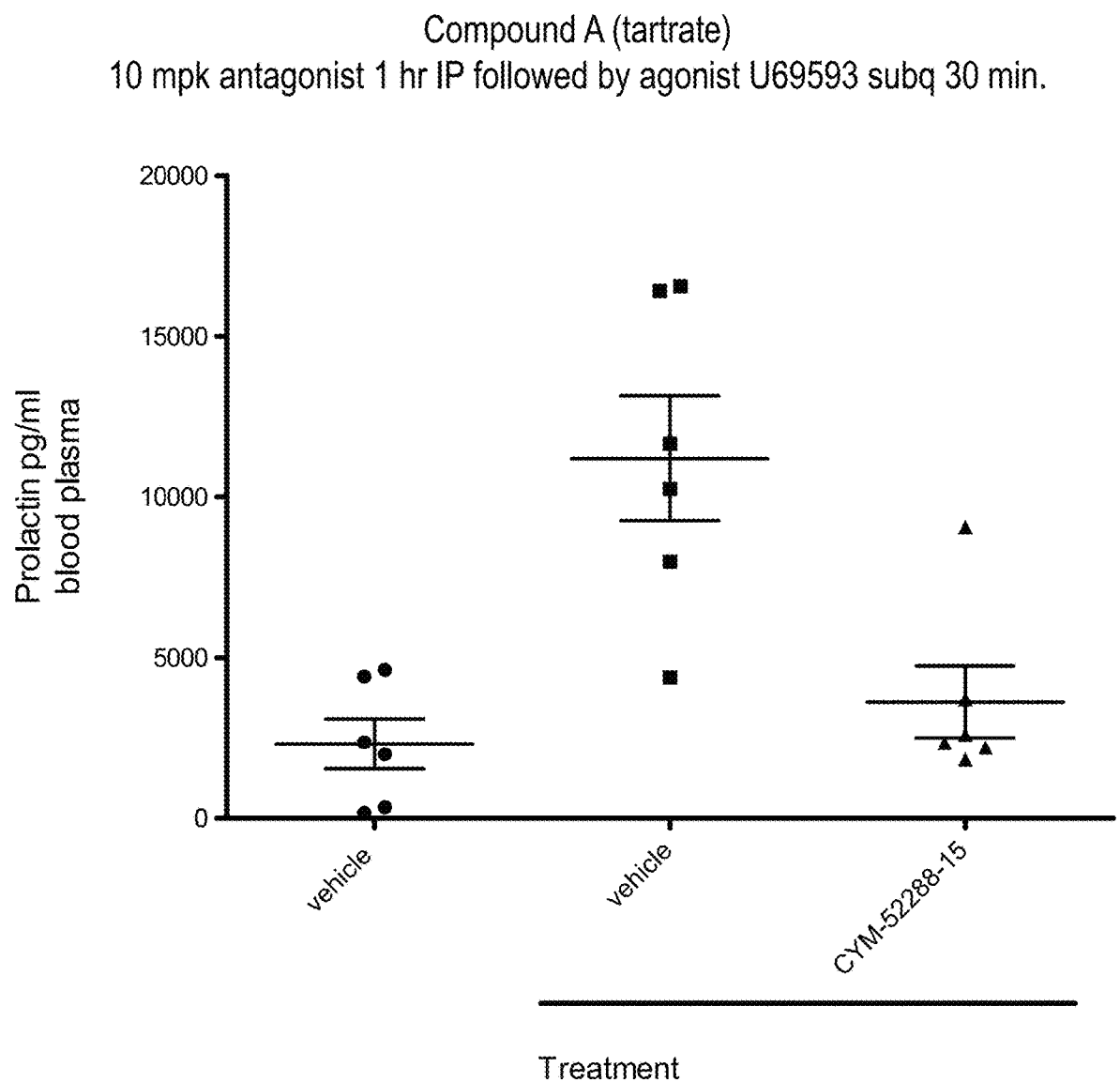
FIG. 6 illustrates the activity of the tartrate salt of Compound A to serve as an antagonist in an OPRK1 agonist-induced prolactin challenge to 8-10 week old male C57BL/6J mice following IP dosing.
Figure 7A:
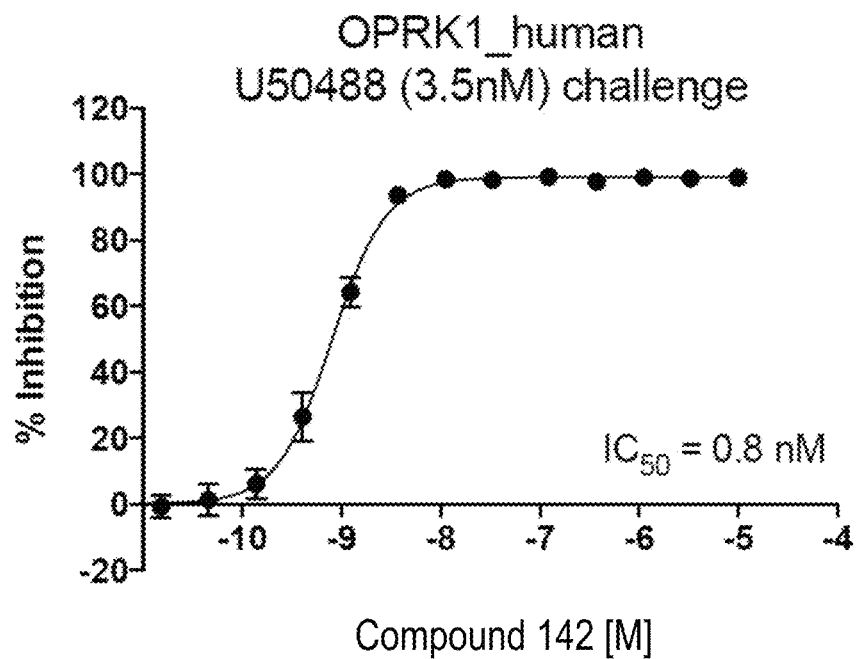
FIGS. 7A and 7B illustrate the activity of a representative compound, Compound 142, to serve as a potent functional antagonist at human OPRK1 in response to (−)-U-50,488 (FIG. 7A) and Dynorphin A (FIG. 7B).
Figure 7B:
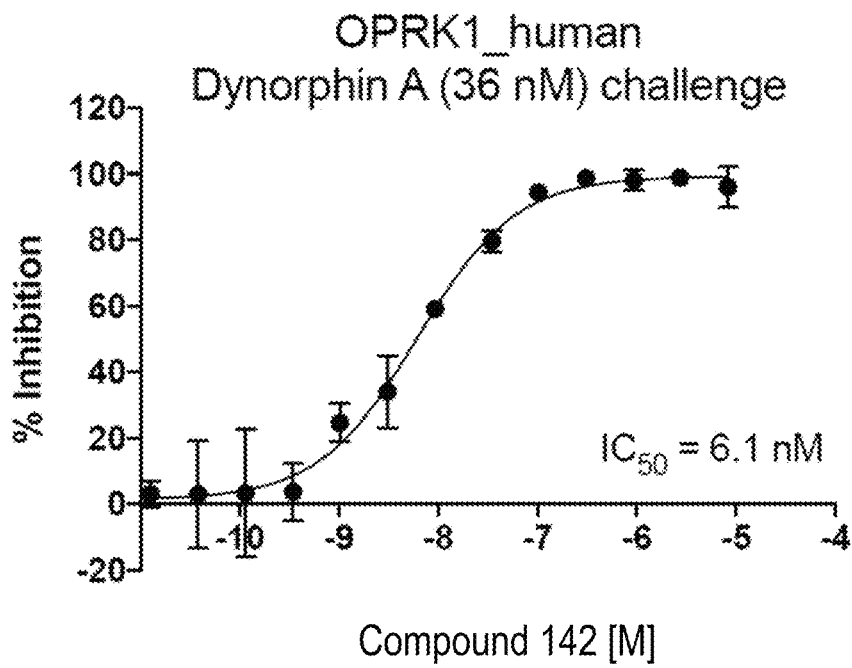
Figure 7C:
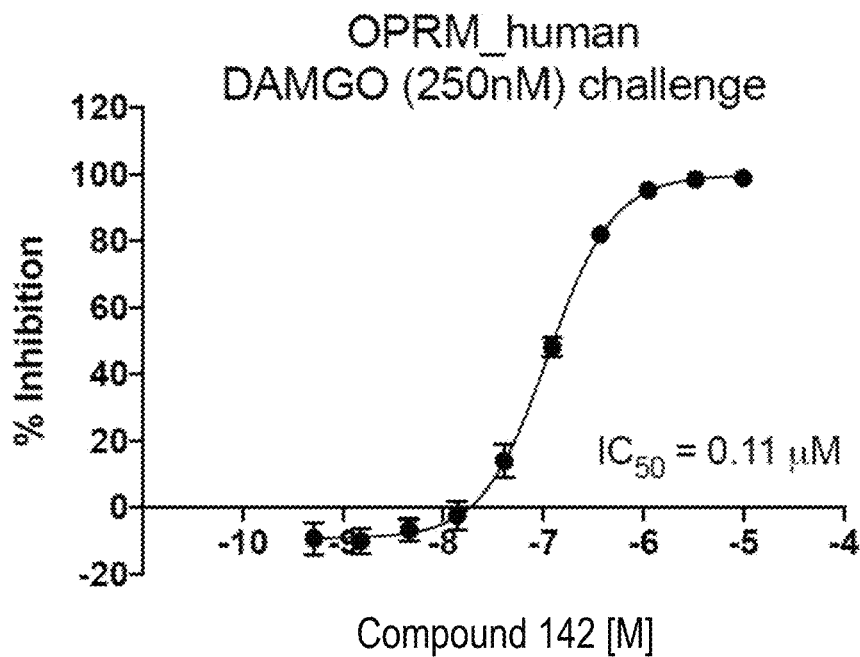
FIGS. 7C and 7D illustrate that Compound 142 is also selective over OPRM1 (FIG. 7C) and OPRD (FIG. 7D).
Figure 7D:
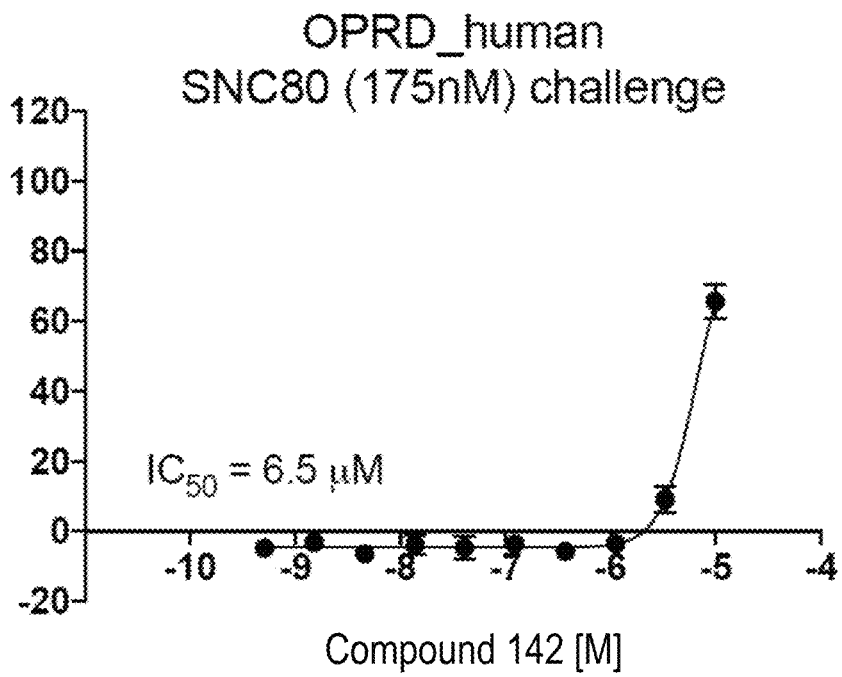

Additional compounds were tested in the same manner. Table 3 shows the results of oral dosing of selected compounds on plasma prolactin levels. Results were assessed based on decrease in prolactin levels as compared to U69593 stimulated and vehicle control measurements: NA indicates no significant reduction, + indicates partial reduction (<50%), ++ indicates reduction (>50%), +++ indicates reduced to vehicle control levels. FIG. 2 shows the results following IP injection (FIG. 2A) or PO administration (FIG. 2B) of Compound 141. FIG. 3 shows the results following IP injection (FIG. 3A) or PO administration (FIG. 3B) of Compound 145. FIG. 4 shows the results following IP injection (FIG. 4A) or PO administration (FIG. 4B) of Compound 146. FIG. 5 shows the results following IP injection (FIG. 5A) or PO administration (FIG. 5B) of Compound 147. FIG. 6 shows the results following IP injection of the tartrate salt of Compound A.

TABLE 3

Oral prolactin data (mouse)

| Compound # | 1 mg/kg | 3 mg/kg | 10 mg/kg | 30 mg/kg | Time |
|---|---|---|---|---|---|
| 34 | | | + | | 2 hr |
| 109 | | NA | NA | NA | 2 hr |
| 110 | | NA | NA | NA | 2 hr |
| 134 | | ++ | + | ++ | 2 hr |
| 136 | | + | ++ | +++ | 2 hr |
| 141 | | + | ++ | +++ | 2 hr |
| 142 | | ++ | +++ | +++ | 2 hr |
| 145 | | + | + | ++ | 2 hr |
| 146 | | ++ | ++ | +++ | 2 hr |
| 147 | | NA | NA | ++ | 2 hr |
| 175 | + | NA | ++ | | 1 hr |
| 176 | NA | NA | + | | 1 hr |
| 181 | | +++ | +++ | | 1 hr |
| 182 | | ++ | +++ | | 1 hr |
| 183 | | NA | +++ | | 1 hr |
| 196 | | | ++ | | 1 hr |
| 197 | ++ | NA | ++ | | 2 hr |
| 214 | | NA | +++ | | 1 hr |
| 215 | | ++ | ++ | | 1 hr |

TABLE 3-continued

Oral prolactin data (mouse)

| Compound # | 1 mg/kg | 3 mg/kg | 10 mg/kg | 30 mg/kg | Time |
|---|---|---|---|---|---|
| 219 |  | +++ | +++ | +++ | 1 hr |
| 220 |  | NA | ++ |  | 1 hr |
| 250 |  | NA | NA | NA | 2 hr |
| 251 |  | NA | ++ | + | 2 hr |

NA: no significant reduction

Rat Prolactin Study

Figure 10:
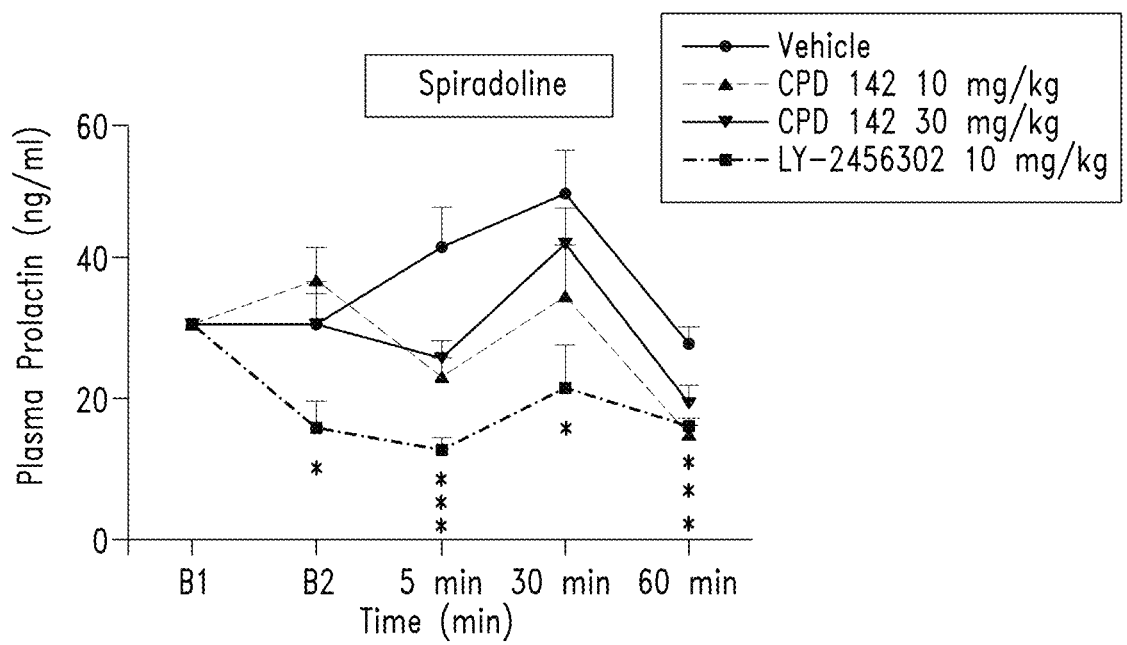
FIG. 10 illustrates that spiradoline (0.32 mg/kg, sc; OPRK1 agonist) significantly increased plasma prolactin concentrations in Sprague-Dawley rats (n=8–10/group) that was suppressed by Compound 142 at the 5 and 60 minutes timepoints, and by LY-2456302/CERC-501 (OPRK1 antagonist) at the 5, 30 and 60 min timepoints (*p≤0.05 vs baseline).

Compound 142 was tested for in vivo antagonist properties using a OPRK1 agonist-induced prolactin challenge approach. In this study, administration of Compound 142 (10 and 30 mg/kg, PO; water [vehicle]; 1 h PTT) to male, Sprague-Dawley rats; n=8-10) was followed by injection of the OPRK1-agonist, spiradoline (0.32 mg/kg, sc; 5% cyclodextran [vehicle]; 0.08 h PTT). Blood samples were taken 5 mins prior to oral dosing (B1) and 5 mins prior to spiradoline dosing (B2) and then 5, 30 and 60 mins after spiradoline administration via a tail vein cannulation. In these studies, spiradoline significantly increased plasma prolactin concentration and Compound 142 suppressed the increase in prolactin with an MED i10 mg/kg at the 5 and 60 minutes timepoints. As a comparator, the OPRK1 antagonist LY-2345302 (10 mg/kg, PO; 1 h PTT) was included and suppressed the spiradoline-induced increase in prolactin at the 5, 30 and 60 min timepoints. FIG. 10.

Rat Stress-Induced Cutaneous Allodynia (Animal Model of Migraine)

The efficacy of Compound 142 following systemic administration was assessed for ability to block bright light stress (BLS)-induced periorbital and hindpaw allodynia in rats with sumatriptan-induced latent sensitization. In this model, rats were infused with sumatriptan (0.6 mg/kg/day, s.c.) for 7 days using osmotic minipumps. At Days (D) 20 and 21 post-sumatriptan infusion, a one hour session of BLS was applied daily for 2 consecutive days. Compound 142 (1 mg/kg, i.p.) or vehicle (10% DMSO/10% Tween 80/80% saline, 5 mL/kg, i.p.) was at 30 min prior to each BLS sessions. Baseline periorbital and hindpaw tactile threshold was assessed at D21 prior to the 2nd Compound 142 administration. Periorbital and hindpaw tactile threshold was assessed hourly for 5 hours after the 2nd stress. The raw data and area over the time effect curve (AOC, calculated from baseline and hourly tactile threshold) were calculated. Compound 142 (1 mg/kg, i.p.) given at 30 min prior to each BLS blocked the development of allodynia in sumatriptan-pretreated rats. Compound 34 (5 mg/kg, p.o.) and compound 196 (5 mg/kg, p.o.) were tested in a similar manner and blocked the development of allodynia in sumatriptan-pretreated rats.

Brain Penetration Study

Figure 11:
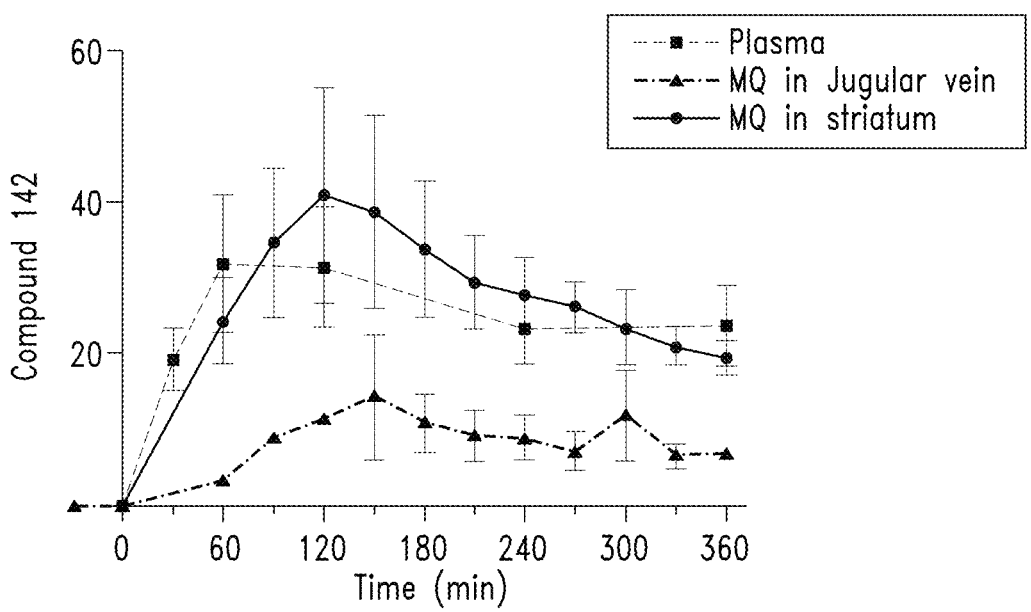
FIG. 11 illustrates that striatal concentrations of Compound 142 (40 nM) were ~3-fold higher than those identified in the jugular vein (~14 nM). Levels of Compound 142 in plasma (total concentration) also were measured. Mean±SEM. N=4/group.

Compound 142 was assessed for brain penetration properties using an in vivo microdialysis procedure in which rats were cannulated in the striatum and the jugular vein and samples were collected every 30 minutes. Striatal exposures of Compound 142 were approximately 4-fold higher than those observed from jugular vein samples collected in the same animals. Surgery: Adult, male Sprague Dawley rats were anesthetized and a jugular vein (JV) MetaQuant (MQ) probe (3 mm membrane) was implanted. Then, the animals were placed in a stereotaxic frame, and a second MQ microdialysis probe (3 mm membrane) was inserted into the striatum: (AP)=+0.9 mm from bregma, lateral (L)=+3.0 mm from midline and ventral (V)=−6.5 mm from dura. Studies were conducted 1 day after surgery. Sample collection and analytics: Probes were perfused with an artificial CSF solution at a flow rate of 0.15 µl/min. Samples were collected every 30 mins and analyzed by LC/MS. Experiments conducted at Brains On-Line, LLC (Brisbane, CA). FIG. 11

Whole Cell Slice Electrophysiology Study

Figure 12:
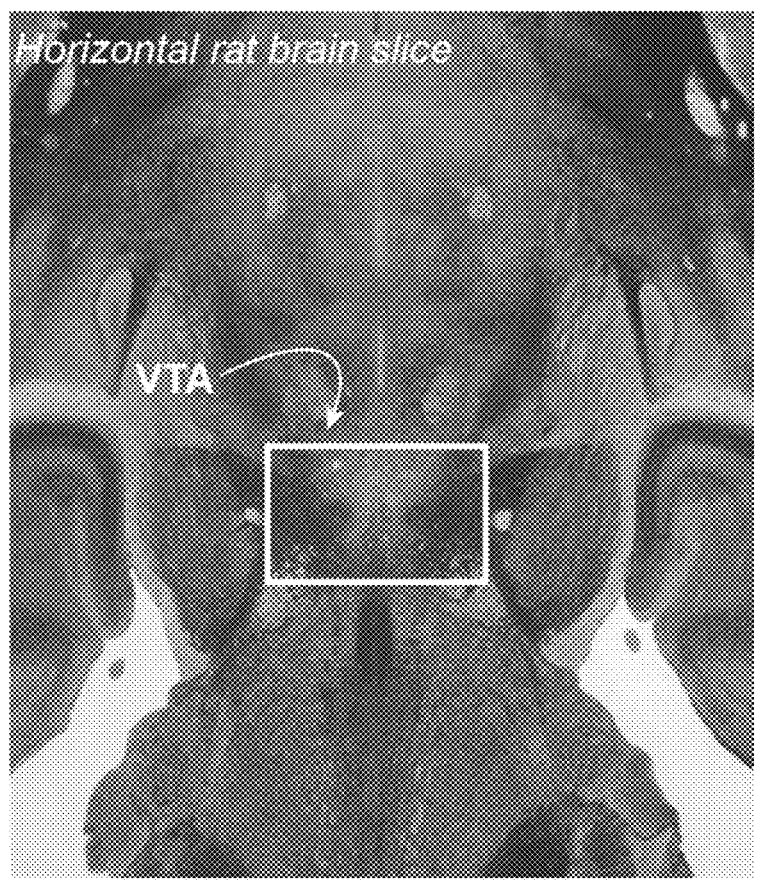
FIG. 12 illustrates native tissue using horizontal brain slices (~150 m) containing the ventral tegmental area (VTA) from male, Sprague-Dawley rats.
Figure 12:
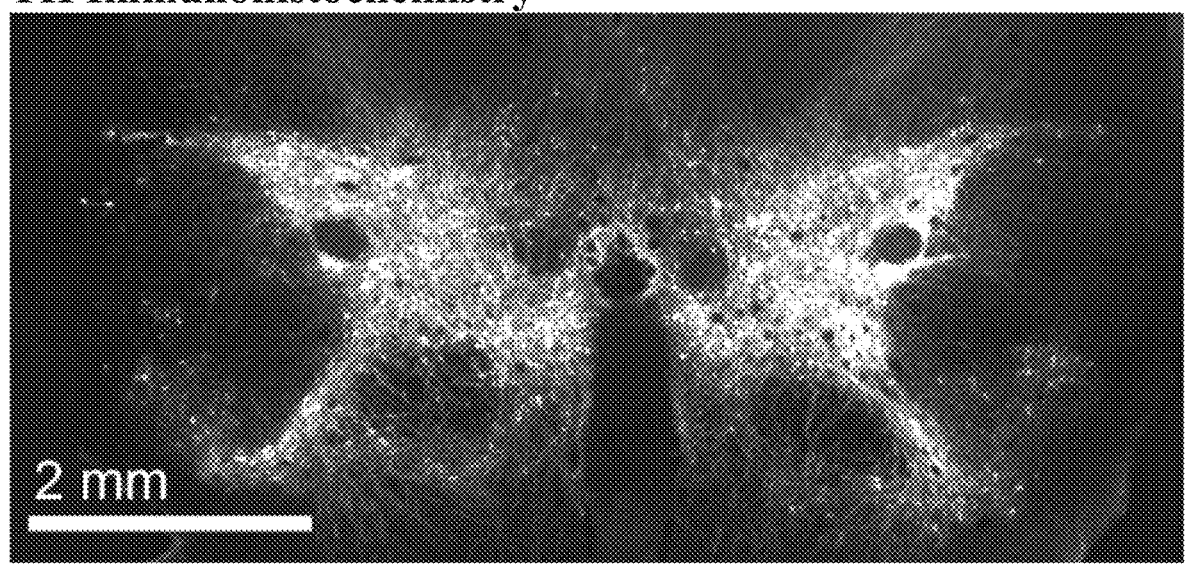

In naïve rats, the KOR selective agonist U69593 causes postsynaptic hyperpolarizations in a subset of ventral tegmental area dopamine (VTA DA) neurons, but not non-DA neurons, via activation of G protein coupled inwardly rectifying K$^+$ channels (GIRKs). The EC$_{50}$ for this U69593 effect is 42 nM. The potency, selectivity and reversibility of Compound 142, Compound A, PF-04455242, and LY2456302 were evaluated in native tissue using horizontal brain slices (~150 m) containing the VTA from male, Sprague-Dawley rats. FIG. 12.

Figure 13:
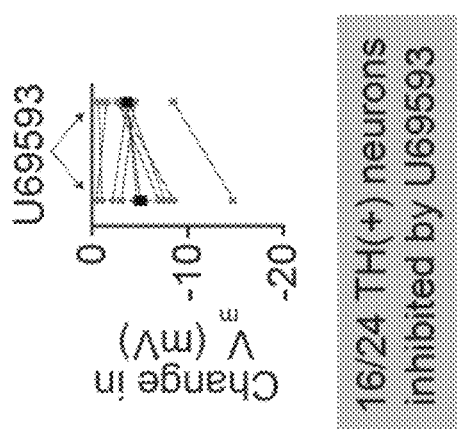
FIG. 13 illustrates the voltage clamp mode (Vm=−60 mV) allowing measurement of firing rate and/or membrane potential of VTA from male, Sprague-Dawley rats.
Figure 13:
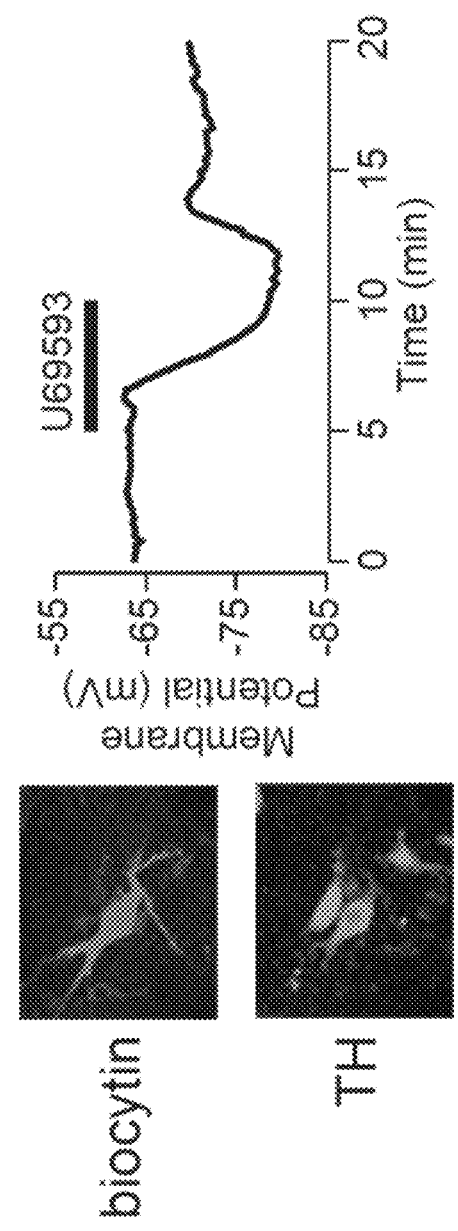

In this study, whole cell recordings were made at 33° C. with a 2.5-4 MQ pipette in voltage clamp mode (Vm=−60 mV) to allow measurement of firing rate and/or membrane potential. FIG. 13. Dose-response data were obtained following bath application of different concentrations of Compound 142, Compound A, PF-04455242, and LY2456302 (0.1-100 nM) in cells followed by administration of the OPRK1 agonist U69593 (1 µM) that was delivered via a pressure ejector placed within 300 µM of the recording site. Each application consisted of 60 seconds of agonist ejection, followed by 30 second of control artificial cerebrospinal fluid (aCSF) washout. The data are reported as % inhibition of U69593-induced outward current produced by the respective antagonist in each responding cell. In control experiments, repeated application of U69593 to VTA neurons results in similar response magnitudes. In probe experiments, each cell was calibrated with at least one baseline U69593 application, and those that showed a time-locked response were used for antagonist characterization.

Figure 14A:
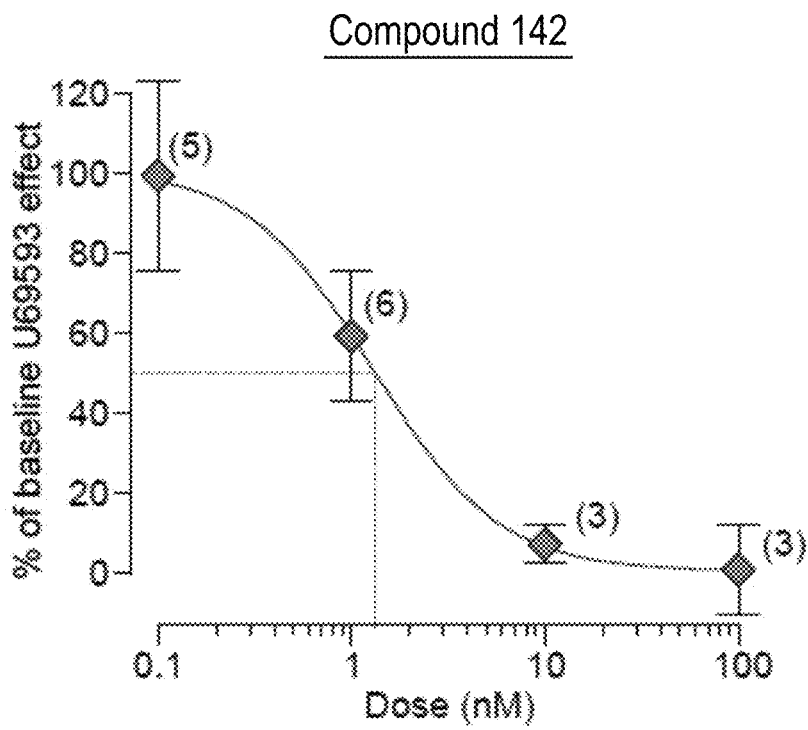
FIGS. 14A, 14B, 14C, and 14D illustrate the dose response curve reported as % inhibition of U69593-induced outward current produced in each responding cell by Compound 142 (FIG. 14A), Compound A (FIG. 14B), PF-04455242 (FIG. 14C), and LY2456302 (FIG. 14D).

In this study, Compound 142 exhibited full antagonist properties and an IC$_{50}$ of 1.3 nM. Both 10 and 100 nM of Compound 142 completely blocked the U69593 response. This is quite similar to the effective concentration in a heterologous system expressing rat KORs, where Compound 142 has an IC$_{50}$ of 3.2 nM for blocking inhibition of adenylyl cyclase by (−)-U-50,488 (3 nM). FIG. 14A.

Figure 14B:
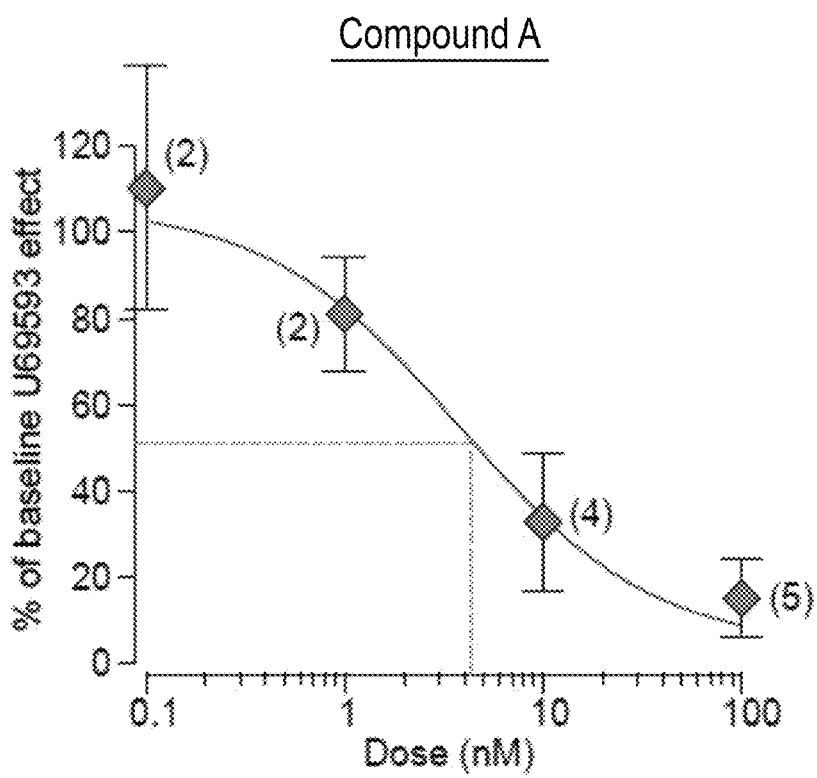

A related compound, Compound A, exhibited an IC$_{50}$ of 4.6 nM. The 100 nM dose of Compound A almost completely blocked U69593 responses. FIG. 14B.

Figure 14C:
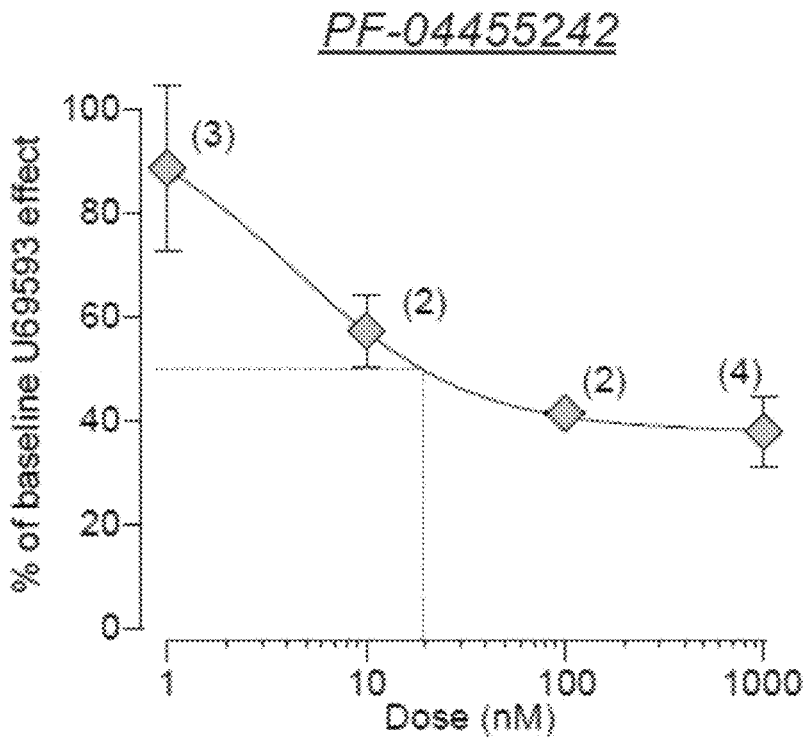

Known KOR antagonist PF-04455242 was also evaluated in this assay. Surprisingly, PF-04455242 only partially blocked the U69593 response. A maximal blockade of 60% of the U69593 response at both 100 nM and 1 µM of PF-04455242, with an absolute IC$_{50}$ of 19.6 nM was observed. The relative IC$_{50}$ was 4.3 nM. FIG. 14C.

Figure 14D:
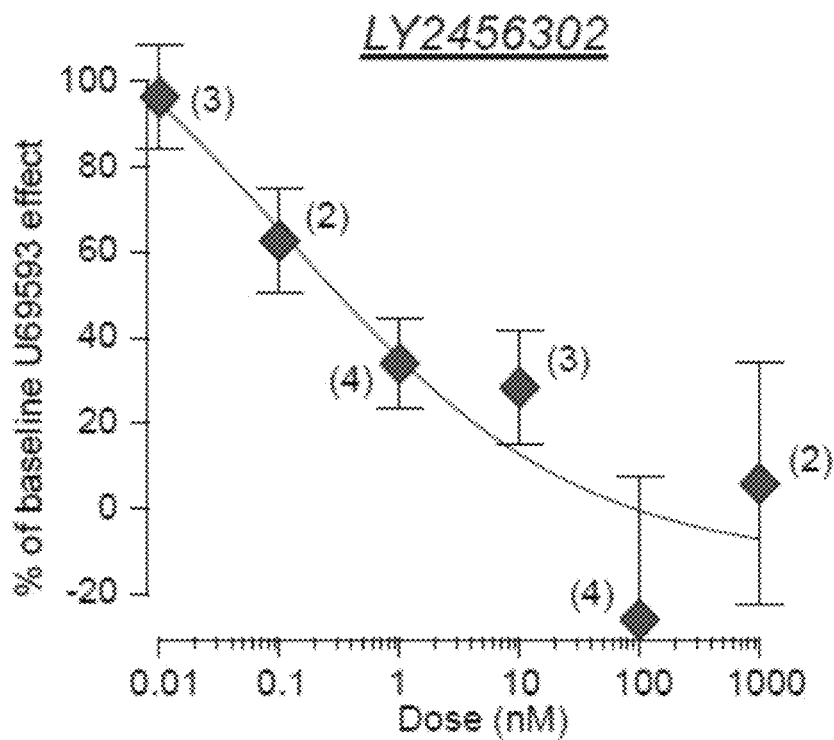

The dose response of LY2456302 was also determined. An absolute IC$_{50}$ of 0.3 nM was found for LY2456302, but the dose response shape was unusual, not well-fit by the Hill equation. FIG. 14D. Another surprising feature of these experiments was that at the 100 nM and 1 µM doses of LY2456302, a subset of cells responded to U69593 with inward currents.

Figure 15:
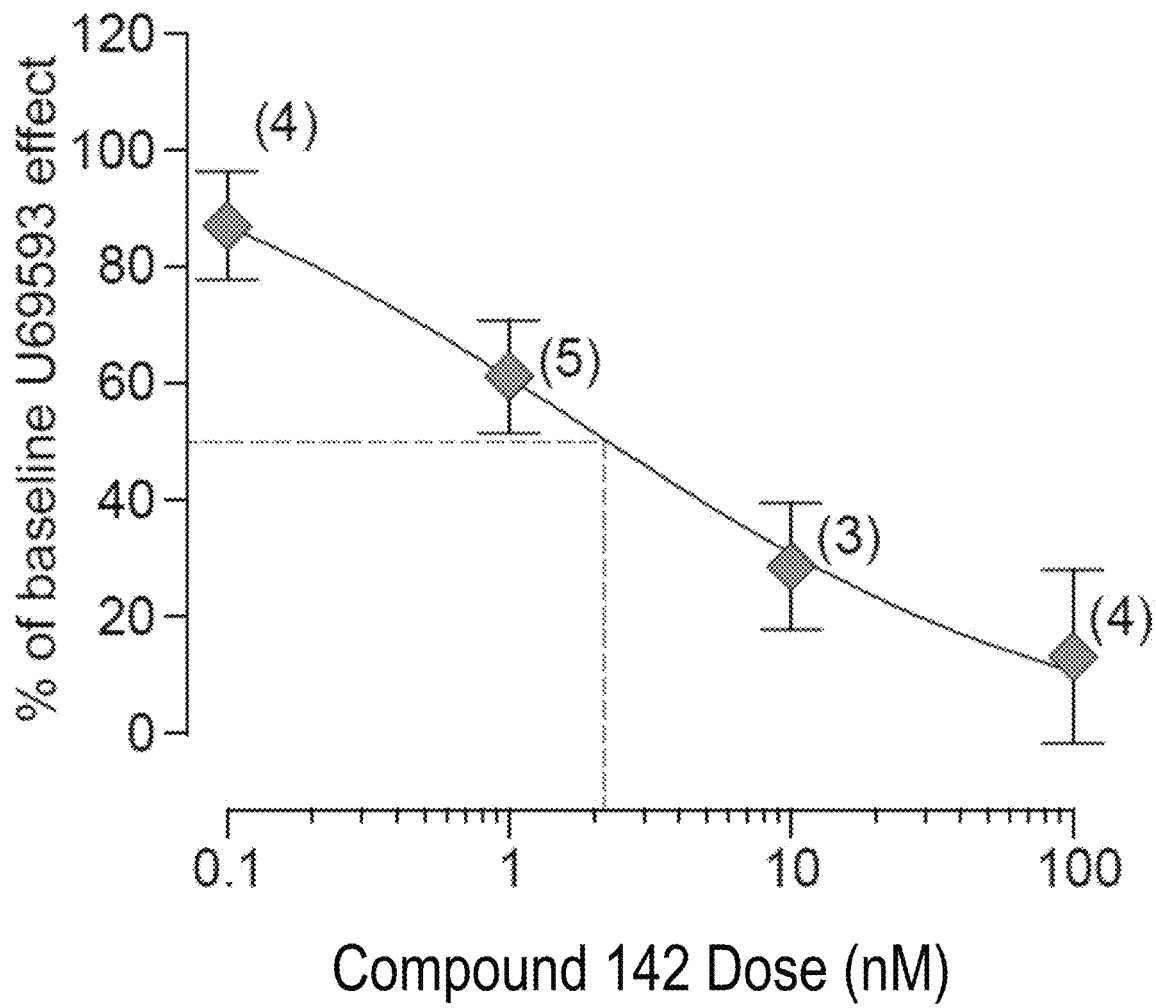
FIG. 15 illustrates the dose response curve of Compound 142's blockade of U69593 response specifically in VTA dopamine (DA) neurons that project to the medial prefrontal cortex (mPFC).

Compound 142 Effectively Blocks KOR Activity in Medial Prefrontal Cortex VTA DA Neurons Compound 142's ability to block U69593-induced responses specifically within VTA DA neurons that project to the medial prefrontal cortex (mPFC) was also measured. The retrograde tracer DiI was injected into the mPFC neurons 7 days prior to whole cell recordings made specifically in retrogradely labeled neurons from the mPFC to the VTA. In these selected neurons, the $IC_{50}$ of Compound 142 was 2.2 nM, within variance of the $IC_{50}$ among non-selected neurons. FIG. 15.

KOR Selectivity of Compound 142 Compared to LY2456302

Figure 16:
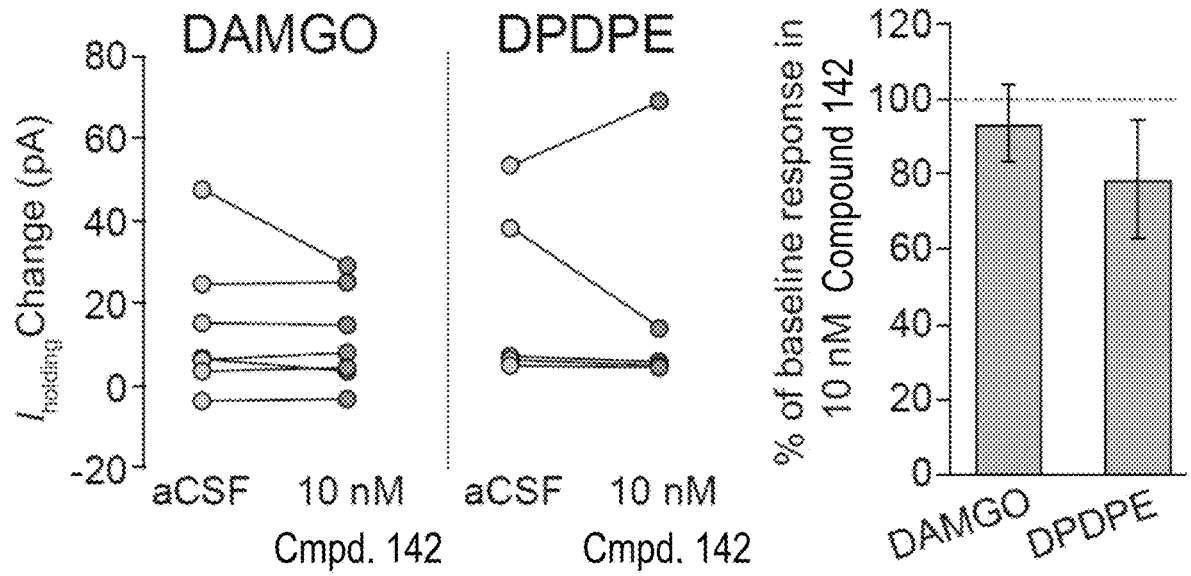
FIG. 16 illustrates the agonist-induced dose response of OPRM1 and OPRD receptors to Compound 142 and LY2456302.
Figure 16:
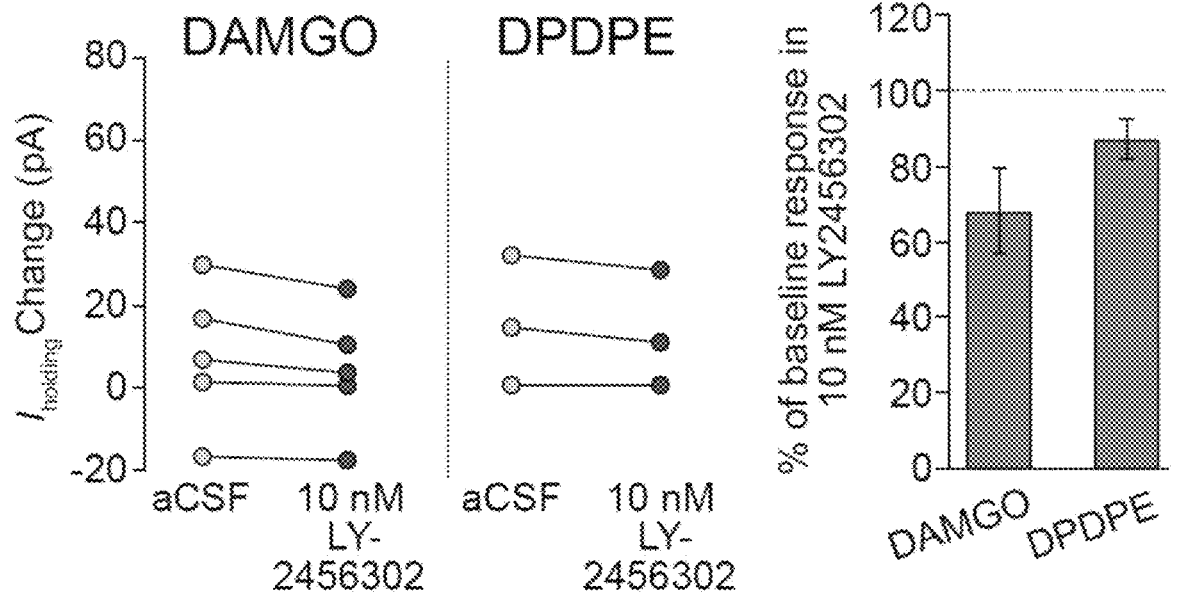

To evaluate the selectivity of Compound 142 and LY2456302 for KOR over MOR and DOR, the ability to block selective agonist-induced responses at these two receptor types in VTA neurons was tested. The MOR selective agonist DAMGO or the DOR selective agonist DPDPE was pressure ejected onto VTA neurons, and in responsive neurons the agonist was reapplied after 10 nM of either antagonist was bath applied for at least 4 minutes. This dose of Compound 142, which completely blocked the KOR response with U69593, did not affect the response to DAMGO or DPDPE. By contrast, 10 nM LY2456302 consistently diminished the response to DAMGO. FIG. 16.

Acute Washout

NorBNI is the most broadly utilized preclinical KOR antagonist tool. One major shortcoming of NorBNI, for many experimental paradigms, is evidence of persistent biological activity after even a single dosing with no measurable amount of compound on board. A short acting (reversible), selective antagonist is not only useful for clinical development, but also for experimental designs that require ligands to clear the brain within hours. In this study, it was tested whether KOR antagonists dissociate from KORs in VTA brain slices rapidly enough to observe washout during whole cell recording.

Figure 17:
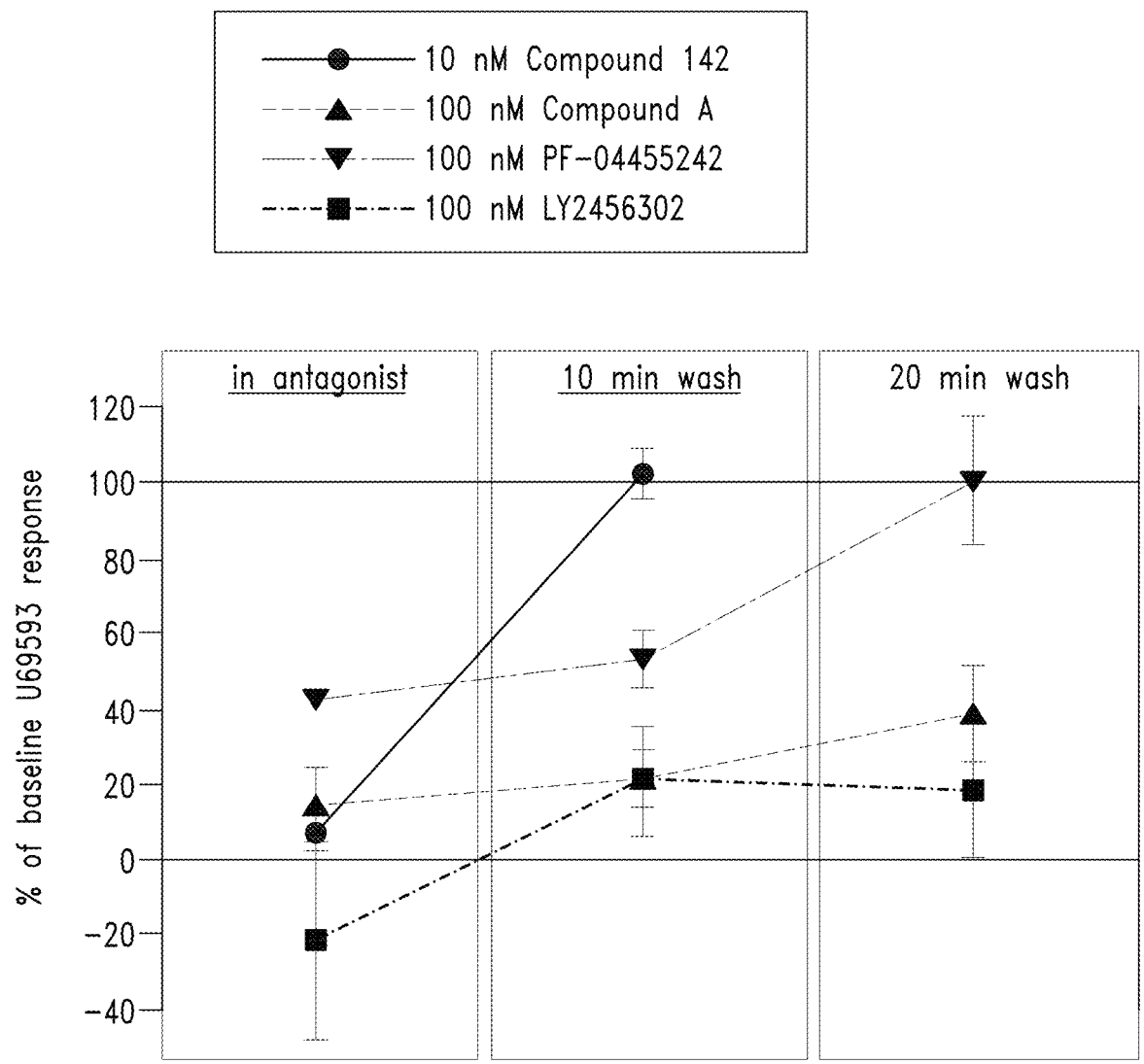
FIG. 17 illustrates baseline response return after washout of Compound 142, Compound A, PF-04455242, and LY2456302.

In each experiment, a baseline U69593 response was measured, then the antagonist was applied to the slice for 5-10 minutes. This interval was sufficient to completely block the U69593 responses, as observed in dose response experiments. U69593 responses were then probed 10 and/or 20 minutes after antagonist washout commenced. As expected, a typical ex vivo dose of NorBNI showed no washout at 20 minutes (−27.13±17.41% of baseline U69593 response, n=4). On the other hand, a 10 nM dose of Compound 142, sufficient to completely block U69593 actions, showed complete washout within 10 min. Interestingly, Compound A did not show significant reversal with up to 20 min washout. These data suggest that there can be differences in the reversible action of compounds within the same chemical series. PF-04455242 showed some washout, with the U69593 response recovering after 20 min, but not 10 min. LY2456302 did not show substantial reversal at 10 or 20 min. FIG. 17.

Results from these studies with additional KOR antagonists suggest PF-04455242 exhibits partial antagonist activity, and also generates an outward current in a subset of neurons via an unknown receptor. Compound A did not show washout of KOR blockade during the slice experiment. Additionally, LY2456302 may have more than one binding site, and a subset of cells responded to U69593 with inward currents in the presence of 100 nM and 1 μM, indicating this is not a neutral antagonist. Together these data provide electrophysiological evidence that Compound 142 is a potent, selective, and short-acting KOR antagonist in neurons that modulate brain circuits commonly dysregulated in neurobehavioral disorders.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A pharmaceutical composition comprising a compound having the following structure, or a pharmaceutically acceptable hydrate, solvate, isotope or salt thereof, together with at least one pharmaceutically acceptable carrier, diluent or excipient:

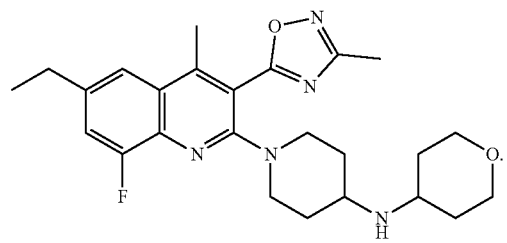 [SMILES: CCc1cc(F)c2nc(N3CCC(NC4CCOCC4)CC3)c(-c3nc(C)no3)c(C)c2c1]

2. The pharmaceutical composition of claim 1 formulated for oral administration.

3. The pharmaceutical composition of claim 2 wherein the oral formulation is a tablet, capsule, troche, lozenge, syrup or emulsion.

4. The pharmaceutical composition of claim 2 wherein the oral formulation is a tablet or capsule.

5. The pharmaceutical composition of claim 3 wherein the tablet or capsule is in a dosage form for administration once a day.

6. The pharmaceutical composition of claim 3 wherein the tablet or capsule is in a dosage form for administration two or three times a day.

* * * * *